(12) United States Patent
Bumcrot et al.

(10) Patent No.: US 7,718,629 B2
(45) Date of Patent: May 18, 2010

(54) COMPOSITIONS AND METHODS FOR INHIBITING EXPRESSION OF EG5 GENE

(75) Inventors: David Bumcrot, Belmont, MA (US); Pamela Tan, Kulmbach (DE); Hans-Peter Vornlocher, Bayreuth (DE); Anke Geick, Bayreuth (DE)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 8 days.

(21) Appl. No.: 11/694,215

(22) Filed: Mar. 30, 2007

(65) Prior Publication Data

US 2007/0281899 A1    Dec. 6, 2007

Related U.S. Application Data

(60) Provisional application No. 60/787,762, filed on Mar. 31, 2006, provisional application No. 60/870,259, filed on Dec. 15, 2006.

(51) Int. Cl.
| | |
|---|---|
| A61K 31/70 | (2006.01) |
| A01N 43/04 | (2006.01) |
| C07H 21/02 | (2006.01) |
| C07H 21/04 | (2006.01) |

(52) U.S. Cl. .................. 514/44; 536/23.1; 536/24.3; 536/24.33; 536/24.5

(58) Field of Classification Search ............ 536/23.1, 536/24.3, 24.33, 24.5; 435/6, 91.1, 325, 435/375; 514/44
See application file for complete search history.

(56) References Cited

U.S. PATENT DOCUMENTS

| | | | |
|---|---|---|---|
| 4,426,330 A | 1/1984 | Sears | |
| 4,534,899 A | 8/1985 | Sears | |
| 4,837,028 A | 6/1989 | Allen | |
| 4,868,116 A | 9/1989 | Morgan et al. | |
| 4,980,286 A | 12/1990 | Morgan et al. | |
| 5,013,556 A | 5/1991 | Woodle et al. | |
| 5,139,941 A | 8/1992 | Muzyczka et al. | |
| 5,213,804 A | 5/1993 | Martin et al. | |
| 5,225,212 A | 7/1993 | Martin et al. | |
| 5,252,479 A | 10/1993 | Srivastava | |
| 5,264,221 A | 11/1993 | Tagawa et al. | |
| 5,328,470 A | 7/1994 | Nabel et al. | |
| 5,334,711 A | 8/1994 | Sproat et al. | |
| 5,356,633 A | 10/1994 | Woodle et al. | |
| 5,540,935 A | 7/1996 | Miyazaki et al. | |
| 5,543,152 A | 8/1996 | Webb et al. | |
| 5,556,948 A | 9/1996 | Tagawa et al. | |
| 5,595,760 A | 1/1997 | Cherif-Cheikh | |
| 5,627,053 A | 5/1997 | Usman et al. | |
| 5,665,710 A | 9/1997 | Rahman et al. | |
| 5,672,659 A | 9/1997 | Shalaby et al. | |
| 5,705,188 A | 1/1998 | Junichi et al. | |
| 5,716,824 A | 2/1998 | Beigelman et al. | |
| 5,854,038 A | 12/1998 | Sullenger et al. | |
| 5,902,880 A | 5/1999 | Thompson | |
| 6,054,299 A | 4/2000 | Conrad | |
| 6,146,886 A | 11/2000 | Thompson | |
| 6,150,092 A | 11/2000 | Uchida et al. | |
| 6,395,713 B1 | 5/2002 | Beigelman et al. | |
| 2003/0203844 A1 | 10/2003 | Delfani et al. | |
| 2004/0018176 A1 | 1/2004 | Tolentino et al. | |
| 2004/0180847 A1 | 9/2004 | Dobie et al. | |
| 2004/0209832 A1 | 10/2004 | McSwiggen et al. | |
| 2005/0255487 A1 | 11/2005 | Khvorova et al. | |
| 2007/0031844 A1 | 2/2007 | Khvorova et al. | |

FOREIGN PATENT DOCUMENTS

| | | |
|---|---|---|
| DE | 101 00 586 | 4/2002 |
| EP | 0 445 131 | 10/1989 |
| EP | 0 496 813 | 10/1990 |
| WO | WO 88/04924 | 7/1988 |
| WO | WO 89/02468 | 3/1989 |
| WO | WO 89/05345 | 6/1989 |
| WO | WO 89/07136 | 8/1989 |
| WO | WO 90/04384 | 5/1990 |
| WO | WO 91/05545 | 5/1991 |
| WO | WO 92/07065 | 4/1992 |
| WO | WO 92/07573 | 5/1992 |

(Continued)

OTHER PUBLICATIONS

Weil et al. Targeting the Kinesin Eg5 to Monitor siRNA Transfection in Mammalian Cells. (BioTechniques, 2002 vol. 33. No. 6(1244-1248).*

(Continued)

*Primary Examiner*—Sean McGarry
*Assistant Examiner*—Terra Cotta Gibbs
(74) *Attorney, Agent, or Firm*—Fenwick & West LLP

(57) ABSTRACT

The invention relates to a double-stranded ribonucleic acid (dsRNA) for inhibiting the expression of the Eg5 gene (Eg5 gene), comprising an antisense strand having a nucleotide sequence which is less that 30 nucleotides in length, generally 19-25 nucleotides in length, and which is substantially complementary to at least a part of the Eg5 gene. The invention also relates to a pharmaceutical composition comprising the dsRNA together with a pharmaceutically acceptable carrier; methods for treating diseases caused by Eg5 expression and the expression of the Eg5 gene using the pharmaceutical composition; and methods for inhibiting the expression of the Eg5 gene in a cell.

33 Claims, No Drawings

FOREIGN PATENT DOCUMENTS

| | | |
|---|---|---|
| WO | WO 93/15187 | 5/1993 |
| WO | WO 93/23569 | 11/1993 |
| WO | WO 93/24641 | 12/1993 |
| WO | WO 94/02595 | 2/1994 |
| WO | WO 94/13788 | 6/1994 |
| WO | WO 94/20073 | 9/1994 |
| WO | WO 96/10390 | 4/1996 |
| WO | WO 96/10391 | 4/1996 |
| WO | WO 96/10392 | 4/1996 |
| WO | WO 96/40062 | 12/1996 |
| WO | WO 97/04787 | 2/1997 |
| WO | WO 97/13499 | 4/1997 |
| WO | WO 97/026270 | 7/1997 |
| WO | WO 97/30731 | 8/1997 |
| WO | WO 98/13526 | 4/1998 |
| WO | WO 99/32619 | 7/1999 |
| WO | WO 99/53050 | 10/1999 |
| WO | WO 99/61631 | 12/1999 |
| WO | WO 00/22113 | 4/2000 |
| WO | WO 00/22114 | 4/2000 |
| WO | WO 00/44895 | 8/2000 |
| WO | WO 00/53722 | 9/2000 |
| WO | WO 03/070910 | 8/2003 |
| WO | WO 2003/070918 A | 8/2003 |
| WO | WO 2004/001193 | 12/2003 |
| WO | WO 2004/007070 | 1/2004 |
| WO | WO 2004/011822 | 2/2004 |
| WO | WO 2004/011829 | 2/2004 |
| WO | WO 2004/064737 | 8/2004 |
| WO | WO 2004/065601 | 8/2004 |
| WO | WO 2004/080406 | 9/2004 |
| WO | WO 2004/094345 | 11/2004 |
| WO | WO 2004/094595 | 11/2004 |
| WO | WO 2004/099410 A2 | 11/2004 |
| WO | WO 2005/014782 A | 2/2005 |
| WO | WO 2005/031002 A2 | 4/2005 |
| WO | WO 2007/115168 A2 | 10/2007 |

OTHER PUBLICATIONS

Elbashir et al. Analysis of Gene Function in Somatic Mammalian Cells using Small Interfering RNAs. (Methods, 2002 vol. 26:199-213).*

Allen et al., "Large Unilamellar Liposomes with Low Uptake into the Reticuloendothelial System," Feb. 23:42-46 (1987).

Anderson et al., "Human Gene Therapy," Nature, 392 (Suppl): 25-30 (1998).

Armentano et al., "Expression of Human Facot IX in Rabbit Hepatocytes by Retrovirus-Mediated Gene Transfer: Potential for Gene Therapy of hemophilia B" Proc. Natl. Acad. Sci. USA 87: 6141-6145 (1990).

Berkner, K., "Development of Adenovirus Vectors for the Expression of Heterologous Genes," Biotechniques, 6(7): 616-629 (1988).

Blume et al., "Liposomes For the Sustained Drug Release in Vivo," Biochimica et Biophysica Acta, 1029:91-97 (1990).

Bucchini et al., "Pancreatic Expression in Human Insulin Gene in Transgenic Mice" Proc. Natl. Acad. Sci. USA, 83: 2511-2515 (1986).

Chen et al., "Gene Therapy for Brain Tumors: Regression of Experimental Gliomas by Adenovirus-Mediated Gene Transfer in vivo", Proc. Natl. Acad. Sci. USA, 91: 3054-3057 (1994).

Chowdhury et al., "Long-Term Improvements of Hypercholesterolemia After ex Vivo Gene Therapy in LDLR-Deficient Rabbits," Science, 254(5039): 1802-1805 (1991).

Cone, R. and Mulligan, R., "High-Efficiency Gene Transfer into Mammalian Cells: Generation of Helper-Free Recombinant Retrovirus with Broad Mammalian Host Range," Proceedings of the National Academy of Sciences of the United States of America, 81(20): 6349-6353 (1984).

Cornetta et al., "Safety Issues Related to Retroviral-Mediated Gene Transfer in Humans," Human Gene Therapy 2:5-14 (1991).

Couture et al., "Anti-Gene Therapy: The Use of Ribozymes to Inhibit Gene Function" TGI 12(12): 510-515 (1996).

Crooke et al., "Pharmacokinetic Properties of Several Novel Oligonucleotide Analogs in Mice" The Journal of Pharmacology and Experimental Therapeutics, 277(2): 923-937 (1996).

Dai et al., "Gene Therapy Via Primary Myoblasts: Long-Term Expression of Factor IX Protein Following Transplantation in vivo" Proc. Natl. Acad. Sci. USA, 89: 10892-10895 (1992).

Danos, O. and Mulligan, R., "Safe and Efficient Generation of Recombinant Retroviruses with Amphotropic and Ecotropic Host Ranges" Proc. Natl. Acad. Sci. USA, 85: 6460-6464 (1988).

Docherty, K. and Clark, A., "Nutrient Regulation of Insulin Gene Expression," The FASEB Journal 8: 20-27 (1994).

Dornburg, R., "Reticuloendotheliosis Viruses and Derived Vectors," Gene Therapy, 2:301-310 (1995).

du Plessis et al., "Topical Delivery of Liposomally Encapsulated Gamma-Interferon," Antiviral Research, 18:259-265 (1992).

Eglitis et al., "Gene Expression in Mice After High Efficiency Retroviral-Mediated Gene Transfer," Science 230(4732): 1395-1398 (1995).

Eglitis et al., "Retroviral Vectors for Introductions of Genes into Mammalian Cells," Biotechniques 6:608-614 (1988).

Elbashir et al., "Functional Anatomy of siRNAs for Mediating Efficient RNAi in Drosophila melanogatser embryo lysate" The EMBO Journal 20(23): 6877-6888 (2001).

El-Hariri et al., "The Mitigating Effects of Phosphatidylcholines on Bile Salt- and Lysophosphatidylcholine-Induced Membrane Damage," J. Pharm. Pharmacol., 44:651-654 (1992).

Ferry et al., "Retroviral-Mediated Gene Transfer into Hepatocytes in vivo" Proc. Natl. Acad. Sci. USA, 88: 8377-8381 (1991).

Fisher et al., "Transduction with Recombinant Adeno-Associated Virus for Gene Therapy is Limited by Leading-Strand Synthesis," Journal of Virology, 70:520-532 (1996).

Gabizon et al., "Liposome Formulations with Prolonged Circulation Time in Blood and Enhanced Uptake by Tumors," Proc. Natl. Acad. Sci. USA 85:3949-3953 (1988).

Gassmann et al., "Maintenance of an Extrachromosomal Plasmid Vecot in Mouse Embryonic Stem Cells" Proc. Natl. Acad. Sci. USA, 92: 1292-1296 (1995).

Hsu et al., "Immunogenicity of Recombinant Adenovirus-Respiratory Syncytial Virus Vaccines with Adenovirus Types 4, 5, and 7 Vecotrs in Dogs and Chimpanzee," The Journal of Infectious Diseases 166:769-775 (1992).

Hu et al., "Topical Delivery of Cyclosporin A from Non-Ionic Liposomal Systems: An In Vovo/In Vitro Correlation Study Using Hairless Mouse Skin," S.T.P. Pharma Sciences, 4: 377-379 (1994).

Huber et al., "Retroviral-Mediated Gene Therapy for the Treatment of Hepatocellular Carcinoma: An Innovative Approach for Cancer Therapy" Proc. Natl. Acad. Sci. USA, 88: 8039-8043 (1991).

Hwu et al., "Functional and Molecular Characterization of Tumor-Infiltrating Lymphocytes Transduced with Tumor Necrosis Factor-$\alpha$ cDNA for the Gene Therapy of Cancer in Humans," The Journal of Immunology 150: 4104-4115 (1993).

Illum et al., "The Organ Uptake of Intravenously Administered Collodial Particles can be Altered Using a Non-Ionic Surfactant (Poloxamer 338)," FEBS 167:79-82 (1984).

Kabanov et al., "A New Class of Antivirals: Antisense Oligonucleotides Combined with a Hydrophobic Substituent Effictively Inhibit Influenza Virus Reproduction and Synthesis of Virus-Specific Proteins in MDCK Cells" FEB 259(2): 327-330 (1990).

Kapoor et al., "Probing Spindle Assembly Mechanisms with Monastrol, A Small Molecule Inhibitor of the Mototic Kinesin, Eg5," The Journal of Cell Biology, 150:975-988 (2000).

Kay et al.., "Hepatic Gene Therapy: Persistent Expression of Human $\alpha$l-Antitypsin in Mice after Direct Gene Delivery in Vivo," Human Gene Therapy 3: 641-647 (1992).

Klibanov et al., "Amphipathic Polyethyleneglycols Effectively Prolong the Circulation Time of Liposomes," FEBS 268:235-237 (1990).

Lee et al., "Mucosal Penetration Enhancers for Facilitation of Peptide and Protein Drug Absorption," Critical Reviews in Therapeutic Drug Carrier Systems, 8:91-192 (1991).

Letsinger et al., "Cholesteryl-Conjugated Oligonucleotides: Synthesis, Properties, and Activity as Inhibitors of replication of Human Immunodeficiency Virus in Cell Culture" *Proc. Natl. Acad. Sci. USA* 86: 6533-6556 (1989).

Manoharan et al., "Chemical Modifications to Improve Uptake and Bioavailability of Anisense Oligonucleotides", *Annals of the New York Academy of Sciences*, 660: 306-308 (1992).

Manoharan et al., "Cholic Acid-Oligonucleotide Conjugates for Antisense Applications" *Bioorganic & Medicinal Chemistry Letters* 4(8): 1053-1060 (1994).

Manoharan et al., "Introduction of a Lipophilic Thioehter Tether in the Minor Groove of Nucleic Acids for Antisense Applications" Bioorganic & Medicinal Chemistry Letters 13(12):2765-2770 (1993).

Manoharan et al., "Lipidic Nucleic Acids" *Tetrahedron Letters* 36(21): 3651-3654 (1995).

Manoharan et al., "Oligonucleotide Conjugates: Alteration of the Pharmacokinetic Properties of Antisense Agents" *Nucleosides & Nucleotides* 14(3-5): 969-973 (1995).

Martin, Pierre, "Streoselektive Sytheses von 2'-o-(2-Methoxyethyl)ribonucleosiden: Nachbargruppenbeteiligung der Methoxyethoxy-Gruppe bei der Ribosylierung von Heterocyclen," *Helvetica Chimica Acta* 79: 1930-1938 (1996).

Mayer et al., "Small Molecule Inhibitor of Mitotic Spindle Bipolarity Identified in a Phenotype-Based Screen," *Science*, 286:971-974 (1999).

Miller, Dusty A., "Retrovirus Packaging Cells," *Human Gene Therapy*, 1:5-14 (1990).

Mishra et al., "Improved Leislunanicidal Effect of Phosphorotioate Antisense Oligonucleotides by LDL-Mediated Delivery" *Biochimica et Biophysica Acta* 1264: 229-237 (1995).

Miyao et al., "Stability and Pharmacokinetic Characteristics of Oligonucleotides Modified at Terminal Linkages in Mice," *Antisense Research and Development*, 5:115-121 (1995).

Muranishi, S., "Absorption Enhancers," *Critical Reviews in Therapeutic Drug Carrier Systems*, 7(1): 1-33 (1990).

Muzyczka, N., "Use of Adeno-Associated Virus as a General Transduction Vector for Mammalian Cells," *Current Topics in Microbiology and Immunology*, 158: 97-129 (1992).

Oberhauser et al., "Effectve Incorporation of 2'-O-Methly-Oligoribonucleotides Into Liposomes and Enhanced Cell Association Through Modification with Thiocholesterol" *Nucleic Acids Research*, 20(3): 533-538 (1992).

Papahadjopoulos et al., "Targeting Liposomes to Tumor Cells in Vivo," *Annals of the New York Academy of Sciences*, 507: 64-74 (1987).

Rabinowitz et al., "Cross-Packaging of a Single Adeno-Associated Virus (AAV) Type 2 Vector Genome into Muliple AAV Serotypes Enables Transduction with Broad Specificity," *Journal of Virology*, 76:791-701 (2002).

Rosenfeld et al., "In Vivo Transfer of the Human Cystic Fibrosis Transmembrane Conductance Regulator Gene to the Airway Epithelium," *Cell* 68:143-155 (1992).

Rubinson et al., "A Lentivirus-Based System to Functionally Silence Genes in Primary Mammalian Cells,. Stem Cells and Transgenic Mice by RNA Interference," *Nature Genetics*, 33: 401-406 (2003).

Saison-Behmoaras et al., "Short Modified Antisense Oligonucleotides Directed Against Ha-ras Point Mutation Induce Selective Cleavage of the mRNA and Inhibit T24 Cells Proliferation" *EMBO J.*, 10: 1111-1118 (1991).

Samulski et al., "A Recombinant Plasmid from Which an Infectious Adeno-Associated Virus Genome Can be Excised in Vitro and Its Use to Study Viral Replication," *Journal of Virology*, 61:3096-3101 (1987).

Samulski et al., "Helper-Free Stocks of Recombinant Adeno-Associated Viruses: Normal Integration Does Not Require Viral Gene Expression," *Journal of Virology* 63:3822-3828 (1989).

Shea et al., "Synthesis, Hybridization Properties and Antiviral Activity of Lipid-Oligodeoxynucleotide Conjugates" *Nucleic Acids Research* 18(13): 3777-3783 (1990).

Sunamoto et al., "Liposomeal Membranes. V. Interaction of Zinc (II) Ion with Egg Phosphatidylcholine Liposomes," *Bull. Chem. Soc. Jpn.*, 53: 2778-2781 (1980).

Svinarchuk et al., "Inhibition of HIV Proloferation in MT-4 Cells by Antisense Oligonucleotide Conjugated to Lipophilic Groups" *Biochimie* 75: 49-54 (1993).

Takahashi et al., "The Use of a Perfluorochemical Emulsion as a Vascular Perfusate in Drug Absorption," *J. Pharm. Phramacol.* 40:252-257 (1988).

Takakura et al., "Uptake Characteristics of Oligonucleotides in the Isolated Rat Liver Perfusion System," *Antisense & Nucleic Acid Drug Development* 6:177-183 (1996).

Van Beusechem et al., "Long-Term Expression of Human Adenosine Deaminase in Rhesus Monkeys Transplanted With Retrovirus-Infected Bone-Marrow Cells" *Proc. Natl. Acad. Sci. USA*, 89: 7640-7644 (1992).

Wang et al., "Plasmid DNA Absorbed to pH-Sensitive Liposomes Efficiently Transforms the Target Cells," *Biochemical and Biophysical Research Communications*, 147:980-985 (1987).

Weiner et al., "Liposomes: A Novel Topical Delivery System for Pharmaceutical and Cosmetic Applications," *Journal of Drug Targeting* 2:405-410 (1994).

Wilson et al., "Retrovirus-Mediated Transduction of Adult Hepatocytes" *Proc. Natl. Acad. Sci. USA*, 85: 3014-3018 (1988).

Xia et al., "siRNA-Mediated Gene Silencing in Vitro and in Vivo," *Nature Biotechnology*, 20:1006-1010 (2002).

Yang et al., "Evidence That Processed Small dsRNAs May Mediate Sequence-Specific mRNA Degradation during RNAi in *Drosophila* embryos" *Current Biology* 10: 1191-1200 (2000).

Zhou et al., "Targeted Delivery of DNA by Liposomes and Polymers, "*Journal of Controlled Release* 19:269-274 (1992).

Akhtar et al. "Cellular uptake and intracellular fate of antisense oligonucleotides" Trends Cell Bio. 2:139-144 (1992).

Aldrian-Herrada et al., "A peptide nucleic acid (PNA) is more rapidly internalized in cultured neurons when coupled to a retro-inverse delivery peptide. The antisense activity depresses the target mRNA and protein in magnocellular oxytocin neurons" Nucleic Acids Res. 26:4910-4916 (1998).

Beigelman et al., "Chemical Modification of Hammerhead Ribozymes" Journal of Biological Chemistry, Oct. 27, 1995, p. 25702-25708, vol. 270, No. 43.

Bernstein et al., "Role for a bidentate ribonuclease in the initiation step of RNA interference" Nature, Jan. 18, 2000, p. 363-366, vol. 409.

Boado, "Antisense drug delivery through the blood-brain barrier" Adv. Drug. Delivery Reviews, 1995, 15:73-107.

Boado et al., "Drug Delivery of Antisense Molecules to the Brain for Treatment of Alzheimer's Disease and Cerebral AIDS" J. Pharm. Sciences, Nov. 1998, p. 1308-1315, vol. 87, No. 11.

Burgin, Jr. et al., "Chemically Modified Hammerhead Ribozymes with Improved Catalytic Rates" Biochemistry, 1996, p. 14090-14097, vol. 35.

Chen et al., "Multitarget-ribozyme directed to cleave at up to nine highly conserved HIV-1 env RNA regions inhibits HIV-1 replication—potential effectiveness against most presently sequenced HIV-1 isolates" Nucleic Acids Research, Sep. 11, 1992, p. 4581-4589, vol. 20, No. 17.

Chowrira et al., "In Vitro and in Vivo Comparison of Hammerhead, Hairpin, and Hepatitis Delta Virus Self-processing Ribozyme Cassettes" J. Biol. Chem., Oct. 1994, p. 25856-25864, vol. 269, No. 41.

Couture et al., "Anti-gene therapy: the use of ribozymes to inhibit gene function" Trends Genet.(TIG), Dec. 1996, p. 510-515, vol. 12, No. 12.

Dropulic et al., "Functional Characterization of a U5 Ribozyme: Intracellular Suppression of Human Immunodeficiency Virus Type I Expression" Journal of Virology, Mar. 1992, p. 1432-1441, vol. 66, No. 3.

Dunn et al., "ARPE-19, A Human Retinal Pigment Epithelial Cell Line with Differentiated Properties" Exp. Eye Res., 1996, p. 155-169, vol. 62.

Earnshaw et al., "Modified Oligoribonucleotides as Site-Specific Probes of RNA Structure and Function" Biopolymers (Nucleic Acid Sciences), 1998, p. 39-55, vol. 48.

Elbashir et al., "Duplexes of 21-nucleotide RNAs mediate RNA interference in cultured mammalian cells" Nature, May 24, 2001, p. 494-498, vol. 411.

Elbashir el al., "RNA interference is mediated by 21- and 22-nucleotide RNAs" Genes & Development, 2001, p. 188-200, vol. 15.

Nykanen et al., "ATP Requirements and Small Interfering RNA Structure in the RNA Interference Pathway" Cell, Nov. 2, 2001, p. 309-321, vol. 107.

Ohkawa et al., "Activities of HIV-RNA targeted ribozymes transcribed from a 'shot-gun' type ribozyme-trimming plasmid" Nucleic Acids Symp. Ser. No. 27, 1992, p. 15-16.

Ojwang at al., "Inhibition of human immunodeficiency virus type I expression by a hairpin ribozyme," Proc. Natl. Acad. Sci. USA, Nov. 1992, p. 10802-10806, vol. 89.

Oku et al., "Real-time analysis of liposomal trafficking in tumor-bearing mice by use of positron emission tomography" Biochimica et Biophysics Acta 1238, 1995, p. 86-90.

Pardridge et al., "Vector-mediated delivery of a polyamide ('peptide') nucleic acid analogue through the blood-brain barrier in vivo" Proc. Natl. Acad. Sci. USA, Jun. 1995, p. 5592-5596, vol. 92.

Perreault et al., "Mixed deoxyribo- and ribo-oligonucleotides with catalytic activity" Nature, Apr. 5, 1990, p. 565-567, col. 344.

Pieken et al., "Kinetic Characterization of Ribonuclease-Resistant 2'-Modified Hammerhead Ribozymes," Science, Jul. 19, 1991, p. 314-317, vol. 253.

Prakash et al., "Synthesis of 2'-O-[2-[(N,M'Dimethylamino)oxy]ethyl] Modified Nucleosides and Olionucleotides" J. Org. Chem., 2002, p. 357-369, vol. 67.

Reich et al., "Small interfering RNA (siRNA) targeting VEGF effectively inhibits ocular neovascularization in a mouse model" Molecular Vision, May 30, 2003, p. 210-216, vol. 9.

Sarver et al., "Ribozymes as Potential Anti-HIV-1 Therapeutic Agents" Science, Mar. 9, 1990, p. 1222-1225, vol. 247.

Scanlon et al., "Ribozyme-mediated cleavage of c-fos mRNA reduces gene expression of DNA synthesis enzymes and metallothionein" Proc. Natl. Acad. Sci. USA, Dec. 1991, p. 10591-10595, vol. 88.

Taira et al., "Construction of a novel RNA-transcript-trimming plasmid which can be used both in vitro in place of run-off and (G)-free transcriptions and in vivo as multi-sequences transcription vectors" Nucleic Acids Research, 1991, p. 5125-5130, vol. 19, No. 19.

Thompson et al., "Improved accumulation and activity of ribozymes expressed from a tRNA-based RNA of erase III promoter" Nucleic Acids Research, 1995, p. 2259-2268, vol. 23, No. 12.

Tyler et al., "Peptide nucleic acids targeted to the neurotensin receptor and administered i.p. cross the blood-brain barrier and specifically reduce gene expression" Proc. Natl. Acad. Sci. USA, Jun. 1999, vol. 96, p. 7053-7058.

Tyler et al., "Specific gene blockade shows that peptide nucleic acids readily enter neuronal cells in vivo," FEBS Letters, 1998, p. 280-284, vol. 421.

Usman et al., "Chemical modification of hammerhead ribozymes: activity and nuclease resistance," Nucleic Acids Symposium Series, 1994, No. 31, p. 163-164.

Usman et al., "Exploiting the chemical synthesis of RNA" Trends Biochem. Sci. 17:334-339 (1992).

Ventura et al., "Activation of HIV-specific ribozyme activity by self-cleavage" Nucleic Acids Research, 1993, p. 3249-3255, vol. 21, No. 14.

Verma et al., "Modified Oligonucleotides: Synthesis and Strategy for Users" Annu. Rev. Biochem. 1998, p. 99-134, vol. 67, No. 99.

Vickers et al., "Efficient Reduction of Target RNAs by Small Interfering RNA and RNase H-dependent Antisense Agents" J. Biol. Chemistry, Feb. 28, 2003, p. 7108-7118, vol. 278.

Weerasinghe et al., "Resistance to Human Immunodeficiency Virus Type I (HIV-1) Infection in Human CD4+ Lymphocyte-Derived Cell Lines Conferred by Using Retroviral Vectors Expressing an HIV-1 RNA-Specific Ribozyme" Journal of Virology, 1991, p. 5531-5534, vol. 65, No. 10.

Wincott et al., "Synthesis, deprotection, analysis and purification of RNA and ribozymes" Nucleic Acids Research, 1995, p. 2677-2684, vol. 23, No. 14.

Bass, B., "The short answer," Nature 411:428-9, May 24, 2001.

Fattal et al., "Ocular delivery of nucleic acids: antisense oligonucleotides aptamers and siRNA," (2006) Advanced Drug Delivery Reviews 58:1203-1223.

Holen et al. "Positional effects of short interfering RNAs targeting the human coagulation trigger Tissue Factor," Nucleic Acid Res. 2002, 30:1757-1766.

Boese et al., "Mechanical Insights Aid Computational Short Interfering RNA Design," Methods in Enzymology 392:73-96, 2005.

Reynolds et al., "Rational siRNA design for RNA interference," Nature Biotechnology 22:326-330, 2004.

Burlina et al, "Chemical Engineering of RNase Resistant and Catalytically Active Hammerhead Ribozymes" Bioorg. Med. Chem. 5(11):1999-2010 (1997).

Filleur et al., "SiRNA-mediated Inhibition of Vascular- Endothelial Growth Factor Severely Limits Tumor Resistance to Antiangiogenic Thrombospondin-1 and Slows Tumor Vascularization and Growth" Cancer Res. 63:3919-3922 (2003).

Fire et al., "Potent specific genetic interference by double-stranded RNA in Caenorhabditis elegans" Nature 391:806-811(1998).

Genbank Accession No. AF214570, "Homo sapiens vascular endothelial growth factor isoform 121 precursor, mRNA, complete cds," Dec. 23, 1999.

Good et al., "Expression of small, therapeutic RNAs in human cell nuclei" Gene Therapy 4:45-54, 1997.

Izant J., et al., "Constitutive and Conditional Suppression of Exogenous and Endogenous Genes by Anti-Sense RNA" Science 229:345-352 (1985).

Karpeisky et al., "Highly Efficient Synthesis of 2'-O-Amino Nucleosides and Their Incorporation In Hammerhead Ribozymes" Tetrahedron Lett. 39:1131-1134 (1998).

Kashani-Sabet et al., "Reversal of the Malignant Phenotype by an Anti-ras Ribozyme" Antisense Res. Dev. 2:3-15 (1992).

Kawaski et al., "Uniformly Modified 2'-Deoxy-2'-fluoro Phosphorothioate Oligonucleotides as Nuclease-Resistant Antisense Compounds with High Affinity and Specificity for RNA Targets" J. Med. Chem. 36:831-841 (1993).

Kumar et al., "Express Protocol for Functionalization of Polymer Supports for Oligonucleotide Synthesis" Nucleosides & Nucleotides 15(4):879-888 (1996).

McGarry T., et al., "Inhibition of heat shock protein synthesis by heat-inducible antisense RNA" Proc. Nat. Acad. Sci. USA 83:399-403, Jan. 1986.

Maurer et al., "Lipid-based systems for the intracellular delivery of genetics Drugs," Molecular Membrane Biology, 16:129-140, 1999.

Liu,Y., et al., "Cationic Liposome-mediated Intravenous Gene Delivery," The Journal of Biological Chemistry, Jun. 30, 1995, p. 24864-24870, vol. 270, No. 42.

Lee, K., et al., "Modified Liposome Formulations for Cytosolic Delivery for Macromolecules," Controlled Drug Delivery, Designing Technologies for the Future, 2000, p. 184-192.

Lasic, D., et al., "Liposomes Revisited," Science, Mar. 3, 1995, 1275-1276, vol. 267.

Lasic, D., et al., "The "Stealth" Liposome: A Prototypical Biomaterial," Chemical Reviews, Dec. 1995, p. 2601-2628, vol. 95, No. 8.

Jolliet-Riant, P., et al., "Drug transfer across the blood-brain barrier and improvement of brain delivery," Fundam. Clin. Pharmacol., 1996, p. 16-26, vol. 13.

Ishiwata, H., et al., "Physical-Chemistry Characteristics and Biodistribution of Poly(ethylene glycol)-Coated Liposomes Using Poly(oxyethylene) Cholesteryl Ether," Pharmaceutical Society of Japan, Jun. 1995, p. 1005-1011, vol. 43.

Gonzalez, H., et al., "New Class of Polymers for the Delivery of Macromolecular Therapeutics," Bioconjugate Chem., 1999, p. 1068-1074, vol. 10.

Hofland, H.E.J. et al., "Formulation and Delivery of Nucleic Acids," Novel Therapeutics from Modern Biotechnology, 1999, p. 166-192.

PCT International Search Report and Written Opinion, PCT/US07/65636, Sep. 30, 2008, 16 Pages.

PCT International Search Report and Written Opinion, PCT/US2009/036223, Sep. 8, 2009, 12 Pages.

Supplementary European Search Report for European Patent Application No. EP 07759825.8, Sep. 25, 2009, 10 Pages.

Harborth, J., et al., "Sequence, chemical, and structural variation of small interfering RNAs and short hairpin RNAs and the effect on mammalian gene silencing," Antisense & Nucleic Acid Drug Development, Apr. 1, 2003, pp. 83-105, vol. 13, No. 2.

Takimoto, C., et al., "Safety and anti-tumor activity of sorafenib (Nexavar ®) in combination with other anti-cancer agents: a review of clinical trials," Cancer Chemotherapy and Pharmacology, Apr. 2008, pp. 535-548, vol. 61, No. 4.

Zimmermann, T., et al., "RNAi-mediated gene silencing in non-human primates," Nature, May 4, 2006, pp. 111-114, vol. 441, No. 7089.

* cited by examiner

SEQUENCE LISTING

<160> NUMBER OF SEQ ID NOS: 1533

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cgaaguguug uuuguccaat t                                               21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 2
uuggacaaac aacacuucgt t                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ugguguuugg agcaucuact t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
guagaugcuc caaacaccat t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ucuaaacuaa cuagaaucct t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ggauucuagu uaguuuagat t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cuuaucgaga aucuaaacut t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
```
aguuuagauu cucgauaagt t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
uugauguuua ccgaagugut t                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
acacuucggu aaacaucaat t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gugagaugca gaccauuuat t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
uaaauggucu gcaucucact t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ucugaguaca uuggaauaut t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
auauuccaau guacucagat t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gaaguguugu uuguccaaut t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
auuggacaaa caacacuuct t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
uuauuagggg cuauaauugt t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
caauuauagc ccauaauaat t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
aaggugaaag gucaccuaat t                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
uuaggugacc uuucaccuut t                                              21

```
<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
uuacaaugga aggugaaagt t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cuuucaccuu ccauuguaat t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aggugaaagg ucaccuaaut t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
auuaggugac cuuucaccut t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggugaaaggu caccuaaugt t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
cauuagguga ccuuucacct t                                              21
```

```
<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ccuuaucgag aaucuaaact t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
guuuagauuc ucgauaaggt t                                              21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
cucuuauuaa ggaguauact t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
guauacuccu uaauaagagt t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gagagauucu gugcuuuggt t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ccaaagcaca gaaucucuct t                                              21
```

```
<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aucuaaacua acuagaauct t                                               21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gauucuaguu aguuuagaut t                                               21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ucaccaaaaa agcucuuaut t                                               21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
auaagagcuu uuuggugat t                                                21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gagcuuuuug aucuucuuat t                                               21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
uaagaagauc aaaagcuct t                                                21

<210> SEQ ID NO 39
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cguacaagaa caucuauaat t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
uuauagaugu ucuuguacgt t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
auugauguuu accgaagugt t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cacuucggua aacaucaaut t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cuaaacuaac uagaauccut t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
aggauucuag uuaguuuagt t                                              21

<210> SEQ ID NO 45
<211> LENGTH: 21
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
accgaagugu uguuugucct t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ggacaaacaa cacuucggut t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ugguggugag augcagacct t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ggucugcauc ucaccaccat t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cauacucuag ucguucccat t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ugggaacgac uagaguaugt t                                              21

<210> SEQ ID NO 51
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 51
agcgcccauu caauaguagt t                                               21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cuacuauuga augggcgcut t                                               21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ggaaagcuag cgcccauuct t                                               21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gaaugggcgc uagcuuucct t                                               21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gaaagcuagc gcccauucat t                                               21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ugaaugggcg cuagcuuuct t                                               21

<210> SEQ ID NO 57
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 57
agaaacuacg auugauggat t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
uccaucaauc guaguuucut t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
uguuccuuau cgagaaucut t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
agauucucga uaaggaacat t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cagauuaccu cugcgagcct t                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ggcucgcaga gguaaucugt t                                              21

<210> SEQ ID NO 63
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 63
gcgcccauuc aauaguagat t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ucuacuauug aaugggcgct t                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
uugcacuauc uuugcguaut t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
auacgcaaag auagugcaat t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cagagcggaa agcuagcgct t                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gcgcuagcuu uccgcucugt t                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 69
agaccuuauu ugguaaucut t         21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
agauuaccaa auaaggucut t         21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
auucucuugg agggcguact t         21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
guacgcccuc caagagaaut t         21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ggcugguaua auccacgut t         21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
acguggaauu auaccagcct t         21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 75
gcggaaagcu agcgcccaut t                                              21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
augggcgcua gcuuccgct t                                               21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ugcacuaucu uugcguaugt t                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
cauacgcaaa gauagugcat t                                              21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
guauaauucc acguacccut t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
aggguacgug gaauuauact t                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 81
agaaucuaaa cuaacuagat t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ucuaguuagu uuagauucut t                                              21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
aggagcugaa uaggguuact t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
guaacccuau ucagcuccut t                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gaaguacaua agaccuuaut t                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
auaaggucuu auguacuuct t                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
```
gacaguggcc gauaagauat t     21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
uaucuuaucg gccacuguct t     21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
aaaccacuua guagugucct t     21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ggacacuacu aagugguuut t     21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
ucccuagacu ucccuauuut t     21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
aaauagggaa gucuagggat t     21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
uagacuuccc uauuucgcut t                                            21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
agcgaaauag ggaagucuat t                                            21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gcgucgcagc caaauucgut t                                            21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
acgaauuugg cugcgacgct t                                            21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
agcuagcgcc cauucaauat t                                            21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
uauugaaugg gcgcuagcut t                                            21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gaaacuacga uugauggagt t                                            21

```
<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
cuccaucaau cguaguuuct t                                              21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
ccgauaagau agaagaucat t                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ugaucuucua ucuuaucggt t                                              21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
uagcgcccau ucaauaguat t                                              21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
uacuauugaa ugggcgcuat t                                              21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
uuugcguaug gccaaacugt t                                              21
```

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
caguuuggcc auacgcaaat t                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
cacguacccu ucaucaaaut t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
auuugaugaa ggguacgugt t                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ucuuugcgua uggccaaact t                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
guuuggccau acgcaaagat t                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ccgaaguguu guuuguccat t                                              21

```
<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
uggacaaaca acacuucggt t                                             21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
agagcggaaa gcuagcgcct t                                             21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ggcgcuagcu uuccgcucut t                                             21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gcuagcgccc auucaauagt t                                             21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
cuauugaaug ggcgcuagct t                                             21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
aaguuagugu acgaacuggt t                                             21

<210> SEQ ID NO 118
```

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 118
ccaguucgua cacuaacuut t                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 119
guacgaacug gaggauuggt t                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 120
ccaauccucc aguucguact t                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 121
acgaacugga ggauuggcut t                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 122
agccaauccu ccaguucgut t                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 123
agauugaugu uuaccgaagt t                                              21

<210> SEQ ID NO 124
<211> LENGTH: 21

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
cuucgguaaa caucaaucut t                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
uaugggcuau aauugcacut t                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
agugcaauua uagcccauat t                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
aucuuugcgu auggccaaat t                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
uuuggccaua cgcaaagaut t                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
acucuagucg uucccacuct t                                              21

<210> SEQ ID NO 130
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 130
gagugggaac gacuagagut t                                            21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
aacuacgauu gauggagaat t                                            21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
uucuccauca aucguaguut t                                            21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gauaagagag cucgggaagt t                                            21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
cuucccgagc ucucuuauct t                                            21

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ucgagaaucu aaacuaacut t                                            21

<210> SEQ ID NO 136
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 136
aguuaguuua gauucucgat t                                              21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
aacuaacuag aauccuccat t                                              21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
uggaggauuc uaguuaguut t                                              21

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ggaucguaag aaggcaguut t                                              21

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
aacugccuuc uuacgaucct t                                              21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
aucguaagaa ggcaguugat t                                              21

<210> SEQ ID NO 142
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 142
ucaacugccu ucuuacgaut t                                              21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
aggcaguuga ccaacacaat t                                              21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
uuguguuggu caacugccut t                                              21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
uggccgauaa gauagaagat t                                              21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
ucuucuaucu uaucggccat t                                              21

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ucuaaggaua uagucaacat t                                              21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 148
uguugacuau auccuuagat t                                              21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
acuaagcuua auugcuuuct t                                              21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
gaaagcaauu aagcuuagut t                                              21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gcccagauca accuuuaaut t                                              21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
auuaaagguu gaucugggct t                                              21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
uuaauuuggc agagcggaat t                                              21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 154
uuccgcucug ccaaauuaat t                                              21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
uuaucgagaa ucuaaacuat t                                              21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
uaguuuagau ucucgauaat t                                              21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
cuagcgccca uucaauagut t                                              21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
acuauugaau gggcgcuagt t                                              21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
aauaguagaa ugugauccut t                                              21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 160
aggaucacau ucuacuauut t                                              21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
uacgaaaaga aguuagugut t                                              21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
acacuaacuu cuuuucguat t                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
agaaguuagu guacgaacut t                                              21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
aguucguaca cuaacuucut t                                              21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
acuaaacaga uugauguuut t                                              21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
```
aaacaucaau cuguuuagut t                                               21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
cuuugcguau ggccaaacut t                                               21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
aguuuggcca uacgcaaagt t                                               21

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
aaugaagagu auaccugggt t                                               21

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
cccagguaua cucuucauut t                                               21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
auaauuccac guacccuuct t                                               21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gaaggguacg uggaauuaut t                                              21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
acguacccuu caucaaauut t                                              21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
aauuugauga aggguacgut t                                              21

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175 cguaccuuc aucaaauuut t                                               21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
aaauuugaug aaggguacgt t                                              21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
guacccuuca ucaaauuuut t                                              21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
aaaauuugau gaaggguact t                                              21

```
<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
aacuuacuga uaauggaact t                                              21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
guaccauuau caguaaguut t                                              21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
uucagucaaa gugucucugt t                                              21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
cagagacacu uugacugaat t                                              21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
uucuuaaucc aucaucugat t                                              21

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
ucagaugaug gauuaagaat t                                              21
```

-continued

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
acaguacaca acaaggaugt t                                              21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
cauccuuguu guguacugut t                                              21

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
aagaaacuac gauugauggt t                                              21

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
ccaucaaucg uaguuucuut t                                              21

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
aaacuacgau ugauggagat t                                              21

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
ucuccaucaa ucguaguuut t                                              21

```
<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
uggagcuguu gauaagagat t                                              21

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ucucuuauca acagcuccat t                                              21

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
cuaacuagaa uccuccaggt t                                              21

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
ccuggaggau ucuaguuagt t                                              21

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gaauaugcuc auagagcaat t                                              21

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
uugcucuaug agcauauuct t                                              21

<210> SEQ ID NO 197
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
augcucauag agcaaagaat t                                              21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
uucuuugcuc uaugagcaut t                                              21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
aaaaauuggu gcuguugagt t                                              21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
cucaacagca ccaauuuuut t                                              21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
gaggagcuga auaggguuat t                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
uaacccuauu cagcuccuct t                                              21

<210> SEQ ID NO 203
<211> LENGTH: 21
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
ggagcugaau aggguuacat t                                              21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
uguaacccua uucagcucct t                                              21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
gagcugaaua ggguuacagt t                                              21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
cuguaacccu auucagcuct t                                              21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
agcugaauag gguuacagat t                                              21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
ucuguaaccc uauucagcut t                                              21

<210> SEQ ID NO 209
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 209
gcugaauagg guuacagagt t                                              21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
cucuguaacc cuauucagct t                                              21

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
ccaaacugga ucguaagaat t                                              21

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212
uucuuacgau ccaguuuggt t                                              21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
gaucguaaga aggcaguugt t                                              21

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
caacugccuu cuuacgauct t                                              21

<210> SEQ ID NO 215
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 215
accuuauuug guaaucugct t                                              21

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
gcagauuacc aaauaaggut t                                              21

<210> SEQ ID NO 217
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
uuagauacca uuacuacagt t                                              21

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
cuguaguaau gguaucuaat t                                              21

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
auaccauuac uacaguagct t                                              21

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
gcuacuguag uaaugguaut t                                              21

<210> SEQ ID NO 221
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 221
uacuacagua gcacuuggat t                                              21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
uccaagugcu acuguaguat t                                              21

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
aaaguaaaac uguacuacat t                                              21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
uguaguacag uuuuacuuut t                                              21

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
cucaagacug aucuucuaat t                                              21

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
uuagaagauc agucuugagt t                                              21

<210> SEQ ID NO 227
<211> LENGTH: 21
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 227
uugacagugg ccgauaagat t                                              21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 228
ucuuaucggc cacugucaat t                                              21

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
ugacaguggc cgauaagaut t                                              21

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
aucuuaucgg ccacugucat t                                              21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
gcaaugugga aaccuaacut t                                              21

<210> SEQ ID NO 232
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
aguuagguuu ccacauugct t                                              21

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 233
ccacuuagua guguccaggt t                                              21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 234
ccuggacacu acuaaguggt t                                              21

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
agaagguaca aaauugguut t                                              21

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
aaccaauuuu guaccuucut t                                              21

<210> SEQ ID NO 237
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
ugguuugacu aagcuuaaut t                                              21

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
auuaagcuua gucaaaccat t                                              21

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 239
gguuugacua agcuuaauut t                                               21

<210> SEQ ID NO 240
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 240
aauuaagcuu agucaaacct t                                               21

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
ucuaagucaa gagccaucut t                                               21

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
agauggcucu ugacuuagat t                                               21

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
ucaucccuau aguucacuut t                                               21

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
aagugaacua uagggaugat t                                               21

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
```

```
caucccuaua guucacuuut t                                              21

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
aaagugaacu auaggaugt t                                               21

<210> SEQ ID NO 247
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
cccuagacuu cccuauuuct t                                              21

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
gaaauaggga agucuagggt t                                              21

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
agacuucccu auuucgcuut t                                              21

<210> SEQ ID NO 250
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
aagcgaaaua gggaagucut t                                              21

<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
```
ucaccaaacc auuuguagat t        21

<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
ucuacaaaug guuuggugat t        21

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
uccuuuaaga ggccuaacut t        21

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
aguuaggccu cuuaaaggat t        21

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
uuuaagaggc cuaacucaut t        21

<210> SEQ ID NO 256
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
augaguuagg ccucuuaaat t        21

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
uuaagaggcc uaacucauut t        21

```
<210> SEQ ID NO 258
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 258
aaugaguuag gccucuuaat t                                              21

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
ggccuaacuc auucacccut t                                              21

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
agggugaaug aguuaggcct t                                              21

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
ugguauuuuu gaucuggcat t                                              21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
ugccagauca aaauaccat t                                               21

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
aguuuagugu guaaaguuut t                                              21
```

```
<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 264
aaacuuuaca cacuaaacut t                                              21

<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
gccaaauucg ucugcgaagt t                                              21

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
cuucgcagac gaauuuggct t                                              21

<210> SEQ ID NO 267
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
aauucgucug cgaagaagat t                                              21

<210> SEQ ID NO 268
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
ucuucuucgc agacgaauut t                                              21

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
ugaaagguca ccuaaugaat t                                              21
```

```
<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 270
uucauuaggu gaccuuucat t                                              21

<210> SEQ ID NO 271
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
cagaccauuu aauuuggcat t                                              21

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
ugccaaauua aauggucugt t                                              21

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
agaccauuua auuuggcagt t                                              21

<210> SEQ ID NO 274
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
cugccaaauu aaauggucut t                                              21

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
aguuauuaug ggcuauaaut t                                              21

<210> SEQ ID NO 276
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 276
auuauagccc auaauaacut t                                              21

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
gcugguauaa uuccacguat t                                              21

<210> SEQ ID NO 278
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
uacguggaau uauaccagct t                                              21

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
auuuaauuug gcagagcggt t                                              21

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
ccgcucugcc aaauuaaaut t                                              21

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
uuuaauuugg cagagcggat t                                              21

<210> SEQ ID NO 282
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 282
uccgcucugc caaauuaaat t                                              21

<210> SEQ ID NO 283
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283
uuuggcagag cggaaagcut t                                              21

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
agcuuuccgc ucugccaaat t                                              21

<210> SEQ ID NO 285
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
uuuuacaaug gaaggugaat t                                              21

<210> SEQ ID NO 286
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
uucaccuucc auuguaaaat t                                              21

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
aauggaaggu gaaggucat t                                               21

<210> SEQ ID NO 288
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 288
ugaccuuuca ccuuccauut t                                              21

<210> SEQ ID NO 289
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
ugagaugcag accauuuaat t                                              21

<210> SEQ ID NO 290
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
uuaaaugguc ugcaucucat t                                              21

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
ucgcagccaa auucgucugt t                                              21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
cagacgaauu uggcugcgat t                                              21

<210> SEQ ID NO 293
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
ggcuauaauu gcacuaucut t                                              21

<210> SEQ ID NO 294
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 294
agauagugca auuauagcct t                                                  21

<210> SEQ ID NO 295
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
auugacagug gccgauaagt t                                                  21

<210> SEQ ID NO 296
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
cuuaucggcc acugucaaut t                                                  21

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
cuagacuucc cuauuucgct t                                                  21

<210> SEQ ID NO 298
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
gcgaaauagg gaagucuagt t                                                  21

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
acuaucuuug cguauggcct t                                                  21

<210> SEQ ID NO 300
<211> LENGTH: 21
<212> TYPE: DNA
<213> ORGANISM: Artificial Sequence
<220> FEATURE:
```

<210> SEQ ID NO 300
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 300
ggccauacgc aaagauagut t         21

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 301
auacucuagu cguucccact t         21

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 302
gugggaacga cuagaguaut t         21

<210> SEQ ID NO 303
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 303
aaagaaacua cgauugaugt t         21

<210> SEQ ID NO 304
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 304
caucaaucgu aguuucuuut t         21

<210> SEQ ID NO 305
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 305
gccuugauuu uuuggcgggt t         21

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic

```
oligonucleotide

<400> SEQUENCE: 306
cccgccaaaa aaucaaggct t                                              21

<210> SEQ ID NO 307
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
cgcccauuca auaguagaat t                                              21

<210> SEQ ID NO 308
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
uucuacuauu gaaugggcgt t                                              21

<210> SEQ ID NO 309
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
ccuuauuugg uaaucugcut t                                              21

<210> SEQ ID NO 310
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
agcagauuac caaauaaggt t                                              21

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
agagacaauu ccggaugugt t                                              21

<210> SEQ ID NO 312
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 312
cacauccgga auugucucut t                                              21

<210> SEQ ID NO 313
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
ugacuuugau agcuaaauut t                                              21

<210> SEQ ID NO 314
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
aauuuagcua ucaaagucat t                                              21

<210> SEQ ID NO 315
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
uggcagagcg gaaagcuagt t                                              21

<210> SEQ ID NO 316
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
cuagcuuucc gcucugccat t                                              21

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
gagcggaaag cuagcgccct t                                              21

<210> SEQ ID NO 318
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 318
gggcgcuagc uuccgcuct t                                                21

<210> SEQ ID NO 319
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
aaagaaguua guguacgaat t                                               21

<210> SEQ ID NO 320
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
uucguacacu aacuucuuut t                                               21

<210> SEQ ID NO 321
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
auugcacuau cuuugcguat t                                               21

<210> SEQ ID NO 322
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
uacgcaaaga uagugcaaut t                                               21

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
gguauaauuc cacguaccct t                                               21

<210> SEQ ID NO 324
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 324
```

```
ggguacgugg aauuauacct t                                             21
```

<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325

```
uacucuaguc guucccacut t                                             21
```

<210> SEQ ID NO 326
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326

```
agugggaacg acuagaguat t                                             21
```

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327

```
uaugaaagaa acuacgauut t                                             21
```

<210> SEQ ID NO 328
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328

```
aaucguaguu ucuuucauat t                                             21
```

<210> SEQ ID NO 329
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329

```
augcuagaag uacauaagat t                                             21
```

<210> SEQ ID NO 330
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330

```
ucuuauguac uucuagcaut t                                              21

<210> SEQ ID NO 331
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
aaguacauaa gaccuuauut t                                              21

<210> SEQ ID NO 332
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
aauaaggucu uauguacuut t                                              21

<210> SEQ ID NO 333
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
acagccugag cuguuaaugt t                                              21

<210> SEQ ID NO 334
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
cauuaacagc ucaggcugut t                                              21

<210> SEQ ID NO 335
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
aaagaagaga caauuccggt t                                              21

<210> SEQ ID NO 336
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
ccggaauugu cucuucuuut t                                              21
```

<210> SEQ ID NO 337
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
cacacuggag aggucuaaat t                                              21

<210> SEQ ID NO 338
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
uuuagaccuc uccagugugt t                                              21

<210> SEQ ID NO 339
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
cacuggagag gucuaaagut t                                              21

<210> SEQ ID NO 340
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
acuuuagacc ucuccagugt t                                              21

<210> SEQ ID NO 341
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
acuggagagg ucuaaagugt t                                              21

<210> SEQ ID NO 342
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
cacuuuagac cucuccagut t                                              21

```
<210> SEQ ID NO 343
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
cgucgcagcc aaauucguct t                                              21

<210> SEQ ID NO 344
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
gacgaauuug gcugcgacgt t                                              21

<210> SEQ ID NO 345
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
gaaggcaguu gaccaacact t                                              21

<210> SEQ ID NO 346
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
guguugguca acugccuuct t                                              21

<210> SEQ ID NO 347
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
cauucacccu gacagaguut t                                              21

<210> SEQ ID NO 348
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
aacucuguca gggugaaugt t                                              21
```

```
<210> SEQ ID NO 349
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
aagaggccua acucauucat t                                               21

<210> SEQ ID NO 350
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
ugaaugaguu aggccucuut t                                               21

<210> SEQ ID NO 351
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
gagacaauuc cggauguggt t                                               21

<210> SEQ ID NO 352
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
ccacauccgg aauugucuct t                                               21

<210> SEQ ID NO 353
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
uuccggaugu ggauguagat t                                               21

<210> SEQ ID NO 354
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
ucuacaucca cauccggaat t                                               21

<210> SEQ ID NO 355
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
aagcuagcgc ccauucaaut t                                               21

<210> SEQ ID NO 356
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
auugaauggg cgcuagcuut t                                               21

<210> SEQ ID NO 357
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
gaaguuagug uacgaacugt t                                               21

<210> SEQ ID NO 358
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
caguucguac acuaacuuct t                                               21

<210> SEQ ID NO 359
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
uauaauucca cguacccuut t                                               21

<210> SEQ ID NO 360
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 360
aaggguacgu ggaauuauat t                                               21

<210> SEQ ID NO 361
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
acaguggccg auaagauagt t                                              21

<210> SEQ ID NO 362
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
cuaucuuauc ggccacugut t                                              21

<210> SEQ ID NO 363
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
ucugucaucc cuauaguuct t                                              21

<210> SEQ ID NO 364
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
gaacuauagg gaugacagat t                                              21

<210> SEQ ID NO 365
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
uucuugcuau gacuugugut t                                              21

<210> SEQ ID NO 366
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 366
acacaaguca uagcaagaat t                                              21

<210> SEQ ID NO 367
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 367
guaagaaggc aguugaccat t                                              21

<210> SEQ ID NO 368
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
uggucaacug ccuucuuact t                                              21

<210> SEQ ID NO 369
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
cauugacagu ggccgauaat t                                              21

<210> SEQ ID NO 370
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
uuaucggcca cugucaaugt t                                              21

<210> SEQ ID NO 371
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
agaaaccacu uaguagugut t                                              21

<210> SEQ ID NO 372
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
acacuacuaa gugguuucut t                                              21

<210> SEQ ID NO 373
<211> LENGTH: 21
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 373
ggauuguuca ucaauuggct t                                              21

<210> SEQ ID NO 374
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gccaauugau gaacaaucct t                                              21

<210> SEQ ID NO 375
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
uaagaggccu aacucauuct t                                              21

<210> SEQ ID NO 376
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gaaugaguua ggccucuuat t                                              21

<210> SEQ ID NO 377
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
aguuagugua cgaacuggat t                                              21

<210> SEQ ID NO 378
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 378
uccaguucgu acacuaacut t                                              21

<210> SEQ ID NO 379
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 379
aguacauaag accuuauuut t                                              21

<210> SEQ ID NO 380
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
aaauaagguc uuauguacut t                                              21

<210> SEQ ID NO 381
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 381
ugagccuugu guauagauut t                                              21

<210> SEQ ID NO 382
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 382
aaucuauaca caaggcucat t                                              21

<210> SEQ ID NO 383
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 383
ccuuuaagag gccuaacuct t                                              21

<210> SEQ ID NO 384
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 384
gaguuaggcc ucuuaaaggt t                                              21

<210> SEQ ID NO 385
<211> LENGTH: 21
<212> TYPE: DNA
<213> ORGANISM: Artificial Sequence
<220> FEATURE:
<223> OTHER INFORMATION: Description of Artificial Sequence: Synthetic

```
                                   -continued
       oligonucleotide

<400> SEQUENCE: 385
accacuuagu aguguccagt t                                              21

<210> SEQ ID NO 386
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 386
cuggacacua cuaaguggut t                                              21

<210> SEQ ID NO 387
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 387
gaaacuucca auuaugucut t                                              21

<210> SEQ ID NO 388
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 388
agacauaauu ggaaguuuct t                                              21

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 389
ugcauacucu agucguucct t                                              21

<210> SEQ ID NO 390
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
ggaacgacua gaguaugcat t                                              21

<210> SEQ ID NO 391
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 391
agaaggcagu ugaccaacat t                                              21

<210> SEQ ID NO 392
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 392
uguuggucaa cugccuucut t                                              21

<210> SEQ ID NO 393
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
guacauaaga ccuuauuugt t                                              21

<210> SEQ ID NO 394
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
caaauaaggu cuuauguact t                                              21

<210> SEQ ID NO 395
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
uauaauugca cuaucuuugt t                                              21

<210> SEQ ID NO 396
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
caaagauagu gcaauuauat t                                              21

<210> SEQ ID NO 397
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 397
ucucuguuac aauacauaut t                                              21

<210> SEQ ID NO 398
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
auauguauug uaacagagat t                                              21

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
uaugcucaua gagcaaagat t                                              21

<210> SEQ ID NO 400
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
ucuuugcucu augagcauat t                                              21

<210> SEQ ID NO 401
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 401
uguuguuugu ccaauucugt t                                              21

<210> SEQ ID NO 402
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
cagaauugga caaacaacat t                                              21

<210> SEQ ID NO 403
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
```

```
acuaacuaga auccuccagt t                                              21

<210> SEQ ID NO 404
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
cuggaggauu cuaguuagut t                                              21

<210> SEQ ID NO 405
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
uguggugucu auacugaaat t                                              21

<210> SEQ ID NO 406
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
uuucaguaua gacaccacat t                                              21

<210> SEQ ID NO 407
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 407
uauuauggga gaccacccat t                                              21

<210> SEQ ID NO 408
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
uggguggucu cccauaauat t                                              21

<210> SEQ ID NO 409
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
```

-continued aaggaugaag ucuaucaaat t                                              21

<210> SEQ ID NO 410
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
uuugauagac uucauccuut t                                              21

<210> SEQ ID NO 411
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
uugauaagag agcucgggat t                                              21

<210> SEQ ID NO 412
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
ucccgagcuc ucuuaucaat t                                              21

<210> SEQ ID NO 413
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413 auguccuua ucgagaauct t                                               21

<210> SEQ ID NO 414
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
gauucucgau aaggaacaut t                                              21

<210> SEQ ID NO 415
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
ggaauaugcu cauagagcat t                                              21

```
<210> SEQ ID NO 416
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
ugcucuauga gcauauucct t                                              21

<210> SEQ ID NO 417
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
ccauuccaaa cuggaucgut t                                              21

<210> SEQ ID NO 418
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
acgauccagu uuggaauggt t                                              21

<210> SEQ ID NO 419
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
ggcaguugac caacacaaut t                                              21

<210> SEQ ID NO 420
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
auuguguugg ucaacugcct t                                              21

<210> SEQ ID NO 421
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
caugcuagaa guacauaagt t                                              21
```

<210> SEQ ID NO 422
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
cuuauguacu ucuagcaugt t                                              21

<210> SEQ ID NO 423
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
cuagaaguac auaagaccut t                                              21

<210> SEQ ID NO 424
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
aggucuuaug uacuucuagt t                                              21

<210> SEQ ID NO 425
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
uuggaucucu cacaucuaut t                                              21

<210> SEQ ID NO 426
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
auagauguga gagauccaat t                                              21

<210> SEQ ID NO 427
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427 aacugguggug ucuauacugt t                                             21

```
<210> SEQ ID NO 428
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
caguauagac accacaguut t                                              21

<210> SEQ ID NO 429
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
ucauugacag uggccgauat t                                              21

<210> SEQ ID NO 430
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
uaucggccac ugucaaugat t                                              21

<210> SEQ ID NO 431
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
auaaagcaga cccauuccct t                                              21

<210> SEQ ID NO 432
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
gggaaugggu cugcuuuaut t                                              21

<210> SEQ ID NO 433
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
acagaaacca cuuaguagut t                                              21

<210> SEQ ID NO 434
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
acuacuaagu gguuucugut t                                                  21

<210> SEQ ID NO 435
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
gaaaccacuu aguaguguct t                                                  21

<210> SEQ ID NO 436
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
gacacuacua agugguuuct t                                                  21

<210> SEQ ID NO 437
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 437
aaaucuaagg auauagucat t                                                  21

<210> SEQ ID NO 438
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
ugacuauauc cuuagauuut t                                                  21

<210> SEQ ID NO 439
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 439
uuauuuauac ccaucaacat t                                                  21

<210> SEQ ID NO 440
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 440
uguugauggg uauaaauaat t                                              21

<210> SEQ ID NO 441
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 441
acagaggcau uaacacacut t                                              21

<210> SEQ ID NO 442
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 442
aguguguuaa ugccucugut t                                              21

<210> SEQ ID NO 443
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 443
acacacugga gagucuaat t                                               21

<210> SEQ ID NO 444
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 444
uuagaccucu ccagugugut t                                              21

<210> SEQ ID NO 445
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 445
acacuggaga ggucuaaagt t                                              21

<210> SEQ ID NO 446
<211> LENGTH: 21
<212> TYPE: DNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 446
cuuuagaccu cuccagugut t                                              21

<210> SEQ ID NO 447
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 447
cgagcccaga ucaaccuuut t                                              21

<210> SEQ ID NO 448
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
aaagguugau cugggcucgt t                                              21

<210> SEQ ID NO 449
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 449
ucccuauuuc gcuuucucct t                                              21

<210> SEQ ID NO 450
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 450
ggagaaagcg aaauagggat t                                              21

<210> SEQ ID NO 451
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 451
ucuaaaauca cugucaacat t                                              21

<210> SEQ ID NO 452
<211> LENGTH: 21
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 452
uguugacagu gauuuuagat t                                              21

<210> SEQ ID NO 453
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 453
agccaaauuc gucugcgaat t                                              21

<210> SEQ ID NO 454
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 454
uucgcagacg aauuggcut t                                               21

<210> SEQ ID NO 455
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 455
cccauucaau aguagaaugt t                                              21

<210> SEQ ID NO 456
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 456
cauucuacua uugaaugggt t                                              21

<210> SEQ ID NO 457
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 457
gaugaaugca uacucuagut t                                              21

<210> SEQ ID NO 458
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 458
acuagaguau gcauucauct t                                              21

<210> SEQ ID NO 459
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 459
cucauguucc uuaucgagat t                                              21

<210> SEQ ID NO 460
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
ucucgauaag gaacaugagt t                                              21

<210> SEQ ID NO 461
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 461
gagaaucuaa acuaacuagt t                                              21

<210> SEQ ID NO 462
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 462
cuaguuaguu uagauucuct t                                              21

<210> SEQ ID NO 463
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 463
uagaaguaca uaagaccuut t                                              21

<210> SEQ ID NO 464
<211> LENGTH: 21
<212> TYPE: DNA
<213> ORGANISM: Artificial Sequence
<220> FEATURE:
<223> OTHER INFORMATION: Description of Artificial Sequence: Synthetic

```
<400> SEQUENCE: 464
aaggucuuau guacuucuat t                                            21

<210> SEQ ID NO 465
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 465
cagccugagc uguuaaugat t                                            21

<210> SEQ ID NO 466
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 466
ucauuaacag cucaggcugt t                                            21

<210> SEQ ID NO 467
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
aagaagagac aauuccggat t                                            21

<210> SEQ ID NO 468
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
uccggaauug ucucuucuut t                                            21

<210> SEQ ID NO 469
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
ugcuggugug gauuguucat t                                            21

<210> SEQ ID NO 470
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 470
ugaacaaucc acaccagcat t                                           21

<210> SEQ ID NO 471
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
aaauucgucu gcgaagaagt t                                           21

<210> SEQ ID NO 472
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
cuucuucgca gacgaauuut t                                           21

<210> SEQ ID NO 473
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
uuucuggaag uugagaugut t                                           21

<210> SEQ ID NO 474
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
acaucucaac uuccagaaat t                                           21

<210> SEQ ID NO 475
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
uacuaaacag auugauguut t                                           21

<210> SEQ ID NO 476
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 476
aacaucaauc uguuuaguat t                                              21

<210> SEQ ID NO 477
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
gauugauguu uaccgaagut t                                              21

<210> SEQ ID NO 478
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
acuucgguaa acaucaauct t                                              21

<210> SEQ ID NO 479
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
gcacuaucuu ugcguauggt t                                              21

<210> SEQ ID NO 480
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
ccauacgcaa agauagugct t                                              21

<210> SEQ ID NO 481
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481
ugguauaauu ccacguacct t                                              21

<210> SEQ ID NO 482
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482
```

```
gguacgugga auuauaccat t                                         21

<210> SEQ ID NO 483
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483
agcaagcugc uuaacacagt t                                         21

<210> SEQ ID NO 484
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484
cuguguuaag cagcuugcut t                                         21

<210> SEQ ID NO 485
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485
cagaaaccac uuaguagugt t                                         21

<210> SEQ ID NO 486
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486
cacuacuaag ugguuucugt t                                         21

<210> SEQ ID NO 487
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487
aacuuauugg agguuguaat t                                         21

<210> SEQ ID NO 488
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488
```

-continued uuacaaccuc caauaaguut t                                         21

<210> SEQ ID NO 489
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
cuggagaggu cuaaaguggt t                                         21

<210> SEQ ID NO 490
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
ccacuuuaga ccucuccagt t                                         21

<210> SEQ ID NO 491
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
aaaaaagaua uaaggcagut t                                         21

<210> SEQ ID NO 492
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
acugccuuau aucuuuuuut t                                         21

<210> SEQ ID NO 493
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
gaauuuugau aucuacccat t                                         21

<210> SEQ ID NO 494
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 494
uggguagaua ucaaaauuct t                                         21

<210> SEQ ID NO 495
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 495
guauuuuuga ucuggcaact t                                              21

<210> SEQ ID NO 496
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 496
guugccagau caaaaauact t                                              21

<210> SEQ ID NO 497
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 497
aggaucccuu ggcugguaut t                                              21

<210> SEQ ID NO 498
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 498
auaccagcca agggauccut t                                              21

<210> SEQ ID NO 499
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 499
ggaucccuug gcugguauat t                                              21

<210> SEQ ID NO 500
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
uauaccagcc aagggaucct t                                              21

```
<210> SEQ ID NO 501
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
caauaguaga augugaucct t                                                  21

<210> SEQ ID NO 502
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
ggaucacauu cuacuauugt t                                                  21

<210> SEQ ID NO 503
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
gcuauaauug cacuaucuut t                                                  21

<210> SEQ ID NO 504
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
aagauagugc aauuauagct t                                                  21

<210> SEQ ID NO 505
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505
uacccuucau caaauuuuut t                                                  21

<210> SEQ ID NO 506
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
aaaaauuuga ugaaggguat t                                                  21
```

```
<210> SEQ ID NO 507
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
agaacauauu gaauaagcct t                                               21

<210> SEQ ID NO 508
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
ggcuuauuca auauguucut t                                               21

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
aaauuggugc uguugaggat t                                               21

<210> SEQ ID NO 510
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
uccucaacag caccaauuut t                                               21

<210> SEQ ID NO 511
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
ugaauagggu uacagaguut t                                               21

<210> SEQ ID NO 512
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
aacucuguaa cccuauucat t                                               21

<210> SEQ ID NO 513
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
aagaacuuga aaccacucat t                                                   21

<210> SEQ ID NO 514
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
ugagugguuu caaguucuut t                                                   21

<210> SEQ ID NO 515
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
aauaaagcag acccauucct t                                                   21

<210> SEQ ID NO 516
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
ggaauggguc ugcuuuauut t                                                   21

<210> SEQ ID NO 517
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
auacccauca acacugguat t                                                   21

<210> SEQ ID NO 518
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 518
uaccaguguu gauggguaut t                                                   21

<210> SEQ ID NO 519
<211> LENGTH: 21
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
uggauuguuc aucaauuggt t                                              21

<210> SEQ ID NO 520
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
ccaauugaug aacaauccat t                                              21

<210> SEQ ID NO 521
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
uggagagguc uaaaguggat t                                              21

<210> SEQ ID NO 522
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
uccacuuuag accucuccat t                                              21

<210> SEQ ID NO 523
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
gucaucccua uaguucacut t                                              21

<210> SEQ ID NO 524
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 524
agugaacuau agggaugact t                                              21

<210> SEQ ID NO 525
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 525
auaauggcua uaauuucuct t                                              21

<210> SEQ ID NO 526
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
gagaaauuau agccauuaut t                                              21

<210> SEQ ID NO 527
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
aucccuuggc ugguauaaut t                                              21

<210> SEQ ID NO 528
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
auuauaccag ccaagggaut t                                              21

<210> SEQ ID NO 529
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
gggcuauaau ugcacuauct t                                              21

<210> SEQ ID NO 530
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 530
gauagugcaa uuauagccct t                                              21

<210> SEQ ID NO 531
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 531
gauucucuug gagggcguat t                                              21

<210> SEQ ID NO 532
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
uacgcccucc aagagaauct t                                              21

<210> SEQ ID NO 533
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
gcaucucuca aucuugaggt t                                              21

<210> SEQ ID NO 534
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
ccucaagauu gagagaugct t                                              21

<210> SEQ ID NO 535
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
cagcagaaau cuaaggauat t                                              21

<210> SEQ ID NO 536
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 536
uauccuuaga uuucugcugt t                                              21

<210> SEQ ID NO 537
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 537
gucaagagcc aucuguagat t                                              21

<210> SEQ ID NO 538
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
ucuacagaug gcucuugact t                                              21

<210> SEQ ID NO 539
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
aaacagaggc auuaacacat t                                              21

<210> SEQ ID NO 540
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
uguguuaaug ccucuguuut t                                              21

<210> SEQ ID NO 541
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
agcccagauc aaccuuuaat t                                              21

<210> SEQ ID NO 542
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
uuaaagguug aucgggcut t                                               21

<210> SEQ ID NO 543
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
<400> SEQUENCE: 543 uauuuugau cuggcaacct t                                              21

<210> SEQ ID NO 544
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
gguugccaga ucaaaaauat t                                             21

<210> SEQ ID NO 545
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
uguuuggagc aucuacuaat t                                             21

<210> SEQ ID NO 546
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
uuaguagaug cuccaaacat t                                             21

<210> SEQ ID NO 547
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
gaaauuacag uacacaacat t                                             21

<210> SEQ ID NO 548
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 548
uguuguguac uguaauuuct t                                             21

<210> SEQ ID NO 549
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 549
acuugaccag uguaaaucut t                                              21

<210> SEQ ID NO 550
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
agauuuacac uggucaagut t                                              21

<210> SEQ ID NO 551
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
accaguguaa aucugaccut t                                              21

<210> SEQ ID NO 552
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
aggucagauu uacacuggut t                                              21

<210> SEQ ID NO 553
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
agaacaauca uuagcagcat t                                              21

<210> SEQ ID NO 554
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
ugcugcuaau gauuguucut t                                              21

<210> SEQ ID NO 555
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 555
caauguggaa accuaacugt t                                              21

<210> SEQ ID NO 556
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
caguuagguu uccacauugt t                                              21

<210> SEQ ID NO 557
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
accaagaagg uacaaaauut t                                              21

<210> SEQ ID NO 558
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558
aauuuuguac cuucuuggut t                                              21

<210> SEQ ID NO 559
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
gguacaaaau ugguugaagt t                                              21

<210> SEQ ID NO 560
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
cuucaaccaa uuuuguacct t                                              21

<210> SEQ ID NO 561
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
```

```
gguguggauu guucaucaat t                                              21

<210> SEQ ID NO 562
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
uugaugaaca auccacacct t                                              21

<210> SEQ ID NO 563
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
agaguucaca aaaagcccat t                                              21

<210> SEQ ID NO 564
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
ugggcuuuuu gugaacucut t                                              21

<210> SEQ ID NO 565
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
ugauagcuaa auuaaaccat t                                              21

<210> SEQ ID NO 566
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
ugguuuaauu uagcuaucat t                                              21

<210> SEQ ID NO 567
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
```
aauaagccug aagugaauct t            21

<210> SEQ ID NO 568
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
gauucacuuc aggcuuauut t            21

<210> SEQ ID NO 569
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
caguugacca acacaaugct t            21

<210> SEQ ID NO 570
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
gcauuguguu ggucaacugt t            21

<210> SEQ ID NO 571
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
ugguguggau uguucaucat t            21

<210> SEQ ID NO 572
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
ugaugaacaa uccacaccat t            21

<210> SEQ ID NO 573
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
auucacccug acagaguuct t            21

<210> SEQ ID NO 574
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
gaacucuguc agggugaaut t                                              21

<210> SEQ ID NO 575
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
uaagaccuua uuugguaaut t                                              21

<210> SEQ ID NO 576
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
auuaccaaau aaggucuuat t                                              21

<210> SEQ ID NO 577
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577
aagcaaugug gaaccuaat t                                               21

<210> SEQ ID NO 578
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
uuagguuucc acauugcuut t                                              21

<210> SEQ ID NO 579
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 579
ucugaaacug gauaucccat t                                              21

-continued

```
<210> SEQ ID NO 580
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
ugggauaucc aguuucagat t                                             21

<210> SEQ ID NO 581

<400> SEQUENCE: 581

000                                                                  3

<210> SEQ ID NO 582
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 582
ccauuacuac aguagcacut t                                             21

<210> SEQ ID NO 583
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 583
agugcuacug uaguaauggt t                                             21

<210> SEQ ID NO 584
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 584
aucuggcaac cauauuucut t                                             21

<210> SEQ ID NO 585
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585
agaaauaugg uugccagaut t                                             21

<210> SEQ ID NO 586
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                    oligonucleotide

<400> SEQUENCE: 586
gauagcuaaa uuaaaccaat t                                              21

<210> SEQ ID NO 587
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
uugguuuaau uuagcuauct t                                              21

<210> SEQ ID NO 588
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
agauaccauu acuacaguat t                                              21

<210> SEQ ID NO 589
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
uacuguagua augguaucut t                                              21

<210> SEQ ID NO 590
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 590
gauuguucau caauuggcgt t                                              21

<210> SEQ ID NO 591
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591
cgccaauuga ugaacaauct t                                              21

<210> SEQ ID NO 592
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 592 gcuucuccu cggcucacut t                                          21

<210> SEQ ID NO 593
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
agugagccga ggagaaagct t                                         21

<210> SEQ ID NO 594
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
ggaggauugg cugacaagat t                                         21

<210> SEQ ID NO 595
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
ucuugucagc caauccucct t                                         21

<210> SEQ ID NO 596
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
uaaugaagag uauaccuggt t                                         21

<210> SEQ ID NO 597
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
ccagguauac ucuucauuat t                                         21

<210> SEQ ID NO 598
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 598
uuucaccaaa ccauuuguat t                                              21

<210> SEQ ID NO 599
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
uacaaauggu uuggugaaat t                                              21

<210> SEQ ID NO 600
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
cuuauuaagg aguauacggt t                                              21

<210> SEQ ID NO 601
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
ccguauacuc cuuaauaagt t                                              21

<210> SEQ ID NO 602
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
gaaaucagau ggacguaagt t                                              21

<210> SEQ ID NO 603
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
cuuacgucca ucugauuuct t                                              21

<210> SEQ ID NO 604
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
```

-continued cagaugucag cauaagcgat t                                      21

<210> SEQ ID NO 605
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
ucgcuuaugc ugacaucugt t                                      21

<210> SEQ ID NO 606
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
aucuaacccu aguuguauct t                                      21

<210> SEQ ID NO 607
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
gauacaacua ggguuagaut t                                      21

<210> SEQ ID NO 608
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
aagagcuugu uaaaaucggt t                                      21

<210> SEQ ID NO 609
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
ccgauuuuaa caagcucuut t                                      21

<210> SEQ ID NO 610
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610

-continued uuaaggagua uacggaggat t                                              21

<210> SEQ ID NO 611
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
uccuccguau acuccuuaat t                                              21

<210> SEQ ID NO 612
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
uugcaaugua aauacguaut t                                              21

<210> SEQ ID NO 613
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
auacguauuu acauugcaat t                                              21

<210> SEQ ID NO 614
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
ucuaacccua guuguaucct t                                              21

<210> SEQ ID NO 615
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
ggauacaacu aggguuagat t                                              21

<210> SEQ ID NO 616
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
cauguaucuu uuucucgaut t                                              21

```
<210> SEQ ID NO 617
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
aucgagaaaa agauacaugt t                                              21

<210> SEQ ID NO 618
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 618
gaugucagca uaagcgaugt t                                              21

<210> SEQ ID NO 619
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 619
caucgcuuau gcugacauct t                                              21

<210> SEQ ID NO 620
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 620
ucccaacagg uacgacacct t                                              21

<210> SEQ ID NO 621
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 621
ggugucguac cuguugggat t                                              21

<210> SEQ ID NO 622
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 622
ugcucacgau gaguuuagut t                                              21
```

<210> SEQ ID NO 623
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 623
acuaaacuca ucgugagcat t                                              21

<210> SEQ ID NO 624
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 624
agagcuuguu aaaaucggat t                                              21

<210> SEQ ID NO 625
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 625
uccgauuuua acaagcucut t                                              21

<210> SEQ ID NO 626
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
gcguacaaga acaucuauat t                                              21

<210> SEQ ID NO 627
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
uauagauguu cuuguacgct t                                              21

<210> SEQ ID NO 628
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
gagguuguaa gccaauguut t                                              21

```
<210> SEQ ID NO 629
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
aacauuggcu ucaaccuct t                                                    21

<210> SEQ ID NO 630
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 630
aacagguacg acaccacagt t                                                   21

<210> SEQ ID NO 631
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
cugugguguc guaccuguut t                                                   21

<210> SEQ ID NO 632
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
aacccuaguu guauccccuct t                                                  21

<210> SEQ ID NO 633
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
gagggauaca acuaggguut t                                                   21

<210> SEQ ID NO 634
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 634
gcauaagcga uggauaauat t                                                   21

<210> SEQ ID NO 635
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635
uauuauccau cgcuuaugct t                                             21

<210> SEQ ID NO 636
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 636
aagcgaugga uaauaccuat t                                             21

<210> SEQ ID NO 637
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 637
uagguauuau ccaucgcuut t                                             21

<210> SEQ ID NO 638
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638
ugauccugua cgaaaagaat t                                             21

<210> SEQ ID NO 639
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639
uucuuuucgu acaggaucat t                                             21

<210> SEQ ID NO 640
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
aaaacauugg ccguucuggt t                                             21

<210> SEQ ID NO 641
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
ccagaacggc caauguuuut t                                              21

<210> SEQ ID NO 642
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 642
cuuggagggc guacaagaat t                                              21

<210> SEQ ID NO 643
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 643
uucuuguacg cccuccaagt t                                              21

<210> SEQ ID NO 644
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
ggcguacaag aacaucuaut t                                              21

<210> SEQ ID NO 645
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
auagauguuc uuguacgcct t                                              21

<210> SEQ ID NO 646
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
acucugagua cauuggaaut t                                              21

<210> SEQ ID NO 647
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 647
auuccaaugu acucagagut t                                              21

<210> SEQ ID NO 648
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 648
uuauuaagga guauacggat t                                              21

<210> SEQ ID NO 649
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649
uccguauacu ccuuaauaat t                                              21

<210> SEQ ID NO 650
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650
uaaggaguau acggaggagt t                                              21

<210> SEQ ID NO 651
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
cuccuccgua uacuccuuat t                                              21

<210> SEQ ID NO 652
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
aaaucaauag ucaacuaaat t                                              21

<210> SEQ ID NO 653
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 653
uuuaguugac uauugauuut t                                            21

<210> SEQ ID NO 654
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 654
aaucaauagu caacuaaagt t                                            21

<210> SEQ ID NO 655
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655 cuuaguuga cuauugauut t                                             21

<210> SEQ ID NO 656
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 656
uucucaguau acuguguaat t                                            21

<210> SEQ ID NO 657
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657
uuacacagua uacugagaat t                                            21

<210> SEQ ID NO 658
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 658
ugugaaacac ucugauaaat t                                            21

<210> SEQ ID NO 659
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 659
uuuaucagag uguuucacat t					21

<210> SEQ ID NO 660
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 660
agaugugaau cucugaacat t					21

<210> SEQ ID NO 661
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 661
uguucagaga uucacaucut t					21

<210> SEQ ID NO 662
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 662
agguuguaag ccaauguugt t					21

<210> SEQ ID NO 663
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 663
caacauuggc uuacaaccut t					21

<210> SEQ ID NO 664
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 664
ugagaaauca gauggacgut t					21

<210> SEQ ID NO 665
<211> LENGTH: 21
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 665
acguccaucu gauuucucat t                                              21

<210> SEQ ID NO 666
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 666
agaaaucaga uggacguaat t                                              21

<210> SEQ ID NO 667
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 667
uuacguccau cugauuucut t                                              21

<210> SEQ ID NO 668
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 668
auaucccaac agguacgact t                                              21

<210> SEQ ID NO 669
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 669
gucguaccug uugggauaut t                                              21

<210> SEQ ID NO 670
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
cccaacaggu acgacaccat t                                              21

<210> SEQ ID NO 671
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671 ugugucgua ccuguugggt t					21

<210> SEQ ID NO 672
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
aguauacuga agaaccucut t					21

<210> SEQ ID NO 673
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 673
agagguucuu caguauacut t					21

<210> SEQ ID NO 674
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 674
auauauauca gccgggcgct t					21

<210> SEQ ID NO 675
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 675
gcgcccggcu gauauauaut t					21

<210> SEQ ID NO 676
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 676
aaucuacccc uaguuguaut t					21

<210> SEQ ID NO 677
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 677
auacaacuag gguuagauut t                                              21

<210> SEQ ID NO 678
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 678
cuaacccuag uuguauccct t                                              21

<210> SEQ ID NO 679
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 679
gggauacaac uagguuagt t                                               21

<210> SEQ ID NO 680
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 680
cuaguuguau cccuccuuut t                                              21

<210> SEQ ID NO 681
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 681
aaaggaggga uacaacuagt t                                              21

<210> SEQ ID NO 682
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 682
agacaucuga cuaauggcut t                                              21

<210> SEQ ID NO 683
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 683

```
agccauuagu cagaugucut t                                              21
```

<210> SEQ ID NO 684
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 684

```
gaagcucaca augauuuaat t                                              21
```

<210> SEQ ID NO 685
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 685

```
uuaaaucauu gugagcuuct t                                              21
```

<210> SEQ ID NO 686
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 686

```
acauguaucu uuucucgat t                                               21
```

<210> SEQ ID NO 687
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 687

```
ucgagaaaaa gauacaugut t                                              21
```

<210> SEQ ID NO 688
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 688

```
ucgauucaaa ucuuaaccct t                                              21
```

<210> SEQ ID NO 689
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 689

-continued

```
ggguuaagau uugaaucgat t                                              21
```

<210> SEQ ID NO 690
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 690

```
ucuuaacccu uaggacucut t                                              21
```

<210> SEQ ID NO 691
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 691

```
agaguccuaa ggguuaagat t                                              21
```

<210> SEQ ID NO 692
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 692

```
gcucacgaug aguuuagugt t                                              21
```

<210> SEQ ID NO 693
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 693

```
cacuaaacuc aucgugagct t                                              21
```

<210> SEQ ID NO 694
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 694

```
cauaagcgau ggauaauact t                                              21
```

<210> SEQ ID NO 695
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 695

```
guauuaucca ucgcuuaugt t                                              21
```

<210> SEQ ID NO 696
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 696
auaagcgaug gauaauacct t                                                 21

<210> SEQ ID NO 697
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 697
gguauuaucc aucgcuuaut t                                                 21

<210> SEQ ID NO 698
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 698
ccuaauaaac ugcccucagt t                                                 21

<210> SEQ ID NO 699
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 699
cugagggcag uuuauuaggt t                                                 21

<210> SEQ ID NO 700
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 700
ucggaaaguu gaacuuggut t                                                 21

<210> SEQ ID NO 701
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
accaaguuca acuuccgat t                                                  21

```
<210> SEQ ID NO 702
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
gaaaacauug gccguucugt t                                                    21

<210> SEQ ID NO 703
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 703
cagaacggcc aauguuuuct t                                                    21

<210> SEQ ID NO 704
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 704
aagacugauc uucuaaguut t                                                    21

<210> SEQ ID NO 705
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
aacuuagaag aucagucuut t                                                    21

<210> SEQ ID NO 706
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
gagcuuguua aaaucggaat t                                                    21

<210> SEQ ID NO 707
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
uuccgauuuu aacaagcuct t                                                    21
```

<210> SEQ ID NO 708
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 708
acauuggccg uucuggagct t              21

<210> SEQ ID NO 709
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 709
gcuccagaac ggccaaugut t              21

<210> SEQ ID NO 710
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 710
aagaacaucu auaauugcat t              21

<210> SEQ ID NO 711
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 711
ugcaauuaua gauguucuut t              21

<210> SEQ ID NO 712
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 712
aaaugugucu acucauguut t              21

<210> SEQ ID NO 713
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 713
aacaugagua gacacauuut t              21

<210> SEQ ID NO 714

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 714 ugcuacuca uguuucucat t                                              21

<210> SEQ ID NO 715
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 715
ugagaaacau gaguagacat t                                             21

<210> SEQ ID NO 716
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 716
guauacugug uaacaaucut t                                             21

<210> SEQ ID NO 717
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 717
agauuguuac acaguauact t                                             21

<210> SEQ ID NO 718
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 718
uauacugugu aacaaucuat t                                             21

<210> SEQ ID NO 719
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 719
uagauuguua cacaguauat t                                             21

<210> SEQ ID NO 720
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 720
cuuaguagug uccaggaaat t                                           21

<210> SEQ ID NO 721
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 721
uuuccuggac acuacuaagt t                                           21

<210> SEQ ID NO 722
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 722
ucagauggac guaaggcagt t                                           21

<210> SEQ ID NO 723
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 723
cugccuuacg uccaucugat t                                           21

<210> SEQ ID NO 724
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 724
agauaaauug auagcacaat t                                           21

<210> SEQ ID NO 725
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 725
uugugcuauc aauuuaucut t                                           21

<210> SEQ ID NO 726
<211> LENGTH: 21
<212> TYPE: DNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 726
caacagguac gacaccacat t                                              21

<210> SEQ ID NO 727
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 727 ugggugucg uaccuguugt t                                               21

<210> SEQ ID NO 728
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 728
ugcaauguaa auacguauut t                                              21

<210> SEQ ID NO 729
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 729
aauacguauu uacauugcat t                                              21

<210> SEQ ID NO 730
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 730
agucagaauu uuaucuagat t                                              21

<210> SEQ ID NO 731
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 731
ucuagauaaa auucugacut t                                              21

<210> SEQ ID NO 732
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 732
cuagaaaucu uuuaacacct t                                              21

<210> SEQ ID NO 733
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 733
gguguuaaaa gauuucuagt t                                              21

<210> SEQ ID NO 734
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 734
aauaaaucua acccuaguut t                                              21

<210> SEQ ID NO 735
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 735
aacuaggguu agauuuauut t                                              21

<210> SEQ ID NO 736
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 736
aauuuucugc ucacgaugat t                                              21

<210> SEQ ID NO 737
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 737
ucaucgugag cagaaaauut t                                              21

<210> SEQ ID NO 738
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 738
gcccucagua aauccauggt t                                              21

<210> SEQ ID NO 739
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 739
ccauggauuu acugagggct t                                              21

<210> SEQ ID NO 740
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 740
acguuuaaaa cgagaucuut t                                              21

<210> SEQ ID NO 741
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 741
aagaucucgu uuuaaacgut t                                              21

<210> SEQ ID NO 742
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
aggagauaga acguuuaaat t                                              21

<210> SEQ ID NO 743
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 743
uuuaaacguu cuaucuccut t                                              21

<210> SEQ ID NO 744
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 744
gaccgucaug gcgucgcagt t                                          21

<210> SEQ ID NO 745
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 745
cugcgacgcc augacgguct t                                          21

<210> SEQ ID NO 746
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 746
accgucaugg cgucgcagct t                                          21

<210> SEQ ID NO 747
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 747
gcugcgacgc caugacggut t                                          21

<210> SEQ ID NO 748
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 748
gaacguuuaa aacgagauct t                                          21

<210> SEQ ID NO 749
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 749
gaucucguuu uaaacguuct t                                          21

<210> SEQ ID NO 750
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 750
uugagcuuaa cauagguaat t                                              21

<210> SEQ ID NO 751
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 751
uuaccuaugu uaagcucaat t                                              21

<210> SEQ ID NO 752
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 752
acuaaauuga ucucguagat t                                              21

<210> SEQ ID NO 753
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 753
ucuacgagau caauuuagut t                                              21

<210> SEQ ID NO 754
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 754
ucguagaauu aucuuaauat t                                              21

<210> SEQ ID NO 755
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 755
uauuaagaua auucuacgat t                                              21

<210> SEQ ID NO 756
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 756
ggagauagaa cguuuaaaat t                                        21

<210> SEQ ID NO 757
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 757
uuuuaaacgu ucuaucucct t                                        21

<210> SEQ ID NO 758
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 758
acaacuuauu ggagguugut t                                        21

<210> SEQ ID NO 759
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 759
acaaccucca auaaguugut t                                        21

<210> SEQ ID NO 760
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 760
ugagcuuaac auagguaaat t                                        21

<210> SEQ ID NO 761
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 761
uuuaccuaug uuaagcucat t                                        21

<210> SEQ ID NO 762
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 762
aucucguaga auuaucuuat t         21

<210> SEQ ID NO 763
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 763
uaagauaauu cuacgagaut t         21

<210> SEQ ID NO 764
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 764
cugcgugcag ucgguccuct t         21

<210> SEQ ID NO 765
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 765
gaggaccgac ugcacgcagt t         21

<210> SEQ ID NO 766
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 766
cacgcagcgc ccgagaguat t         21

<210> SEQ ID NO 767
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 767
uacucucggg cgcugcgugt t         21

<210> SEQ ID NO 768
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 768
aguaccaggg agacuccggt t                                    21

<210> SEQ ID NO 769
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 769
ccggagucuc ccugguacut t                                    21

<210> SEQ ID NO 770
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 770
acggaggaga uagaacguut t                                    21

<210> SEQ ID NO 771
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 771
aacguucuau cuccuccgut t                                    21

<210> SEQ ID NO 772
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 772
agaacguuua aaacgagaut t                                    21

<210> SEQ ID NO 773
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 773
aucucguuuu aaacguucut t                                    21

<210> SEQ ID NO 774
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 774
aacguuuaaa acgagaucut t                                    21

```
<210> SEQ ID NO 775
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 775
agaucucguu uuaaacguut t                                              21

<210> SEQ ID NO 776
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 776
agcuugagcu uaacauaggt t                                              21

<210> SEQ ID NO 777
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 777
ccuauguuaa gcucaagcut t                                              21

<210> SEQ ID NO 778
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 778
agcuuaacau agguaaauat t                                              21

<210> SEQ ID NO 779
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 779
uauuuaccua uguuaagcut t                                              21

<210> SEQ ID NO 780
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 780
uagagcuaca aaaccuauct t                                              21
```

```
<210> SEQ ID NO 781
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 781
gauagguuuu guagcucuat t                                                    21

<210> SEQ ID NO 782
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 782
uaguuguauc ccuccuuuat t                                                    21

<210> SEQ ID NO 783
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 783
uaaaggaggg auacaacuat t                                                    21

<210> SEQ ID NO 784
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 784
accacccaga caucugacut t                                                    21

<210> SEQ ID NO 785
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 785
agucagaugu cuggguggut t                                                    21

<210> SEQ ID NO 786
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 786
agaaacuaaa uugaucucgt t                                                    21
```

```
<210> SEQ ID NO 787
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 787
cgagaucaau uuaguuucut t                                              21

<210> SEQ ID NO 788
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 788
ucucguagaa uuaucuuaat t                                              21

<210> SEQ ID NO 789
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 789
uuaagauaau ucuacgagat t                                              21

<210> SEQ ID NO 790
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 790
caacuuauug gagguuguat t                                              21

<210> SEQ ID NO 791
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 791
uacaaccucc aauaaguugt t                                              21

<210> SEQ ID NO 792
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 792
uuguaucccu ccuuuaagut t                                              21

<210> SEQ ID NO 793
```

<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 793
acuuaaagga gggaucaaut t                                              21

<210> SEQ ID NO 794
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 794
ucacaacuua uuggagguut t                                              21

<210> SEQ ID NO 795
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 795
aaccuccaau aaguugugat t                                              21

<210> SEQ ID NO 796
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 796
agaacuguac ucuucucagt t                                              21

<210> SEQ ID NO 797
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 797
cugagaagag uacaguucut t                                              21

<210> SEQ ID NO 798
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 798
gagcuuaaca uagguaaaut t                                              21

<210> SEQ ID NO 799
<211> LENGTH: 21

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 799
auuuaccuau guuaagcuct t                                              21

<210> SEQ ID NO 800
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 800
caccaacauc uguccuuagt t                                              21

<210> SEQ ID NO 801
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 801
cuaaggacag auguuggugt t                                              21

<210> SEQ ID NO 802
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 802
aaagcccacu uuagaguaut t                                              21

<210> SEQ ID NO 803
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 803
auacucuaaa gugggcuuut t                                              21

<210> SEQ ID NO 804
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 804
aagcccacuu uagaguauat t                                              21

<210> SEQ ID NO 805
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 805
uauacucuaa agugggcuut t                                              21

<210> SEQ ID NO 806
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 806
gaccuuauuu gguaaucugt t                                              21

<210> SEQ ID NO 807
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 807
cagauuacca aauaagguct t                                              21

<210> SEQ ID NO 808
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 808
gauuaaugua cucaagacut t                                              21

<210> SEQ ID NO 809
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 809
agucuugagu acauuaauct t                                              21

<210> SEQ ID NO 810
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 810
cuuuaagagg ccuaacucat t                                              21

<210> SEQ ID NO 811
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 811
ugaguuaggc cucuuaaagt t                                              21

<210> SEQ ID NO 812
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 812
uuaaaccaaa cccuauugat t                                              21

<210> SEQ ID NO 813
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 813
ucaauagggu uugguuuaat t                                              21

<210> SEQ ID NO 814
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 814
ucuguuggag aucuauaaut t                                              21

<210> SEQ ID NO 815
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 815
auuauagauc uccaacagat t                                              21

<210> SEQ ID NO 816
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 816
cugauguuuc ugagagacut t                                              21

<210> SEQ ID NO 817
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 817
agucucucag aaacaucagt t                                                 21

<210> SEQ ID NO 818
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 818
gcauacucua gucguuccct t                                                 21

<210> SEQ ID NO 819
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 819
gggaacgacu agaguaugct t                                                 21

<210> SEQ ID NO 820
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 820
guuccuuauc gagaaucuat t                                                 21

<210> SEQ ID NO 821
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 821
uagauucucg auaaggaact t                                                 21

<210> SEQ ID NO 822
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 822
gcacuuggau cucucacaut t                                                 21

<210> SEQ ID NO 823
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 823
augugagaga uccaagugct t                                              21

<210> SEQ ID NO 824
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 824
aaaaaaggaa cuagauggct t                                              21

<210> SEQ ID NO 825
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 825
gccaucuagu uccuuuuuut t                                              21

<210> SEQ ID NO 826
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 826
agagcagauu accucugcgt t                                              21

<210> SEQ ID NO 827
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 827
cgcagaggua aucugcucut t                                              21

<210> SEQ ID NO 828
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 828
agcagauuac cucugcgagt t                                              21

<210> SEQ ID NO 829
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 829
cucgcagagg uaaucugcut t                                              21

<210> SEQ ID NO 830
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 830
cccugacaga guucacaaat t                                              21

<210> SEQ ID NO 831
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 831
uuugugaacu cugucagggt t                                              21

<210> SEQ ID NO 832
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 832
guuuaccgaa guguuguuut t                                              21

<210> SEQ ID NO 833
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 833
aaacaacacu ucgguaaact t                                              21

<210> SEQ ID NO 834
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 834
uuacaguaca caacaaggat t                                              21

<210> SEQ ID NO 835
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 835
uccuuguugu guacuguaat t                                               21

<210> SEQ ID NO 836
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 836
acuggaucgu aagaaggcat t                                               21

<210> SEQ ID NO 837
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 837
ugccuucuua cgauccagut t                                               21

<210> SEQ ID NO 838
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 838
gagcagauua ccucugcgat t                                               21

<210> SEQ ID NO 839
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 839
ucgcagaggu aaucugcuct t                                               21

<210> SEQ ID NO 840
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 840
aaaagaaguu aguguacgat t                                               21

<210> SEQ ID NO 841
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 841
ucguacacua acuucuuuut t          21

<210> SEQ ID NO 842
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 842
gaccauuuaa uuuggcagat t          21

<210> SEQ ID NO 843
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 843
ucugccaaau uaaaugguct t          21

<210> SEQ ID NO 844
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 844
gagaggagug auaauuaaat t          21

<210> SEQ ID NO 845
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 845
uuuaauuauc acuccucuct t          21

<210> SEQ ID NO 846
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 846
cuggaggauu ggcugacaat t          21

<210> SEQ ID NO 847
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 847

-continued uugucagcca auccuccagt t					21

<210> SEQ ID NO 848
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 848
cucuagucgu ucccacucat t					21

<210> SEQ ID NO 849
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 849
ugagugggaa cgacuagagt t					21

<210> SEQ ID NO 850
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 850
gauaccauua cuacaguagt t					21

<210> SEQ ID NO 851
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 851
cuacuguagu aaugguauct t					21

<210> SEQ ID NO 852
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 852
uucgucugcg aagaagaaat t					21

<210> SEQ ID NO 853
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 853
uuucuucuuc gcagacgaat t					21

```
<210> SEQ ID NO 854
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 854
gaaaagaagu uaguguacgt t                                              21

<210> SEQ ID NO 855
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 855
cguacacuaa cuucuuuuct t                                              21

<210> SEQ ID NO 856
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 856
ugauguuuac cgaaguguut t                                              21

<210> SEQ ID NO 857
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 857
aacacuucgg uaaacaucat t                                              21

<210> SEQ ID NO 858
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 858
uguuugucca auucuggaut t                                              21

<210> SEQ ID NO 859
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 859
auccagaauu ggacaaacat t                                              21
```

```
<210> SEQ ID NO 860
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 860
augaagagua uaccugggat t                                              21

<210> SEQ ID NO 861
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 861
ucccagguau acucuucaut t                                              21

<210> SEQ ID NO 862
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 862
gcuacucuga ugaaugcaut t                                              21

<210> SEQ ID NO 863
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 863
augcauucau cagaguagct t                                              21

<210> SEQ ID NO 864
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 864
gcccuuguag aaagaacact t                                              21

<210> SEQ ID NO 865
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 865
guguucuuuc uacaagggct t                                              21
```

```
<210> SEQ ID NO 866
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 866
ucauguuccu uaucgagaat t                                              21

<210> SEQ ID NO 867
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 867
uucucgauaa ggaacaugat t                                              21

<210> SEQ ID NO 868
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 868
gaauaggguu acagaguugt t                                              21

<210> SEQ ID NO 869
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 869
caacucugua acccuauuct t                                              21

<210> SEQ ID NO 870
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 870
caaacuggau cguaagaagt t                                              21

<210> SEQ ID NO 871
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 871
cuucuuacga uccaguuugt t                                              21

<210> SEQ ID NO 872
```

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 872
cuuauuuggu aaucugcugt t                                              21

<210> SEQ ID NO 873
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 873
cagcagauua ccaaauaagt t                                              21

<210> SEQ ID NO 874
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 874
agcaaugugg aaaccuaact t                                              21

<210> SEQ ID NO 875
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 875
guuagguuuc cacauugcut t                                              21

<210> SEQ ID NO 876
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 876
acaauaaagc agacccauut t                                              21

<210> SEQ ID NO 877
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 877
aaugggucug cuuuauugut t                                              21

<210> SEQ ID NO 878
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 878
aaccacuuag uaguguccat t                                              21

<210> SEQ ID NO 879
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 879
uggacacuac uaagugguut t                                              21

<210> SEQ ID NO 880
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 880
agucaagagc caucuguagt t                                              21

<210> SEQ ID NO 881
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 881
cuacagaugg cucuugacut t                                              21

<210> SEQ ID NO 882
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 882
cucccuagac ucccuauut t                                               21

<210> SEQ ID NO 883
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 883
aauagggaag ucuagggagt t                                              21

<210> SEQ ID NO 884
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 884
auagcuaaau uaaaccaaat t                                              21

<210> SEQ ID NO 885
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 885
uuugguuuaa uuuagcuaut t                                              21

<210> SEQ ID NO 886
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 886
uggcugguau aauuccacgt t                                              21

<210> SEQ ID NO 887
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 887
cguggaauua uaccagccat t                                              21

<210> SEQ ID NO 888
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 888
uuauuuggua aucugcugut t                                              21

<210> SEQ ID NO 889
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 889
acagcagauu accaaauaat t                                              21

<210> SEQ ID NO 890
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 890
aacuagaugg cuuucucagt t                                              21

<210> SEQ ID NO 891
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 891
cugagaaagc caucuaguut t                                              21

<210> SEQ ID NO 892
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 892
ucauggcguc gcagccaaat t                                              21

<210> SEQ ID NO 893
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 893
uuuggcugcg acgccaugat t                                              21

<210> SEQ ID NO 894
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 894
acuggaggau uggcugacat t                                              21

<210> SEQ ID NO 895
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 895
ugucagccaa uccuccagut t                                              21

<210> SEQ ID NO 896
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 896
cuauaauugc acuaucuuut t                                              21

<210> SEQ ID NO 897
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 897
aaagauagug caauuauagt t                                              21

<210> SEQ ID NO 898
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 898
aaaggucacc uaaugaagat t                                              21

<210> SEQ ID NO 899
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 899
ucuucauuag gugaccuuut t                                              21

<210> SEQ ID NO 900
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 900
augaaugcau acucuaguct t                                              21

<210> SEQ ID NO 901
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 901
gacuagagua ugcauucaut t                                              21

<210> SEQ ID NO 902
<211> LENGTH: 21
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 902
aacauauuga auaagccugt t                                              21

<210> SEQ ID NO 903
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 903
caggcuuauu caauauguut t                                              21

<210> SEQ ID NO 904
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 904
aagaaggcag uugaccaact t                                              21

<210> SEQ ID NO 905
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 905
guuggucaac ugccuucuut t                                              21

<210> SEQ ID NO 906
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 906
gauacuaaaa gaacaaucat t                                              21

<210> SEQ ID NO 907
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 907
ugauuguucu uuuaguauct t                                              21

<210> SEQ ID NO 908
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 908
auacugaaaa ucaauaguct t                                              21

<210> SEQ ID NO 909
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 909
gacuauugau uuucaguaut t                                              21

<210> SEQ ID NO 910
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 910
aaaaaggaac uagauggcut t                                              21

<210> SEQ ID NO 911
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 911
agccaucuag uuccuuuuut t                                              21

<210> SEQ ID NO 912
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 912
gaacuagaug gcuuucucat t                                              21

<210> SEQ ID NO 913
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 913
ugagaaagcc aucuaguuct t                                              21

<210> SEQ ID NO 914
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 914
gaaaccuaac ugaagaccut t                                              21

<210> SEQ ID NO 915
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 915
aggucuucag uuagguuuct t                                              21

<210> SEQ ID NO 916
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 916
uacccaucaa cacugguaat t                                              21

<210> SEQ ID NO 917
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 917
uuaccagugu ugauggguat t                                              21

<210> SEQ ID NO 918
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 918
auuuugauau cuacccauut t                                              21

<210> SEQ ID NO 919
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 919
aauggguaga uaucaaaaut t                                              21

<210> SEQ ID NO 920
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 920
```
aucccuauag uucacuuugt t                                                    21

<210> SEQ ID NO 921
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 921
caaagugaac uauagggaut t                                                    21

<210> SEQ ID NO 922
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 922
augggcuaua auugcacuat t                                                    21

<210> SEQ ID NO 923
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 923
uagugcaauu auagcccaut t                                                    21

<210> SEQ ID NO 924
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 924
agauuaccuc ugcgagccct t                                                    21

<210> SEQ ID NO 925
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 925
gggcucgcag agguaaucut t                                                    21

<210> SEQ ID NO 926
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 926
uaauuccacg uacccuucat t    21

<210> SEQ ID NO 927
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 927
ugaaggguac guggaauuat t    21

<210> SEQ ID NO 928
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 928
gucguuccca cucaguuuut t    21

<210> SEQ ID NO 929
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 929
aaaacugagu gggaacgact t    21

<210> SEQ ID NO 930
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 930
aaaucaaucc cuguugacut t    21

<210> SEQ ID NO 931
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 931
agucaacagg gauugauuut t    21

<210> SEQ ID NO 932
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 932
ucauagagca aagaacauat t    21

<210> SEQ ID NO 933
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 933
uauguucuuu gcucuaugat t                                              21

<210> SEQ ID NO 934
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 934
uuacuacagu agcacuuggt t                                              21

<210> SEQ ID NO 935
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 935
ccaagugcua cuguaguaat t                                              21

<210> SEQ ID NO 936
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 936 auuggaaac cuaacugaat t                                               21

<210> SEQ ID NO 937
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 937
uucaguuagg uuuccacaut t                                              21

<210> SEQ ID NO 938
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 938
uguggaaacc uaacugaagt t                                              21

```
<210> SEQ ID NO 939
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 939
cuucaguuag guuuccacat t                                             21

<210> SEQ ID NO 940
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 940
ucuuccuuaa augaaagggt t                                             21

<210> SEQ ID NO 941
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 941
cccuuucauu uaaggaagat t                                             21

<210> SEQ ID NO 942
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 942
ugaagaaccu cuaagucaat t                                             21

<210> SEQ ID NO 943
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 943
uugacuuaga gguucuucat t                                             21

<210> SEQ ID NO 944
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 944
agaggucuaa aguggaagat t                                             21
```

<210> SEQ ID NO 945
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 945
ucuuccacuu uagaccucut t                                               21

<210> SEQ ID NO 946
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 946
auaucuaccc auuuuucugt t                                               21

<210> SEQ ID NO 947
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 947
cagaaaaaug gguagauaut t                                               21

<210> SEQ ID NO 948
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 948
uaagccugaa gugaaucagt t                                               21

<210> SEQ ID NO 949
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 949
cugauucacu ucaggcuuat t                                               21

<210> SEQ ID NO 950
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 950
agaugcagac cauuuaauut t                                               21

<210> SEQ ID NO 951

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 951
aauuaaaugg ucugcaucut t                                              21

<210> SEQ ID NO 952
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 952
aguguuguuu guccaauuct t                                              21

<210> SEQ ID NO 953
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 953
gaauuggaca aacaacacut t                                              21

<210> SEQ ID NO 954
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 954
cuauaaugaa gagcuuuuut t                                              21

<210> SEQ ID NO 955
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 955
aaaaagcucu ucauuauagt t                                              21

<210> SEQ ID NO 956
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 956
agaggaguga uaauuaaagt t                                              21

<210> SEQ ID NO 957
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 957
cuuuaauuau cacuccucut t                                              21

<210> SEQ ID NO 958
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 958
uuucucuguu acaauacaut t                                              21

<210> SEQ ID NO 959
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 959
auguauugua acagagaaat t                                              21

<210> SEQ ID NO 960
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 960
aacaucuaua auugcaacat t                                              21

<210> SEQ ID NO 961
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 961
uguugcaauu auagauguut t                                              21

<210> SEQ ID NO 962
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 962
ugcuagaagu acauaagact t                                              21

<210> SEQ ID NO 963
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 963
gucuuaugua cuucuagcat t                                                21

<210> SEQ ID NO 964
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 964
aauguacuca agacugauct t                                                21

<210> SEQ ID NO 965
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 965
gaucagucuu gaguacauut t                                                21

<210> SEQ ID NO 966
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 966
guacucaaga cugaucuuct t                                                21

<210> SEQ ID NO 967
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 967
gaagaucagu cuugaguact t                                                21

<210> SEQ ID NO 968
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 968
cacucugaua aacucaaugt t                                                21

<210> SEQ ID NO 969
<211> LENGTH: 21
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 969
cauugaguuu aucagagugt t                                          21

<210> SEQ ID NO 970
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 970
aagagcagau uaccucugct t                                          21

<210> SEQ ID NO 971
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 971
gcagagguaa ucugcucuut t                                          21

<210> SEQ ID NO 972
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 972
ucugcgagcc cagaucaact t                                          21

<210> SEQ ID NO 973
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 973
guugaucugg gcucgcagat t                                          21

<210> SEQ ID NO 974
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 974
aacuugagcc uuguguauat t                                          21

<210> SEQ ID NO 975
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 975
uauacacaag gcucaaguut t                                              21

<210> SEQ ID NO 976
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 976
gaauauauau aucagccggt t                                              21

<210> SEQ ID NO 977
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 977
ccggcugaua uauauauuct t                                              21

<210> SEQ ID NO 978
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 978
ugucaucccu auaguucact t                                              21

<210> SEQ ID NO 979
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 979
gugaacuaua gggaugacat t                                              21

<210> SEQ ID NO 980
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 980
gaucuggcaa ccauauuuct t                                              21

<210> SEQ ID NO 981
<211> LENGTH: 21
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 981
gaaauauggu ugccagauct t                                              21

<210> SEQ ID NO 982
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 982
uggcaaccau auuucuggat t                                              21

<210> SEQ ID NO 983
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 983
uccagaaaua ugguugccat t                                              21

<210> SEQ ID NO 984
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 984
gauguuuacc gaaguguugt t                                              21

<210> SEQ ID NO 985
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 985
caacacuucg guaaacauct t                                              21

<210> SEQ ID NO 986
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 986
uuccuuaucg agaaucuaat t                                              21

<210> SEQ ID NO 987
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 987
uuagauucuc gauaaggaat t                                                21

<210> SEQ ID NO 988
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 988
agcuuaauug cuuucuggat t                                                21

<210> SEQ ID NO 989
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 989
uccagaaagc aauuaagcut t                                                21

<210> SEQ ID NO 990
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 990
uugcuauuau gggagaccat t                                                21

<210> SEQ ID NO 991
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 991
uggucuccca uaauagcaat t                                                21

<210> SEQ ID NO 992
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 992
gucauggcgu cgcagccaat t                                                21

<210> SEQ ID NO 993
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 993
uuggcugcga cgccaugact t                                              21

<210> SEQ ID NO 994
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 994
uaauugcacu aucuuugcgt t                                              21

<210> SEQ ID NO 995
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 995
cgcaaagaua gugcaauuat t                                              21

<210> SEQ ID NO 996
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 996
cuaucuuugc guauggccat t                                              21

<210> SEQ ID NO 997
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 997
uggccauacg caaagauagt t                                              21

<210> SEQ ID NO 998
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 998
ucccuauagu ucacuuugut t                                              21

<210> SEQ ID NO 999
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 999
```

-continued acaaagugaa cuauagggat t                                              21

<210> SEQ ID NO 1000
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1000
ucaaccuuua auucacuugt t                                              21

<210> SEQ ID NO 1001
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1001
caagugaauu aaagguugat t                                              21

<210> SEQ ID NO 1002
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1002
ggcaaccaua uuucuggaat t                                              21

<210> SEQ ID NO 1003
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1003
uuccagaaau augguugcct t                                              21

<210> SEQ ID NO 1004
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1004
auguacucaa gacugaucut t                                              21

<210> SEQ ID NO 1005
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1005

-continued agaucagucu ugaguacaut t    21

<210> SEQ ID NO 1006
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1006
gcagaccauu uaauuuggct t    21

<210> SEQ ID NO 1007
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1007
gccaaauuaa auggucugct t    21

<210> SEQ ID NO 1008
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1008
ucugagagac uacagaugut t    21

<210> SEQ ID NO 1009
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1009
acaucuguag ucucucagat t    21

<210> SEQ ID NO 1010
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1010
ugcucauaga gcaaagaact t    21

<210> SEQ ID NO 1011
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1011
guucuuugcu cuaugagcat t    21

```
<210> SEQ ID NO 1012
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1012
acauaagacc uuauuuggut t                                              21

<210> SEQ ID NO 1013
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1013
accaaauaag gucuuaugut t                                              21

<210> SEQ ID NO 1014
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1014
uuugugcuga uucugauggt t                                              21

<210> SEQ ID NO 1015
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1015
ccaucagaau cagcacaaat t                                              21

<210> SEQ ID NO 1016
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1016
ccaucaacac ugguaagaat t                                              21

<210> SEQ ID NO 1017
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1017
uucuuaccag uguugauggt t                                              21
```

<210> SEQ ID NO 1018
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1018
agacaauucc ggauguggat t                                              21

<210> SEQ ID NO 1019
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1019
uccacauccg gaauugucut t                                              21

<210> SEQ ID NO 1020
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1020
gaacuugagc cuuguguaut t                                              21

<210> SEQ ID NO 1021
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1021
auacacaagg cucaaguuct t                                              21

<210> SEQ ID NO 1022
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1022
uaauuuggca gagcggaaat t                                              21

<210> SEQ ID NO 1023
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1023
uuuccgcucu gccaaauuat t                                              21

<210> SEQ ID NO 1024
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1024
uggaugaagu auuaugggt t     21

<210> SEQ ID NO 1025
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1025
cccauaauaa cuucauccat t     21

<210> SEQ ID NO 1026
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1026
aucuacauga acuacaagat t     21

<210> SEQ ID NO 1027
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1027
ucuuguaguu cauguagaut t     21

<210> SEQ ID NO 1028
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1028
gguauuuuug aucuggcaat t     21

<210> SEQ ID NO 1029
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1029
uugccagauc aaaaauacct t     21

<210> SEQ ID NO 1030

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1030
cuaaugaaga guauaccugt t                                          21

<210> SEQ ID NO 1031
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1031
cagguauacu cuucauuagt t                                          21

<210> SEQ ID NO 1032
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1032
uuugagaaac uuacugauat t                                          21

<210> SEQ ID NO 1033
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1033
uaucaguaag uuucucaaat t                                          21

<210> SEQ ID NO 1034
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1034
cgauaagaua gaagaucaat t                                          21

<210> SEQ ID NO 1035
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1035
uugaucuucu aucuuaucgt t                                          21

<210> SEQ ID NO 1036
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1036
cuggcaacca uauuucuggt t                                              21

<210> SEQ ID NO 1037
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1037
ccagaaauau gguugccagt t                                              21

<210> SEQ ID NO 1038
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1038
uagauaccau uacuacagut t                                              21

<210> SEQ ID NO 1039
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1039
acuguaguaa ugguaucuat t                                              21

<210> SEQ ID NO 1040
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1040
guauuaaauu ggguuucaut t                                              21

<210> SEQ ID NO 1041
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1041
augaaaccca auuuaauact t                                              21

<210> SEQ ID NO 1042
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1042
aagaccuuau uugguaauct t                                              21

<210> SEQ ID NO 1043
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1043
gauuaccaaa uaaggucuut t                                              21

<210> SEQ ID NO 1044
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1044
gcuguugaua agagagcuct t                                              21

<210> SEQ ID NO 1045
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1045
gagcucucuu aucaacagct t                                              21

<210> SEQ ID NO 1046
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1046
uacucauguu ucucagauut t                                              21

<210> SEQ ID NO 1047
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1047
aaucugagaa acaugaguat t                                              21

<210> SEQ ID NO 1048
<211> LENGTH: 21
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 1048
cagauggacg uaaggcagct t                                             21

<210> SEQ ID NO 1049
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1049
gcugccuuac guccaucugt t                                             21

<210> SEQ ID NO 1050
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1050
uaucccaaca gguacgacat t                                             21

<210> SEQ ID NO 1051
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1051
ugucguaccu guugggauat t                                             21

<210> SEQ ID NO 1052
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1052
cauugcuauu augggagact t                                             21

<210> SEQ ID NO 1053
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1053
gucucccaua auagcaaugt t                                             21

<210> SEQ ID NO 1054
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 1054
cccucaguaa auccauggut t                                                    21

<210> SEQ ID NO 1055
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1055
accauggauu uacugagggt t                                                    21

<210> SEQ ID NO 1056
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1056
ggucauuacu gcccuuguat t                                                    21

<210> SEQ ID NO 1057
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1057
uacaagggca guaaugacct t                                                    21

<210> SEQ ID NO 1058
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1058
aaccacucaa aaacauuugt t                                                    21

<210> SEQ ID NO 1059
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1059
caaauguuuu ugagugguut t                                                    21

<210> SEQ ID NO 1060
<211> LENGTH: 21
<212> TYPE: DNA
<213> ORGANISM: Artificial Sequence
<220> FEATURE:
<223> OTHER INFORMATION: Description of Artificial Sequence: Synthetic -continued

```
      oligonucleotide

<400> SEQUENCE: 1060
uuugcaaguu aaugaaucut t                                             21

<210> SEQ ID NO 1061
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1061
agauucauua acuugcaaat t                                             21

<210> SEQ ID NO 1062
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1062
uuauuuucag uagucagaat t                                             21

<210> SEQ ID NO 1063
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1063
uucugacuac ugaaaauaat t                                             21

<210> SEQ ID NO 1064
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1064
uuuucucgau ucaaaucuut t                                             21

<210> SEQ ID NO 1065
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1065
aagauuugaa ucgagaaaat t                                             21

<210> SEQ ID NO 1066
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1066
guacgaaaag aaguuagugt t                                              21

<210> SEQ ID NO 1067
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1067
cacuaacuuc uuuucguact t                                              21

<210> SEQ ID NO 1068
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1068
uuuaaaacga gaucuugcut t                                              21

<210> SEQ ID NO 1069
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1069
agcaagaucu cguuuuaaat t                                              21

<210> SEQ ID NO 1070
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1070
gaauugauua auguacucat t                                              21

<210> SEQ ID NO 1071
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1071
ugaguacauu aaucaauuct t                                              21

<210> SEQ ID NO 1072
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1072
gauggacgua aggcagcuct t                                              21

<210> SEQ ID NO 1073
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1073
gagcugccuu acguccauct t                                              21

<210> SEQ ID NO 1074
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1074
caucugacua auggcucugt t                                              21

<210> SEQ ID NO 1075
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1075
cagagccauu agucagaugt t                                              21

<210> SEQ ID NO 1076
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1076
gugauccugu acgaaaagat t                                              21

<210> SEQ ID NO 1077
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1077
ucuuuucgua caggaucact t                                              21

<210> SEQ ID NO 1078
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1078
```
agcucuuauu aaggaguaut t      21

<210> SEQ ID NO 1079
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1079
auacuccuua auaagagcut t      21

<210> SEQ ID NO 1080
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1080
gcucuuauua aggaguauat t      21

<210> SEQ ID NO 1081
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1081
uauacuccuu aauaagagct t      21

<210> SEQ ID NO 1082
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1082
ucuuauuaag gaguauacgt t      21

<210> SEQ ID NO 1083
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1083
cguauacucc uuaauaagat t      21

<210> SEQ ID NO 1084
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1084

-continued uauuaaggag uauacggagt t							21

<210> SEQ ID NO 1085
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1085
cuccguauac uccuuaauat t							21

<210> SEQ ID NO 1086
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1086
cugcagcccg ugagaaaaat t							21

<210> SEQ ID NO 1087
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1087
uuuuucucac gggcugcagt t							21

<210> SEQ ID NO 1088
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1088
ucaagacuga ucuucuaagt t							21

<210> SEQ ID NO 1089
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1089
cuuagaagau cagucuugat t							21

<210> SEQ ID NO 1090
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1090
cuucuaaguu cacuggaaat t							21

```
<210> SEQ ID NO 1091
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1091
uuuccaguga acuuagaagt t                                              21

<210> SEQ ID NO 1092
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1092
ugcaaguuaa ugaaucuuut t                                              21

<210> SEQ ID NO 1093
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1093
aaagauucau uaacuugcat t                                              21

<210> SEQ ID NO 1094
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1094
aaucuaagga uauagucaat t                                              21

<210> SEQ ID NO 1095
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1095
uugacuauau ccuuagauut t                                              21

<210> SEQ ID NO 1096
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1096
aucucugaac acaagaacat t                                              21
```

```
<210> SEQ ID NO 1097
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1097
uguucuugug uucagagaut t                                              21

<210> SEQ ID NO 1098
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1098
uucugaacag uggguaucut t                                              21

<210> SEQ ID NO 1099
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1099
agauacccac uguucagaat t                                              21

<210> SEQ ID NO 1100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1100
aguuauuuau acccaucaat t                                              21

<210> SEQ ID NO 1101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1101
uugaugggua uaaauaacut t                                              21

<210> SEQ ID NO 1102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1102
augcuaaacu guucagaaat t                                              21
```

```
<210> SEQ ID NO 1103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1103
uuucugaaca guuuagcaut t                                                    21

<210> SEQ ID NO 1104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1104
cuacagagca cuugguuact t                                                    21

<210> SEQ ID NO 1105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1105
guaaccaagu gcucuguagt t                                                    21

<210> SEQ ID NO 1106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1106
uauauaucag ccgggcgcgt t                                                    21

<210> SEQ ID NO 1107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1107
cgcgcccggc ugauauaut t                                                     21

<210> SEQ ID NO 1108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1108
auguaaauac guauuucuat t                                                    21

<210> SEQ ID NO 1109
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1109
uagaaauacg uauuuacaut t                                              21

<210> SEQ ID NO 1110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1110
uuuuucucga uucaaaucut t                                              21

<210> SEQ ID NO 1111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1111
agauuugaau cgagaaaaat t                                              21

<210> SEQ ID NO 1112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1112
aaucuuaacc cuuaggacut t                                              21

<210> SEQ ID NO 1113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1113
aguccuaagg guuaagauut t                                              21

<210> SEQ ID NO 1114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1114
ccuuaggacu cugguauuut t                                              21

<210> SEQ ID NO 1115
<211> LENGTH: 21
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1115
aaauaccaga guccuaaggt t                                              21

<210> SEQ ID NO 1116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1116
aauaaacugc ccucaguaat t                                              21

<210> SEQ ID NO 1117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1117
uuacugaggg caguuuauut t                                              21

<210> SEQ ID NO 1118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1118
gauccuguac gaaagaagt t                                               21

<210> SEQ ID NO 1119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1119
cuucuuuucg uacaggauct t                                              21

<210> SEQ ID NO 1120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1120
aaugugaucc uguacgaaat t                                              21

<210> SEQ ID NO 1121
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1121
uuucguacag gaucacauut t                                              21

<210> SEQ ID NO 1122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1122
gugaaaacau uggccguuct t                                              21

<210> SEQ ID NO 1123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1123
gaacggccaa uguuuucact t                                              21

<210> SEQ ID NO 1124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1124
cuugaggaaa cucugaguat t                                              21

<210> SEQ ID NO 1125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1125
uacucagagu uuccucaagt t                                              21

<210> SEQ ID NO 1126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1126
cguuuaaaac gagaucuugt t                                              21

<210> SEQ ID NO 1127
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1127
caagaucucg uuuuaaacgt t                                              21

<210> SEQ ID NO 1128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1128
uuaaaacgag aucuugcugt t                                              21

<210> SEQ ID NO 1129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1129
cagcaagauc ucguuuuaat t                                              21

<210> SEQ ID NO 1130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1130
aaagauguau cuggucucct t                                              21

<210> SEQ ID NO 1131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1131
ggagaccaga uacaucuuut t                                              21

<210> SEQ ID NO 1132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1132
cagaaaaugu gucuacucat t                                              21

<210> SEQ ID NO 1133
<211> LENGTH: 21
<212> TYPE: DNA
<213> ORGANISM: Artificial Sequence
<220> FEATURE:
```

-continued

<223> OTHER INFORMATION: Description of Artificial Sequence: Synthetic
     oligonucleotide

<400> SEQUENCE: 1133
ugaguagaca cauuucugt t                                              21

<210> SEQ ID NO 1134
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 1134
caggaauuga uuaauguact t                                             21

<210> SEQ ID NO 1135
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 1135
guacauuaau caauuccugt t                                             21

<210> SEQ ID NO 1136
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 1136
agucaacuaa agcauauuut t                                             21

<210> SEQ ID NO 1137
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 1137
aaauaugcuu uaguugacut t                                             21

<210> SEQ ID NO 1138
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 1138
uguguaacaa ucuacaugat t                                             21

<210> SEQ ID NO 1139
<211> LENGTH: 21
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 1139
ucauguagau uguuacacat t                                              21

<210> SEQ ID NO 1140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1140
auaccauuug uuccuuggut t                                              21

<210> SEQ ID NO 1141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1141
accaaggaac aaaugguaut t                                              21

<210> SEQ ID NO 1142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1142
gcagaaaucu aaggauauat t                                              21

<210> SEQ ID NO 1143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1143
uauauccuua gauuucugct t                                              21

<210> SEQ ID NO 1144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1144
uggcuucuca caggaacuct t                                              21

<210> SEQ ID NO 1145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1145
gaguuccugu gagaagccat t                                              21

<210> SEQ ID NO 1146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1146
gagaugugaa ucucugaact t                                              21

<210> SEQ ID NO 1147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1147
guucagagau ucacaucuct t                                              21

<210> SEQ ID NO 1148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1148
uguaagccaa uguugugagt t                                              21

<210> SEQ ID NO 1149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1149
cucacaacau uggcuuacat t                                              21

<210> SEQ ID NO 1150
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1150
agccaauguu gugaggcuut t                                              21

<210> SEQ ID NO 1151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 1151
aagccucaca acauuggcut t                                              21

<210> SEQ ID NO 1152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1152
uugugaggcu ucaaguucat t                                              21

<210> SEQ ID NO 1153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1153
ugaacuugaa gccucacaat t                                              21

<210> SEQ ID NO 1154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1154
aggcagcuca ugagaaacat t                                              21

<210> SEQ ID NO 1155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1155
uguuucucau gagcugccut t                                              21

<210> SEQ ID NO 1156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1156
auaaauugau agcacaaaat t                                              21

<210> SEQ ID NO 1157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1157
```
uuuugugcua ucaauuuaut t                          21

<210> SEQ ID NO 1158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1158
acaaaaucua gaacuuaaut t                          21

<210> SEQ ID NO 1159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1159
auuaaguucu agauuuugut t                          21

<210> SEQ ID NO 1160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1160
gauaucccaa cagguacgat t                          21

<210> SEQ ID NO 1161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1161
ucguaccugu ugggauauct t                          21

<210> SEQ ID NO 1162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1162
aaguuauuua uacccaucat t                          21

<210> SEQ ID NO 1163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1163

-continued ugauggguau aaauaacuut t    21

<210> SEQ ID NO 1164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1164
uguaaauacg uauuucuagt t    21

<210> SEQ ID NO 1165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1165
cuagaaauac guauuuacat t    21

<210> SEQ ID NO 1166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1166
ucuaguuuuc auauaaagut t    21

<210> SEQ ID NO 1167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1167
acuuuauaug aaaacuagat t    21

<210> SEQ ID NO 1168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1168
auaaaguagu ucuuuuauat t    21

<210> SEQ ID NO 1169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1169 uauaaagaa cuacuuuaut t    21

<210> SEQ ID NO 1170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1170
ccauuuguag agcuacaaat t                                              21

<210> SEQ ID NO 1171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1171
uuuguagcuc uacaaauggt t                                              21

<210> SEQ ID NO 1172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1172
uauuuucagu agucagaaut t                                              21

<210> SEQ ID NO 1173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1173
auucugacua cugaaaauat t                                              21

<210> SEQ ID NO 1174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1174
aaaucuaacc cuaguuguat t                                              21

<210> SEQ ID NO 1175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1175
uacaacuagg guuagauuut t                                              21

```
<210> SEQ ID NO 1176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1176
cuuuagagua uacauugcut t                                                 21

<210> SEQ ID NO 1177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1177
agcaauguau acucuaaagt t                                                 21

<210> SEQ ID NO 1178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1178
aucugacuaa uggcucugut t                                                 21

<210> SEQ ID NO 1179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1179
acagagccau uagucagaut t                                                 21

<210> SEQ ID NO 1180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1180
cacaaugauu uaaggacugt t                                                 21

<210> SEQ ID NO 1181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1181
caguccuuaa aucauugugt t                                                 21
```

```
<210> SEQ ID NO 1182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1182 ucuuuucuc gauucaaaut t                                              21

<210> SEQ ID NO 1183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1183
auuugaaucg agaaaaagat t                                             21

<210> SEQ ID NO 1184
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1184 cuuuucucg auucaaauct t                                              21

<210> SEQ ID NO 1185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1185
gauuugaauc gagaaaaagt t                                             21

<210> SEQ ID NO 1186
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1186
auuuucugcu cacgaugagt t                                             21

<210> SEQ ID NO 1187
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1187
cucaucguga gcagaaaaut t                                             21

<210> SEQ ID NO 1188
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1188
uuucugcuca cgaugaguut t                                              21

<210> SEQ ID NO 1189
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1189
aacucaucgu gagcagaaat t                                              21

<210> SEQ ID NO 1190
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1190
agagcuacaa aaccuaucct t                                              21

<210> SEQ ID NO 1191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1191
ggauagguuu uguagcucut t                                              21

<210> SEQ ID NO 1192
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1192
gagccaaagg uacaccacut t                                              21

<210> SEQ ID NO 1193
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1193 aguggguac cuuuggcuct t                                               21

<210> SEQ ID NO 1194
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1194
gccaaaggua caccacuact t                                              21

<210> SEQ ID NO 1195
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1195
guaguggugu accuuuggct t                                              21

<210> SEQ ID NO 1196
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1196
gaacuguacu cuucucagct t                                              21

<210> SEQ ID NO 1197
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1197
gcugagaaga guacaguuct t                                              21

<210> SEQ ID NO 1198
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1198
agguaaauau caccaacaut t                                              21

<210> SEQ ID NO 1199
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1199
auguggguga uauuuaccut t                                              21

<210> SEQ ID NO 1200
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 1200
agcuacaaaa ccuauccuut t                                              21

<210> SEQ ID NO 1201
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1201
aaggauaggu uuguagcut t                                               21

<210> SEQ ID NO 1202
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1202
ugugaaagca uuuaauucct t                                              21

<210> SEQ ID NO 1203
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1203
ggaauuaaau gcuuucacat t                                              21

<210> SEQ ID NO 1204
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1204
gcccacuuua gaguauacat t                                              21

<210> SEQ ID NO 1205
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1205
uguauacucu aaagugggct t                                              21

<210> SEQ ID NO 1206
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1206
ugugccacac uccaagacct t                                              21

<210> SEQ ID NO 1207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1207
ggucuuggag uguggcacat t                                              21

<210> SEQ ID NO 1208
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1208
aaacuaaauu gaucucguat t                                              21

<210> SEQ ID NO 1209
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1209
uacgagauca auuuaguuut t                                              21

<210> SEQ ID NO 1210
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1210
ugaucucgua gaauuaucut t                                              21

<210> SEQ ID NO 1211
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1211
agauaauucu acgagaucat t                                              21

<210> SEQ ID NO 1212
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1212
gcgugcaguc gguccuccat t                                              21

<210> SEQ ID NO 1213
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1213
uggaggaccg acugcacgct t                                              21

<210> SEQ ID NO 1214
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1214
aaaguuuaga gacaucugat t                                              21

<210> SEQ ID NO 1215
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1215
ucagaugucu cuaaacuuut t                                              21

<210> SEQ ID NO 1216
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1216
cagaaggaau auguacaaat t                                              21

<210> SEQ ID NO 1217
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1217
uuuguacaua uuccuucugt t                                              21

<210> SEQ ID NO 1218
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
<400> SEQUENCE: 1218
cgcccgagag uaccagggat t                                              21

<210> SEQ ID NO 1219
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1219
ucccugguac ucucgggcgt t                                              21

<210> SEQ ID NO 1220
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1220
cggaggagau agaacguuut t                                              21

<210> SEQ ID NO 1221
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1221
aaacguucua ucuccuccgt t                                              21

<210> SEQ ID NO 1222
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1222
agauagaacg uuuaaaacgt t                                              21

<210> SEQ ID NO 1223
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1223
cguuuuaaac guucuaucut t                                              21

<210> SEQ ID NO 1224
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 1224
ggaacaggaa cuucacaact t                                              21

<210> SEQ ID NO 1225
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1225
guugugaagu uccuguucct t                                              21

<210> SEQ ID NO 1226
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1226
gugagccaaa gguacaccat t                                              21

<210> SEQ ID NO 1227
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1227
ugguguaccu uuggcucact t                                              21

<210> SEQ ID NO 1228
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1228
auccucccua gacuucccut t                                              21

<210> SEQ ID NO 1229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1229
agggaagucu agggaggaut t                                              21

<210> SEQ ID NO 1230
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 1230
cacacuccaa gaccugugct t                                              21

<210> SEQ ID NO 1231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1231
gcacaggucu uggagugugt t                                              21

<210> SEQ ID NO 1232
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1232
acagaaggaa uauguacaat t                                              21

<210> SEQ ID NO 1233
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1233
uuguacauau uccuucugut t                                              21

<210> SEQ ID NO 1234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1234
uuagagacau cugacuuugt t                                              21

<210> SEQ ID NO 1235
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1235
caaagucaga ugucucuaat t                                              21

<210> SEQ ID NO 1236
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1236
aauugaucuc guagaauuat t                     21

<210> SEQ ID NO 1237
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1237
uaauucuacg agaucaauut t                     21

<210> SEQ ID NO 1238
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1238
accgaagugu uguuugucct t                     21

<210> SEQ ID NO 1239
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1239
ggacaaacaa cacuucggut t                     21

<210> SEQ ID NO 1240
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1240
ucgagaaucu aaacuaacut t                     21

<210> SEQ ID NO 1241
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1241
aguuaguuua gauucucgat t                     21

<210> SEQ ID NO 1242
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1242

```
gcacauagga gagaugagcu u                                                 21

<210> SEQ ID NO 1243
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1243
aagcucaucu cuccuaugug cug                                               23

<210> SEQ ID NO 1244
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1244
accgaagugu uguuugucca auu                                               23

<210> SEQ ID NO 1245
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1245
uaugguguuu ggagcaucua cua                                               23

<210> SEQ ID NO 1246
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1246
aaucuaaacu aacagaauc cuc                                                23

<210> SEQ ID NO 1247
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1247
uccuuaucga gaaucuaaac uaa                                               23

<210> SEQ ID NO 1248
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1248
gauugauguu uaccgaagug uug                                               23
```

```
<210> SEQ ID NO 1249
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1249
uggugagaug cagaccauuu aau                                              23

<210> SEQ ID NO 1250
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1250
acucugagua cauuggaaua ugc                                              23

<210> SEQ ID NO 1251
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1251
ccgaaguguu guuguccaa uuc                                               23

<210> SEQ ID NO 1252
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1252
aguuauuaug ggcuauaauu gca                                              23

<210> SEQ ID NO 1253
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1253
ggaaggugaa aggucaccua aug                                              23

<210> SEQ ID NO 1254
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1254
uuuuacaaug gaaggugaaa ggu                                              23
```

-continued

<210> SEQ ID NO 1255
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1255
gaaggugaaa ggucaccuaa uga                                           23

<210> SEQ ID NO 1256
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1256
aaggugaaag gucaccuaau gaa                                           23

<210> SEQ ID NO 1257
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1257
uuccuuaucg agaaucuaaa cua                                           23

<210> SEQ ID NO 1258
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1258
agcucuuauu aaggaguaua cgg                                           23

<210> SEQ ID NO 1259
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1259
cagagagauu cugugcuuug gag                                           23

<210> SEQ ID NO 1260
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1260
gaaucuaaac uaacuagaau ccu                                           23

```
<210> SEQ ID NO 1261
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1261
acucaccaaa aaagcucuua uua                                              23

<210> SEQ ID NO 1262
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1262
aagagcuuuu ugaucuucuu aau                                              23

<210> SEQ ID NO 1263
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1263
ggcguacaag aacaucuaua auu                                              23

<210> SEQ ID NO 1264
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1264
agauugaugu uuaccgaagu guu                                              23

<210> SEQ ID NO 1265
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1265
aucuaaacua acuagaaucc ucc                                              23

<210> SEQ ID NO 1266
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1266
uuaccgaagu guuguuuguc caa                                              23

<210> SEQ ID NO 1267
```

-continued

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1267
ggugguggug agaugcagac cau                                          23

<210> SEQ ID NO 1268
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1268
cauacucuag ucguuccca                                               19

<210> SEQ ID NO 1269
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1269
agcgcccauu caauaguag                                               19

<210> SEQ ID NO 1270
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1270
ggaaagcuag cgcccauuc                                               19

<210> SEQ ID NO 1271
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1271
gaaagcuagc gcccauuca                                               19

<210> SEQ ID NO 1272
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1272
agaaacuacg auugaugga                                               19

<210> SEQ ID NO 1273
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1273
uguuccuuau cgagaaucu                                                19

<210> SEQ ID NO 1274
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1274
cagauuaccu cugcgagcc                                                19

<210> SEQ ID NO 1275
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1275
gcgcccauuc aauaguaga                                                19

<210> SEQ ID NO 1276
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1276
uugcacuauc uuugcguau                                                19

<210> SEQ ID NO 1277
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1277
cagagcggaa agcuagcgc                                                19

<210> SEQ ID NO 1278
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1278
agaccuuauu ugguaaucu                                                19

<210> SEQ ID NO 1279
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1279
auucucuugg agggcguac                                                 19

<210> SEQ ID NO 1280
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1280
ggcugguaua auuccacgu                                                 19

<210> SEQ ID NO 1281
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1281
gcggaaagcu agcgcccau                                                 19

<210> SEQ ID NO 1282
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1282
ugcacuaucu uugcguaug                                                 19

<210> SEQ ID NO 1283
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1283
guauaauucc acguacccu                                                 19

<210> SEQ ID NO 1284
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1284
agaaucuaaa cuaacuaga                                                 19

<210> SEQ ID NO 1285
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1285
aggagcugaa uaggguuac                                                19

<210> SEQ ID NO 1286
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1286
gaaguacaua agaccuuau                                                19

<210> SEQ ID NO 1287
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1287
gacaguggcc gauaagaua                                                19

<210> SEQ ID NO 1288
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1288
aaaccacuua guagugucc                                                19

<210> SEQ ID NO 1289
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1289
ucccuagacu ucccuauuu                                                19

<210> SEQ ID NO 1290
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1290
uagacuuccc uauuucgcu                                                19

<210> SEQ ID NO 1291
<211> LENGTH: 19
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 1291
gcgucgcagc caaauucgu                                               19

<210> SEQ ID NO 1292
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1292
agcuagcgcc cauucaaua                                               19

<210> SEQ ID NO 1293
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1293
gaaacuacga uugauggag                                               19

<210> SEQ ID NO 1294
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1294
ccgauaagau agaagauca                                               19

<210> SEQ ID NO 1295
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1295
uagcgcccau ucaauagua                                               19

<210> SEQ ID NO 1296
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1296
uuugcguaug gccaaacug                                               19

<210> SEQ ID NO 1297
<211> LENGTH: 19
<212> TYPE: RNA
<213> ORGANISM: Artificial Sequence
<220> FEATURE:
<223> OTHER INFORMATION: Description of Artificial Sequence: Synthetic

```
<400> SEQUENCE: 1297
cacguacccu ucaucaaau                                                19

<210> SEQ ID NO 1298
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1298
ucuuugcgua uggccaaac                                                19

<210> SEQ ID NO 1299
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1299
ccgaaguguu guuugucca                                                19

<210> SEQ ID NO 1300
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1300
agagcggaaa gcuagcgcc                                                19

<210> SEQ ID NO 1301
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1301
gcuagcgccc auucaauag                                                19

<210> SEQ ID NO 1302
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1302
aaguuagugu acgaacugg                                                19

<210> SEQ ID NO 1303
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1303
guacgaacug gaggauugg                                              19

<210> SEQ ID NO 1304
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1304
acgaacugga ggauuggcu                                              19

<210> SEQ ID NO 1305
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1305
agauugaugu uuaccgaag                                              19

<210> SEQ ID NO 1306
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1306
uaugggcuau aauugcacu                                              19

<210> SEQ ID NO 1307
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1307
aucuuugcgu auggccaaa                                              19

<210> SEQ ID NO 1308
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1308
acucuagucg uucccacuc                                              19

<210> SEQ ID NO 1309
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 1309
aacuacgauu gauggagaa                                            19

<210> SEQ ID NO 1310
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1310
gauaagagag cucgggaag                                            19

<210> SEQ ID NO 1311
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1311
ucgagaaucu aaacuaacu                                            19

<210> SEQ ID NO 1312
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1312
aacuaacuag aauccucca                                            19

<210> SEQ ID NO 1313
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1313
ggaucguaag aaggcaguu                                            19

<210> SEQ ID NO 1314
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1314
aucguaagaa ggcaguuga                                            19

<210> SEQ ID NO 1315
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1315
```
aggcaguuga ccaacacaa                      19

<210> SEQ ID NO 1316
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1316
uggccgauaa gauagaaga                      19

<210> SEQ ID NO 1317
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1317
ucuaaggaua uagucaaca                      19

<210> SEQ ID NO 1318
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1318
acuaagcuua auugcuuuc                      19

<210> SEQ ID NO 1319
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1319
gcccagauca accuuuaau                      19

<210> SEQ ID NO 1320
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1320
uuaauuuggc agagcggaa                      19

<210> SEQ ID NO 1321
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1321

-continued uuaucgagaa ucuaaacua                                                 19

<210> SEQ ID NO 1322
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1322
cuagcgccca uucaauagu                                                 19

<210> SEQ ID NO 1323
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1323
aauaguagaa ugugauccu                                                 19

<210> SEQ ID NO 1324
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1324
uacgaaaaga aguuagugu                                                 19

<210> SEQ ID NO 1325
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1325
agaaguuagu guacgaacu                                                 19

<210> SEQ ID NO 1326
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1326
acuaaacaga uugauguuu                                                 19

<210> SEQ ID NO 1327
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1327
cuuugcguau ggccaaacu                                                 19

<210> SEQ ID NO 1328
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1328
aaugaagagu auaccuggg                                                19

<210> SEQ ID NO 1329
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1329
auaauuccac guacccuuc                                                19

<210> SEQ ID NO 1330
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1330
acguacccuu caucaaauu                                                19

<210> SEQ ID NO 1331
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1331
cguacccuuc aucaaauuu                                                19

<210> SEQ ID NO 1332
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1332
guacccuuca ucaaauuuu                                                19

<210> SEQ ID NO 1333
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1333
aacuuacuga uaaugguac                                                19

```
<210> SEQ ID NO 1334
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1334
uucagucaaa gugucucug                                                   19

<210> SEQ ID NO 1335
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1335
uucuuaaucc aucaucuga                                                   19

<210> SEQ ID NO 1336
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1336
acaguacaca acaaggaug                                                   19

<210> SEQ ID NO 1337
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1337
aagaaacuac gauugaugg                                                   19

<210> SEQ ID NO 1338
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1338
aaacuacgau ugauggaga                                                   19

<210> SEQ ID NO 1339
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1339
uggagcuguu gauaagaga                                                   19
```

```
<210> SEQ ID NO 1340
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1340
cuaacuagaa uccuccagg                                                       19

<210> SEQ ID NO 1341
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1341
gaauaugcuc auagagcaa                                                       19

<210> SEQ ID NO 1342
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1342
augcucauag agcaaagaa                                                       19

<210> SEQ ID NO 1343
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1343
aaaaauuggu gcguugag                                                        19

<210> SEQ ID NO 1344
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1344
gaggagcuga auaggguua                                                       19

<210> SEQ ID NO 1345
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1345
ggagcugaau aggguuaca                                                       19

<210> SEQ ID NO 1346
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1346
gagcugaaua ggguuacag                                            19

<210> SEQ ID NO 1347
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1347
agcugaauag gguuacaga                                            19

<210> SEQ ID NO 1348
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1348
gcugaauagg guuacagag                                            19

<210> SEQ ID NO 1349
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1349
ccaaacugga ucguaagaa                                            19

<210> SEQ ID NO 1350
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1350
gaucguaaga aggcaguug                                            19

<210> SEQ ID NO 1351
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1351
accuuauuug guaaucugc                                            19

<210> SEQ ID NO 1352
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1352
uuagauacca uuacuacag                                                    19

<210> SEQ ID NO 1353
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1353
auaccauuac uacaguagc                                                    19

<210> SEQ ID NO 1354
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1354
uacuacagua gcacuugga                                                    19

<210> SEQ ID NO 1355
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1355
aaaguaaaac uguacuaca                                                    19

<210> SEQ ID NO 1356
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1356
cucaagacug aucuucuaa                                                    19

<210> SEQ ID NO 1357
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1357
uugacagugg ccgauaaga                                                    19

<210> SEQ ID NO 1358
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1358
ugacaguggc cgauaagau                                                    19

<210> SEQ ID NO 1359
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1359
gcaaugugga aaccuaacu                                                    19

<210> SEQ ID NO 1360
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1360
ccacuuagua guguccagg                                                    19

<210> SEQ ID NO 1361
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1361
agaagguaca aaauugguu                                                    19

<210> SEQ ID NO 1362
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1362
ugguuugacu aagcuuaau                                                    19

<210> SEQ ID NO 1363
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1363
gguuugacua agcuuaauu                                                    19

<210> SEQ ID NO 1364
<211> LENGTH: 19
<212> TYPE: RNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 1364
ucuaagucaa gagccaucu                                                  19

<210> SEQ ID NO 1365
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1365
ucaucccuau aguucacuu                                                  19

<210> SEQ ID NO 1366
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1366
caucccuaua guucacuuu                                                  19

<210> SEQ ID NO 1367
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1367
cccuagacuu cccuauuuc                                                  19

<210> SEQ ID NO 1368
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1368
agacuucccu auuucgcuu                                                  19

<210> SEQ ID NO 1369
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1369
ucaccaaacc auuuguaga                                                  19

<210> SEQ ID NO 1370
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 1370
uccuuuaaga ggccuaacu                                                 19

<210> SEQ ID NO 1371
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1371
uuuaagaggc cuaacucau                                                 19

<210> SEQ ID NO 1372
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1372
uuaagaggcc uaacucauu                                                 19

<210> SEQ ID NO 1373
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1373
ggccuaacuc auucacccu                                                 19

<210> SEQ ID NO 1374
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1374
ugguauuuuu gaucuggca                                                 19

<210> SEQ ID NO 1375
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1375
aguuuagugu guaaaguuu                                                 19

<210> SEQ ID NO 1376
<211> LENGTH: 19
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 1376
gccaaauucg ucugcgaag                                                19

<210> SEQ ID NO 1377
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1377
aauucgucug cgaagaaga                                                19

<210> SEQ ID NO 1378
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1378
ugaaagguca ccuaaugaa                                                19

<210> SEQ ID NO 1379
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1379
cagaccauuu aauuuggca                                                19

<210> SEQ ID NO 1380
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1380
agaccauuua auuuggcag                                                19

<210> SEQ ID NO 1381
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1381
aguuauuaug ggcuauaau                                                19

<210> SEQ ID NO 1382
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 1382
gcugguauaa uuccacgua                                                19

<210> SEQ ID NO 1383
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1383
auuuaauuug gcagagcgg                                                19

<210> SEQ ID NO 1384
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1384
uuuaauuugg cagagcgga                                                19

<210> SEQ ID NO 1385
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1385
uuuggcagag cggaaagcu                                                19

<210> SEQ ID NO 1386
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1386
uuuuacaaug gaaggugaa                                                19

<210> SEQ ID NO 1387
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1387
aauggaaggu gaaagguca                                                19

<210> SEQ ID NO 1388
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1388
ugagaugcag accauuuaa                                              19

<210> SEQ ID NO 1389
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1389
ucgcagccaa auucgucug                                              19

<210> SEQ ID NO 1390
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1390
ggcuauaauu gcacuaucu                                              19

<210> SEQ ID NO 1391
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1391
auugacagug gccgauaag                                              19

<210> SEQ ID NO 1392
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1392
cuagacuucc cuauuucgc                                              19

<210> SEQ ID NO 1393
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1393
acuaucuuug cguauggcc                                              19

<210> SEQ ID NO 1394
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1394
```

-continued auacucuagu cguucccac                                               19

<210> SEQ ID NO 1395
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1395
aaagaaacua cgauugaug                                               19

<210> SEQ ID NO 1396
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1396
gccuugauuu uuuggcggg                                               19

<210> SEQ ID NO 1397
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1397
cgcccauuca auaguagaa                                               19

<210> SEQ ID NO 1398
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1398
ccuuauuugg uaaucugcu                                               19

<210> SEQ ID NO 1399
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1399
agagacaauu ccggaugug                                               19

<210> SEQ ID NO 1400
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1400

-continued ugacuuugau agcuaaauu                                    19

<210> SEQ ID NO 1401
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1401
uggcagagcg gaaagcuag                                    19

<210> SEQ ID NO 1402
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1402
gagcggaaag cuagcgccc                                    19

<210> SEQ ID NO 1403
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1403
aaagaaguua guguacgaa                                    19

<210> SEQ ID NO 1404
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1404
auugcacuau cuuugcgua                                    19

<210> SEQ ID NO 1405
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1405
gguauaauuc cacguaccc                                    19

<210> SEQ ID NO 1406
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1406
uacucuaguc guucccacu                                    19

<210> SEQ ID NO 1407
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1407
uaugaaagaa acuacgauu                                              19

<210> SEQ ID NO 1408
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1408
augcuagaag uacauaaga                                              19

<210> SEQ ID NO 1409
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1409
aaguacauaa gaccuuauu                                              19

<210> SEQ ID NO 1410
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1410
acagccugag cuguuaaug                                              19

<210> SEQ ID NO 1411
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1411
aaagaagaga caauuccgg                                              19

<210> SEQ ID NO 1412
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1412
cacacuggag aggucuaaa                                              19

```
<210> SEQ ID NO 1413
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1413
cacuggagag gucuaaagu                                                    19

<210> SEQ ID NO 1414
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1414
acuggagagg ucuaaagug                                                    19

<210> SEQ ID NO 1415
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1415
cgucgcagcc aaauucguc                                                    19

<210> SEQ ID NO 1416
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1416
gaaggcaguu gaccaacac                                                    19

<210> SEQ ID NO 1417
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1417
cauucacccu gacagaguu                                                    19

<210> SEQ ID NO 1418
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1418
aagaggccua acucauuca                                                    19
```

```
<210> SEQ ID NO 1419
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1419
gagacaauuc cggaugugg                                                  19

<210> SEQ ID NO 1420
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1420
uuccggaugu ggauguaga                                                  19

<210> SEQ ID NO 1421
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1421
aagcuagcgc ccauucaau                                                  19

<210> SEQ ID NO 1422
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1422
gaaguuagug uacgaacug                                                  19

<210> SEQ ID NO 1423
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1423
uauaauucca cguacccuu                                                  19

<210> SEQ ID NO 1424
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1424
acaguggccg auaagauag                                                  19

<210> SEQ ID NO 1425
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1425 ucugcaucc cuauaguuc                                                    19

<210> SEQ ID NO 1426
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1426
uucuugcuau gacuugugu                                                   19

<210> SEQ ID NO 1427
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1427
guaagaaggc aguugacca                                                   19

<210> SEQ ID NO 1428
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1428
cauugacagu ggccgauaa                                                   19

<210> SEQ ID NO 1429
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1429
agaaaccacu uaguagugu                                                   19

<210> SEQ ID NO 1430
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1430
ggauuguuca ucaauuggc                                                   19

<210> SEQ ID NO 1431
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1431
uaagaggccu aacucauuc                                              19

<210> SEQ ID NO 1432
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1432
aguuagugua cgaacugga                                              19

<210> SEQ ID NO 1433
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1433
aguacauaag accuuauuu                                              19

<210> SEQ ID NO 1434
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1434
ugagccuugu guauagauu                                              19

<210> SEQ ID NO 1435
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1435
ccuuuaagag gccuaacuc                                              19

<210> SEQ ID NO 1436
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1436
accacuuagu aguguccag                                              19

<210> SEQ ID NO 1437
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1437
gaaacuucca auuaugucu                                                    19

<210> SEQ ID NO 1438
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1438
ugcauacucu agucguucc                                                    19

<210> SEQ ID NO 1439
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1439
agaaggcagu ugaccaaca                                                    19

<210> SEQ ID NO 1440
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1440
guacauaaga ccuuauuug                                                    19

<210> SEQ ID NO 1441
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1441
uauaauugca cuaucuuug                                                    19

<210> SEQ ID NO 1442
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1442
ucucuguuac aauacauau                                                    19

<210> SEQ ID NO 1443
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1443
uaugcucaua gagcaaaga                                                    19

<210> SEQ ID NO 1444
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1444
uguuguuugu ccaauucug                                                    19

<210> SEQ ID NO 1445
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1445
acuaacuaga auccuccag                                                    19

<210> SEQ ID NO 1446
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1446
uguggugucu auacugaaa                                                    19

<210> SEQ ID NO 1447
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1447
uauuauggga gaccaccca                                                    19

<210> SEQ ID NO 1448
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1448
aaggaugaag ucuaucaaa                                                    19

<210> SEQ ID NO 1449
<211> LENGTH: 19
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 1449
uugauaagag agcucggga                                                19

<210> SEQ ID NO 1450
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1450 auguccuua ucgagaauc                                                 19

<210> SEQ ID NO 1451
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1451
ggaauaugcu cauagagca                                                19

<210> SEQ ID NO 1452
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1452
ccauuccaaa cuggaucgu                                                19

<210> SEQ ID NO 1453
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1453
ggcaguugac caacacaau                                                19

<210> SEQ ID NO 1454
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1454
caugcuagaa guacauaag                                                19

<210> SEQ ID NO 1455
<211> LENGTH: 19
<212> TYPE: RNA
<213> ORGANISM: Artificial Sequence
<220> FEATURE:
<223> OTHER INFORMATION: Description of Artificial Sequence: Synthetic

```
            oligonucleotide

<400> SEQUENCE: 1455
cuagaaguac auaagaccu                                                    19

<210> SEQ ID NO 1456
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1456
uuggaucucu cacaucuau                                                    19

<210> SEQ ID NO 1457
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1457
aacuguggug ucuauacug                                                    19

<210> SEQ ID NO 1458
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1458
ucauugacag uggccgaua                                                    19

<210> SEQ ID NO 1459
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1459
auaaagcaga cccauuccc                                                    19

<210> SEQ ID NO 1460
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1460
acagaaacca cuuaguagu                                                    19

<210> SEQ ID NO 1461
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1461
gaaaccacuu aguaguguc                                               19

<210> SEQ ID NO 1462
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1462
aaaucuaagg auauaguca                                               19

<210> SEQ ID NO 1463
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1463
uuauuuauac ccaucaaca                                               19

<210> SEQ ID NO 1464
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1464
acagaggcau uaacacacu                                               19

<210> SEQ ID NO 1465
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1465
acacacugga gagucuaa                                                19

<210> SEQ ID NO 1466
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1466
acacuggaga ggucuaaag                                               19

<210> SEQ ID NO 1467
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1467
cgagcccaga ucaaccuuu                                            19

<210> SEQ ID NO 1468
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1468
ucccuauuuc gcuucucc                                             19

<210> SEQ ID NO 1469
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1469
ucuaaaauca cugucaaca                                            19

<210> SEQ ID NO 1470
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1470
agccaaauuc gucugcgaa                                            19

<210> SEQ ID NO 1471
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1471
cccauucaau aguagaaug                                            19

<210> SEQ ID NO 1472
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1472
gaugaaugca uacucuagu                                            19

<210> SEQ ID NO 1473
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1473
```

-continued cucauguucc uuaucgaga                    19

<210> SEQ ID NO 1474
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1474
gagaaucuaa acuaacuag                    19

<210> SEQ ID NO 1475
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1475
uagaaguaca uaagaccuu                    19

<210> SEQ ID NO 1476
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1476
cagccugagc uguuaauga                    19

<210> SEQ ID NO 1477
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1477
aagaagagac aauuccgga                    19

<210> SEQ ID NO 1478
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1478
ugcuggugug gauuguuca                    19

<210> SEQ ID NO 1479
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1479
aaauucgucu gcgaagaag                                              19

<210> SEQ ID NO 1480
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1480
uuucuggaag uugagaugu                                              19

<210> SEQ ID NO 1481
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1481
uacuaaacag auugauguu                                              19

<210> SEQ ID NO 1482
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1482
gauugauguu uaccgaagu                                              19

<210> SEQ ID NO 1483
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1483
gcacuaucuu ugcguaugg                                              19

<210> SEQ ID NO 1484
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1484
ugguauaauu ccacguacc                                              19

<210> SEQ ID NO 1485
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1485
agcaagcugc uuaacacag                                              19

<210> SEQ ID NO 1486
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1486
cagaaaccac uuaguagug                                                19

<210> SEQ ID NO 1487
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1487
aacuuauugg agguuguaa                                                19

<210> SEQ ID NO 1488
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1488
cuggagaggu cuaaagugg                                                19

<210> SEQ ID NO 1489
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1489
aaaaaagaua uaaggcagu                                                19

<210> SEQ ID NO 1490
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1490
gaauuuugau aucaccca                                                 19

<210> SEQ ID NO 1491
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1491
guauuuuuga ucuggcaac                                                19

```
<210> SEQ ID NO 1492
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1492
aggaucccuu ggcugguau                                                19

<210> SEQ ID NO 1493
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1493
ggaucccuug gcugguaua                                                19

<210> SEQ ID NO 1494
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1494
caauaguaga augugaucc                                                19

<210> SEQ ID NO 1495
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1495
gcuauaauug cacuaucuu                                                19

<210> SEQ ID NO 1496
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1496
uacccuucau caaauuuuu                                                19

<210> SEQ ID NO 1497
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1497
agaacauauu gaauaagcc                                                19
```

```
<210> SEQ ID NO 1498
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1498
aaauuggugc uguugagga                                               19

<210> SEQ ID NO 1499
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1499
ugaauagggu uacagaguu                                               19

<210> SEQ ID NO 1500
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1500
aagaacuuga aaccacuca                                               19

<210> SEQ ID NO 1501
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1501
aauaaagcag acccauucc                                               19

<210> SEQ ID NO 1502
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1502
auacccauca acacuggua                                               19

<210> SEQ ID NO 1503
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1503
uggauuguuc aucaauugg                                               19

<210> SEQ ID NO 1504
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1504
uggagagguc uaaagugga                                                  19

<210> SEQ ID NO 1505
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1505
gucaucccua uaguucacu                                                  19

<210> SEQ ID NO 1506
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1506
auaauggcua uaauuucuc                                                  19

<210> SEQ ID NO 1507
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1507
aucccuuggc ugguauaau                                                  19

<210> SEQ ID NO 1508
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1508
gggcuauaau ugcacuauc                                                  19

<210> SEQ ID NO 1509
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1509
gauucucuug gagggcgua                                                  19

<210> SEQ ID NO 1510
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1510
gcaucucuca aucuugagg                                                    19

<210> SEQ ID NO 1511
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1511
cagcagaaau cuaaggaua                                                    19

<210> SEQ ID NO 1512
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1512
gucaagagcc aucuguaga                                                    19

<210> SEQ ID NO 1513
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1513
aaacagaggc auuaacaca                                                    19

<210> SEQ ID NO 1514
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1514
agcccagauc aaccuuuaa                                                    19

<210> SEQ ID NO 1515
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1515 uauuuugau cuggcaacc                                                     19

<210> SEQ ID NO 1516
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1516
uguuuggagc aucuacuaa                                                       19

<210> SEQ ID NO 1517
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1517
gaaauuacag uacacaaca                                                       19

<210> SEQ ID NO 1518
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1518
acuugaccag uguaaaucu                                                       19

<210> SEQ ID NO 1519
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1519
accaguguaa aucugaccu                                                       19

<210> SEQ ID NO 1520
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1520
agaacaauca uuagcagca                                                       19

<210> SEQ ID NO 1521
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1521
caauguggaa accuaacug                                                       19

<210> SEQ ID NO 1522
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1522
accaagaagg uacaaaauu                                                    19

<210> SEQ ID NO 1523
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1523
gguacaaaau ugguugaag                                                    19

<210> SEQ ID NO 1524
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1524 ggugugggauu guucaucaa                                                   19

<210> SEQ ID NO 1525
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1525
agaguucaca aaaagccca                                                    19

<210> SEQ ID NO 1526
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1526
ugauagcuaa auuaaacca                                                    19

<210> SEQ ID NO 1527
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1527
aauaagccug aagugaauc                                                    19

<210> SEQ ID NO 1528
<211> LENGTH: 19
<212> TYPE: RNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 1528
caguugacca acacaaugc                                                    19

<210> SEQ ID NO 1529
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1529
ugguguggau uguucauca                                                    19

<210> SEQ ID NO 1530
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1530
auucacccug acagaguuc                                                    19

<210> SEQ ID NO 1531
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1531
uaagaccuua uuugguaau                                                    19

<210> SEQ ID NO 1532
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1532
aagcaaugug gaaaccuaa                                                    19

<210> SEQ ID NO 1533
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1533
ucugaaacug gauauccca                                                    19

COMPOSITIONS AND METHODS FOR INHIBITING EXPRESSION OF EG5 GENE

RELATED APPLICATIONS

This application claims the benefit of U.S. Provisional Application No. 60/787,762, filed Mar. 31, 2006, and U.S. Provisional Application No. 60/870,259, filed Dec. 15, 2006. Both prior applications are incorporated herein by reference in their entirety.

FIELD OF THE INVENTION

This invention relates to double-stranded ribonucleic acid (dsRNA), and its use in mediating RNA interference to inhibit the expression of the Eg5 gene and the use of the dsRNA to treat pathological processes mediated by Eg5 expression, such as cancer, alone or in combination with a dsRNA targeting vacular endothelian growth factor (VEGF).

BACKGROUND OF THE INVENTION

The maintenance of cell populations within an organism is governed by the cellular processes of cell division and programmed cell death. Within normal cells, the cellular events associated with the initiation and completion of each process is highly regulated. In proliferative disease such as cancer, one or both of these processes may be perturbed. For example, a cancer cell may have lost its regulation (checkpoint control) of the cell division cycle through either the overexpression of a positive regulator or the loss of a negative regulator, perhaps by mutation.

Alternatively, a cancer cell may have lost the ability to undergo programmed cell death through the overexpression of a negative regulator. Hence, there is a need to develop new chemotherapeutic drugs that will restore the processes of checkpoint control and programmed cell death to cancerous cells.

One approach to the treatment of human cancers is to target a protein that is essential for cell cycle progression. In order for the cell cycle to proceed from one phase to the next, certain prerequisite events must be completed. There are checkpoints within the cell cycle that enforce the proper order of events and phases. One such checkpoint is the spindle checkpoint that occurs during the metaphase stage of mitosis. Small molecules that target proteins with essential functions in mitosis may initiate the spindle checkpoint to arrest cells in mitosis. Of the small molecules that arrest cells in mitosis, those which display anti-tumor activity in the clinic also include apoptosis, the morphological changes associated with programmed cell death. An effective chemotherapeutic for the treatment of cancer may thus be one which induces checkpoint control and programmed cell death. Unfortunately, there are few compounds available for controlling these processes within the cell. Most compounds known to cause mitotic arrest and apoptosis act as tubulin binding agents. These compounds alter the dynamic instability of microtubules and indirectly alter the function/structure of the mitotic spindle thereby causing mitotic arrest. Because most of these compounds specifically target the tubulin protein which is a component of all microtubules, they may also affect one or more of the numerous normal cellular processes in which microtubules, they may also affect one or more of the numerous normal cellular processes in which microtubules have a role. Hence, there is also a need for small molecules that more specifically target proteins associated with proliferating cells.

Eg5 is one of several kinesin-like motor proteins that are localized to the mitotic spindle and known to be required for formation and/or function of the bipolar mitotic spindle. Recently, there was a report of a small molecule that disturbs bipolarity of the mitotic spindle (Mayer, T. U. et. al. 1999. Science 286(5441) 971-4, herein incorporated by reference). More specifically, the small molecule induced the formation of an aberrant mitotic spindle wherein a monoastral array of microtubules emanated from a central pair of centrosomes, with chromosomes attached to the distal ends of the microtubules. The small molecule was dubbed "monastrol" after the monoastral array. This monoastral array phenotype had been previously observed in mitotic cells that were immunodepleted of the Eg5 motor protein. This distinctive monoastral array phenotype facilitated identification of monastrol as a potential inhibitor of Eg5. Indeed, monastrol was further shown to inhibit the Eg5 motor-driven motility of microtubules in an in vitro assay. The Eg5 inhibitor monastrol had no apparent effect upon the related kinesin motor or upon the motor(s) responsible for golgi apparatus movement within the cell. Cells that display the monoastral array phenotype either through immunodepletion of Eg5 or monastrol inhibition of Eg5 arrest in M-phase of the cell cycle. However, the mitotic arrest induced by either immunodepletion or inhibition of Eg5 is transient (Kapoor, T. N., 2000, J Cell Biol 150(5) 975-80). Both the monoastral array phenotype and the cell cycle arrest in mitosis induced by monastrol are reversible. Cells recover to form a normal bipolar mitotic spindle, to complete mitosis and to proceed through the cell cycle and normal cell proliferation. These data suggest that a small molecule inhibitor of Eg5 which induced a transient mitotic arrest may not be effective for the treatment of cancer cell proliferation. Nonetheless, the discovery that monastrol causes mitotic arrest is intriguing and hence there is a need to further study and identify compounds which can be used to modulate the Eg5 motor protein in a manner that would be effective in the treatment of human cancers. There is also a need to explore the use of these compounds in combination with other antineoplastic agents.

VEGF (also known as vascular permeability factor, VPF) is a multifunctional cytokine that stimulates angiogenesis, epithelial cell proliferation, and endothelial cell survival. VEGF can be produced by a wide variety of tissues, and its overexpression or aberrant expression can result in a variety disorders, including cancers and retinal disorders such as age-related macular degeneration and other angiogenic disorders.

Recently, double-stranded RNA molecules (dsRNA) have been shown to block gene expression in a highly conserved regulatory mechanism known as RNA interference (RNAi)). WO 99/32619 (Fire et al.) discloses the use of a dsRNA of at least 25 nucleotides in length to inhibit the expression of genes in *C. elegans*. dsRNA has also been shown to degrade target RNA in other organisms, including plants (see, e.g., WO 99/53050, Waterhouse et al., and WO 99/61631, Heifetz et al.), *Drosophila* (see e.g., Yang, D., et al., *Curr. Biol.* (2000) 10:1191-1200), and mammals (see WO 00/44895, Limmer; and DE 101 00 586.5, Kreutzer et al.). This natural mechanism has now become the focus for the development of a new class of pharmaceutical agents for treating disorders that are caused by the aberrant or unwanted regulation of a gene.

Despite significant advances in the field of RNAi and advances in the treatment of pathological processes mediated by Eg5 expression, there remains a need for an agent that can selectively and efficiently silence the Eg5 gene using the cell's own RNAi machinery that has both high biological activity and in vivo stability, and that can effectively inhibit expression of a target Eg5 gene for use in treating pathological processes mediated by Eg5 expression.

SUMMARY OF THE INVENTION

The invention provides double-stranded ribonucleic acid (dsRNA), as well as compositions and methods for inhibiting the expression of the Eg5 gene in a cell or mammal using such dsRNA, alone or in combination with a dsRNA targeting VEGF. The invention also provides compositions and methods for treating pathological conditions and diseases caused by the expression of the Eg5 gene, such as in cancer. The dsRNA of the invention comprises an RNA strand (the antisense strand) having a region which is less than 30 nucleotides in length, generally 19-24 nucleotides in length, and is substantially complementary to at least part of an mRNA transcript of the Eg5 gene.

In one embodiment, the invention provides double-stranded ribonucleic acid (dsRNA) molecules for inhibiting the expression of the Eg5 gene. The dsRNA comprises at least two sequences that are complementary to each other. The dsRNA comprises a sense strand comprising a first sequence and an antisense strand comprising a second sequence. The antisense strand comprises a nucleotide sequence which is substantially complementary to at least part of an mRNA encoding Eg5, and the region of complementarity is less than 30 nucleotides in length, generally 19-24 nucleotides in length. The dsRNA, upon contacting with a cell expressing the Eg5, inhibits the expression of the Eg5 gene by at least 40%.

For example, the dsRNA molecules of the invention can be comprised of a first sequence of the dsRNA that is selected from the group consisting of the sense sequences of Tables 1-3 and the second sequence is selected from the group consisting of the antisense sequences of Tables 1-3. The dsRNA molecules of the invention can be comprised of naturally occurring nucleotides or can be comprised of at least one modified nucleotide, such as a 2'-O-methyl modified nucleotide, a nucleotide comprising a 5'-phosphorothioate group, and a terminal nucleotide linked to a cholesteryl derivative. Alternatively, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Generally, such modified sequence will be based on a first sequence of said dsRNA selected from the group consisting of the sense sequences of Tables 1-3 and a second sequence selected from the group consisting of the antisense sequences of Tables 1-3.

In another embodiment, the invention provides a cell comprising one of the dsRNAs of the invention. The cell is generally a mammalian cell, such as a human cell.

In another embodiment, the invention provides a pharmaceutical composition for inhibiting the expression of the Eg5 gene in an organism, generally a human subject, comprising one or more of the dsRNA of the invention and a pharmaceutically acceptable carrier or delivery vehicle.

In another embodiment, the invention provides a method for inhibiting the expression of the Eg5 gene in a cell, comprising the following steps:
 (a) introducing into the cell a double-stranded ribonucleic acid (dsRNA), wherein the dsRNA comprises at least two sequences that are complementary to each other. The dsRNA comprises a sense strand comprising a first sequence and an antisense strand comprising a second sequence. The antisense strand comprises a region of complementarity which is substantially complementary to at least a part of a mRNA encoding Eg5, and wherein the region of complementarity is less than 30 nucleotides in length, generally 19-24 nucleotides in length, and wherein the dsRNA, upon contact with a cell expressing the Eg5, inhibits expression of the Eg5 gene by at least 40%; and
 (b) maintaining the cell produced in step (a) for a time sufficient to obtain degradation of the mRNA transcript of the Eg5 gene, thereby inhibiting expression of the Eg5 gene in the cell.

In another embodiment, the invention provides methods for treating, preventing or managing pathological processes mediated by Eg5 expression, e.g. cancer, comprising administering to a patient in need of such treatment, prevention or management a therapeutically or prophylactically effective amount of one or more of the dsRNAs of the invention.

In another embodiment, the invention provides vectors for inhibiting the expression of the Eg5 gene in a cell, comprising a regulatory sequence operable linked to a nucleotide sequence that encodes at least one strand of one of the dsRNA of the invention.

In another embodiment, the invention provides a cell comprising a vector for inhibiting the expression of the Eg5 gene in a cell. The vector comprises a regulatory sequence operably linked to a nucleotide sequence that encodes at least one strand of one of the dsRNA of the invention.

In a further embodiment, the invention provides the Eg5 dsRNA and the uses thereof as described above in combination with a second dsRNA targeting the VEGF mRNA. A combination of a dsRNA targeting Eg5 and a second dsRNA targeting VEGF provides complementary and synergiatic activity for treating hyperproliferative discords, particulary hepatic carcinoma.

BRIEF DESCRIPTION OF THE FIGURES

No Figures are presented.

DETAILED DESCRIPTION OF THE INVENTION

The invention provides double-stranded ribonucleic acid (dsRNA), as well as compositions and methods for inhibiting the expression of the Eg5 gene in a cell or mammal using the dsRNA. The invention also provides compositions and methods for treating pathological conditions and diseases in a mammal caused by the expression of the Eg5 gene using dsRNA. dsRNA directs the sequence-specific degradation of mRNA through a process known as RNA interference (RNAi). The invention further provides this dsRNA in combination with a second dsRNA that inhibits the expression of the VEGF gene.

The dsRNAs of the invention comprises an RNA strand (the antisense strand) having a region which is less than 30 nucleotides in length, generally 19-24 nucleotides in length, and is substantially complementary to at least part of an mRNA transcript of the Eg5 gene. The use of these dsRNAs enables the targeted degradation of mRNAs of genes that are implicated in replication and or maintenance of cancer cells in mammals. Using cell-based and animal assays, the present invention have demonstrated that very low dosages of these dsRNA can specifically and efficiently mediate RNAi, resulting in significant inhibition of expression of the Eg5 gene. Thus, the methods and compositions of the invention comprising these dsRNAs are useful for treating pathological processes mediated by EG5 expression, e.g. cancer, by targeting a gene involved in mitotic division.

The following detailed description discloses how to make and use the dsRNA and compositions containing dsRNA to inhibit the expression of the Eg5 gene, as well as compositions and methods for treating diseases and disorders caused by the expression of Eg5, such as cancer, alone or in combination with a second dsRNA targeting the VEGF gene. The pharmaceutical compositions of the invention comprise a dsRNA having an antisense strand comprising a region of complementarity which is less than 30 nucleotides in length, generally 19-24 nucleotides in length, and is substantially complementary to at least part of an RNA transcript of the Eg5 gene, together with a pharmaceutically acceptable carrier. As discussed above, such compositions can further include a second dsRNA targeting VEGF.

Accordingly, certain aspects of the invention provide pharmaceutical compositions comprising the dsRNA of the invention together with a pharmaceutically acceptable carrier, methods of using the compositions to inhibit expression of the Eg5 gene, and methods of using the pharmaceutical compositions to treat diseases caused by expression of the Eg5 gene. The invention further provides the above pharmaceutical compositions further containing a second dsRNA designed to inhibit the expression of VEGF.

I. Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A" and "U" each generally stand for a nucleotide that contains guanine, cytosine, adenine, and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, "Eg5" refers to the human kinesine family member 11, which is also known in KIF11, Eg5, KNSL1 or TRIP5. Eg5 sequence can be found as NCBI GeneID:3832, HGNC ID: HGNC:6388 and RefSeq ID number NM_004523.

As used herein, "target sequence" refers to a contiguous portion of the nucleotide sequence of an mRNA molecule formed during the transcription of the Eg5 gene, including mRNA that is a product of RNA processing of a primary transcription product.

As used hereing, VEGF, also known as vascular permeability factor, is an angiogenic growth factor. VEGF is a homodimeric 45 kDa glycoprotein that exists in at least three different isoforms. VEGF isoforms are expressed in endothelial cells. The VEGF gene contains 8 exons that express a 189-amino acid portein isoform. A 165-amino acid isoform lacks the residues encoded by exon 6, whereas a 121-amino acid isoform lacks the residues encoded by exons 6 and 7. VEGF145 is an isoform predicted to contain 145 amino acids and to lack exon 7. VEGF can act on endothelial cells by binding to an endothelial tyrosine kinase receptor, such as Flt-1 (VEGFR-1) or KDR/flk-1 (VEGFR-2). VEGFR-2 is expressed in endothelial cells and is involved in endothelial cell differentiation and vasculogenesis. A third receptor, VEGFR-3 has been implicated in lymphogenesis.

The various isoforms have different biologic activities and clinical implications. For example, VEGF145 includes angiogenesis and like VEGF189 (but unlike VEGF165) VEGF145 binds efficiently to the extracellular matrix by a mechanism that is not dependent on extracellular matrix-associated heparin sulfates. VEGF displays activity as an endothelial cell mitogen and chemoattractant in vitro and induces vascular permeability and angiogenesis in vivo. VEGF is secreted by a wide variety of cancer cell types and promotes the growth of tumors by inducing the development of tumor-associated vasculature. Inhibition of VEGF function has been shown to limit both the growth of primary experimental tumors as well as the incidence of metastases in immunocompromised mice. Various dsRNAs directed to VEGF are described in co-pending U.S. Ser. Nos. 11/078,073 and 11/340,080, herein incorporated by reference).

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two-sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes of the invention.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide which is "substantially complementary to at least part of" a messenger RNA (mRNA) refers to a polynucleotide which is substantially complementary to a contiguous portion of the mRNA of interest (e.g., encoding Eg5). For example, a polynucleotide is complementary to at least a part of a Eg5 mRNA if the sequence is substantially complementary to a non-interrupted portion of a mRNA encoding Eg5.

The term "double-stranded RNA" or "dsRNA", as used herein, refers to a complex of ribonucleic acid molecules, having a duplex structure comprising two anti-parallel and substantially complementary, as defined above, nucleic acid strands,. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'end of the respective other strand forming the duplex structure, the connecting RNA chain is referred to as a "hairpin loop". Where the two strands are connected covalently by means other than an uninterrupted chain of nucleotides between the 3'-end of one strand and the 5'end of the respective other strand forming the duplex structure, the connecting structure is referred to as a "linker". The RNA strands may have the same or a different number of nucleotides. The maximum number of base pairs is the number of nucleotides in the shortest strand of the dsRNA minus any overhangs that are present in the duplex. In addition to the duplex structure, a dsRNA may comprise one or more nucleotide overhangs.

As used herein, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "sense strand," as used herein, refers to the strand of a dsRNA that includes a region that is substantially complementary to a region of the antisense strand.

"Introducing into a cell", when referring to a dsRNA, means facilitating uptake or absorption into the cell, as in understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. In vitro introduction into a cell includes methods known in the art such as electroporation and lipofection.

The terms "silence" and "inhibit the expression of", in as far as they refer to the Eg5 gene, herein refer to the at least partial suppression of the expression of the Eg5 gene, as manifested by a reduction of the amount of mRNA transcribed from the Eg5 gene which may be isolated from a first cell or group of cells in which the Eg5 gene is transcribed and which has or have been treated such that the expression of the Eg5 gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\%$$

Alternatively, the degree of inhibition may be given in terms of a reduction of a parameter that is functionally linked to Eg5 gene transcription, e.g. the amount of protein encoded by the Eg5 gene which is secreted by a cell, or the number of cells displaying a certain phenotype, e.g. apoptosis. In principle, Eg5 gene silencing may be determined in any cell expressing the target, either constitutively or by genomic engineering, and by any appropriate assay. However, when a reference is needed in order to determine whether a given dsRNA inhibits the expression of the Eg5 gene by a certain degree and therefore is encompassed by the instant invention, the assay provided in the Examples below shall serve as such reference.

For example, in certain instances, expression of the Eg5 gene (or VEGF gene) is suppressed by at least about 20%, 25%, 35%, or 50% by administration of the double-stranded oligonucleotide of the invention. In some embodiment, the Eg5 gene is suppressed by at least about 60%, 70%, or 80% by administration of the double-stranded oligonucleotide of the invention. In some embodiments, the Eg5 gene is suppressed by at least about 85%, 90%, or 95% by administration of the double-stranded oligonucleotide of the invention. Tables 1-3 provides values for inhibition of expression using various Eg5 dsRNA molecules at various concentrations.

As used herein in the context of Eg5 expression, the terms "treat", "treatment", and the like, refer to relief from or alleviation of pathological processes mediated by Eg5 expression. In the context of the present invention insofar as it relates to any of the other conditions recited herein below (other than pathological processes mediated by Eg5 expression), the terms "treat", "treatment", and the like mean to relieve or alleviate at least one symptom associated with such condition, or to slow or reverse the progression of such condition, such as the slowing and progression of hepatic carcinoma.

As used herein, the phrases "therapeutically effective amount" and "prophylactically effective amount" refer to an amount that provides a therapeutic benefit in the treatment, prevention, or management of pathological processes mediated by Eg5 expression or an overt symptom of pathological processes mediated by Eg5 expression (alone or in combination with VEGF expression). The specific amount that is therapeutically effective can be readily determined by ordinary medical practitioner, and may vary depending on factors known in the art, such as, e.g. the type of pathological processes mediated by Eg5 expression, the patient's history and age, the stage of pathological processes mediated by Eg5 expression, and the administration of other anti-pathological processes mediated by Eg5 expression agents.

As used herein, a "pharmaceutical composition" comprises a pharmacologically effective amount of a dsRNA and a pharmaceutically acceptable carrier. As used herein, "pharmacologically effective amount," "therapeutically effective amount" or simply "effective amount" refers to that amount of an RNA effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

As used herein, a "transformed cell" is a cell into which a vector has been introduced from which a dsRNA molecule may be expressed.

II. Double-stranded Ribonucleic Acid (dsRNA)

In one embodiment, the invention provides double-stranded ribonucleic acid (dsRNA) molecules for inhibiting the expression of the Eg5 gene (alone or incombination with a second dsRNA for inhibiting the expression of VEGF) in a cell or mammal, wherein the dsRNA comprises an antisense strand comprising a region of complementarity which is complementary to at least a part of an mRNA formed in the expression of the Eg5 gene, and wherein the region of complementarity is less than 30 nucleotides in length, generally 19-24 nucleotides in length, and wherein said dsRNA, upon contact with a cell expressing said Eg5 gene, inhibits the expression of said Eg5 gene by at least 40%. The dsRNA comprises two RNA strands that are sufficiently complementary to hybridize to form a duplex structure. One strand of the dsRNA (the antisense strand) comprises a region of complementarity that is substantially complementary, and generally fully complementary, to a target sequence, derived from the sequence of an mRNA formed during the expression of the Eg5 gene, the other strand (the sense strand) comprises a region which is complementary to the antisense strand, such that the two strands hybridize and form a duplex structure when combined under suitable conditions. Generally, the duplex structure us between 15 and 30, more generally between 18 and 25, yet more generally between 19 and 24, and most generally between 19 and 21 base pairs in length. Similarly, the region of complementarity to the target sequence is between 15 and 30, more generally between 18 and 25, yet more generally between 19 and 24, and most generally between 19 and 21 nucleotides in length. The dsRNA of the invention may further comprise one or more single-stranded nucleotide overhang(s). The dsRNA can be synthesized by stranded methods known in the art as further discussed below, e.g., by use of an automated DNA synthesizer, such as are commercially available from, for example, Biosearch, Applied Biosystems, Inc. In a preferred embodiment, the Eg5 gene is the human Eg5 gene. In specific embodiments, the antisense strand of the dsRNA comprises the sense sequences of Tables 1-3 and the second sequence is selected from the group consisting of the antisense sequences of Tables 1-3. Alternative antisense agents that target elsewhere in the target sequence provided in Tables 1-3 can readily be determined using the target sequence and the flanking Eg5 sequence. In embodiments using a second dsRNA targeting VEGF, such agents are exemplified in the Examples and in co-pending U.S. Ser. Nos. 11/078,073 and 11/340,080, herein incorporated by reference.

The dsRNA will comprise at least two nucleotide sequence selected from the groups of sequences provided in Tables 1-3. One of the two sequences is complementary to the other of the two sequences, with one of the sequences being substantially complementary to a sequence of an mRNA generated in the expression of the Eg5 gene. As such, the dsRNA will comprises two oligonucleotides, wherein one oligonucleotide is described as the sense strand in Tables 1-3 and the second oligonucleotide is described as the antisense strand in Tables 1-3.

The skilled person is well aware that dsRNAs comprising a duplex structure of between 20 and 23, but specifically 21, base pairs have been hailed as particularly effective in inducing RNA interference (Elbashir et al., EMBO 2001, 20:6877-6888). However, others have found that shorter or longer dsRNAs can be effective as well. In the embodiments described above, by virtue of the nature of the oligonucleotide sequences provided in Tables 1-3, the dsRNAs of the invention can comprise at least one strand of a length of minimally 21 nt. It can be reasonably expected that shorter dsRNAs comprising one of the sequences of Tables 1-3 minus only a few nucleotides on one or both ends may be similarly effective as compared to the dsRNAs described above. Hence, dsRNAs comprising a partial sequence of at least 15, 16, 17, 18, 19, 20, or more contiguous nucleotides from one of the sequences of Tables 1-3, and differing in their ability to inhibit the expression of the Eg5 gene in a FACS assay as described herein below by not more than 5, 10, 15, 20, 25, or 30% inhibition from a dsRNA comprising the full sequence, are contemplated by the invention. Further dsRNAs that cleave within the target sequence provided in Tables 1-3 can readily be made using the Eg5 sequence and the target sequence provided.

In addition, the RNAi agents provided in Tables 1-3 identify a site in the Eg5 mRNA that is susceptible to RNAi based cleavage. As such the present invention further includes RNAi agents that target within the sequence targeted by one of the agents of the present invention. As used herein a second RNAi agent is said to target within the sequence of a first RNAi agent if the second RNAi agent cleaves the message anywhere within the mRNA that is complementary to the antisense strand of the first RNAi agent. Such a second agent will generally consist of at least 15 contiguous nucleotides from one of the sequences provided in Tables 1-3 coupled to additional nucleotide sequences taken from the region contiguous to the selected sequence in the Eg5 gene. For example, the last 15 nucleotides of SEQ ID NO:1 combined with the next 6 nucleotides from the target Eg5 gene produces a single strand agent of 21 nucleotides that is based on one of the sequences provided in Tables 1-3.

The dsRNA of the invention can contain one or more mismatches to the target sequence. In a preferred embodiment, the dsRNA of the invention contains no more than 3 mismatches. If the antisense strand of the dsRNA contains mismatches to a target sequence, it is preferable that the area of mismatch not be located in the center of the region of complementarity. If the antisense strand of the dsRNA contains mismatches to the target sequence, it is preferable that the mismatch be restricted to 5 nucleotides from either end, for example 5, 4, 3, 2, or 1 nucleotide from either the 5' or 3' end of the region of complementarity. For example, for a 23 nucleotide dsRNA strand which is complementary to a region of the Eg5 gene, the dsRNA generally does not contain any mismatch within the central 13 nucleotides. The methods described within the invention can be used to determine whether a dsRNA containing a mismatch to a target sequence is effective in inhibiting the expression of the Eg5 gene. Consideration of the efficacy of dsRNAs with mismatches in inhibiting expression of the Eg5 gene is important, especially if the particular region of complementarity in the Eg5 gene is known to have polymorphic sequence variation within the population.

In one embodiment, at least one end of the dsRNA has a single-stranded nucleotide overhang of 1 to 4, generally 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in vivo, as well as in a variety of cells, cell culture mediums, blood, and serum. Generally, the single-stranded overhang is located at the 3'-terminal end of the antisense strand or, alternatively, at the 3'-terminal end of the sense strand. The dsRNA may also have a blunt end, generally located at the 5'-end of the antisense strand. Such dsRNAs have improved stability and inhibitory activity, thus allowing administration at low dosages, e.g., less than 5 mg/kg body weight of the recipient per day. Generally, the antisense strand of the dsRNA has a nucleotide overhang at the 3'-end, and the 5'-end is blunt. In another embodiment, one or more of the nucleotides in the overhang is replaced with a nucleoside thiophosphate.

In yet another embodiment, the dsRNA is chemically modified to enhance stability. The nucleic acids of the invention may be synthesized and/or modified by methods well established in the art, such as those described in "Current protocols in nucleic acid chemistry", Beaucage, S. L. et al. (Edrs.), John Wiley & Sons, Ind., New York, N.Y., USA, which is hereby incorporated herein by reference. Specific examples of preferred dsRNA compounds useful in this invention include dsRNAs containing modified backbones or no natural internucleoside linkages. As defined in this specification, dsRNAs having modified backbones include those that retain a phosphorus atom in the backbone and those that do not have a phosphorus atom in the backbone. For the purposes of this specification, and as sometimes referenced in the art, modified dsRNAs that do not have a phosphorus atom in their internucleoside backbone can also be considered to be oligonucleosides.

Preferred modified dsRNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; and 5,625,050, each of which in herein incorporated by reference.

Preferred modified dsRNA backbones that do not include a phosphorus atom therein have backbones that are formed by short chain alkyl or cycloakyl internucleoside linkages, mixed heteroatoms and alkyl or cycloalkyl internucleoside linkages, or ore or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other preferred dsRNA mimetics, both the sugar and the internucleoside linkage, i.e., the backbone, of the nucleotide units are replaced with novel groups. The base units are maintained for hybridization with an appropriate nucleic acid target compound. One such oligomeric compound, and dsRNA mimetic that has been shown to have excellent hybridization properties, is referred to as a peptide nucleic acid (PNA). In PNA compounds, the sugar backbone of an dsRNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262; each of which is herein incorporated by reference. Further teaching of PNA compounds can be found in Nielsen et al., Science, 1991, 254, 1497-1500.

Most preferred embodiments of the invention are dsRNAs with phosphorothioate backbones and oligonucleosides with heteroatom backbones, and in particular —CH.sub.2-NH—CH.sub.2-, —CH.sub.2-N(CH.sub.3)-O—CH.sub.2-[known as a methylene (methylimino) or MMI backbone], —CH.sub.2-O—N(CH.sub.3)-CH.sub.2-, —CH.sub.2-N(CH.sub.3)-N(CH.sub.3)—CH.sub.2- and -N(CH.sub.3)-CH.sub.2-CH.sub.2-[wherein the native phosphodiester backbone is represented as —O—P—O—CH.sub.2-] of the above-referenced U.S. Pat. No. 5,489,677, and the amide backbones of the above-referenced U.S. Pat. No. 5,602,240. Also preferred are dsRNAs having morepholino backbone structures of the above-referenced U.S. Pat. No. 5,034,506.

Modified dsRNAs may also contain one or more substituted sugar moieties. Preferred dsRNAs comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $(CH_2)$.ub.nOCH$_3$, $O(CH_2)_nNH_2$, $O(CH_2)$.xub.nCH$_3$, $O(CH_2)_nONH_2$, and $O(CH_2)_nON[(CH_2)_nCH_{su-b.3})]_2$, where n and m are from 1 to about 10. Other preferred dsRNAs comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an dsRNA, or a group for improving the pharmacodynamic properties of an dsRNA, and other substituents having similar properties. A preferred modification includes 2'-methoxyethoxy (2'-O—$CH_2CH_2OCH_3$, also known as 2'-O-(2)methoxyethyl) or 2'-MOE) (Martin et al., Helv. Chim. Acta, 1995, 78, 486-504) i.e., an alkozy-alkoxy group. A further preferred modification includes 2'-dimethylaminooxyethoxy, i.e., a $O(CH_2)_2ON(CH_3)_2$ group, also known as 2'-DNAOE, as described in examples hereinbelow, and 2'-dimethylaminothoxyethoxy (also known in the art as 2'-O-dimethylaminoethoxyethyl or 2'-DMAEOE), i.e., 2'-O—$CH_2$-O—$CH_2$-N$(CH_2)_2$, also described in examples hereinbelow.

Other preferred modifications include 2'-methoxy (2'-$OCH_3$), 2'-aminopropoxy (2'-$OCH_2CH_2NH_2$) and 2'-fluoro (2'-F). Similar modifications may also be made at other positions on the dsRNA, particularly the 3' position of the sugar on the 3' terminal nulceotide or in 2'-5' linked dsRNAs and the 5' position of 5' terminal nucleotide. DsRNAs may also have sugar mimetics such as cyclobutul moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

DsRNAs may also include nucleobase (often referred to in the art simply as "base") modifications or substitutions. As used herein, "unmodified" or "natural" nucleobases include the puring bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouacil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and sytosines, 7-methylguanine and 7-methyladenine, 8-azaguanine and 8-azaadenine, 7-deazaguanine and 7-daazaadenine and 3-deazaguanine and 3-deazaadenin. Further nucleobases include those disclosed in U.S. Pat. No. 3,687,808, those disclosed in The Concise Encyclopedia Of Polymer Science And Engineering, pages 858-859, Kroschwitz, J. L, ed. John Wiley & Sons. 1990, these disclosed by Englisch et al., Angewandti Chemie, International Edition, 1991, 30, 613, and those disclosed by Sanghvi, Y S., Chapter 15, DsRNA Research and Applications, pages 289-302, Crooke, S. T. and Lebleu, B., Ed., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, including 2-aminopropyladenine, 5-propynyluracil and 5-propynyleytosine, 5-methylcytosine substitutions have been shown to increase nucleic acid duplex stability by 0.6-1.2.degree. C. (Sanghvi, Y. S., Crooke, S. T. and Lebleu, B., Eds., DsRNA Research and Applications, CRC Press, Boca Raton, 1993, pp. 276-278) and are presently preferred base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, each of which is herein incorporated by reference, and U.S. Pat. No. 5,750,692, also herein incorporated by reference.

Another modification of the dsRNAs of the invention involves chemically linking to the dsRNA one or more moieties or conjugates which enhance the activity, cellular distribution or cellular uptake of the dsRNA. Such moieties include but are not limited to lipid moieties such as a cholesterol moiety (Letsinger et al., Proc. Natl. Acid. Sci. USA, 199, 86, 6553-6556), cholic acid (Mancharan et al., Biorg. Med. Chem. Let., 1994 4 1053-1060), a thioether, e.g., beryl-S-triylthiol (Manoharan et al., Ann, N.Y. Acad. Sci., 1992, 660, 306-309; Manoharan et al., Biorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J, 1991, 10, 1111-1118; Kabanov et al., FEBS Lett., 1990, 259, 327-330; Svinarchuk et al., Biochimic, 1993, 75, 49-54), a phospholipid, e.g., di-hexadecyl-rac-hlycerol or triethyl-ammonium 1,2-di-O-hexadecyl-rac-glycero-3-Hphosphonate (Manoharan et al., Tetrahedron Lett., 1995, 36, 3651-3654; Shen et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyloxycholesterol moiety (Crooke et al., J. Pharmacol. Exp. Ther., 1996, 277, 923-937).

Representative U.S. patents that teach the preparation of such dsRNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735;

5,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,345,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

It is not necessary for all positions in a given compound to be uniformly modified, and in fact more than one of the aforementioned modifications may be incorporated in a single compound or even at a single nucleoside within an dsRNA. The present invention also includes dsRNA compounds which are chimeric compounds. "Chimeric" dsRNA compounds or "chimeras," in the context of this invention, are dsRNA compounds, particularly dsRNAs, which contain two or more chemically distinct regions, each made up of at least one monomer unit, i.e., a nucleotide in the case of an dsRNA compound. These dsRNAs typically contain at least one region wherein the dsRNA is modified so as to confer upon the dsRNA increased resistance to nuclease degradation, increased cellular uptake, and/or increased binding affinity for the target nucleic acid. An additional region of the dsRNA may serve as a substrate for anzymes capable of cleaving RNA-DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of dsRNA inhibition of gene expression. Consequently, comparable results can often be obtained with shorter dsRNAs when chimeric dsRNAs are used, compared to phosphorothioate deoxydsRNAs hybridizing to the same target region. Cleavage of the RNA target can be routinely detected by gel electrophoresis and, if necessary, associated nucleic acid hybridization techniques known in the art.

In certain instances, the dsRNA may be modified by a non-ligand group. A number of non-ligand molecules have been conjugated to dsRNAs in order to enhance the activity, cellular distribution or cellular uptake of the dsRNA, and procedures for performing such conjugations are available in the scientific literature. Such non-ligand moieties have included lipid moieties, such as cholesterol (Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad, Sci., 1992, 660-306; Manoharan et al., Bioorg. Med. Chem. Let. 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-hlycero-3-H-phosphonate (Manoharan et al., Tetrahedron Lett., 1995, 36:3651; Shen et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim, Biophys. Acta, 1995, 1264:229), or an octadecylamine or hexylamino-carbonyl-oxycholesterol moiety (Crooke et al., J. Pharmacel. Exp. Ther., 1996, 277:923). Representative United States patents that teach the preparation of such dsRNA conjugates have been listed above. Typical conjugation protocols involve the synthesis of dsRNAs bearing an aminolinker at one or more positions of the sequence. The amino group is then reacted with the molecule being conjugated using appropriate coupling or activating reagents. The conjugation reaction may be performed either with the dsRNA still bound to the solid support or following cleavage of the dsRNA in solution phase. Purification of the dsRNA conjugate by HPLC typically affords the pure conjugate.

Vector Encoded RNAi Agents

The dsRNA of the invention can also be expressed from recombinant viral vectors intracellularly in vivo. The recombinant viral vectors of the invention comprise sequences encoding the dsRNA of the invention and any suitable promoter for expressing the dsRNA sequences. Suitable promoters include, for example, the U6 or H1 RNA pol III promoter sequences and the cytomegalovirus promoter. Selection of other suitable promoters is within the skill in the art. The recombinant viral vectors of the invention can also comprise inducible or regulatable promoters for expression of the dsRNA in a particular tissue or in a particular intracellular environment. The use of recombinant viral vectors to deliver dsRNA of the invention to cells in vivo is discussed in more detail below.

dsRNA of the invention can be expressed from a recombinent viral vector either as two separate, complementary RNA molecules, or as a single RNA molecule with two complementary regions.

Any viral vector capable of accepting the coding sequences for the dsRNA molecule(s) so be expressed can be used, for example vectors derived from adenovirus (AV); adeno-associated virus (AAV); retroviruses (e.g, lentiviruses (LV), Rhabdoviruses, murine leukemia virus); harpes virus, and the like. The tropism of viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokela, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the dsRNA into the vector, and methods of delivering the viral vector to the cells of interest are within the skill in the art. See, for example, Dornburg R (1995), Gene Therap. 2: 301-310, Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Preferred viral vectors are those derived from AV and AAV. In a particularly preferred embodiment, the dsRNA of the invention is expressed as two separate, complementary single-stranded RNA molecules from a recombinant AAV vector comprising, for example, either the U6 or H1 RNA promoters, or the cytomegalovirus (CMV) promoter.

A suitable AV vector for expressing the dsRNA of the invention, a method for constructing the recombinant AV vector, and a method for delivering the vector into target cells, are described in Xia H et al. (2002), Nat. Biotech. 20: 1006-1010.

Suitable AAV vectors for expressing the dsRNA of the invention, methods for constructing the recombinant AV vector, and methods for delivering the vectors into target cells are described in Samulski R et al. (1987), J. Virol. 61: 3096-3101; Fisher K. J et al. (1996), J. Virol, 70: 520-532; Samulski R et al. (1989), J. Virol. 63: 3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference.

III. Pharmaceutical Compositions Comprising dsRNA

In one embodiment, the invention provides pharmaceutical compositions comprising a dsRNA, as described herein, and a pharmaceutically acceptable carrier. The pharmaceutical composition comprising the dsRNA is useful for treating a disease or disorder associated with the expression or activity of the Eg5 gene, such as pathological processes mediated by Eg5 expression. Such pharmaceutical composition are formulated based on the mode of delivery. One example is compositions that are formulated for systemic administration via parenteral delivery.

In another embodiment, such compositions will further comprise a second dsRNA that inhibits VEGF expression. dsRNA directed to VEGF are described in the Examples and in co-pending U.S. Ser. Nos. 11/078,073 and 11/340,080.

The pharmaceutical compositions of the invention are administered to dosages sufficient to inhibit expression of the Eg5 gene (and VEGF expression when a second dsRNA is included). In general, a suitable dose of dsRNA will be in the range of 0.01 to 5.0 milligrams per kilogram body weight of the recipient per day, generally in the range of 1 microgram to 1 mg per kilogram body weight per day. The pharmaceutical composition may be administered once daily or the dsRNA may be administered as two, three, or more sub-doses at appropriate intervals throughout the day or even using continuous infusion or delivery through a controlled release formulation. In that case, the dsRNA contained in each sub-dose must be correspondingly smaller in order to achieve the total daily dosage. The dosage unit can also be compounded for delivery over several days, e.g., using a conventional sustained release formulation which provides sustained release of the dsRNA over a several day period. Sustained release formulations are well known in the art and are particularly useful for delivery of agents at a particular site, such as could be used with the agents of the present invention. In this embodiment, the dosage unit contains a corresponding multiple of the daily dose.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual dsRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes mediated by Eg5 expression. Such models are used for in vivo testing of dsRNA, as well as for determining a therapeutically effective dose.

The present invention also includes pharmaceutical compositions and formulations which include the dsRNA compounds of the invention. The pharmaceutical compositions of the present invention may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the dsRNAs of the invention are in admixture with a topical delivery agent such as lipids, liposomes, fatty acids, fatty acid esters, steroids, chelating agents and sufactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). DsRNAs of the invention may be encapsulated within liposomes or may form complexes thereto, in particular to cationic liposomes. Alternatively, dsRNAs may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dieaprate, tricaprate, monoolein, dilaurin, glyceryl 1-monocaprate, 1-dodecylazacycloheptan-2-one, an acylcamitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which dsRNAs of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-digydro-fusidate and sodium glycodihydrofusidate. Preferred fatty acids include arachidonic acid, undecanoic acid, oleic acid, lauric acid, caprylic acid, capric acid, myristic acid palmitic acid, stearic acid, linoleic acid, linolenic acid, dicaprate, tricaprate, monoolein, dilaurin, glycerly 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. DsRNAs of the invention may be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkyleyanoacrylates; cationized gelatins, albumins, starches, acrylates, polyethyleneglycols (PEG) and starches; polyalkylcyanoacrylates; DEAE-derivatized polimines, pollulans, celluloses and starches. Particularly preferred complexing agents include chitosan, N-trimethylchitosan, poly-L-lysine, polyhistidine, polyomithine, polyspermines, protamine, polyvinylpyridine, polythiodiethylaminomethylethylene P(TDAE), polyaminostyrene (e.g. p-amino), poly(methyleyanoacrylate), poly(ethylcyanoacrylate), poly(butylcayanoacrylate), poly(isobutylcyanoacrylate), poly(isohexyleynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. application Ser. No. 08/886,829 (filed Jul. 1, 1997), Ser. No. 09/108,673 (filed Jul. 1, 1998), Ser No. 09/256,515 (filed Feb. 23, 1999), Ser. No. 09/082,624 (filed May 21, 1998) and Ser. No. 09/315,298 (filed May 20, 1999), each of which is incorporated herein by reference in their entirety.

Compositions and formulations for parenteral, intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which may conventeitly be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and the, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Emulsions

The compositions of the present invention may be prepared and formulated as emulsions. Emulsions are typically heterogenous systems of one liquid dispersed in another in the form of droplets usually exceeding 0.1.mu.m in diameter (Idson, in Pharmaceutical Dosage Forms, Lieberman, Rieger and Bander (Eds.), 1988, Marcel Dekker, Inc., New York, N.Y., volumn 1, p. 199; Rosoff, in Pharmaceutical Dosage Forms, Leiberman, Rieger and Banker (Eds.), 1988, Marcel Dekker, INc., New York, N.Y., Volume 1, p. 245; Block in Pharmaceutical Dosage Forms, Leiberman, Rieger and Banker (Eds.), 1988, Marcel Dekker, Inc., New York, N.Y., Volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marchel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volumn 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their sermisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin montmorillonite, colloidal aluminum silicate and colloidal magnesium aluminum silicate, pigments and nonpolar solids such as carbon or glyceryl tristearate.

A large variety of non-emulsifying materials are also included in eulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Bander (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the ixternal phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent detreioration of the formulation. Antioxidants used may be free radical scavengers such as tocopherols, alkyl gallates, butylated hydroxyanisole, butylated hydroxytoluene, or reducing agents such as ascorbic acid and sodium metabisulite, and antioxidant synergists such as citric acid, tartaric acid, and lecithin.

The application of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of dsRNAs and nucleic acids are formulated as microemulsions. A microemulsion may be defined as a system of water, oil and amphiphile which is a single optically isotropic and thermodynamically stable liquid solution (Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active moleculses (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyehtylene oleyl ethers, plyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The sosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipis based microemulsions (both o/w and w/o) have been proposed to enhance the oral bioavailibility of drugs, including peptides (Constrantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solic dosage forms, improved clinical potency, and decreased toxicity (Constantinides et al.,Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, piptides or dsRNAs. Microemulsions have also been effective in the transdermal delivery of active components in both cosmetic and pharmaceutical applications. It is expected that the microemulsion compositions and formulations of the present invention will facilitate the increased systemic absorption of dsRNAs and nucleic acids from the gastrointestinal tract, as well as improve the local cellular uptake of dsRNAs and nucleic acids.

Microemulsions of the present invention may also contain additional components and additives such as sorbitan monostearate (Grill 3), Labrasol, and penetration enhancers to improve the properties of the formulation and to enhance the absorption of the dsRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Lipsomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type of formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome.TM.I (glyceryl dilaurate/cholesterol/po-lyoxy-ethylene-10-stearyl ether) and Novasome.TM.II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P.Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G.sub.M1$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papagadjopoulos et al. (Ann. N.Y. Acad. Sci., 1987, 507, 64) reported the ability of monosialoganglioside $G.sub.M1$, galactocerebrodside sulfate and phosphatidylinositol to improve blood half-lives of liposomes. These findings were expounded upon by Gabizon et al. (Proc. Natl. Acad. Sci. U.S.A., 1988, 85, 6949), U.S. Pat. No. 4,837,028 and WO 88/04924, both to Allen et al., disclose liposomes comprising (1) sphingomyelin and (2) the ganglioside $G.sub.M1$ or a galactocerebroside sulfate ester. U.S. Pat. No. 5,543,152 (Webb et al.) discloses liposomes comprising sphingomyelin. Liposomes comprising 1,2-sn-dimyristoylphosphat-idylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C.sub.1215G$, that contains a PEG moiety. Illum et al. (FEBS Lett., 1984, 167, 79) noted that hydrophilic couting of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophsica Acta, 1990, 1029, 91) extended such observations to other PEG-derivatized phospholipids, e.g., DSPE-PEG, formed from the combination of distearoylphosphatidylethanolamine (DSPE) and PEG.Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an dsRNA RNA. U.S. Pat. No. 5,665,710 to Rahman et al. describes certain methods of encapsulating oligodeoxynucleotides in liposomes. WO 97/04787 to Love et al. discloses liposomes comprising dsRNA dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y. 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is disolved or dispersed in water, the surfactant is classified as anionic. Anionic surfactants include carboxylates such as soaps, acyl lactylates, acyl amides of amino acids, esters of sulfuric acid such as alkyl sufates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positve charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Penetration Enhancers

In one embodiment, the present invention employs various penetration enhancers to effect the efficient delivery of nucleic acids, particularly dsRNAs, to the skin of animals. Most drugs are present in solution in both ionized and non-ionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of dsRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., Critical Reviews in Therapeutic Drug Carrier Systems, 1991, p. 92); and perfluouochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (N-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylearnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., Critical Reviews in Therapeutic Drug Carryier Systems, 1991, p. 92; Muranishi, Critical Reviews in Terapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxyeholic acid (sodium glycodeoxycholate), taurocholic acid (sodium taurocholate), taurodeoxycholic acid (sodium taurodeoxycholate), chanodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., Critical Reviews in therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 79, 579-583).

Chelating Agents: Chelating agents, as used in connection with the present invention, can be defined as compounds that remove metallic ions from solution by forming complexes therewith, with the result that absorption of dsRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of dsRNAs through the alimentary mucose (Muranishi, Critical Reviews in Therapeutic Drug Carrier Systems, 1990, 7, 1-33). This class of penetration enhancers include, for example unsaturated cyclic ureas, 1-alkyl- and 1-alkenylazacycle-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of dsRNAs at the cellular level may also be added to the pharmaceutical and other compositions of the present invention. For example cationic lipids, such as lipodectin (Junichi et al, U.S. Pat. No. 5,705,188), cationic hlycerol derivatives, and polycationic molecules, such as polylysine (Lollo et al., PCT Application WO 97/30731), are also known to enhance the cellular uptake of dsRNAs.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polyytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solic and is selected, with the planned manner of administration in mind, so as to provide for the desired bulk, consistency, etc., When combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for toptical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipurities, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, decarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, The Merck Manual of Diagnosis and Therapy, 15th Ed. 1987, pp. 1206-1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, The Merck Manual of Diagnosis and Therapy, 15th Ed., Berkow et al., eds., 1987, Rahway, N.J., pages 2499-2506 and 46-49, respectively). Other non-antisense chemotherapeutic agents are also within the scope of this invention. Two or more combined compounds may be used together or sequentially.

Toxicity and therapeutic efficacy of such compounds can be determined by standard pharmaceutical procedures in cell cultures or experimental animals, e.g., for determining the LD50 (the dose lethal to 50% of the population) and the Ed50

(the dose therapeutically effective in 50% of the population). The dose ration between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies generally within a range of circulating concentrations that include the Ed50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, as discussed above, the dsRNAs of the invention can be administered in combination with other known agents effective in treatment of pathological processes mediated by Eg5 expression. In any event, the administering physician can adjust the amount and timing of dsRNA administration on the basis of results observed using standard measures of efficacy known in the art or described herein.

Methods for Treating Diseases Caused by Expression of the Eg5 Gene

The invention relates in particular to the use of a dsRNA or a pharmaceutical composition prepared therefrom for the treatment of cancer, e.g., for inhibiting tumor growth and tumor metastasis. For example, the dsRNA or a pharmaceutical composition prepared therefrom may be used for the treatment of solid tumors, like breast cancer, lung cancer, head and neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma and for the treatment of skin cancer, like melanoma, for the treatment of lymphormas and blood cancer. The invention further relates to the use of an dsRNA according to the invention or a pharmaceutical composition prepared therefrom for inhibiting eg5 expression and/or for inhibiting accumulation of ascites fluid and plural effusion in different types of cancer, e.g., breast cancer, lung cancer, head cancer, neck cancer, brain cancer, abdominal cancer, colon cancer, colorectal cancer, esophagus cancer, gastrointestinal cancer, glioma, liver cancer, tongue cancer, neuroblastoma, osteosarcoma, ovarian cancer, pancreatic cancer, prostate cancer, retinoblastoma, Wilm's tumor, multiple myeloma, skin cancer, melanoma, lymphomas and blood cancer. Owing to the inhibitory effect on eg5 expression, an dsRNA according to the invention or a pharmaceutical composition prepared thereform can enhance the quality of life.

The invention futhermore relates to the use of an dsRNA or a pharmaceutical composition thereof, e.g., for treating cancer or for preventing tumor metastasis, in combination with other pharmaceuticals and/or other therapeutic methods, e.g., with known pharmaceuticals and/or known therapeutic methods, such as, for example, those which are currently employed for treating cancer and/or for preventing tumor metastasis. Preference is given to a combination with radiation therapy and chemotherapeutic agents, such as cisplatin, cyclophosphamide, 5-fluoroacil, adriamycin, daunorabicin or tamoxifen. Other embodiments include the use of a second dsRNA used to inhibit the expression of VEGF.

The invention can also be practiced by including with a specific RNAi agent, in combination with another anti-cancer chemotherapeutic agent, such as any conventional chemotherapeutic: agent, or another dsRNA used to inhibit the expression of VEGF. The combination of a specific binding agent with such other agents can potentiate the chemotherapeutic protocol. Numerous chemotherapeutic protocols will present themselves in the mind of the skilled practitioner as being capable of incorporation into the method of the invention. Any chemotherapeutic agent can be used, including alkylating agents, antimetabolites, hormones and antagonists, radioisotopes, as well as natural products. For example, the compound of the invention can be administered with antibiotics such as doxorubicin and other anthracycline analogs, nitrogen mustards such as cyclophosphamide, pyrimidine analogs such as 5-fluorouracil, cisplatin, hydroxyurea, traxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of a tetracycline compound with another treatment modality, e.g., surgery, radiation, etc., also referred to herein as "adjunct antineoplastic modalities." Thus, the method of the invention can be employed with such conventional regimens with the benefit of reducing side effects and enhancing efficacy.

Methods for Inhibiting Expression of the Eg5 Gene

In yet another aspect, the invention provides a method for inhibiting the expression of the Eg5 gene in a mammal. The method comprises administering a composition of the invention to the mammal such that expression of the target Eg5 gene is silenced. Because of their high specificity, the dsRNAs of the invention specifically target RNAs (primary or processed) of the target Eg5 gene. Compositions and methods for inhibiting the expression of these Eg5 genes using dsRNAs can be performed as described elsewhere herein.

In one embodiment, the method comprises administering a composition comprising a dsRNA, wherein the dsRNA comprises a nucleotide sequence which is complementary to at least a part of an RNA transcript of the Eg5 gene of the mammal to be treated. When the organism to be treated is a mammal such as a human, the compositions may be administered by any means known in the art including, but not limited to oral or parenteral routes, including intravenous, intramuscular, subcutaneous, transdermal, airway (aerosol), nasal, rectal, and topical (including buccal and sublingual) administration. In preferred embodiments, the compositions are administered by intravenous infusion or injection.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Gene Walking of the Eg5 Gene

Initial Screening Set siRNA design was carried out to identify siRNAs targeting Eg5 (also known as KIF11, HSKP, KNSL1 and TRIP5). Human mRNA sequences to Eg5, RefSeq ID number:NM_004523, was used.

siRNA duplexes cross-reactive to human and mouse Eg5 were designed. Twenty-four duplexes were synthesized for screening. (Table 1).

Expanded Screening Set

A second screening set was defined with 266 siRNAs targeting human EG5, as well as its rhesus monkey ortholog (Table 2). An expanded screening set was selected with 328 siRNA targeting human EG5, with no necessity to hit any EG5 mRNA of other species (Table 3).

The sequences for human and a partial rhesus EG5 mRNAs were downloaded from NCBI Nucleotide database and the human sequence was further on used as reference sequence (Human EG5:NM_004523.2, 4908 bp, and Rhesus EG5: XM_001087644.1, 878 bp (only 5' part of human EG5).

For identification of further rhesus EG5 sequences a mega blast search with the human sequence was conducted at NCBI against rhesus reference genome. The downloaded rhesus sequence and the hit regions in the blast hit were assembled to a rhesus consensus sequence with ~92% identity to human EG5 over the full-length.

All possible 19 mers were extracted from the human mRNA sequence, resulting in the pool of candidate target sites corresponding to 4890 (sense strand) sequences of human-reactive EG5 siRNAs.

Human-rhesus cross-reactivity as prerequisite for in silico selection of siRNAs for an initial screening set out of this candidate pool. To determine rhesus-reactive siRNAs, each candidate siRNA target site was searched for presence in the assembled rhesus sequence. Further, the predicted specificity of the siRNA as criterion for selection of out the pool of human-rhesus cross-reactive siRNAs, manifested by targeting human EG5 mRNA sequences, but not other human mRNAs.

The specificity of an siRNA can be expressed via its potential to target other genes, which are referred to as "off-target genes".

For predicting the off-target potential of an siRNA, the following assumptions were made:

1) off-target potential of a strand can be deduced from the number and distribution of mismatches to an off-target
2) the most relevant off-target, that is the gene predicted to have the highest probability to be silenced due to tolerance of mismatches, determines the off-target potential of the strand
3) positions 2 to 9 (counting 5' to 3') of a strand (seed region) may contribute more to off-target potential than rest of sequence (that is non-seed and cleavage site region)
4) positions 10 and 11 (counting 5' to 3') of a strand (cleavage site region) may contribute more to off-target potential than non-seed region (that is positions 12 to 18, counting 5' to 3')
5) position 1 and 19 of each strand are not relevant for off-target interactions
6) off-target potential can be expressed by the off-target score of the most relevant off-target, calculated based on number and position of mismatches of the strand to the most homologous region in the off-target gene considering assumptions 3 to 5
7) off-target potential of antisense and sense strand will be relevant, whereas potential abortion of sense strand activity by internal modifications introduced is likely siRNAs with low off-target potential were defined as preferable and assumed to be more specific.

In order to identify human EG5-specific siRNAs, all other human transcripts, which were all considered potential off-targets, were searched for potential target regions for human-rhesus cross-reactive 19 mer sense strand sequences as well as complementary antisense strands. For this, the fastA algorithm was used to determine the most homologues hit region in each sequence of the human RefSeq database, which we assume to represent the comprehensive human transcriptome.

To rank all potential off-targets according to assumptions 3 to 5, and by this identify the most relevant off-target gene and its off-target score, fastA output files were analyzed further by a perl script.

The script extracted the following off-target properties for each 19 mer input sequence and each off-target gene to calculate the off-target score:

Number of mismatches in non-seed region

Number of mismatches in seed region

Number of mismatches in cleavage site region

The off-target score was calculated by considering assumptions 3 to 5 as follows:

$$\text{Off-target score} = \text{number of seed mismatches} * 10 + \\ \text{number of cleavage site mismatches} * 1.2 + \\ \text{number of non-seed mismatches} * 1$$

The most relevant off-target gene for each 19 mer sequence was defined as the gene with the lowest off-target score. Accordingly, the lowest off-target score was defined as representative for the off-target potential of a strand.

For the screening set in Table 2, an off-target score of 3 or more for the antisense strand and 2 or more for the sense strand was chosen as prerequisite for selection of siRNAs, whereas all sequences containing 4 or more consecutive G's (poly-G sequences) were excluded. 266 human-rhesus cross-reactive sequences passing the specificity criterion, were selected based on this cut-off (see Table 2).

For definition of the expended screening set the cross-reactivity to rhesus was disgarded, re-calculated the predicted specificity based on the newly available human RefSeq database and selected only those 328 non-poly-G siRNAs with off-target score of 2,2 or more for the antisense and sense strand (see Table 3).

For the Tables: Key: A,G,C,U-ribonucleotides: T-deoxythymidine: u,c-2'-O-mehtyl nucleotides: s-phosphorothioate linkage dsRNA Synthesis Source of Reagents Where the source of a reagent is not specifically given herein, such reagent may be obtained from any supplier of reagents for molecular biology at a quality/purity standard for application in molecular biology.

siRNA Synthesis

Single-stranded RNAs were produced by solid phase synthesis on a scale of 1 µmole using an Expedite 8909 synthesizer (Applied Biosystems, Applera Deutschland GmbH, Darmstadt, Germany) and controlled pore glass (CPG, 500 Å, Proligo Biochemie GmbH, Hamburg, Germany) as solid support. RNA and RNA containing 2'-O-methyl nucleotides were generated by solid phase synthesis employing the corresponding phosphoramidites and 2'-O-methyl phosphoramidites, respectively (Proligo Biochemic GmbH, Hamburg, Germany). These building blocks were incorporated at selected sites within the sequence of the oligoribonucleotide chain using standard nucleoside phosphoramidite chemistry such as descried in Current protocols in nucleic acid chemistry, Beaucage, S. L. et al. (Edrs.), John Wiley & Sons, Ind., New York, N.Y., USA. Phosphorothioate linkages were introduced by replacement of the iodine oxidizer solution with a solution of the Beaucage reagent (Chruachem Ltd, Glasgow, UK) in acetonitrile (1%). Further ancillary reagents were obtained from Mallinckrodt Baker (Griesheim, Germany).

Deprotection and purification of the crude oligoribonucleotides by anion exchange HPLC were carried out according to established procedures. Yields and concentrations were determined by UV absorption of a solution of the respective RNA at a wavelength of 260 nm using a spectral photometer (DU 640B, Beckman Coulter GmbH, Unterschleißheim, Germany). Double stranded RNA was generated by mixing an equimolar solution of complementary strands in annealing buffer (20 mM sodium phosphate, pH 6.8; 100 mM sodium chloride), beated in a water bath at 85-90° C. for 3 minutes and cooled to room temperature over a period of 3-4 hours. The annealed RNA solution was stored at −20° C. until use.

For the synthesis of 3'-cholesterol-conjugated siRNAs (herein referred to as -Chol-3'), an appropriately modified solid support was used for RNA synthesis. The modified solid support was prepared as follows:

Diethyl-2-azabutane-1,4-dicarboxylate AA

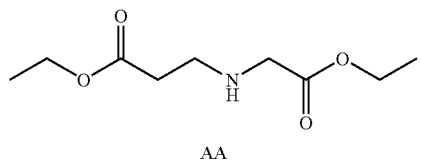

AA

A 4.7 M aqueous solution of sodium hydroxide (50 mL) was added into a stirred, ice-cooled solution of ehtyl glycinate hydrochloride (32.19 g, 0.23 mole) in water (50 mL). Then, ethyl acrylate (23.1 g, 0.23 mole) was added and the mixture was stirred at room temperature until completion of the reaction was ascertained by TLC. After 19 h the solution was partitioned with dichloromethane (3×100 mL). The organic layer was dried with anhydrous sodium sulfate, filtered and evaporated. The residue was distilled to afford AA (28.8 g, 61%).

3-{Ethoxycarbonylmethyl-[6-(9H-fluoren-9-yl-methoxycarbonyl-amino)-hexanoyl]-amino}-propionic acid ethyl ester AB

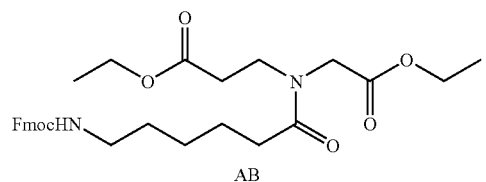

AB

Fmoc-6-amino-hexanoic acid (9.12 g, 25.83 mmol) was dissolved in dichloromethane (50 mL) and cooled with ice. Diisopropylcarbodiimde (3.25 g, 3.99 mL, 25.83 mmol) was added to the solution at 0° C. It was then followed by the addition of Diethyl-azabutane-1,4-dicarboxylate (5 g, 24.6 mmol) and dimethylamino pyridine (0.305 g, 2.5 mmol). The solution was brought to room temperature and stirred further for 6 h. Completion of the reaction was ascertained by TLC. The reaction mixture was concentrated under vacuum and ethyl acetate was added to precipitate diisopropyl area. The suspension was filtered. The filtrate was washed with 5% aqueous hydrochloric acid, 5% sodium bicarbonate and water. The combined organic layer was dried over sodium sulfate and concentrated to give the crude product which was purified by column chromatography (50% EtOAC/Hexanes) to yield 11.87 g (88%) of AB.

3-[(6-Amino-hexanoyl)-ethoxycarbonylmethyl-amino]-propionic acid ethyl ester AC

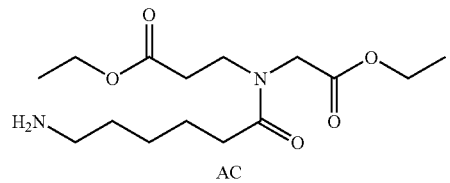

AC

3-{Ethoxycarbonylmethyl-[6-(9H-fluoren-9-ylmethoxycarbonylamino)-hexanoyl]-amino}-propionic acid ethyl ester AB (11.5 g, 21.3 mmol) was dissolved in 20% piperidine in dimethylformamide at 0° C. The solution was continued stirring for 1 h. The reaction mixture was concentrated under vacuum, water was added to the residue, and the product was extracted with ethyl acetate. The crude product was purified by conversion into its hydrochloride salt.

3-({6-[17-1,5-Dimethyl-hexyl)-10,13-dimethyl-2,3,
4,7,8,9,10,11,12,13,14,15,16,17-tetradecahydro-1H-
cyclopenta[a]phenanthren-3-yloxycarbonylamino]-
hexanoyl} ethoxycarbonylmethyl-amino)-propionic
acid ethyl ester AD

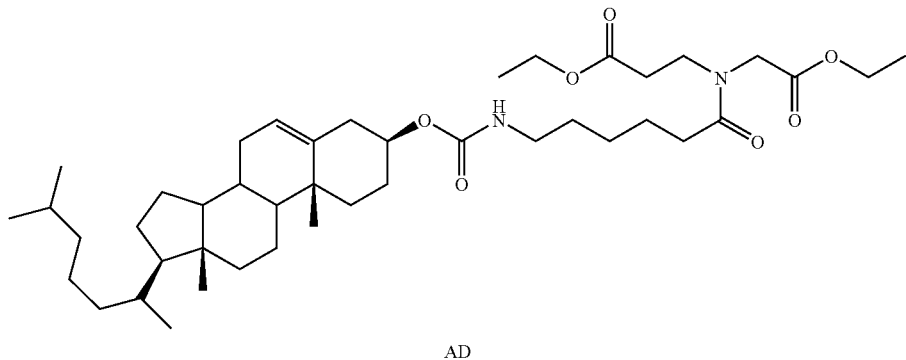

AD

The hyrdochloride salt of 3-[(6-Amino-hexanoyl)-ethoxycarbonylmethyl-amino]-propionic acid ethyl ester AC(4.7 g, 14.8 mmol) was taken up in dichloromethane. The suspension was cooled to 0° C. on ice. To the suspension diisopropylethylamine (3.87 g, 5.2 mL, 30 mmol) was added. To the resulting solution cholesteryl chloroformate (6.675 g, 14.8 mmol) was added. The reaction mixture was stirred overnight. The reaction mixture was diluted with dichloromethane and washed with 10% hydrochloric acid. The product was purified by flash chromatography (10.3 g, 92%).

1-{6-[17-(1,5-Dimethyl-hexyl)-10,13-dimethyl-2,3,
4,7,8,9,10,11,12,13,14,15,16,17-tetradecahydro-1H-
cyclopents[a] phenanthren-3-yloxycarbonylamino]-
hexanoyl}-4-oxo-pyrrolidine-3-carboxylic acid ethyl
ester AE Potassium t-butoxide (1.1 g, 9.8 mmol) was slurried in 30 mL of dry toluene. The mixture was cooed to 0° C. on ice and 5 g (6.6 mmol) of diester AD was added slowly with stirring within 20 mins. The temperature was kept below 5° C. during the addition. The stirring was continued for 30 mins at 0° C. and 1 mL of glacial acetic acid was added, immediately followed by 4 g of $NaH_2PO_4.H_2O$ in 40 mL of water. The resultant mixture was extracted twice with 100 mL of dichloromethane each and the combined organic extracts were washed twice with 10 mL of phosphate buffer each, dried, and evaporated to dryness. The residue was dissolved in 60 mL of toluene, cooled to 0° C. and extracted with three 50 mL portions of cold pH 9.5 carbonate buffer. The aqueous extracts were adjusted to pH 3 with phosphoric acid, and extracted with five 40 mL portions of chloroform which were combined, dried and evaporated to dryness. The residue was purified by column chromatography using 25% ethylacetate/hexane to afford 1.9 g of b-detoester (39%).

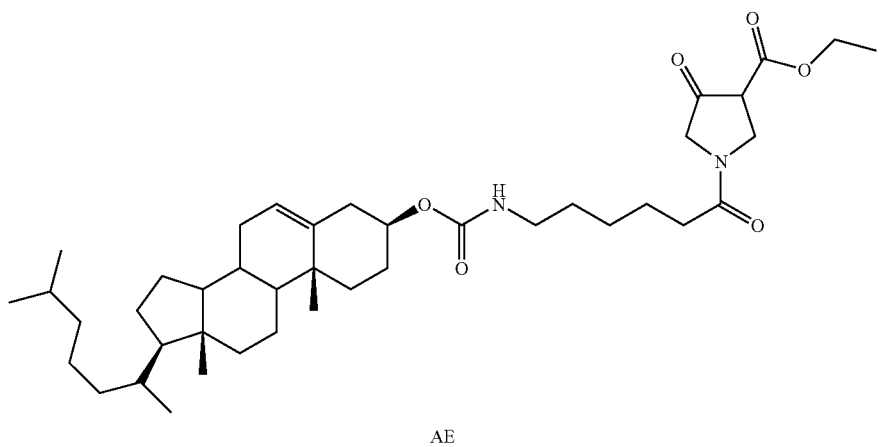

AE

[6-(3-Hydroxy-4-hydroxymethyl-pyrrolidin-1-yl)-6-oxo-hexyl]-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AF (6-{3-[Bis-(4-methoxy-phenyl)-phenyl-methoxymethyl]-4-hydroxy-pyrrolidin-1-yl}-6-oxo-hexyl)-carbamic acid 17-(1,5-dimethyl-hexyl)-10,13-dimethyl-2,3,4,7,8,9,10,11,12,13,14,15,16,17-tetradecahydro-1H-cyclopenta[a]phenanthren-3-yl ester AG

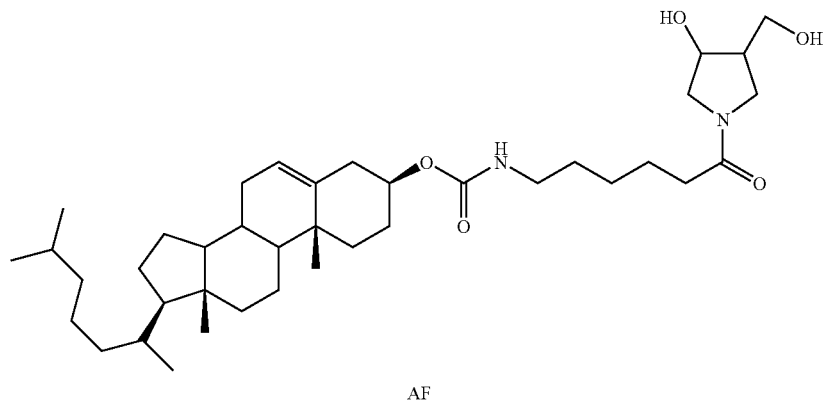

AF

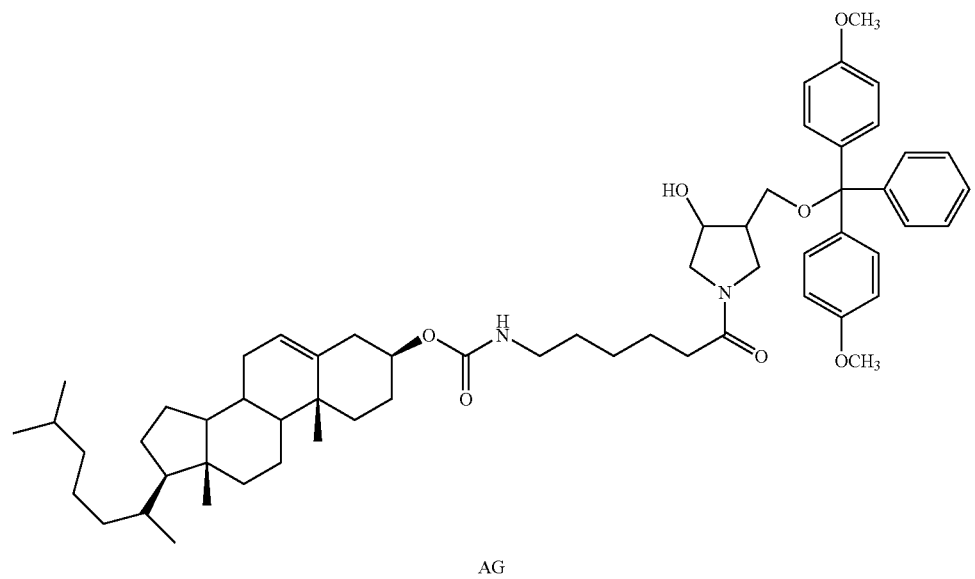

AG

Methanol (2.) was added dropwise over a period of 1 h to a refluxing mixture of b-ketoester AE (1.5 g, 2.2 mmol) and sodium borohydride (0.226 g, 6 mmol) in tetrahydrofuran (10 mL). Stirring was continued at reflux temperature for 1 h. After cooling to room temperature, 1 N NCl (12.5 mL) was added, the mixture was extracted with ethylacetate (3×40 mL). The combined ethylacetate layer was dried over anhydrous sodium sulfate and concentrated under vacuum to yield the product which was purified by column chromatography (10% MeOH/CHCl₃) (89%).

Diol AF (1.25 g, 1.994 mmol) was dried by evaporating with pyridine (2×5 mL) in vacuo. Anhydrous pyridine (10 mL) and 4,4'-dimethoxytritylchloride (0.724 g, 2.13 mmol) were added with stirring. The reaction was carried out at room temperature overnight. The reaction was quenched by the addition of methanol. The reaction mixture was concentrated under vacuum and to the residue dichloromethane (50 mL) was added. The organic layer was washed with 1 M aqueous sodium bicarbonate. The organic layer was dried over anhydrous sodium sulfate, filtered and concentrated. The residual pyridine was removed by evaporating with toluene. The crude product was purified by column chromatography (2% MeOH/Chloroform, Rf=0.5 in 5% MeOH/CHCl₃) (1.75 g, 95%).

Succinic acid mono-(4-[bos-(4-methoxy-phenyl-methoxymethyl]-1-{6-[17-(1,5-dimethyl-hexyl)-10,13-dimethyl 2,3,4,7,8,9,10,11,12,13,14,15,16,17-tetradecahydro-1H cyclopenta[a]phenanthren-3-yloxycarbonylamino]-hexanoyl}-pyrrolidin-3-yl) ester AH

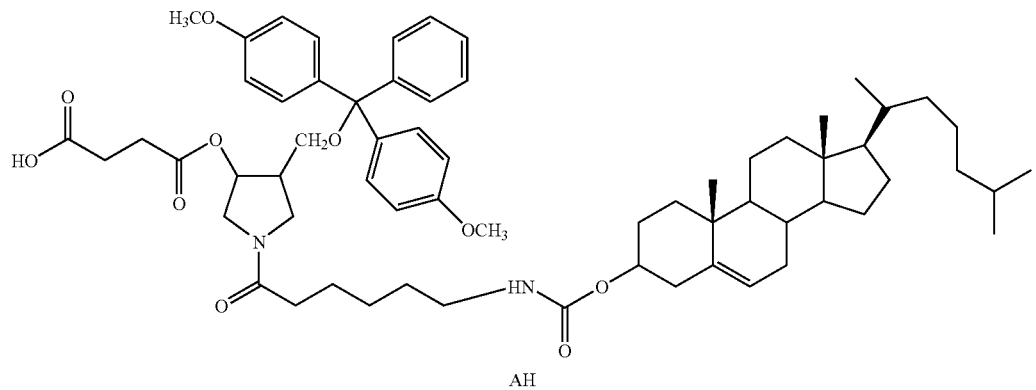

AH

Compound AG (1.0 g, 1.05 mmol) was mixed with succinic anhydride (0.150 g, 1.5 mmol) and DMAP (0.073 g, 0.6 mmol) and dried in a vacuum at 40° C. overnight. The mixture was dissolved in anhydrous dichloroethane (3 mL), triethylamine (0.318 g, 0.0440 mL, 3.15 mmol) was added and the solution was stirred at room temperature under argon atmosphere for 16 h. It was then diluted with dichloromethane (40 mL) and washed with ice cold aqueous citric acid (5 wt %, 30 mL) and water (2×20 mL). The organic phase was dried over anhydrous sodium sulfate and concentrated to dryness. The residue was used as such for the next step.

Cholesterol Derivatised CPG AI

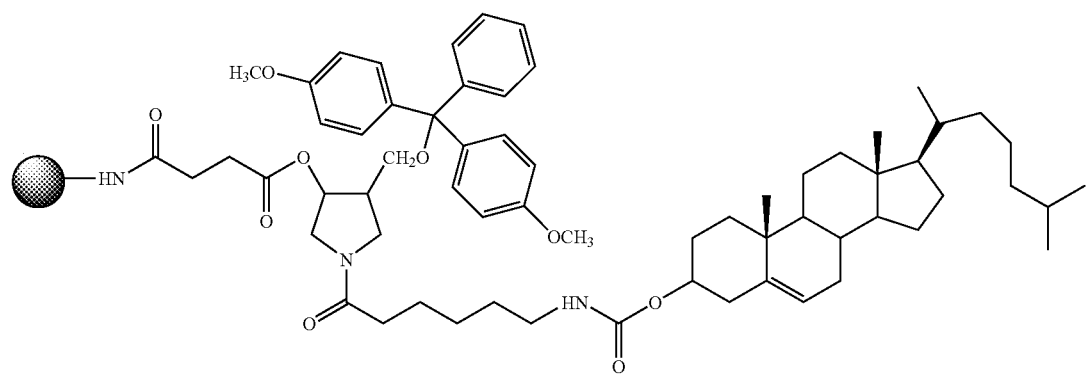

AI

Succinate AH (0.254 g, 0.242 mmol) was dissolved in a mixture of dichloromethane/acetonitrile (3:2, 3 mL). To that solution DMAP (0.0296 g, 0.242 mmol) in acetonitrile (1.25 mL), 2,2'-Dithio-bis(5-nitropyridine) (0.075 g, 0.242 mmol) in acetonitrile/dichloroethane (3:1, 1.25 mL) were added successively. To the resulting solution triphenylphosphine (0.064 g, 0.242 mmol) in acetonitrile (0.6 ml) was added. The reaction mixture turned bright orange in color. The solution was agitated briefly using a wrist-action shaker (5 mins). Long chain alkyl amine-CPG (LCAA-CPG) (1.5 g, 61 mM) was added. The suspension was agitated for 2 h. The CPG was filtered through a sintered funnel and washed with acetonitrile, dichloromethane and ether successively. Unreacted amino groups were masked using acetic anhydride/hyridine. The achieved loading of the CPG was measured by taking UV measurement (37 mM/g).

The synthesis of siRNAs bearing a 5'-12-dodecanoic acid bisdecylamide group (herein referred to as "5'-C32-") or a 5'-cholesteryl derivative group (herein referred to as "5'-Chol-") was performed as described in WO 2004/065601, except that, for the cholesteryl derivative, the oxidation step was performed using the Beaucage reagent in order to introduce a phosphorothioate linkage at the 5'-end of the nucleic acid oligomer.

Nucleic acid sequences are represented below using standard nomenclature, and specifically the abbreviations of Table 4.

TABLE 4

Abbreviations of nucleotide monomers used in nucleic acid sequence representation. It will be understood that these monomers, when present in an oligonucleotide, are mutually linked by 5'-3'-phosphodiester bonds.

| Abbreviation[3] | Nucleotide (s) |
|---|---|
| A, a | 2'-deoxy-adenosine-5'-phosphate, adenosine-5'-phosphate |
| C, c | 2'-deoxy-cytidine-5'-phosphate, cytidine-5'-phosphate |
| G, g | 2'-deoxy-guanosino-5'-phosphate, guanosine-5'-phosphate |
| T, t | 2'-deoxy-thymidine-5'-phosphate, thymidine-5'-phosphate |
| U, u | 2'-deoxy-uridine-5'-phosphate, uridine-5'-phosphate |
| N, n | any 2'-deoxy-nucleotide/nucleotide (G, A, C, or T, g, a, c or u) |
| Am | 2'-O-methyladenosine-5'-phosphate |
| Cm | 2'-O-methylcytidine phosphate |
| Gm | 2'-O-methylguanosine-5'-phosphate |
| Tm | 2'-O-methyl-thymidine-5'-phosphate |
| Um | 2'-O-methyluridine-5'-phosphate |
| Af | 2'-fluoro-2'-deoxy-adenosine-5'-phosphate |
| Cf | 2'-fluoro-2'-deoxy-cytidine-5'-phosphate |
| Gf | 2'-fluoro-2'-deoxy-guanosine-5'-phosphate |
| Tf | 2'-fluoro-2'-deoxy-thymidine-5'-phosphate |
| Uf | 2'-fluoro-2'-deoxy-uridine-5'-phosphate |
| A, C, G, T, U, a, c, g, t, u | underlined: nucleoside-5'-phosphorothioate |
| am, cm, gm, tm, um | underlined: 2-O-methyl-nucleoside-5'-phosphorothioate |

[3]capital letters represent 2'-deoxribonucletides (DNA), lower case letters represent ribonucleotides (RNA)

dsRNA Expression Vectors

In another aspect of the invention, Eg5 specific dsRNA molecules that modulate Eg5 gene expression activity are expressed from transcription units inserted into DNA or RNA vectors (see, e.g., Couture, A, et al., EIG. (1996), 12:5-10; Skillern, A., et al., International PCT Publication No. WO 00/22113, Conrad, International PCT Publicatoin No. WO 00/22114, and Conrad, U.S. Pat. No. 6,054,299). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann, et al., *Proc. Natl. Acad. Sci. USA* (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In preferred embodiment, a dsRNA is expressed as an inverted repeat joined by a linker polynucleotide sequence such that the dsRNA has a stem and loop structure.

The recombination dsRNA expression vectors are generally DNA plasmids or viral vectors. dsRNA expressing viral vectors can be constructed based on, but not limited to, adeno-associated virus (for a review, see Muzyezka, et al., *Curr. Topics Micro. Immunol.* (1992) 158:97-129)); adenovirus (see, for example, Berkner, et al., BioTechniques (1998) 6:616), Rosenfeld et al. (1991, Science 252:431-434), and Rosenfeld et al. (1992), *Cell* 68:143-155)); or alphavirus as well as others known in the art. Retroviruses have been used to introduce a vieriety of genes into many different cell types, including epithelial cells, in vitro and/or in vivo and/or in vivo (see, e.g., Eglitis, et al., *Science* (1985) 230:1395-1398; Danos and Mulligan, *Proc. Natl. Acad. Sci. USA* (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 354:1802-1805; van Beusechem. et al., 1992, Proc. Nad. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Ummunol. 150: 4104-4115; U.S. Pat. No. 4,868,116; U.S. Pat. No. 4,980,286; PCT Application WO 89/07136; PCT Application WO 89/02468; PCT Application WO 89/05344; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Invectious Disease, 166:769), and also have the advantage of not requiring mitotically active cells for infection.

The promoter driving dsRNA expression in either a DNA plasmid or viral vector of the invention may be a eukaryotic RNA polymerase I (e.g. ribosomal RNA promoter), RNA polymerase II (e.g. CNV early promoter or actin promoter or U1 snRNA promoter) or generally RNA polymerase III prometer (e.g. U6 snRNA or 7SK RNA promoter) or a prokaryotic promoter, for example the T7 promoter, provided the expression plasmid also encodes T7 RNA polymerase required for transcription from a T7 Promoter. The promoter can also direct transgene expression to the pancreas (see, e.g. the insulin regulatory sequence for pancreas (Bucchini et al., 1986, Proc, Natl. Acad. Sci. USA 83:2511-2515)).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., 1994, FASWV J. 8:20-24). Such inducible expression systems, suitable for the control of transgene expression in cells or in mammals include regulation by ecdysone, by estrogen, progesterone, tetracycline, chemical inducers of dierization, and isopropyl-beta-D1-thiogalactopyranoside (EPTG). A person skilled in the art would be able to choose the appropriate regulatory/promoter sequence based on the intended use of the dsRNA transgene.

Generally, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g., Oligofectamine) or non-cationic lipid-based carriers (e.g. Transit-TKO™). Multiple lipid transfections for dsRNA-mediated knockdowns targeting different regions of a single Eg5 gene or multiple Eg5 genes over a period of a week or more are also contemplated by the invention. Successful introduction of the vectors of the invention into host cells can be monitored using various known methods. For example, transient transfection, can be signaled with a reporter, such as a flourescent marker, such as Green Fluorescent Protein (GFP). Stable transfection of ex vivo cells can be ensured using markers that provide the transfected cell with resistance to specific environmental factors (e.g., antibiotics and drugs), such as hygromycin B resistance.

The Eg5 dsRNA molecules can also be inserted into vectors and sued as gene therapy vectors for human patients. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3045-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Eg5 siRNA in vitro Screening via Cell Proliferation

As silencing of Eg5 has been shown to cause mitotic arrest (Weil, D, et al [2002] Biotechniques 33: 1244-8), a cell viability assay was used for siRNA activity screening. HeLa cells (14000 per well [Screens 1 and 3] or 10000 per well [Screen2])) were seeded in 96-well plates and simultaneously transfected with Lipofectamine 2000 (Invitrogen) at a final siRNA concentration in the well of 30 nM and at final concentrations of 50 nM ($1^{st}$ screen) and 25 nM ($2^{nd}$ screen). A subset of duplexes was tested at 25 nM in a third screen (Table 5).

Seventy-two hours post-transfection, cell proliferation was assayed the addition of WST-1 reagent (Roche) to the culture medium, and subsequent absorbance measurement at 450 nm. The absorbance value for control (non-transfected) cells was considered 100 percent, and absorbances for the siRNA transfected wells were compared to the control value. Assays were performed in sextuplicate for each of three screens. A subset of the siRNAs was further tested at a range of siRNA concentrations. Assays were performed in HeLa cells (14000 per well; method same as above, Table 5).

TABLE 5

| Duplex | Relative absorbance at 450 nm | | | | | |
|---|---|---|---|---|---|---|
|  | Screen I mean | sd | Screen II Mean | sd | Screen III mean | Sd |
| AL-DP-6226 | 20 | 10 | 28 | 11 | 43 | 9 |
| AL-DP-6227 | 66 | 27 | 96 | 41 | 108 | 33 |
| AL-DP-6228 | 56 | 28 | 76 | 22 | 78 | 18 |
| AL-DP-6229 | 17 | 3 | 31 | 9 | 48 | 13 |
| AL-DP-6230 | 48 | 8 | 75 | 11 | 73 | 7 |
| AL-DP-6231 | 8 | 1 | 21 | 4 | 41 | 10 |
| AL-DP-6232 | 16 | 2 | 37 | 7 | 52 | 14 |
| AL-DP-6233 | 31 | 9 | 37 | 6 | 49 | 12 |
| AL-DP-6234 | 103 | 40 | 141 | 29 | 164 | 45 |
| AL-DP-6235 | 107 | 34 | 140 | 27 | 195 | 75 |
| AL-DP-6236 | 48 | 12 | 54 | 12 | 56 | 12 |
| AL-DP-6237 | 73 | 14 | 108 | 18 | 154 | 37 |
| AL-DP-6238 | 64 | 9 | 103 | 10 | 105 | 24 |
| AL-DP-6239 | 9 | 1 | 20 | 4 | 31 | 11 |
| AL-DP-6240 | 99 | 7 | 139 | 16 | 194 | 43 |
| AL-DP-6241 | 43 | 9 | 54 | 12 | 66 | 19 |
| AL-DP-6242 | 6 | 1 | 15 | 7 | 36 | 8 |
| AL-DP-6243 | 7 | 2 | 19 | 5 | 33 | 13 |
| AL-DP-6244 | 7 | 2 | 19 | 3 | 37 | 13 |
| AL-DP-6245 | 25 | 4 | 45 | 10 | 58 | 9 |
| AL-DP-6246 | 34 | 8 | 65 | 10 | 66 | 13 |
| AL-DP-6247 | 53 | 6 | 78 | 14 | 105 | 20 |
| AL-DP-6248 | 7 | 0 | 22 | 7 | 39 | 12 |
| AL-DP-6249 | 36 | 8 | 48 | 13 | 61 | 7 |

TABLE 5-continued

The nine siRNA duplexes that showed the greatest growth inhibition in Table 5 were re-tested at a range of siRNA concentrations in HeLa cells. The siRNA concentrations tested were 100 nM, 33.3 nM, 11.1 nM, 3.70 nM, 1.23 nM, 0.41 nM and 0.046 nM. Assays were performed in sextuplicate, and the concentration of each siRNA resulting in fifty percent inhibition of cell proliferation ($IC_{50}$) was calculated. This dose-response analysis was performed between two and four times for each duplex. Mean $IC_{50}$ values (nM) are given in Table 6.

TABLE 6

| Duplex | Mean $IC_{50}$ |
|---|---|
| AL-DP-6226 | 15.5 |
| AL-DP-6229 | 3.4 |
| AL-DP-6231 | 4.2 |
| AL-DP-6232 | 17.5 |
| AL-DP-6239 | 4.4 |
| AL-DP-6242 | 5.2 |
| AL-DP-6243 | 2.6 |
| AL-DP-6244 | 8.3 |
| AL-DP-6248 | 1.9 |

Eg5 siRNA in vitro Screening via Cell Proliferation

Directly before transfection, Hela S3 (ATCC-Number: CCL-2:2, LCG Promochem GmbH, Wesel, Germany) cells were seeded at $1.5 \times 10^4$ cells/well on 96-well plates (Greiner Bio-One GmbH, Frickenhausen, Germany) in 75 µl of growth medium (Ham's F12, 10% fetal calf serum, 100 u penicillin/100 µg/ml streptomycin, all from Biochrom AG, Berlin, Germany). Transfections were performed in quadruplicates. For each well 0.5 µl Lipofectamine2000 (Invitrogen GmbH, Darlsruhe, Germany) were mixed with 12 µl Opti-MEM (Invitrogen) and incubated for 15 min at room temperature. For the siRNA concentration being 50 nM in the 100 µl transfection volume, 1 µl of a 5 µM siRNA were mixed with 11.5 µl Opti-MEM per well, combined with the Lipofectamine2000-Opti-MEM mixture and again incubated for 15 minutes at room temperature, siRNA-Lipofectamine2000-complexes were applied completely (25 µl each per well) to the cells and cells were incubated for 24 h at 37° C. and 5% $CO_2$ in a humidified incubator (Heracus GmbH, Hanau). The single dose screen was done once at 50 nM and at 25 nM, respectively.

Cells were harvested by applying 50 µl of lysis mixture (content of the QuantiGene bDNA-kit from Genospectra, Fremont, USA) to each well containing 100 µl of growth medium and were lysed at 53° C. for 30 min. Afterwards, 50 µl of the lysates were incubated with probesets specific to human Eg5 and human GAPDH and proceeded according to the manufacturer's protocol for QuantiGene. In the end chemoluminescence was measured in a Victor2-Light (Perkin Elmer, Wiesbaden, Germany) as RLUs (relative light units) and values obtained with the hEg5 probeset were normalized to the respective GAPDH values for each well. Values obtained with siRNAs directed against Eg5 were related to the value obtained with an unspecific siRNA (directed against HCV) which was set to 100% (Tables 1, 2, and 3).

Effective siRNAs from the screen were further characterized by dose response curves. Transfections of dose response curves were performed at the following concentrations: 100 nM, 16.7 nM, 2.8 nM, 0.46 nM, 77 picoM, 12.8 picoM, 2.1 picoM, 0.35 picoM, 59.5 fM, 9.9 fM and mock (no siRNA) and diluted with Opti-MEM to a final concentration of 12.5 µl according to the above protocol. Data analysis was performed by using the Microsoft Excel add-in software XL-fit 4.2 (IDBS, Guildford, Surrey, UK) and applying the dose response model number 205 (Tables 1, 2 and 3).

The lead siRNA AD12115 was additionally analyzed by applying the WST-proliferation assay from Roche (as previously described).

A subset of 34 duplexes from Table 2 that showed greatest activity was assayed by transfection in HeLa cells at final concentrations ranging from 100 nM to 10 fM. Transfections were performed in quadruplicate. Two dose-response assays were performed for each duplex. The concentration giving 20% (IC20), 50% (IC50) and 80% (IC80) reduction of KSP mRNA was calculated for each duplex. (Table 7).

TABLE 7

| | Concentrations given in pM | | | | | |
|---|---|---|---|---|---|---|
| | IC20s | | IC50s | | IC80s | |
| Duplex name | $1^{st}$ screen | $2^{nd}$ screen | 1st screen | 2nd screen | 1st screen | 2nd screen |
| AD12077 | 1.19 | 0.80 | 6.14 | 10.16 | 38.36 | 76.16 |
| AD12078 | 25.43 | 25.43 | 156.18 | 156.18 | ND | ND |
| AD12085 | 9.08 | 1.24 | 40.57 | 8.52 | 257.68 | 81.26 |
| AD12095 | 1.03 | 0.97 | 9.84 | 4.94 | 90.31 | 60.47 |
| AD12113 | 4.00 | 5.94 | 17.18 | 28.14 | 490.83 | 441.30 |
| AD12115 | 0.60 | 0.41 | 3.79 | 3.39 | 23.45 | 23.45 |
| AD12125 | 31.21 | 22.02 | 184.28 | 166.15 | 896.85 | 1008.11 |
| AD12134 | 2.59 | 5.51 | 17.87 | 22.00 | 116.36 | 107.03 |
| AD12149 | 0.72 | 0.50 | 4.51 | 3.91 | 30.29 | 40.89 |
| AD12151 | 0.53 | 6.84 | 4.27 | 10.72 | 22.88 | 43.01 |
| AD12152 | 155.45 | 7.56 | 867.36 | 66.69 | 13165.27 | ND |
| AD12157 | 0.30 | 26.23 | 14.60 | 92.08 | 14399.22 | 693.31 |
| AD12166 | 0.20 | 0.93 | 3.71 | 3.86 | 46.28 | 20.59 |
| AD12180 | 28.85 | 28.85 | 101.06 | 101.06 | 847.21 | 847.21 |
| AD12185 | 2.60 | 0.42 | 15.55 | 13.91 | 109.80 | 120.63 |
| AD12194 | 2.08 | 1.11 | 5.37 | 5.09 | 53.03 | 30.92 |
| AD12211 | 5.27 | 4.52 | 11.73 | 18.93 | 26.74 | 191.07 |
| AD12257 | 4.56 | 5.20 | 21.68 | 22.75 | 124.69 | 135.82 |
| AD12280 | 2.37 | 4.53 | 6.89 | 20.23 | 64.80 | 104.82 |
| AD12281 | 8.81 | 8.65 | 19.68 | 42.89 | 119.01 | 356.08 |
| AD12282 | 7.71 | 456.42 | 20.09 | 558.00 | ND | ND |
| AD12285 | ND | 1.28 | 57.30 | 7.31 | 261.79 | 42.53 |
| AD12292 | 40.23 | 12.00 | 929.11 | 109.10 | ND | ND |
| AD12252 | 0.02 | 18.63 | 6.35 | 68.24 | 138.09 | 404.91 |
| AD12275 | 25.76 | 25.04 | 123.89 | 133.10 | 1054.54 | 776.25 |
| AD12266 | 4.85 | 7.80 | 10.00 | 32.94 | 41.67 | 162.65 |
| AD12267 | 1.39 | 1.21 | 12.00 | 4.67 | 283.03 | 51.12 |
| AD12264 | 0.92 | 2.07 | 8.56 | 15.12 | 56.36 | 196.78 |
| AD12268 | 2.29 | 3.67 | 22.16 | 25.64 | 258.27 | 150.84 |
| AD12279 | 1.11 | 28.54 | 23.19 | 96.87 | 327.28 | 607.27 |
| AD12256 | 7.20 | 33.52 | 46.49 | 138.04 | 775.54 | 1076.76 |
| AD12259 | 2.16 | 8.31 | 8.96 | 40.12 | 50.05 | 219.42 |
| AD12276 | 19.49 | 6.14 | 89.60 | 59.60 | 672.51 | 736.72 |
| AD12321 | 4.67 | 4.91 | 24.88 | 19.43 | 139.50 | 89.49 |

ND-not determined

Silencing of Liver Eg5/KSP in Juvenile Rats Following Single-bolus Administration of LNP01 Formulated siRNA From birth until approximately 23 days of age, Eg5/KSP expression can be detected in the growing rat liver. Target silencing with a formulated Eg5/KSP siRNA was evaluated in juvenile rats.

KSP Duplex Tested

| Duplex ID | Target | Sense | Antisense |
|---|---|---|---|
| AD6248 | Eg5 | AccGAAGuGuuGuuuGuccTsT (SEQ ID NO:1238) | GGAcAAAcAAcACUUCGGUTsT (SEQ ID NO:1239) |

Methods

Dosing of animals. Male, juvenile Sprague-Dawley rats (19 days old) were administered single doses of lipidoid ("LNP01") formulated siRNA via tail vein injection. Groups of ten animals received doses of 10 milligrams per kilogram (mg/kg) bodyweight of either AD6248 or an unspecific siRNA. Dose level refers to the amount of siRNA duplex administered in the formulation. A third group received phosphate-buffered saline. Animals were sacrificed two days after siRNA administration. Livers were dissected, flash frozen in liquid Nitrogen and pulverized into powders.

mRNA measurements. Levels of Eg5/KSP mRNA were measured in livers from all treatment groups. Samples of each liver powder (approximately ten milligrams) were homogenized in tissue lysis buffer containing proteinase K. Levels of Eg5/KSP and GAPDH mRNA were measured in triplicate for each sample using the Quantigene branched DNA assay (GenoSpectra). Mean values for Eg5/KSP were normalized to mean GAPDH values for each sample. Group means were determined and normalized to the PBS group for each experiment.

Statistical analysis. Significance was determined by ANOVA followed by the Tukey post-hoc test Results Data Summary Mean values (±standard deviation) for Eg5/KSP mRNA are given. Statistical significance (p value) versus the PBS group is shown (ns, not significant [p>0.05]).

Experiment 1

| | | VEGF/GAPDH | p value |
|---|---|---|---|
| PBS | | 1.0 ± 0.47 | |
| AD6248 | 10 mg/kg | 0.47 ± 0.12 | <0.001 |
| unspec | 10 mg/kg | 1.0 ± 0.26 | ns |

A statistically significant reduction in liver Eg5/KSP mRNA was obtained following treatment with formulated AD6248 at a dose of 10 mg/kg.

Silencing of Rat Liver VEGF Following Intravenous Infusion of LNP01 Formulated siRNA Duplexes A "lipidoid" formulation comprising an equimolar mixture of two siRNAs was administered to rats. One siRNA (AD3133) was directed towards VEGF. The other (AD12115) was directed towards Eg5/KSP. Since Eg5/KSP expression is nearly undetectable in the adult rat liver, only VEGF levels were measured following siRNA treatment.

siRNA Duplexes Administered

| Duplex ID | Target | Sense | Antisense |
|---|---|---|---|
| AD12115 | Eg5/KSP | ucGAGAAucuAAAcuAAcuTsT (SEQ ID NO:1240) | AGUuAGUUuAGAUUCUCGATsT (SEQ ID NO:1241) |
| AD3133 | VEGF | GcAcAuAGGAGAGAuGAGCUsU (SEQ ID NO:1242) | AAGCUcAUCUCUCCuAuGuG CusG (SEQ ID NO:1243) |

Key: A, G, C, U - ribonucleotides; c, u - 2'-O-Me ribonucleotides; s-phosphorothioate.

Methods

Dosing of animals. Adult, female Sprague-Dawley rats were administered lipidoid ("LNP01") formulated siRNA by a two-hour infusion into the femoral vein. Groups of four animals received doses of 5, 10 and 15 milligrams per kilogram (mg/kg) bodyweight of formulated siRNA. Dose level refers to the total amount of siRNA duplex administered in the formulation. A fourth group received phosphate-buffered saline. Animals were sacrificed 72 hours after the end of the siRNA infusion. Livers were dissected, flash frozen in liquid Nitrogen and pulverized into powders.

Formulation Procedure

The lipidoid ND98-4HCl (MW 1487) (Formula 1), Cholesterol (Sigma-Aldrich), and PEG-Ceramide C16 (Avanti Polar Lipids) were used to prepare lipid-siRNA nanoparticles. Stock solutions of each in ethanol were prepared: ND98, 133 mg/mL; Cholesterol, 25 mg/mL, PEG-Ceramide C16, 100 mg/mL. ND98, Cholesterol, and PEG-Ceramide C16 stock solutions were then combined in a 42:48:10 molar ratio. Combined lipid solution was mixed rapidly with aqueous siRNA (in sodium acetate pH 5) such that the final ethanol concentration was 35-45% and the final sodium acetate concentration was 100-300 mM. Lipid-siRNA nanoparticles formed spontaneously upon mixing. Depending on the desired particle size distribution, the resultant nanoparticle mixture was in some cases extruded through a polycarbonate membrane (100 nm cut-off) using a thermobarrel extruder (Lipex Extruder, Northern Lipids, Inc). In other cases, the extrusion step was omitted. Ethanol removal and simultaneous buffer exchange was accomplished by either dialysis or tangential flow filtration. Buffer was exchanged to phosphate buffered saline (PBS) pH 7.2.

Triton-X100. The total siRNA in the formulation is determined by the signal from the sample containing the surfactant, relative to a standard curve. The entrapped fraction is determined by subtracting the "free" siRNA content (as measured by the signal in the absence of surfactant) from the total siRNA content. Percent entrapped siRNA is typically >85%.

mRNA measurements. Samples of each liver powder (approximately ten milligrams) were homogenized in tissue lysis buffer containing proteinase K. Levels of VEGF and GAPDH mRNA were measured in triplicate for each sample using the Quantigene branched DNA assay (GenoSpectra). Mean values for VEGF were normalized to mean GAPDH values for each sample. Group means were determined and normalized to the PBS group for each experiment.

Protein measurements. Samples of each liver powder (approximately 60 milligrams) were homogenized in 1 ml RIPA buffer. Total protein concentrations were determined using the MicroBCA protein assay kit (Pierce). Samples of total protein from each animal was used to determine VEGF protein levels using a VEGF ELISA assay (R&D systems). Group means were determined and normalized to the PBS group for each experiment.

Statistical analysis. Significance was determined by ANOVA followed by the Tukey post-hoc test Results Data Summary Mean values (±standard deviation) for mRNA (VEGF/GAPDH) and protein (rel. VEGF) are shown for each treatment group. Statistical significance (p value) versus the PBS group for each experiment is shown.

Formula I

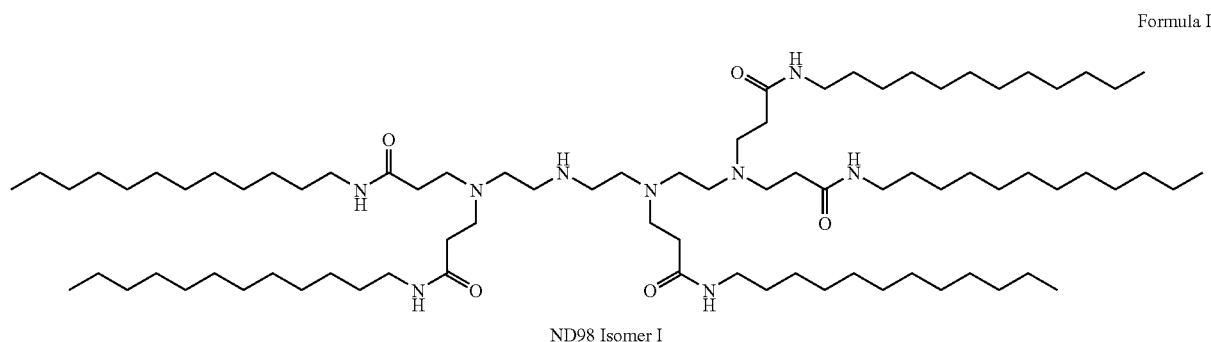

ND98 Isomer I

Characterization of Formulations

Formulations prepared by either the standard or extrusion-free method are characterized in a similar manner. Formulations are first characterized by visual inspection. They should be whitish translucent solutions free from aggregates or sediment. Particle size and particle size distribution of lipid-nanoparticles are measured by dynamic light scattering using a Malvern Zetasizer Nano ZS (Malvern, USA). Particles should be 20-300 nm, and ideally, 40-100 nm in size. The particle size distribution should be unimodal. The total siRNA concentration in the formulation, as well as the entrapped fraction, is estimated using a dye exclusion assay. A sample of the formulated siRNA is incubated with the RNA-binding dye Ribogreen (Molecular Probes) in the presence or absence of a formulation disrupting surfactant, 0.5%

|  | VEGF/GAPDH | p value | rel VEGF | p value |
|---|---|---|---|---|
| PBS | 1.0 ± 0.17 |  | 1.0 ± 0.17 |  |
| 5 mg/kg | 0.74 ± 0.12 | <0.05 | 0.23 ± 0.03 | <0.001 |
| 10 mg/kg | 0.65 ± 0.12 | <0.005 | 0.22 ± 0.03 | <0.001 |
| 15 mg/kg | 0.49 ± 0.17 | <0.001 | 0.20 ± 0.04 | <0.001 |

Statistically significant reductions in liver VEGF mRNA and protein were measured at all three siRNA dose levels.

TABLE 1

| position in human access. # | sequence of total 23 mer target site | SEQ I | sense sequence (5'-3') |
|---|---|---|---|
| 385-407 | ACCGAAGUGUUGUUUGUCCAAUU | 1 | cGAAGuGuuGuuuGuccAATsT |
| 347-369 | UAUGGUGUUUGGAGCAUCUACUA | 3 | uGGuGuuuGGAGcAucuAcTsT |
| 1078-1100 | AAUCUAAACUAACUAGAAUCCUC | 5 | ucuAAAcuAAcuAGAAuccTsT |
| 1067-1089 | UCCUUAUCGAGAAUCUAAACUAA | 7 | cuuAucGAGAAucuAAAcuTsT |
| 374-396 | GAUUGAUGUUUACCGAAGUGUUG | 9 | uuGAuGuuuAccGAAGuGuTsT |
| 205-227 | UGGUGAGAUGCAGACCAUUUAAU | 11 | GuGAGAuGcAGAccAuuuATsT |
| 1176-1198 | ACUCUGAGUACAUUGGAAUAUGC | 13 | ucuGAGuAcAuuGGAAuAuTsT |
| 386-408 | CCGAAGUGUUGUUUGUCCAAUUC | 15 | GAAGuGuuGuuuGccAAuTsT |
| 416-438 | AGUUAUUAUGGGCUAUAAUUGCA | 17 | uuAuuAuGGGcuAuAAuuGTsT |
| 485-507 | GGAAGGUGAAAGGUCACCUAAUG | 19 | AAGGuGAAAGGucAccuAATsT |
| 476-498 | UUUUACAAUGGAAGGUGAAAGGU | 21 | uuAcAAuGGAAGGuGAAAGTsT |
| 486-508 | GAAGGUGAAAGGUCACCUAAUGA | 23 | AGGuGAAAGGucAccuAAuTsT |
| 487-509 | AAGGUGAAAGGUCACCUAAUGAA | 25 | GGuGAAAGGucAccuAAuGTsT |
| 1066-1088 | UUCCUUAUCGAGAAUCUAAACUA | 27 | ccuuAucGAGAAucuAAAcTsT |
| 1256-1278 | AGCUCUUAUUAAGGAGUAUACGG | 29 | cucuuAuuAAGGAGuAuAcTsT |
| 2329-2351 | CAGAGAGAUUCUGUGCUUUGGAG | 31 | GAGAGAuucuGuGcuuuGGTsT |
| 1077-1099 | GAAUCUAAACUAACUAGAAUCCU | 33 | AucuAAAcuAAcuAGAAucTsT |
| 1244-1266 | ACUCACCAAAAAAGCUCUUAUUA | 35 | ucAccAAAAAAGcucuuAuTsT |
| 637-659 | AAGAGCUUUUUGAUCUUCUUAAU | 37 | GAGcuuuuuGAucuucuuATsT |
| 1117-1139 | GGCGUACAAGAACAUCUAUAAUU | 39 | cGuAcAAGAAcAucuAuAATsT |
| 373-395 | AGAUUGAUGUUUACCGAAGUGUU | 41 | AuuGAuGuuuAccGAAGuGTsT |
| 1079-1101 | AUCUAAACUAACUAGAAUCCUCC | 43 | cuAAAcuAAcuAGAAuccuTsT |
| 383-405 | UUACCGAAGUGUUGUUUGUCCAA | 45 | AccGAAGuGuuGuuuGccTsT |
| 200-222 | GGUGGUGGUGAGAUGCAGACCAU | 47 | uGGuGGuGAGAuGcAGAccTsT |

| position in human access. # | SEQ I | antisense sequence (5'-3') | duplex name | single dose screen @ 25 nM [% residual mRNA] | SDs 2nd screen (among quadruplicates) |
|---|---|---|---|---|---|
| 385-407 | 2 | UUGGAcAAAcAAcACUUCGTsT | AL-DP-6226 | 23% | 3% |
| 347-369 | 4 | GuAGAUGCUCcAAAcACcATsT | AL-DP-6227 | 69% | 10% |
| 1078-1100 | 6 | GGAUUCuAGUuAGUUuAGATsT | AL-DP-6228 | 33% | 2% |
| 1067-1089 | 8 | AGUUuAGAUUCUCGAuAAGTsT | AL-DP-6229 | 2% | 2% |
| 374-396 | 10 | AcACUUCGGuAAAcAUcAATsT | AL-DP-6230 | 66% | 11% |
| 205-227 | 12 | uAAAUGGUCUGcAUCUcACTsT | AL-DP-6231 | 17% | 1% |
| 1176-1198 | 14 | AuAUUCcAAUGuACUcAGATsT | AL-DP-6232 | 9% | 3% |
| 386-408 | 16 | AUUGGAcAAAcAAcACUUCTsT | AL-DP-6233 | 24% | 6% |
| 416-438 | 18 | cAAUuAuAGCCcAuAAuAATsT | AL-DP-6234 | 91% | 2% |
| 485-507 | 20 | UuAGGUGACCUUUcACCUUTsT | AL-DP-6235 | 112% | 4% |
| 476-498 | 22 | CUUUcACCUUCcAUUGuAATsT | AL-DP-6236 | 69% | 4% |
| 486-508 | 24 | AUuAGGUGACCUUUcACCUTsT | AL-DP-6237 | 42% | 2% |
| 487-509 | 26 | cAUuAGGUGACCUUUcACCTsT | AL-DP-6238 | 45% | 2% |
| 1066-1088 | 28 | GUUuAGAUUCUCGAuAAGGTsT | AL-DP-6239 | 2% | 1% |
| 1256-1278 | 30 | GuAuACUCCUuAAuAAGAGTsT | AL-DP-6240 | 48% | 2% |
| 2329-2351 | 32 | CcAAAGcAcAGAAUCUCUCTsT | AL-DP-6241 | 41% | 2% |
| 1077-1099 | 34 | GAUUUuAGUuAGUUuAGAUTsT | AL-DP-6242 | 8% | 2% |
| 1244-1266 | 36 | AuAAGAGCUUUUUUGGUGATsT | AL-DP-6243 | 7% | 1% |
| 637-659 | 38 | uAAGAAGAUcAAAAAGCUCTsT | AL-DP-6244 | 6% | 2% |
| 1117-1139 | 40 | UuAuAGAUGUUCUUGuACGTsT | AL-DP-6245 | 12% | 2% |
| 373-395 | 42 | cACUUCGGuAAAcAUcAAUTsT | AL-DP-6246 | 28% | 3% |
| 1079-1101 | 44 | AGGAUUCuAGUuAGUUuAGTsT | AL-DP-6247 | 71% | 4% |
| 383-405 | 46 | GGAcAAAcAAcACUUCGGUTsT | AL-DP-6248 | 5% | 2% |
| 200-222 | 48 | GGUCUGcAYCUcACcACcATsT | AL-DP-6249 | 28% | 3% |

TABLE 2A

| position in human access. # | SEQ ID NO: | sequence of total 19mer target site | SEQ ID NO: | sense sequence (5'-3') | SEQ ID NO: | sense sequence (5'-3') | duplex name |
|---|---|---|---|---|---|---|---|
| 829-847 | 1268 | CAUACUCAUGUCGUUCCCA | 49 | cAuAcucuAGucGuucccATsT | 50 | UGGGAACGACuAGAGuAUGTsT | AD-12072 |
| 246-264 | 1269 | AGCGCCCAUUCAAUAGUA-G | 51 | AGcGcccAuucAAuAGuAGTsT | 52 | CuACuAUUGAAUGGGCGCUTsT | AD-12073 |
| 238-256 | 1270 | GGAAAGCUAGCGCCCAUUC | 53 | GGAAAGcuAGcGcccAuucTsT | 54 | GAAUGGGCGCuAGCUUUCCTsT | AD-12074 |
| 239-257 | 1271 | GAAAGCUAGCGCCCAUUCA | 55 | GAAAGcuAGcGcccAuucATsT | 56 | UGAAUGGGCGCuAGCUUUCTsT | AD-12075 |
| 878-896 | 1272 | AGAAACUACGAUUGAUGG-A | 57 | AGAAAcuAcGAuuGAuGGATsT | 58 | UCcAUcAAUCGuAGUUUCUTsT | AD-12076 |
| 1064-1082 | 1273 | UGUUCCUUAUCGAGAAUC-U | 59 | uGuuccuuAucGAGAAucuTsT | 60 | AGAUUCUCGAuAAGGAAcATsT | AD-12077 |
| 3278-3296 | 1274 | CAGAUUACCUCUGCGAGCC | 61 | cAGAuuAccucuGcGAGccTsT | 62 | GGCUCGcAGAGGuAAUCUGTsT | AD-12078 |
| 247-265 | 1275 | GCGCCCAUUCAAUAGUAG-A | 63 | GcGcccAuucAAuAGuAGATsT | 64 | UCuACuAUUGAAUGGGCGCTsT | AD-12079 |
| 434-452 | 1276 | UUGCACUAUCUUUGCGUA-U | 65 | uuGcAcuAucuuuGcGuAuTsT | 66 | AuACGcAAAGAuAGUGcAATsT | AD-12080 |
| 232-250 | 1277 | CAGAGCGGAAAGCUAGCG-C | 67 | cAGAGcGGAAAGcuAGcGcTsT | 68 | GCGCuAGCUUUCCGCUCUGTsT | AD-12081 |
| 1831-1849 | 1278 | AGACCUUAUUUGGUAAUC-U | 69 | AGAccuuAuuuGGuAAucuTsT | 70 | AGAUuAccAAAuAAGGUCUTsT | AD-12082 |
| 1105-1123 | 1279 | AUUCUCUUGGAGGGCGUA-C | 71 | AuucucuuGGAGGGcGuAcTsT | 72 | GuACGCCCUCcAAGAGAAUTsT | AD-12083 |
| 536-554 | 1280 | GGCUGGUAUAAUUCCACG-U | 73 | GGcuGGuAuAAuuccAcGuTsT | 74 | ACGUGGAAUuAuACcAGCCTsT | AD-12084 |
| 236-254 | 1281 | GCGGAAAGCUAGCGCCCAU | 75 | GcGGAAAGcuAGcGcccAuTsT | 76 | AUGGGCGCuAGCUUUCCGCTsT | AD-12085 |
| 435-453 | 1282 | UGCACUAUCUUUGCGUAU-G | 77 | uGcAcuAucuuuGcGuAuGTsT | 78 | cAuACGcAAAGAuAGUGcATsT | AD-12086 |
| 541-559 | 1283 | GUAUAAUUCCACGUACCCU | 79 | GuAuAAuuccAcGuAcccuTsT | 80 | AGGGuACGUGGAAUuAuACTsT | AD-12087 |
| 1076-1094 | 1284 | AGAAUCUAAACUAACUAG-A | 81 | AGAAucuAAAcuAAcuAGATsT | 82 | UCuAGUuAGUUuAGAUUCUTsT | AD-12088 |
| 1432-1450 | 1285 | AGGAGCUGAAUAGGGUUA-C | 83 | AGGAGcuGAAuAGGGuuAcTsT | 84 | GuAACCCuAUUcAGCUCCUTsT | AD-12089 |
| 1821-1839 | 1286 | GAAGUACAUAAGACCUUA-U | 85 | GAAGuAcAuAAGAccuuAuTsT | 86 | AuAAGGUCUuAUGuACUUCTsT | AD-12090 |
| 2126-2144 | 1287 | GACAGUGGCCGAUAAGAU-A | 87 | GAcAGuGGccGAuAAGAuATsT | 88 | uAUCUuAUCGGccACUGUCTsT | AD-12091 |
| 2373-2391 | 1288 | AAACCACUUAGUAGUGUC-C | 89 | AAAccAcuuAGuAGuGuccTsT | 90 | GGAcACuACuAAGUGGUUUTsT | AD-12092 |
| 4026-4044 | 1289 | UCCCUAGACUUCCCUAUUU | 91 | ucccuAGAcuucccuAuuuTsT | 92 | AAAuAGGGAAGUCuAGGGATsT | AD-12093 |

TABLE 2A-continued

| position in human access. # | SEQ ID NO: | sequence of total 19mer target site | SEQ ID NO: | sense sequence (5'-3') | SEQ ID NO: | sense sequence (5'-3') | duplex name |
|---|---|---|---|---|---|---|---|
| 4030-4048 | 1290 | UAGACUUCCCUAUUUCGCU | 93 | uAGAcuucccuAuuucGcuTsT | 94 | AGCGAAAuAGGGAAGUCuATsT | AD-12094 |
| 144-162 | 1291 | GCGUCGCAGCCAAAUUCGU | 95 | GcGucGcAGccAAAuucGuTsT | 96 | ACGAAUUUGGCUGCGACGCTsT | AD-12095 |
| 242-260 | 1292 | AGCUAGCGCCCAUUCAAUA | 97 | AGcuAGcGcccAuucAAuATsT | 98 | uAUUGAAuGGGCGCuAGCUTsT | AD-12096 |
| 879-897 | 1293 | GAAACUACGAUUGAUGGA-G | 99 | GAAAcuAcGAuuGAuGGAGTsT | 100 | CUCcAUcAAUCGuAGUUUCTsT | AD-12097 |
| 2134-2152 | 1294 | CCGAUAAGAUAGAAGAUC-A | 101 | ccGAuAAGAuAGAAGAucATsT | 102 | UGAUCUUCuAUCUuAUCGGTsT | AD-12098 |
| 245-263 | 1295 | UAGCGCCCAUUCAAUAGU-A | 103 | uAGcGcccAuucAAuAGuATsT | 104 | uACuAUUGAAuGGGCGCuATsT | AD-12099 |
| 444-462 | 1296 | UUUGCGUAUGGCCAAACU-G | 195 | uuuGcGuAuGGccAAAcuGTsT | 106 | cAGUUUGGCcAuACGcAAATsT | AD-12100 |
| 550-568 | 1297 | CACGUACCCUUCAUCAAAU | 107 | cAcGuAcccuucAucAAAuTsT | 108 | AUUUGAuGAAGGGuACGUGTsT | AD-12101 |
| 442-460 | 1298 | UCUUUGCGUAUGGCCAAA-C | 109 | ucuuuGcGuAuGGccAAAcTsT | 110 | GUUUGGCcAuACGcAAAGATsT | AD-12102 |
| 386-440 | 1299 | CCGAAGUGUUGUUUGUCC-A | 111 | ccGAAGuGuuGuuuGuccATsT | 112 | UGGAcAAAcAAcACUUCGGTsT | AD-12103 |
| 233-251 | 1300 | AGAGCGGAAAGCUAGCGC-C | 113 | AGAGcGGAAAGcuAGcGccTsT | 114 | GGCGCuAGCUUUCCGCUCUTsT | AD-12104 |
| 243-261 | 1301 | GCUAGCGCCCAUUCAAUAG | 115 | GcuAGcGcccAuucAAuAGTsT | 116 | CuAUUGAAuGGGCGCuAGCTsT | AD-12105 |
| 286-304 | 1302 | AAGUUAGUGUACGAACUG-G | 117 | AAGuuAGuGuAcGAAcuGGTsT | 118 | CcAGUUCGuAcACuAACUUTsT | AD-12106 |
| 294-312 | 1303 | GUACGAACUGGAGGAUUG | 119 | GuAcGAAcuGGAGGAuuGGTsT | 120 | CcAAUCCUCcAGUUCGuACTsT | AD-12107 |
| 296-314 | 1304 | ACGAACUGGAGGAUUGGC-U | 121 | AcGAAcuGGAGGAuuGGcuTsT | 122 | AGCcAAUCCUCcAGUUCGUTsT | AD-12108 |
| 373-391 | 1305 | AGAUUGAUGUUUACCGAA-G | 123 | AGAuuGAuGuuuAccGAAGTsT | 124 | CUUCGGuAAAcAUcAAUCUTsT | AD-12109 |
| 422-440 | 1306 | UAUGGGCUAUAAUUGCAC-U | 125 | uAuGGGcuAuAAuuGcAcuTsT | 126 | AGUGcAAUuAuAGCCCAuATsT | AD-12110 |
| 441-459 | 1307 | AUCUUUGCGUAUGGCCAA-A | 127 | AucuuuGcGuAuGGccAAATsT | 128 | UUUGGCcAuACGcAAAGAUTsT | AD-12111 |
| 832-850 | 1308 | ACUCUAGUCGUUCCCACUC | 129 | AcucuAGucGuucccAcucTsT | 130 | GAGUGGGAACGACuAGAGUTsT | AD-12112 |
| 881-899 | 1309 | AACUACGAUUGAUGGAGA-A | 131 | AAcuAcGAuuGAuGGAGAATsT | 132 | UUCUCcAUcAAUCGuAGUUTsT | AD-12113 |
| 975-993 | 1310 | GAUAAGAGAGCUCGGGAA-G | 133 | GAuAAGAGAGcucGGGAAGTsT | 134 | CUUCCCGAGCUCUCUuAUCTsT | AD-12114 |
| 1073-1091 | 1311 | UCGAGAAUCUAAACUAAC-U | 135 | ucGAGAAucuAAAcuAAcuTsT | 136 | AGUuAGUUuAGAUUCUCGATsT | AD-12115 |
| 1084-1102 | 1312 | AACUAACUAGAAUCCUCCA | 137 | AAcuAAcuAGAAuccuccATsT | 138 | UGGAGGAUUCuAGUuAGUUTsT | AD-12116 |

TABLE 2A-continued

| position in human access. # | SEQ ID NO: | sequence of total 19mer target site | SEQ ID NO: | sense sequence (5'-3') | SEQ ID NO: | sense sequence (5'-3') | duplex name |
|---|---|---|---|---|---|---|---|
| 1691-1709 | 1313 | GGAUCGUAAGAAGGCAGU-U | 139 | GGAucGuAAGAAGGcAGuuTsT | 140 | AACUGCCUUCUuACGAUCCTsT | AD-12117 |
| 1693-1711 | 1314 | AUCGUAAGAAGGCAGUUG-A | 141 | AucGuAAGAAGGcAGuuGATsT | 142 | UcAACUGCCUUCUuACGAUTsT | AD-12118 |
| 1702-1720 | 1315 | AGGCAGUUGACCAACACA-A | 143 | AGGcAGuuGAccAAcAcAATsT | 144 | UUGUGUUGGUcAACUGCCUTsT | AD-12119 |
| 2131-2149 | 1316 | UGGCCGAUAAGAUAGAAG-A | 145 | uGGccGAuAAGAuAGAAGATsT | 146 | UCUUCuAUCUuAUCGGCcATsT | AD-12120 |
| 2412-2430 | 1317 | UCUAAGGAUAUAGUCAAC-A | 147 | ucuAAGGAuAuAGucAAcATsT | 148 | UGUUGACuAuAUCCUuAGATsT | AD-12121 |
| 2859-2877 | 1318 | ACUAAGCUUAAUUGCUUU-C | 149 | AcuAAGcuuAAuuGcuuucTsT | 150 | GAAAGcAAUuAAGCUuAGUTsT | AD-12122 |
| 3294-3312 | 1319 | GCCCAGAUCAACCUUUAAU | 151 | GcccAGAucAAccuuuAAuTsT | 153 | AUuAAAGGUUGAUCUGGGCTsT | AD-12123 |
| 223-241 | 1320 | UUAAUUGGGCAGAGCGGA-A | 153 | uuAAuuuGGcAGAGcGGAATsT | 154 | UUCCGCUCUGCcAAAUuAATsT | AD-12124 |
| 1070-1088 | 1321 | UUAUCGAGAAUCUAAACU-A | 155 | uuAucGAGAAucuAAAcuATsT | 156 | uAGUUuAGAUUCUCGAuAATsT | AD-12125 |
| 244-262 | 1322 | CUAGCGCCCAUUCAAUAGU | 157 | cuAGcGcccAuucAAuAGuTsT | 158 | ACuAUUGAAUGGGCGCuAGTsT | AD-12126 |
| 257-275 | 1323 | AAUAGUAGAAUGUGAUCC-U | 159 | AAuAGuAGAAuGuGAuccuTsT | 160 | AGGAUcAcAUUCuACuAUUTsT | AD-12127 |
| 277-295 | 1324 | UACGAAAAGAAGUUAGUG-U | 161 | uAcGAAAAGAAGuuAGuGuTsT | 162 | AcACuAACUUCUUUUCGuATsT | AD-12128 |
| 284-302 | 1325 | AGAAGUUAGUGUACGAAC-U | 163 | AGAAGuuAGuGuAcGAAcuTsT | 164 | AGUUCGuAcACuAACUUCUTsT | AD-12129 |
| 366-384 | 1326 | ACUAAACAGAUUGAUGUU-U | 165 | AcuAAAcAGAuuGAuGuuuTsT | 166 | AAAcAUcAAUCUGUUuAGUTsT | AD-12130 |
| 443-461 | 1327 | CUUUGCGUAUGGCCAAAC-U | 167 | cuuuGcGuAuGGccAAAcuTsT | 168 | AGUUUGGCcAuACGcAAAGTsT | AD-12131 |
| 504-522 | 1328 | AAUGAAGAGUAUACCUGG-G | 169 | AAuGAAGAGuAuAccuGGGTsT | 170 | CCcAGGuAuACUCUUcAUUTsT | AD-12132 |
| 543-561 | 1329 | AUAAUUCCACGUACCCUUC | 171 | AuAAuuccAcGuAcccuucTsT | 172 | GAAGGGuACGUGGAAUuAUTsT | AD-12133 |
| 551-569 | 1330 | ACGUACCCUUCAUCAAAUU | 173 | AcGuAcccuucAucAAAuuTsT | 174 | AAUUUGAuGAAGGGuACGUTsT | AD-12134 |
| 552-570 | 1331 | CGUACCCUUCAUCAAAUUU | 175 | cGuAcccuucAucAAAuuuTsT | 176 | AAAUUUGAuGAAGGGuACGTsT | AD-12135 |
| 553-571 | 1332 | GUACCCUUCAUCAAAUUU-U | 177 | GuAcccuuucAucAAAuuuuTsT | 178 | AAAAUUUGAuGAAGGGuACTsT | AD-12136 |
| 577-595 | 1333 | AACUUACUGAUAAUGGUA-C | 179 | AAcuuAcuGAuAAuGGuAcTsT | 180 | GuAccAUuAUcAGuAAGUUTsT | AD-12137 |
| 602-620 | 1334 | UUCAGUCAAAGUGUCUCU-G | 181 | uucAGucAAAGuGucucuGTsT | 182 | cAGAGAcACUUUGACUGAATsT | AD-12138 |

TABLE 2A-continued

| position in human access. # | SEQ ID NO: | sequence of total 19mer target site | SEQ ID NO: | sense sequence (5'-3') | SEQ ID NO: | sense sequence (5'-3') | duplex name |
|---|---|---|---|---|---|---|---|
| 652-670 | 1335 | UUCUUAAUCCAUCAUCUGA | 183 | uucuuAAuccAucAucuGATsT | 184 | UcAGAUGAUGGAUuAAGAATsT | AD-12139 |
| 747-765 | 1336 | ACAGUACACAACAAGGAUG | 185 | AcAGuAcAcAAcAAGGAuGTsT | 186 | cAUCCUUGUUGUGuACUGUTsT | AD-12140 |
| 877-895 | 1337 | AAGAAACUACGAUUGAUGG | 187 | AAGAAAcuAcGAuuGAuGGTsT | 188 | CcAUcAAUCGuAGUUUCUUTsT | AD-12141 |
| 880-898 | 1338 | AAACUACGAUUGAUGGAGA | 189 | AAAcuAcGAuuGAuGGAGATsT | 190 | UCUCcAUcAAUCGuAGUUUTsT | AD-12142 |
| 965-983 | 1339 | UGGAGCUGUUGAUAAGAGA | 191 | uGGAGcuGuuGAuAAGAGATsT | 192 | UCUCUuAUcAAcAGCUCcATsT | AD-12143 |
| 1086-1104 | 1340 | CUAACUAGAAUCCUCCAGG | 193 | cuAAcuAGAAuccuccAGGTsT | 194 | CCUGGAGGAUUCuAGUuAGTsT | AD-12144 |
| 1191-1209 | 1341 | GAAUAUGCUCAUAGAGCAA | 195 | GAAuAuGcucAuAGAGcAATsT | 196 | UUGCUCuAUGAGcAuAUUCTsT | AD-12145 |
| 1195-1213 | 1342 | AUGCUCAUAGAGCAAAGAA | 197 | AuGcucAuAGAGcAAAGAATsT | 198 | UUCUUUGCUCuAUGAGcAUTsT | AD-12146 |
| 1412-1430 | 1343 | AAAAAUUGGUGCUGUUGAG | 199 | AAAAAuuGGuGcuGuuGAGTsT | 200 | CUcAAcAGcACcAAUUUUUTsT | AD-12147 |
| 1431-1449 | 1344 | GAGGAGCUGAAUAGGGUUA | 201 | GAGGAGcuGAAuAGGGuuATsT | 202 | uAACCCuAUUcAGCUCCUCTsT | AD-12148 |
| 1433-1451 | 1345 | GGAGCUGAAUAGGGUUACA | 203 | GGAGcuGAAuAGGGuuAcATsT | 204 | UGuAACCCuAUUcAGCUCCTsT | AD-12149 |
| 1434-1452 | 1346 | GAGCUGAAUAGGGUUACAG | 205 | GAGcuGAAuAGGGuuAcAGTsT | 206 | CUGuAACCCuAUUcAGCUCTsT | AD-12150 |
| 1435-1453 | 1347 | AGCUGAAUAGGGUUACAGA | 207 | AGcuGAAuAGGGuuAcAGATsT | 208 | UCUGuAACCCuAUUcAGCUTsT | AD-12151 |
| 1436-1454 | 1348 | GCUGAAUAGGGUUACAGAG | 209 | GcuGAAuAGGGuuAcAGAGTsT | 210 | CUCUGuAACCCuAUUcAGCTsT | AD-12152 |
| 1684-1702 | 1349 | CCAAACUGGAUCGUAAGAA | 211 | ccAAAcuGGAucGuAAGAATsT | 212 | UUCUuACGAUCcAGUUUGGTsT | AD-12153 |
| 1692-1710 | 1350 | GAUCGUAAGAAGGCAGUUG | 213 | GAucGuAAGAAGGcAGuuGTsT | 214 | cAACUGCCUUCUuACGAUCTsT | AD-12154 |
| 1833-1851 | 1351 | ACCUUAUUUGGUAAUCUGC | 215 | AccuuAuuuGGuAAucuGcTsT | 216 | GcAGAUuAccAAAuAAGGUTsT | AD-12155 |
| 1872-1890 | 1352 | UUAGAUACCAUUACUACAG | 217 | uuAGAuAccAuuAcuAcAGTsT | 218 | CUGuAGuAAUGGuAUCuAATsT | AD-12156 |
| 1876-1894 | 1353 | AUACCAUUACUACAGUAGC | 219 | AuAccAuuAcuAcAGuAGcTsT | 220 | GCuACUGuAGuAAUGGuAUTsT | AD-12157 |
| 1883-1901 | 1354 | UACUACAGUAGCACUUGGA | 221 | uAcuAcAGuAGcAcuuGGATsT | 222 | UCcAAGUGCuACUGuAGuATsT | AD-12158 |

TABLE 2A-continued

| position in human access. # | SEQ ID NO: | sequence of total 19mer target site | SEQ ID NO: | sense sequence (5'-3') | SEQ ID NO: | sense sequence (5'-3') | duplex name |
|---|---|---|---|---|---|---|---|
| 1987-2005 | 1355 | AAAGUAAAACUGUACUACA | 223 | AAAGuAAAAcuGuAcuAcATsT | 224 | UGuAGuAcAGUUUuACUUUTsT | AD-12159 |
| 2022-2040 | 1356 | CUCAAGACUGAUCUUCUAA | 225 | cucAAGAcuGAucuucuAATsT | 226 | UuAGAAGAUcAGUCUUGAGTsT | AD-12160 |
| 2124-2142 | 1357 | UUGACAGUGGCCGAUAAGA | 227 | uuGAcAGuGGccGAuAAGATsT | 228 | UCUuAUCGGCcACUGUcAATsT | AD-12161 |
| 2125-2143 | 1358 | UGACAGUGGCCGAUAAGAU | 229 | uGAcAGuGGccGAuAAGAUsT | 230 | AUCUuAUCGGCcACUGUcATsT | AD-12162 |
| 2246-2264 | 1359 | GCAAUGGGAAACCUAACU | 231 | GcAAuGuGGAAAccuAAcuTsT | 232 | AGUuAGGUUUCcAcAUUGCTsT | AD-12163 |
| 2376-2394 | 1360 | CCACUUAGUAGUGGCCAGG | 233 | ccAcuuAGuAGuGuccAGGTsT | 234 | CCUGGAcACuACuAAGUGGTsT | AD-12164 |
| 2504-2522 | 1361 | AGAAGGUACAAAAUUGGUG | 235 | AGAAGGuAcAAAAuuGGuuTsT | 236 | AACcAAUUUUGuACCUUCUTsT | AD-12165 |
| 2852-2870 | 1362 | UGGUUUGACUAAGCUUAAG | 237 | uGGuuuGAcuAAGcuuAAuTsT | 238 | AUuAAGCUuAGUCAAACcATsT | AD-12166 |
| 2853-2871 | 1363 | GGUUUGACUAAGCUUAAUG | 239 | GGuuuGAcuAAGcuuAAuuTsT | 240 | AAUuAAGCUuAGUcAAACCTsT | AD-12167 |
| 3110-3128 | 1364 | UCUAAGUCAAGAGCCAUCU | 241 | ucuAAGucAAGAGccAucuTsT | 242 | AGAUGGCUCUUGACUuAGATsT | AD-12168 |
| 3764-3782 | 1365 | UCAUCCCUAUAGUUCACUU | 243 | ucAucccuAuAGuucAcuuTsT | 244 | AAGUGAACuAuAGGGAUGATsT | AD-12169 |
| 3765-3783 | 1366 | CAUCCCUAUAGUUCACUUU | 245 | cAucccuAuAGuucAcuuuTsT | 246 | AAAGUGAACuAuAGGGAUGTsT | AD-12170 |
| 4027-4045 | 1367 | CCCUAGACUUCCCUAUUUC | 247 | cccuAGAcuucccuAuuucTsT | 248 | GAAAuAGGGAAGUCuAGGGTsT | AD-12171 |
| 4031-4049 | 1368 | AGACUUCCCUAUUUCGCUU | 249 | AGAcuucccuAuuucGcuuTsT | 250 | AAGCGAAAuAGGGAAGUCUTsT | AD-12172 |
| 4082-4100 | 1369 | UCACCAAACCAUUUGUAGA | 251 | ucAccAAAccAuuuGuAGATsT | 252 | UCuAcAAAUGGUUUGGUGATsT | AD-12173 |
| 4272-4290 | 1370 | UCCUUUAAGAGGCCUAACU | 253 | uccuuuAAGAGGccuAAcuTsT | 254 | AGUuAGGCCUCUuAAAGGATsT | AD-12174 |
| 4275-4293 | 1371 | UUUAAGAGGCCUAACUCAU | 255 | uuuAAGAGGccuAAcucAuTsT | 256 | AUGAGUuAGGCCUCUuAAATsT | AD-12175 |
| 4276-4294 | 1372 | UUAAGAGGCCUAACUCAUU | 257 | uuAAGAGGccuAAcucAuuTsT | 258 | AAUGAGUuAGGCCUCUuAATsT | AD-12176 |
| 4282-4300 | 1373 | GGCCUAACUCAUUCACCCU | 259 | GGccuAAcucAuucAcccuTsT | 260 | AGGGUGAAUGAGUuAGGCCTsT | AD-12177 |

TABLE 2A-continued

| position in human access. # | SEQ ID NO: | sequence of total 19mer target site | SEQ ID NO: | sense sequence (5'-3') | SEQ ID NO: | sense sequence (5'-3') | duplex name |
|---|---|---|---|---|---|---|---|
| 4571-4589 | 1374 | UGGUAUUUUUGAUCUGGC-A | 261 | uGGuAuuuuuGAucuGGcATsT | 262 | UGCcAGAUcAAAAAuACcATsT | AD-12178 |
| 4677-4695 | 1375 | AGUUUAGUGUGUAAAGUU-U | 263 | AGuuuAGuGuGuAAAGuuuTsT | 264 | AAACUUuAcAcACuAAACUTsT | AD-12179 |
| 152-170 | 1376 | GCCAAAUUCGUCUGCGAA-G | 265 | GccAAAuucGucuGcGAAGTsT | 266 | CUUCGcAGACGAAUUUGGCTsT | AD-12180 |
| 156-174 | 1377 | AAUUCGUCUGCGAAGAAG-A | 267 | AAuucGucuGcGAAGAAGATsT | 268 | UCUUCUUCGcAGACGAAUUTsT | AD-12181 |
| 491-509 | 1378 | UGAAAGGUCACCUAAUGA-A | 269 | uGAAAGGucAccuAAuGAATsT | 270 | UUcAUuAGGUGACCUUUcATsT | AD-12182 |
| 215-233 | 1379 | CAGACCAUUUAAUUGGC-A | 271 | cAGAccAuuuAAuuGGcATsT | 272 | UGCcAAAUuAAAUGGUCUGTsT | AD-12183 |
| 216-234 | 1380 | AGACCAUUUAAUUGGCA-G | 273 | AGAccAuuuAAuuGGcAGTsT | 274 | CUGCcAAAUuAAAUGGUCUTsT | AD-12184 |
| 416-434 | 1381 | AGUUAUUAUGGGCUAUAA-U | 275 | AGuuAuuAuGGGcuAuAATsT | 276 | AUuAuAGCCcAuAAuAACUTsT | AD-12185 |
| 537-555 | 1382 | GCUGGUAUAAUUCCACGU-A | 277 | GcuGGuAuAAuuccAcGuATsT | 278 | uACGUGGAAUuAuACcAGCTsT | AD-12186 |
| 221-239 | 1383 | AUUUAAUUGGCAGAGCG-G | 279 | AuuuAAuuGGcAGAGcGGTsT | 280 | CCGCUCUGCcAAAuUAAAUTsT | AD-12187 |
| 222-240 | 1384 | UUUAAUUGGCAGAGCGG-A | 281 | uuuAAuuGGcAGAGcGGATsT | 282 | UCCGCUCUGCcAAAuUAAATsT | AD-12188 |
| 227-245 | 1385 | UUUGGCAGAGCGGAAAGC-U | 283 | uuuGGcAGAGcGGAAAGcuTsT | 284 | AGCUUUCCGCUCUGCcAAATsT | AD-12189 |
| 476-494 | 1386 | UUUUACAAGGGAAGGUGA-A | 285 | uuuuAcAAGGGAAGGuGAATsT | 286 | UUcACCUUCcAUUGuAAAATsT | AD-12190 |
| 482-500 | 1387 | AAUGGAAGGUGAAAGGUC-A | 287 | AAuGGAAGGuGAAAGGucATsT | 288 | UGACCUUUcACCUUCcAUUTsT | AD-12191 |
| 208-226 | 1388 | UGAGAUGCAGACCAUUUA-A | 289 | uGAGAuGcAGAccAuuuAATsT | 290 | UuAAAUGGUCUGcAUCUcATsT | AD-12192 |
| 147-165 | 1389 | UCGCAGCCAAAUUCGUCUG | 291 | ucGcAGccAAAuucGucuGTsT | 292 | cAGACGAAUUUGGCUGCGATsT | AD-12193 |
| 426-444 | 1390 | GGCUAUAAUUGCACUAUC-U | 293 | GGcuAuAAuuGcAcuAucuTsT | 294 | AGAuAGUGcAAUuAuAGCCTsT | AD-12194 |
| 2123-2141 | 1391 | AUUGACAGUGGCCGAUAA-G | 295 | AuuGAcAGuGGccGAuAAGTsT | 296 | CUuAUCGGCcACUGUcAAUTsT | AD-12195 |
| 4029-4047 | 1392 | CUAGACUUCCCUAUUUCGC | 297 | cuAGAcuucccuAuuucGcTsT | 298 | GCGAAAuAGGGAAGUCuAGTsT | AD-12196 |
| 438-456 | 1393 | ACUAUCUUUGCGUAUGGC-C | 299 | AcuAucuuuGcGuAuGGccTsT | 300 | GGCcAuACGcAAAGAuAGUTsT | AD-12197 |
| 830-848 | 1394 | AUACUCUAGUCGUUCCCAC | 301 | AuAcucuAGucGuucccAcTsT | 302 | GUGGGAACGACuAGAGuAUTsT | AD-12198 |
| 876-894 | 1395 | AAAGAAACUACGAUUGAU-G | 303 | AAAGAAAcuAcGAuuGAuGTsT | 304 | cAUcAAUCGuAGUUUCUUUTsT | AD-12199 |
| 115-133 | 1396 | GCCUUGAUUUUUGGCGG-G | 305 | GccuuGAuuuuuGGcGGGTsT | 306 | CCCGCcAAAAAAUcAAGGCTsT | AD-12200 |

TABLE 2A-continued

| position in human access. # | SEQ ID NO: | sequence of total 19mer target site | SEQ ID NO: | sense sequence (5'-3') | SEQ ID NO: | sense sequence (5'-3') | duplex name |
|---|---|---|---|---|---|---|---|
| 248-266 | 1397 | CGCCCAUUCAAUAGUAGA-A | 307 | cGcccAuucAAuAGuAGAATsT | 308 | UUCuACuAUUGAAUGGGCGTsT | AD-12201 |
| 1834-1852 | 1398 | CCUUAUUUGGUAAUCUGC-U | 309 | ccuuAuuuGGuAAucuGcuTsT | 310 | AGcAGAUuACcAAAuAAGGTsT | AD-12202 |
| 3050-3068 | 1399 | AGAGACAAUUCCGGAUGU-G | 311 | AGAGAcAAuuccGGAuGuGTsT | 312 | cAcAUCCGGAAUUGUCUCUTsT | AD-12203 |
| 4705-4723 | 1400 | UGACUUUGAUAGCUAAAU-U | 313 | uGAcuuuGAuAGcuAAAuuTsT | 314 | AAUUuAGCuAUcAAAGUcATsT | AD-12204 |
| 229-247 | 1401 | UGGCAGAGCGGAAAGCUA-G | 315 | uGGcAGAGcGGAAAGcuAGTsT | 316 | CuAGCUUUCCGCUCUGCcATsT | AD-12205 |
| 234-252 | 1402 | GAGCGGAAAGCUAGCGCCC | 317 | GAGcGGAAAGcuAGcGcccTsT | 318 | GGGCGCuAGCUUUCCGCUCTsT | AD-12206 |
| 282-300 | 1403 | AAAGAAGUUAGUGUACGA-A | 319 | AAAGAAGuuAGuGuAcGAATsT | 320 | UUCGuAcACuAACUUCUUUTsT | AD-12207 |
| 433-451 | 1404 | AUUGCACUAUCUUUGCGU-A | 321 | AuuGcAcuAucuuuGcGuATsT | 322 | uACGcAAAGAuAGUGcAAUTsT | AD-12208 |
| 540-558 | 1405 | GGUAUAAUUCCACGUACCC | 323 | GGuAuAAuuccAcGuAcccTsT | 324 | GGGuACGUGGAAUuAuACCTsT | AD-12209 |
| 831-849 | 1406 | UACUCUAGUCGUUCCCACU | 325 | uAcucuAGucGuucccAcuTsT | 326 | AGUGGGAACGACuAGAGuATsT | AD-12210 |
| 872-890 | 1407 | UAUGAAAGAAACUACGAU-U | 327 | uAuGAAAGAAAcuAcGAuuTsT | 328 | AAUCGuAGUUUCUUUcAuATsT | AD-12211 |
| 1815-1833 | 1408 | AUGCUAGAAGUACAUAAG-A | 329 | AuGcuAGAAGuAcAuAAGATsT | 330 | UCUuAUGuACUUCuAGcAUTsT | AD-12212 |
| 1822-1840 | 1409 | AAGUACAUAAGACCUUAU-U | 331 | AAGuAcAuAAGAccuuAuuTsT | 332 | AAuAAGGUCUuAUGuACUUTsT | AD-12213 |
| 3002-3020 | 1410 | ACAGCCUGAGCUGUUAAU-G | 333 | AcAGccuGAGcuGuuAAuGTsT | 334 | cAUuAAcAGCUcAGGCUGUTsT | AD-12214 |
| 3045-3063 | 1411 | AAAGAAGAGACAAUUCCG-G | 335 | AAAGAAGAGAcAAuuccGGTsT | 336 | CCGGAAUUGUCUCUUCUUUTsT | AD-12215 |
| 3224-3242 | 1412 | CACACUGGAGAGGUCUAA-A | 337 | cAcAcuGGAGAGGucuAAATsT | 338 | UUuAGACCUCUCcAGUGUGTsT | AD-12216 |
| 3226-3244 | 1413 | CACUGGAGAGGUCUAAAG-U | 339 | cAcuGGAGAGGucuAAAGuTsT | 340 | ACUuAGACCUCUCcAGUGTsT | AD-12217 |
| 3227-3245 | 1414 | ACUGGAGAGGUCUAAAGU-G | 341 | AcuGGAGAGGucuAAAGuGTsT | 342 | cACUuAGACCUCUCcAGUTsT | AD-12218 |
| 145-163 | 1415 | CGUCGCAGCCAAAUUCGUC | 343 | cGucGcAGccAAAuucGucTsT | 344 | GACGAAUUUGGCUGCGACGTsT | AD-12219 |
| 1700-1718 | 1416 | GAAGGCAGUUGACCAACA-C | 345 | GAAGGcAGuuGAccAAcAcTsT | 346 | GUGUUGGUcAACUGCCUUCTsT | AD-12220 |
| 4291-4309 | 1417 | CAUUCACCCUGACAGAGUU | 347 | cAuucAcccuGAcAGAGuuTsT | 348 | AACUCUGUcAGGGUGAAUGTsT | AD-12221 |

TABLE 2A-continued

| position in human access. # | SEQ ID NO: | sequence of total 19mer target site | SEQ ID NO: | sense sequence (5'-3') | SEQ ID NO: | sense sequence (5'-3') | duplex name |
|---|---|---|---|---|---|---|---|
| 4278-4296 | 1418 | AAGAGGCCUAACUCAUUCA | 349 | AAGAGGccuAAcucAuucATsT | 350 | UGAAUGAGUuAGGCCUCUUTsT | AD-12222 |
| 3051-3069 | 1419 | GAGACAAUUCCGGAUGUGG | 351 | GAGAcAAuuccGGAuGuGGTsT | 352 | CcAcAUCCGGAAUUGUCUCTsT | AD-12223 |
| 3058-3076 | 1420 | UUCCGGAUGUGGAUGUAGA | 353 | uuccGGAuGuGGAuGuAGATsT | 354 | UCuAcAUCcAcAUCCGGAATsT | AD-12224 |
| 241-259 | 1421 | AAGCUAGCGCCCAUUCAAU | 355 | AAGcuAGcGcccAuucAAuTsT | 356 | AUUGAAuGGGCGCuAGCUUTsT | AD-12225 |
| 285-303 | 1422 | GAAGUUAGUGUACGAACUG | 357 | GAAGuuAGuGuAcGAAcuGTsT | 358 | cAGUUCGuAcACuAACUUCTsT | AD-12226 |
| 542-560 | 1423 | UAUAAUUCCACGUACCUU | 359 | uAuAAuuccAcGuAccuuTsT | 360 | AAGGGuACGUGGAAUuAuATsT | AD-12227 |
| 2127-2145 | 1424 | ACAGUGGCCGAUAAGAUAG | 361 | AcAGuGGccGAuAAGAuAGTsT | 362 | CuAUCUuAUCGGCcACUGUTsT | AD-12228 |
| 3760-3778 | 1425 | UCUGUCAUCCCUAUAGUUC | 363 | ucuGucAuccccuAuAGuucTsT | 364 | GAAcuAuAGGGAuGAcAGATsT | AD-12229 |
| 3993-4011 | 1426 | UUCUUGCUAUGACUUGUGU | 365 | uucuuGcuAuGAcuuGuGuTsT | 366 | AcAcAAGUcAuAGcAAGAATsT | AD-12230 |
| 1696-1714 | 1427 | GUAAGAAGGCAGUUGACCA | 367 | GuAAGAAGGcAGuuGAccATsT | 368 | UGGUcAACUGCCUUCUuACTsT | AD-12231 |
| 2122-2140 | 1428 | CAUUGACAGUGGCCGAUAA | 369 | cAuuGAcAGuGGccGAuAATsT | 370 | UuAUCGGCcACUGUcAAUGTsT | AD-12232 |
| 2371-2389 | 1429 | AGAAACCACUUAGUAGUGU | 371 | AGAAAccAcuuAGuAGuGuTsT | 372 | AcACuACuAAGUGGUUUCUTsT | AD-12233 |
| 3143-3161 | 1430 | GGAUUGUUCAUCAAUUGGC | 373 | GGAuuGuucAucAAuuGGcTsT | 374 | GCcAAUUGAUGAAcAAUCCTsT | AD-12234 |
| 4277-4295 | 1431 | UAAGAGGCCUAACUCAUUC | 375 | uAAGAGGccuAAcucAuucTsT | 376 | GAAUGAGUuAGGCCUCUuATsT | AD-12235 |
| 287-305 | 1432 | AGUUAGUGUACGAACUGGA | 377 | AGuuAGuGuAcGAAcuGGATsT | 378 | UCcAGUUCGuAcACuAACUTsT | AD-12236 |
| 1823-1841 | 1433 | AGUACAUAAGACCUUAUUU | 379 | AGuAcAuAAGAccuuAuuuTsT | 380 | AAAuAAGGUCUuAUGuACUTsT | AD-12237 |
| 3379-3397 | 1434 | UGAGCCUUGUGUAUAGAUU | 381 | uGAGccuuGuGuAuAGAuuTsT | 382 | AAUCuAuAcAcAAGGCUcATsT | AD-12238 |
| 4273-4291 | 1435 | CCUUUAAGAGGCCUAACUC | 383 | ccuuuAAGAGGccuAAcucTsT | 384 | GAGUuAGGCCUCUuAAAGGTsT | AD-12239 |
| 2375-2393 | 1436 | ACCACUUAGUAGUGUCCAG | 385 | AccAcuuAGuAGuGuccAGTsT | 386 | CUGGAcACuACuAAGUGGUTsT | AD-12240 |
| 4439-4457 | 1437 | GAAACUUCCAAUUAUGUCU | 387 | GAAAcuuccAAuuAuGucuTsT | 388 | AGAcAuAAUUGGAAGUUUCTsT | AD-12241 |

TABLE 2A-continued

| position in human access. # | SEQ ID NO: | sequence of total 19mer target site | SEQ ID NO: | sense sequence (5'-3') | SEQ ID NO: | sense sequence (5'-3') | duplex name |
|---|---|---|---|---|---|---|---|
| 827-845 | 1438 | UGCAUACUCUAGUCGUUCC | 389 | uGcAuAcucuAGucGuuccTsT | 390 | GGAACGACuAGAGuAUGcATsT | AD-12242 |
| 1699-1717 | 1439 | AGAAGGCAGUUGACCAAC-A | 391 | AGAAGGcAGuuGAccAAcATsT | 392 | UGUUGGUcAACUGCCUUCUTsT | AD-12243 |
| 1824-1842 | 1440 | GUACAUAAGACCUUAUUU-G | 393 | GuAcAuAAGAccuuAuuuGTsT | 394 | cAAAuAAGGUCUuAUGuACTsT | AD-12244 |
| 429-447 | 1441 | UAUAAUUGCACUAUCUUU-G | 395 | uAuAAuuGcAcuAucuuuGTsT | 396 | cAAAGAuAGUGcAAUuAuATsT | AD-12245 |
| 856-874 | 1442 | UCUCUGUUACAAUACAUA-U | 397 | ucucuGuuAcAAuAcAuAuTsT | 398 | AuAUGuAUUGuAAcAGAGATsT | AD-12246 |
| 1194-1212 | 1443 | UAUGCUCAUAGAGCAAAG-A | 399 | uAuGcucAuAGAGcAAAGATsT | 400 | UCUUUGCUCuAUGAGcAuATsT | AD-12247 |
| 392-410 | 1444 | UGUUGUUUGUCCAAUUCU-G | 401 | uGuuGuuuGuccAAuucuGTsT | 402 | cAGAAUUGGAcAAAcAAcATsT | AD-12248 |
| 1085-1103 | 1445 | ACUAACUAGAAUCCUCCAG | 403 | AcuAAcuAGAAuccuccAGTsT | 404 | CUGGAGGAUUCuAGUuagutsT | AD-12249 |
| 2069-2087 | 1446 | UGUGGUGUCUAUACUGAA-A | 405 | uGuGGuGucuAuAcuGAAATsT | 406 | UUUcAGuAuAGAcACcAcATsT | AD-12250 |
| 4341-4359 | 1447 | UAUUAUGGGAGACCACCC-A | 407 | uAuuAuGGGAGAccAcccATsT | 408 | UGGGUGGUCUCCcAuAAuATsT | AD-12251 |
| 759-777 | 1448 | AAGGAUGAAGUCUAUCAA-A | 409 | AAGGAuGAAGucuAucAAATsT | 410 | UUUGAuAGACUUcAUCCUUTsT | AD-12252 |
| 973-991 | 1449 | UUGAUAAGAGAGCUCGGG-A | 411 | uuGAuAAGAGAGcucGGGATsT | 412 | UCCCGAGCUCUCUuAUcAATsT | AD-12253 |
| 1063-1081 | 1450 | AUGUUCCUUAUCGAGAAU-C | 413 | AuGuuccuuAucGAGAAucTsT | 414 | GAUUCUCGAuAAGGAAcAUTsT | AD-12254 |
| 1190-1208 | 1451 | GGAAUAUGCUCAUAGAGC-A | 415 | GGAAuAuGcucAuAGAGcATsT | 416 | UGCUCuAUGAGcAuAUUCCTsT | AD-12255 |
| 1679-1697 | 1452 | CCAUUCCAAACUGGAUCGU | 417 | ccAuuccAAAcuGGAucGuTsT | 418 | ACGAUCcAGUUUGGAAUGGTsT | AD-12256 |
| 1703-1721 | 1453 | GGCAGUUGACCAACACAA-U | 419 | GGcAGuuGAccAAcAcAAuTsT | 420 | AUUGUGUUGGUcAACUGCCTsT | AD-12257 |
| 1814-1832 | 1454 | CAUGCUAGAAGUACAUAA-G | 421 | cAuGcuAGAAGuAcAuAAGTsT | 422 | CUuAUGuACUUCuAGcAUGTsT | AD-12258 |
| 1818-1836 | 1455 | CUAGAAGUACAUAAGACC-U | 423 | cuAGAAGuAcAuAAGAccuTsT | 424 | AGGUCUuAUGuACUUCuAGTsT | AD-12259 |
| 1897-1915 | 1456 | UUGGAUCUCUCACAUCUA-U | 425 | uuGGAucucucAcAucuAuTsT | 426 | AuAGAUGUGAGAGAUCcAATsT | AD-12260 |
| 2066-2084 | 1457 | AACUGGGUGUCUAUACU-G | 427 | AAcuGGGuGucuAuAcuGTsT | 428 | cAGuAuAGAcACcAcAGUUTsT | AD-12261 |

TABLE 2A-continued

| position in human access. # | SEQ ID NO: | sequence of total 19mer target site | SEQ ID NO: | sense sequence (5'-3') | SEQ ID NO: | sense sequence (5'-3') | duplex name |
|---|---|---|---|---|---|---|---|
| 2121-2139 | 1458 | UCAUUGACAGUGGCCGAUA | 429 | ucAuuGAcAGuGGccGAuATsT | 430 | uAUCGGCcACUGUcAAUGATsT | AD-12262 |
| 2280-2298 | 1459 | AUAAAGCAGACCCAUUCCC | 431 | AuAAAGcAGAcccAuuccccTsT | 432 | GGGAAUGGGUCUGCUUuAUTsT | AD-12263 |
| 2369-2387 | 1460 | ACAGAAACCACUUAGUAGG | 433 | AcAGAAAccAcuuAGuAGGTsT | 434 | ACuACuAAGUGGUUUCUGUTsT | AD-12264 |
| 2372-2390 | 1461 | GAAACCACUUAGUAGUGUC | 435 | GAAAccAcuuAGuAGuGucTsT | 436 | GAcACuACuAAGUGGUUUCTsT | AD-12265 |
| 2409-2427 | 1462 | AAAUCUAAGGAUAUAGUCA | 437 | AAAucuAAGGAuAuAGucATsT | 438 | UGACuAuAUCCUuAGAUUUTsT | AD-12266 |
| 2933-2951 | 1463 | UUAUUUAUACCCAUCAACA | 439 | uuAuuuAuAccccAucAAcATsT | 440 | UGUUGAUGGGuAuAAAuAATsT | AD-12267 |
| 3211-3229 | 1464 | ACAGAGGCAUUAACACACU | 441 | AcAGAGGcAuuAAcAcAcuTsT | 442 | AGUGUGUuAAUGCCUCUGUTsT | AD-12268 |
| 3223-3241 | 1465 | ACACACUGGAGAGGUCUAA | 443 | AcAcAcuGGAGAGGucuAATsT | 444 | UuAGACCUCUCcAGUGUGUTsT | AD-12269 |
| 3225-3243 | 1466 | ACACUGGAGAGGUCUAAAG | 445 | AcAcuGGAGAGGucuAAAGTsT | 446 | CUUuAGACCUCUCcAGUGUTsT | AD-12270 |
| 3291-3309 | 1467 | CGAGCCCAGAUCAACCUUU | 447 | cGAGcccAGAucAAccuuuTsT | 448 | AAAGGUUGAUCUGGGCUCGTsT | AD-12271 |
| 4036-4054 | 1468 | UCCCUAUUUCGCUUUCUCC | 449 | ucccuAuuucGcuuucuccTsT | 450 | GGAGAAAGCGAAAuAGGGATsT | AD-12272 |
| 4180-4198 | 1469 | UCUAAAAUCACUGUCAACA | 451 | ucuAAAAucAcuGucAAcATsT | 452 | UGUUGAcAGUGAUUUuAGATsT | AD-12273 |
| 151-169 | 1470 | AGCCAAAUUCGUCUGCGAA | 453 | AGccAAAuucGucuGcGAATsT | 454 | UUCGcAGACGAAUUUGGCUTsT | AD-12274 |
| 250-268 | 1471 | CCCAUUCAAUAGUAGAAUG | 455 | cccAuucAAuAGuAGAAuGTsT | 456 | cAUUCuAcuAUUGAAUGGGTsT | AD-12275 |
| 821-839 | 1472 | GAUGAAUGCAUACUCUAGU | 457 | GAuGAAuGcAuAcucuAGuTsT | 458 | ACuAGAGuAUGcAUUcAUCTsT | AD-12276 |
| 1060-1078 | 1473 | CUCAUGUUCCUUAUCGAGA | 459 | cucAuGuuccuuAucGAGATsT | 460 | UCUCGAuAAGGAAcAUGAGTsT | AD-12277 |
| 1075-1093 | 1474 | GAGAAUCUAAACUAACUAG | 461 | GAGAAucuAAAcuAAcuAGTsT | 462 | CuAGUuAGUUuAGAUUCUCTsT | AD-12278 |
| 1819-1837 | 1475 | UAGAAGUACAUAAGACCUU | 463 | uAGAAGuAcAuAAGAccuuTsT | 464 | AAGGUCUuAUGuACUUCuATsT | AD-12279 |
| 3003-3021 | 1476 | CAGCCUGAGCUGUUAAUGA | 465 | cAGccuGAGcuGuuAAuGATsT | 466 | UcAUuAAcAGCUcAGGCUGTsT | AD-12280 |

TABLE 2A-continued

| position in human access. # | SEQ ID NO: | sequence of total 19mer target site | SEQ ID NO: | sense sequence (5'-3') | SEQ ID NO: | sense sequence (5'-3') | duplex name |
|---|---|---|---|---|---|---|---|
| 3046-3064 | 1477 | AAGAAGAGACAAUUCCGGA | 467 | AAGAAGAGAcAAuccGGATsT | 468 | UCCGGAAUUGUCUCUUCUUTsT | AD-12281 |
| 3134-3152 | 1478 | UGCUGGUGUGGAUUGUUCA | 469 | uGcuGGuGuGGAuuGuucATsT | 470 | UGAAcAAUCcAcACcAGcATsT | AD-12282 |
| 155-173 | 1479 | AAAUUCGUCUGCGAAGAAG | 471 | AAAuucGucuGcGAAGAAGTsT | 472 | CUUCUUCGcAGACGAAUUUTsT | AD-12283 |
| 4596-4614 | 1480 | UUUCUGGAAGUUGAGAUGU | 473 | uuucuGGAAGuuGAGAuGuTsT | 474 | AcAUCUcAACUUCcAGAAATsT | AD-12284 |
| 365-383 | 1481 | UACUAAACAGAUUGAUGUU | 475 | uAcuAAAcAGAuuGAuGuuTsT | 476 | AAcAUcAAUCUGUUuAGuATsT | AD-12285 |
| 374-392 | 1482 | GAUUGAUGUUUACCGAAGU | 477 | GAuuGAuGuuuAccGAAGuTsT | 478 | ACUUCGGuAAAcAUcAAUCTsT | AD-12286 |
| 436-454 | 1483 | GCACUAUCUUUGCGUAUGG | 479 | GcAcuAucuuuGcGuAuGGTsT | 480 | CcAuACGcAAAGAuAGUGCTsT | AD-12287 |
| 539-557 | 1484 | UGGUAUAAUUCCACGUACC | 481 | uGGuAuAAuuccAcGuAccTsT | 482 | GGuACGUGGAAUuAuACcATsT | AD-12288 |
| 1629-1647 | 1485 | AGCAAGCUGCUUAACACAG | 483 | AGcAAGcuGcuuAAcAcAGTsT | 484 | CUGUGUuAAGcAGCUUGCUTsT | AD-12289 |
| 2370-2388 | 1486 | CAGAAACCACUUAGUAGUG | 485 | cAGAAAccAcuuAGuAGuGTsT | 486 | cACuACuAAGUGGUUUCUGTsT | AD-12290 |
| 2676-2694 | 1487 | AACUUAUUGGAGGUUGGAA | 487 | AAcuuAuuGGAGGuuGGAATsT | 488 | UuAcAACCUCcAAuAAGUUTsT | AD-12291 |
| 3228-3246 | 1488 | CUGGAGAGGUCUAAAGUGG | 489 | cuGGAGAGGucuAAAGuGGTsT | 490 | CcACUUuAGACCUCUCcAGTsT | AD-12292 |
| 3703-3721 | 1489 | AAAAAGAUAUAAGGCAGU | 491 | AAAAAGAuAuAAGGcAGuTsT | 492 | ACUGCCUuAuAUCUUUUUTsT | AD-12293 |
| 3737-3755 | 1490 | GAAUUUUGAUAUCUACCCA | 493 | GAAuuuuGAuAucuAcccATsT | 494 | UGGGuAGAuAUcAAAAUUCTsT | AD-12294 |
| 4573-4591 | 1491 | GUAUUUUGAUCUGGCAAC | 495 | GuAuuuuGAucuGGcAAcTsT | 496 | GUUGCcAGAUcAAAAAuACTsT | AD-12295 |
| 526-544 | 1492 | AGGAUCCCUUGGCUGGUAU | 497 | AGGAucccuuGGcuGGuAuTsT | 498 | AcACcAGCcAAGGGAUCCUTsT | AD-12296 |
| 527-545 | 1493 | GGAUCCCUUGGCUGGUAUA | 499 | GGAucccuuGGcuGGuAuATsT | 500 | uAuAccAGCcAAGGGAUCCTsT | AD-12297 |
| 256-274 | 1494 | CAAUAGUAGAAUGUGAUCC | 501 | cAAuAGuAGAAuGuGAuccTsT | 502 | GGAUcAcAUUCrACuAUUGTsT | AD-12298 |
| 427-445 | 1495 | GCUAUAAUUGCACUAUCUU | 503 | GcuAuAAuuGcAcuAucuuTsT | 504 | AAGAuAGUGcAAUuAuAGCTsT | AD-12299 |
| 554-572 | 1496 | UACCCUUCAUCAAAUUUUU | 505 | uAcccuucAucAAAuuuuuTsT | 506 | AAAAAUUUGAUGAAGGGuATsT | AD-12300 |
| 1210-1228 | 1497 | AGAACAUAUUGAAUAAGCC | 507 | AGAAcAuAuuGAAuAAGccTsT | 508 | GGCUuAUUcAAuAUGUUCUTsT | AD-12301 |

TABLE 2A-continued

| position in human access. # | SEQ ID NO: | sequence of total 19mer target site | SEQ ID NO: | sense sequence (5'-3') | SEQ ID NO: | sense sequence (5'-3') | duplex name |
|---|---|---|---|---|---|---|---|
| 1414-1432 | 1498 | AAAUUGGUGCUGUUGAGGA | 509 | AAAuuGGuGcuGuuGAGGATsT | 510 | UCCUcAAcAGcACcAAUUUTsT | AD-12302 |
| 1438-1456 | 1499 | UGAAUAGGGUUACAGAGUU | 511 | uGAAuAGGGuuAcAGAGuuTsT | 512 | AACUCUGuAACCCuAUUcATsT | AD-12303 |
| 1516-1534 | 1500 | AAGAACUUGAAACCACUCA | 513 | AAGAAcuuGAAAccAcucATsT | 514 | UGAGUGGUUUcAAGUUCUUTsT | AD-12304 |
| 2279-2297 | 1501 | AAUAAAGCAGACCCAUUCC | 515 | AAuAAAGcAGAcccAuuccTsT | 516 | GGAAUGGGUCUGCUUuAUUTsT | AD-12305 |
| 2939-2957 | 1502 | AUACCCAUCAACACUGGUA | 517 | AuAcccAucAAcAcuGGuATsT | 518 | uACcAGUGUUGAUGGGuAUTsT | AD-12306 |
| 3142-3160 | 1503 | UGGAUUGUUCAUCAAUUGG | 519 | uGGAuuGuucAucAAuuGGTsT | 520 | CcAAUUGAUGAAcAAUCcATsT | AD-12307 |
| 3229-3247 | 1504 | UGGAGAGGUCUAAAGUGGA | 521 | uGGAGAGGucuAAAGuGGATsT | 522 | UCcACUUuAGACCUCUCcATsT | AD-12308 |
| 3763-3781 | 1505 | GUCUACCCUAUAGUUCACU | 523 | GucuAcccuAuAGuucAcuTsT | 524 | AGUGAACuAuAGGGAUGACTsT | AD-12309 |
| 4801-4819 | 1506 | AUAAUGGCUAUAAUUUCUC | 525 | AuAAuGGcuAuAAuuucucTsT | 526 | GAGAAAuAuAGCcAUuAUTsT | AD-12310 |
| 529-547 | 1507 | AUCCCUUGGCUGGUAUAAU | 527 | AucccuuGGcuGGuAuAAuTsT | 528 | AUuAuAcUAGCcAAGGGAUTsT | AD-12311 |
| 425-443 | 1508 | GCGCUAUAAUUGCACUAUC | 529 | GcGcuAuAAuuGcAcuAucTsT | 530 | GAuAGUGcAAUuAuAGCCCTsT | AD-12312 |
| 1104-1122 | 1509 | GAUUCUCUGGGAGGGCGUA | 531 | GAuucucuGGGAGGGcGuATsT | 532 | uACGCCCUCcAAGAGAAUCTsT | AD-12313 |
| 1155-1173 | 1510 | GCAUCUCUCAAUCUUGAGG | 533 | GcAucucucAAucuuGAGGTsT | 534 | CCUcAAGAUUGAGAGAUGCTsT | AD-12314 |
| 2403-2421 | 1511 | CAGCAGAAAUCUAAGGAUA | 535 | cAGcAGAAAucuAAGGAuATsT | 536 | uAUCCUuAGAUUUCUGCUGTsT | AD-12315 |
| 3115-3133 | 1512 | GUCAAGAGCCAUCUGUAGA | 537 | GucAAGAGccAucuGuAGATsT | 538 | UCuAcAGAUGGCUCUUGACTsT | AD-12316 |
| 3209-3227 | 1513 | AAACAGAGGCAUUAACACA | 539 | AAAcAGAGGcAuuAAcAcATsT | 540 | UGUGUuAAUGCCUCUGUUUTsT | AD-12317 |
| 3293-3311 | 1514 | AGCCCAGAUCAACCUUUAA | 541 | AGcccAGAucAAccuuuAATsT | 542 | UuAAAGGUUGAUCUGGGCUTsT | AD-12318 |
| 4574-4592 | 1515 | UAUUUUUGAUCUGGCAACC | 543 | uAuuuuuGAucuGGcAAccTsT | 544 | GGUUGCcAGAUcAAAAAuATsT | AD-12319 |
| 352-370 | 1516 | UGUGUGGAGCAUCUACUAA | 545 | uGuGuGGAGcAucuAcuAATsT | 546 | UuAGuAGAUGCUCcAcAcATsT | AD-12320 |
| 741-759 | 1517 | GAAAUUACAGUACACAACA | 547 | GAAAuuAcAGuAcAcAAcATsT | 548 | UGUUGUGuACUGuAAUUUCTsT | AD-12321 |

TABLE 2A-continued

| position in human access. # | SEQ ID NO: | sequence of total 19mer target site | SEQ ID NO: | sense sequence (5'-3') | SEQ ID NO: | sense sequence (5'-3') | duplex name |
|---|---|---|---|---|---|---|---|
| 1478-1496 | 1518 | ACUUGACCAGUGUAAAUCU | 549 | AcuuGAccAGuGuAAAucuTsT | 550 | AGAUUuAcACUGGUcAAGUTsT | AD-12322 |
| 1483-1501 | 1519 | ACCAGUGUAAAUCUGACCU | 551 | AccAGuGuAAAucuGAccuTsT | 552 | AGGUcAGAUUuAcACUGGUTsT | AD-12323 |
| 1967-1985 | 1520 | AGAACAAUCAUUAGCAGCA | 553 | AGAAcAAucAuuAGcAGcATsT | 554 | UGCUGCuAAUGAUUGUUCUTsT | AD-12324 |
| 2247-2265 | 1521 | CAAUGUGGAAACCUAACUG | 555 | cAAuGuGGAAAccuAAcuGTsT | 556 | cAGUuAGGUUUCcAcAUUGTsT | AD-12325 |
| 2500-2518 | 1522 | ACCAAGAAGGUACAAAAUU | 557 | AccAAGAAGGuAcAAAAuuTsT | 558 | AAUUUUGuACCUUCUUGGUTsT | AD-12326 |
| 2508-2526 | 1523 | GGUACAAAAUUGGUUGAAG | 559 | GGuAcAAAAuuGGuuGAAGTsT | 560 | CUUcAAccAAUUUUGuACCTsT | AD-12327 |
| 3138-3156 | 1524 | GGUGUGGAUUGUUCAUCAA | 561 | GGuGuGGAuuGuucAucAATsT | 562 | UUGAUGAAcAAUCcAcACCTsT | AD-12328 |
| 4304-4322 | 1525 | AGAGUUCACAAAAAGCCCA | 563 | AGAGuucAcAAAAAGcccATsT | 564 | UGGGCUUUUUGUGAACUCUTsT | AD-12329 |
| 4711-4729 | 1526 | UGAUAGCUAAAUUAAACCA | 565 | uGAuAGcuAAAuuAAAccATsT | 566 | UGGUUuAAUUuAGCuAUcATsT | AD-12330 |
| 1221-1239 | 1527 | AAUAAGCCUGAAGUGAAUC | 567 | AAuAAGccuGAAGuGAAucTsT | 568 | GAUUcACUuCAGGCUuAUUTsT | AD-12331 |
| 1705-1723 | 1528 | CAGUUGACCAACACAAUGC | 569 | cAGuuGAccAAcAcAAuGcTsT | 570 | GcAUUGUGUUGGUcAACUGTsT | AD-12332 |
| 3137-3155 | 1529 | UGGUGUGGAUUGUUCAUCA | 571 | uGGuGuGGAuuGuucAucATsT | 572 | UGAUGAAcAAUCcAcACcATsT | AD-12333 |
| 4292-4310 | 1530 | AUUCACCCUGACAGAGUUC | 573 | AuucAcccuGAcAGAGuucTsT | 574 | GAACUCUGUcAGGGUGAAUTsT | AD-12334 |
| 1829-1847 | 1531 | UAAGACCUUAUUUGGUAAU | 575 | uAAGAccuuAuuuGGuAAuTsT | 576 | AUuACcAAAuAAGGUCUuATsT | AD-12335 |
| 2244-2262 | 1532 | AAGCAAUGUGGAAACCUAA | 577 | AAGcAAuGuGGAAAccuAATsT | 578 | UuAGGUUUCcAcAUUGCUUTsT | AD-12336 |
| 2888-2906 | 1533 | UCUGAAACUGGAUAUCCCA | 579 | ucuGAAAcuGGAuAucccATsT | 580 | UGGGAuAUCcAGUUUcAGATsT | AD-12337 |

TABLE 2B

| duplex name | 1st single dose screen @ 50 nM [% residual mRNA] | SDs 1st screen (among quadruplicates) | 2nd single dose screen @ 25 nM [% residual mRNA] | SDs 2nd screen (among quadruplicates) | 3rd single dose screen @25 nM | SDs 3rd screen (among quadruplicates) |
|---|---|---|---|---|---|---|
| AD-12072 | 65% | 2% | 82% | 5% | | |
| AD-12073 | 84% | 1% | 61% | 6% | | |
| AD-12074 | 51% | 3% | 36% | 9% | | |
| AD-12075 | 56% | 4% | 36% | 4% | | |
| AD-12076 | 21% | 4% | 13% | 3% | | |
| AD-12077 | 11% | 2% | 6% | 1% | | |
| AD-12078 | 22% | 3% | 9% | 2% | | |
| AD-12079 | 22% | 10% | 15% | 7% | | |
| AD-12080 | 68% | 4% | 52% | 13% | | |
| AD-12081 | 34% | 8% | 35% | 24% | | |
| AD-12082 | 20% | 2% | 92% | 5% | | |
| AD-12083 | 85% | 6% | 63% | 10% | | |
| AD-12084 | 18% | 6% | 17% | 4% | | |
| AD-12085 | 13% | 4% | 12% | 4% | | |
| AD-12086 | 26% | 5% | 17% | 3% | | |
| AD-12087 | 95% | 4% | 80% | 4% | | |
| AD-12088 | 29% | 6% | 29% | 2% | | |
| AD-12089 | 69% | 5% | 64% | 7% | | |
| AD-12090 | 46% | 15% | 34% | 5% | | |
| AD-12091 | 16% | 6% | 17% | 3% | | |
| AD-12092 | 82% | 26% | 63% | 5% | | |
| AD-12093 | 84% | 4% | 70% | 4% | | |
| AD-12094 | 46% | 3% | 34% | 3% | | |
| AD-12095 | 14% | 2% | 13% | 1% | | |
| AD-12096 | 26% | 11% | 17% | 1% | | |
| AD-12097 | 23% | 2% | 21% | 1% | | |
| AD-12098 | 41% | 14% | 17% | 3% | | |
| AD-12099 | 57% | 2% | 48% | 6% | | |
| AD-12100 | 101% | 11% | 98% | 8% | | |
| AD-12101 | 46% | 7% | 32% | 2% | | |
| AD-12102 | 96% | 17% | 88% | 18% | | |
| AD-12103 | 19% | 5% | 20% | 2% | | |
| AD-12104 | 40% | 8% | 24% | 2% | | |
| AD-12105 | 39% | 2% | 35% | 10% | | |
| AD-12106 | 87% | 6% | 79% | 19% | | |
| AD-12107 | 29% | 2% | 32% | 16% | | |
| AD-12108 | 38% | 4% | 39% | 8% | | |
| AD-12109 | 49% | 3% | 44% | 10% | | |
| AD-12110 | 85% | 5% | 80% | 14% | | |
| AD-12111 | 64% | 6% | 71% | 18% | | |
| AD-12112 | 48% | 4% | 41% | 5% | | |
| AD-12113 | 13% | 0% | 14% | 3% | | |
| AD-12114 | 32% | 6% | 16% | 4% | | |
| AD-12115 | 8% | 4% | 7% | 5% | | |
| AD-12116 | 74% | 5% | 61% | 7% | | |
| AD-12117 | 21% | 4% | 20% | 2% | | |
| AD-12118 | 44% | 4% | 42% | 6% | | |
| AD-12119 | 37% | 4% | 24% | 3% | | |
| AD-12120 | 22% | 2% | 15% | 4% | | |
| AD-12121 | 32% | 1% | 22% | 2% | | |
| AD-12122 | 36% | 16% | 10% | 5% | | |
| AD-12123 | 28% | 1% | 16% | | | |
| AD-12124 | 28% | 2% | 16% | | | |
| AD-12125 | 15% | 1% | 14% | | | |
| AD-12126 | 51% | 22% | 27% | | | |
| AD-12127 | 54% | 4% | 42% | 9% | | |
| AD-12128 | 29% | 1% | 20% | 2% | | |
| AD-12129 | 22% | 3% | 19% | 3% | | |
| AD-12130 | 53% | 6% | 42% | 7% | | |
| AD-12131 | 28% | 5% | 22% | 3% | | |
| AD-12132 | 88% | 2% | 90% | 18% | | |
| AD-12133 | 34% | 2% | 26% | 6% | | |
| AD-12134 | 18% | 3% | 14% | 2% | | |
| AD-12135 | 50% | 6% | 37% | 4% | | |
| AD-12136 | 42% | 19% | 22% | 2% | | |
| AD-12137 | 85% | 12% | 92% | 4% | | |
| AD-12138 | 47% | 6% | 49% | 1% | | |
| AD-12139 | 80% | 5% | 72% | 4% | | |
| AD-12140 | 97% | 22% | 67% | 9% | | |
| AD-12141 | 120% | 4% | 107% | 10% | | |

TABLE 2B-continued

| duplex name | 1st single dose screen @ 50 nM [% resudual mRNA] | SDs 1st screen (among quadruplicates) | 2nd single dose screen @ 25 nM [% resudual mRNA] | SDs 2nd screen (among quadruplicates) | 3rd single dose screen @25 nM | SDs 3rd screen (among quadruplicates) |
|---|---|---|---|---|---|---|
| AD-12142 | 55% | 8% | 33% | 4% | | |
| AD-12143 | 64% | 34% | 19% | 2% | | |
| AD-12144 | 58% | 29% | 17% | 2% | | |
| AD-12145 | 27% | 8% | 18% | 2% | | |
| AD-12146 | 19% | 20% | 15% | 1% | | |
| AD-12147 | 29% | 9% | 35% | 3% | | |
| AD-12148 | 30% | 3% | 56% | 5% | | |
| AD-12149 | 8% | 2% | 12% | 3% | | |
| AD-12150 | 31% | 2% | 31% | 7% | | |
| AD-12151 | 9% | 5% | 14% | 2% | | |
| AD-12152 | 3% | 3% | 23% | 3% | | |
| AD-12153 | 20% | 6% | 34% | 4% | | |
| AD-12154 | 24% | 7% | 44% | 3% | | |
| AD-12155 | 33% | 6% | 53% | 11% | | |
| AD-12156 | 35% | 5% | 40% | 5% | | |
| AD-12157 | 8% | 3% | 23% | 4% | | |
| AD-12158 | 13% | 2% | 22% | 5% | | |
| AD-12159 | 34% | 6% | 46% | 5% | | |
| AD-12160 | 19% | 3% | 31% | 4% | | |
| AD-12161 | 88% | 4% | 83% | 7% | | |
| AD-12162 | 26% | 7% | 32% | 7% | | |
| AD-12163 | 55% | 9% | 40% | 3% | | |
| AD-12164 | | | 21% | 3% | | |
| AD-12165 | 30% | 3% | 41% | 4% | | |
| AD-12166 | 9% | 10% | 22% | 9% | | |
| AD-12167 | 26% | 3% | 30% | 2% | | |
| AD-12168 | 54% | 4% | 59% | 20% | | |
| AD-12169 | 41% | 4% | 51% | 16% | | |
| AD-12170 | 43% | 4% | 52% | 20% | | |
| AD-12171 | 67% | 3% | 73% | 25% | | |
| AD-12172 | 53% | 15% | 37% | 2% | | |
| AD-12173 | 39% | 0% | 39% | 0% | | |
| AD-12174 | 41% | 5% | 27% | 0% | | |
| AD-12175 | 29% | 0% | 38% | 14% | | |
| AD-12176 | 43% | 2% | 56% | 25% | | |
| AD-12177 | 68% | 6% | 74% | 30% | | |
| AD-12178 | 41% | 4% | 41% | 6% | | |
| AD-12179 | 53% | 5% | 44% | 5% | | |
| AD-12180 | 16% | 2% | 13% | 4% | | |
| AD-12181 | 19% | 3% | 14% | 2% | | |
| AD-12182 | 16% | 4% | 18% | 8% | | |
| AD-12183 | 26% | 3% | 19% | 4% | | |
| AD-12184 | 54% | 2% | 77% | 8% | | |
| AD-12185 | 8% | 1% | 9% | 1% | | |
| AD-12186 | 35% | 3% | 41% | 6% | | |
| AD-12187 | 34% | 17% | 27% | 1% | | |
| AD-12188 | 30% | 3% | 27% | 4% | | |
| AD-12189 | 51% | 4% | 48% | 5% | | |
| AD-12190 | 33% | 2% | 26% | 4% | | |
| AD-12191 | 20% | 2% | 13% | 0% | | |
| AD-12192 | 21% | 1% | 23% | 10% | | |
| AD-12193 | 64% | 8% | 98% | 6% | | |
| AD-12194 | 8% | 2% | 15% | 4% | | |
| AD-12195 | 34% | 2% | 48% | 3% | | |
| AD-12196 | 34% | 2% | 51% | 3% | | |
| AD-12197 | 75% | 4% | 93% | 6% | | |
| AD-12198 | 55% | 5% | 48% | 2% | | |
| AD-12199 | 102% | 6% | 118% | 9% | | |
| AD-12200 | 75% | 6% | 60% | 12% | | |
| AD-12201 | 42% | 3% | 16% | 4% | | |
| AD-12202 | 29% | 4% | 9% | 3% | | |
| AD-12203 | 114% | 14% | 89% | 20% | | |
| AD-12204 | 64% | 7% | 26% | 5% | | |
| AD-12205 | 66% | 12% | 35% | 4% | | |
| AD-12206 | 46% | 3% | 32% | 12% | | |
| AD-12207 | 57% | 5% | 40% | 6% | | |
| AD-12208 | 30% | 8% | 10% | 5% | | |
| AD-12209 | 101% | 6% | 102% | 23% | | |
| AD-12210 | 38% | 11% | 27% | 14% | | |
| AD-12211 | 16% | 6% | 10% | 5% | | |

TABLE 2B-continued

| duplex name | 1st single dose screen @ 50 nM [% residual mRNA] | SDs 1st screen (among quadruplicates) | 2nd single dose screen @ 25 nM [% residual mRNA] | SDs 2nd screen (among quadruplicates) | 3rd single dose screen @25 nM | SDs 3rd screen (among quadruplicates) |
|---|---|---|---|---|---|---|
| AD-12212 | 59% | 8% | 65% | 5% | | |
| AD-12213 | 24% | 9% | 12% | 2% | | |
| AD-12214 | 67% | 14% | 70% | 12% | | |
| AD-12215 | 29% | 13% | 13% | 4% | | |
| AD-12216 | 36% | 4% | 13% | 1% | | |
| AD-12217 | 36% | 9% | 11% | 2% | | |
| AD-12218 | 35% | 5% | 17% | 3% | | |
| AD-12219 | 41% | 9% | 14% | 1% | | |
| AD-12220 | 37% | 5% | 23% | 3% | | |
| AD-12221 | 58% | 7% | 39% | 6% | | |
| AD-12222 | 74% | 9% | 53% | 3% | | |
| AD-12223 | 74% | 10% | 67% | 7% | | |
| AD-12224 | 24% | 2% | 11% | 2% | | |
| AD-12225 | 75% | 5% | 76% | 14% | | |
| AD-12226 | 45% | 8% | 40% | 3% | | |
| AD-12227 | 61% | 6% | 47% | 5% | | |
| AD-12228 | 28% | 3% | 25% | 5% | | |
| AD-12229 | 54% | 13% | 37% | 6% | | |
| AD-12230 | 70% | 17% | 65% | 4% | | |
| AD-12231 | 32% | 12% | 22% | 6% | | |
| AD-12232 | 30% | 3% | 17% | 2% | | |
| AD-12233 | 38% | 2% | 32% | 3% | | |
| AD-12234 | 90% | 5% | 95% | 7% | | |
| AD-12235 | 57% | 7% | 46% | 3% | | |
| AD-12236 | 34% | 8% | 16% | 2% | | |
| AD-12237 | 42% | 9% | 32% | 8% | | |
| AD-12238 | 42% | 6% | 34% | 6% | | |
| AD-12239 | 42% | 3% | 40% | 4% | | |
| AD-12240 | 47% | 6% | 36% | 5% | | |
| AD-12241 | 69% | 5% | 70% | 8% | | |
| AD-12242 | 61% | 2% | 47% | 3% | | |
| AD-12243 | 26% | 7% | 15% | 1% | | |
| AD-12244 | 25% | 6% | 15% | 1% | | |
| AD-12245 | 65% | 6% | 83% | 13% | | |
| AD-12246 | 29% | 7% | 31% | 6% | | |
| AD-12247 | 57% | 13% | 50% | 3% | | |
| AD-12248 | 36% | 8% | 20% | 3% | 15% | 7% |
| AD-12249 | 44% | 3% | 70% | 11% | 103% | 34% |
| AD-12250 | 47% | 5% | 18% | 5% | 17% | 4% |
| AD-12251 | 121% | 28% | 35% | 8% | 60% | 42% |
| AD-12252 | 94% | 15% | 8% | 3% | 5% | 3% |
| AD-12253 | 94% | 33% | 42% | 8% | 49% | 27% |
| AD-12254 | 101% | 58% | 70% | 5% | 80% | 32% |
| AD-12255 | 163% | 37% | 38% | 6% | 36% | 10% |
| AD-12256 | 112% | 62% | 18% | 3% | 9% | 4% |
| AD-12257 | 10% | 4% | 9% | 2% | 6% | 2% |
| AD-12258 | 27% | 9% | 18% | 3% | 20% | 6% |
| AD-12259 | 20% | 5% | 12% | 2% | 13% | 5% |
| AD-12260 | 22% | 7% | 81% | 7% | 65% | 13% |
| AD-12261 | 122% | 11% | 66% | 7% | 80% | 22% |
| AD-12262 | 57% | 30% | 33% | 6% | 44% | 18% |
| AD-12263 | 177% | 57% | 85% | 11% | 84% | 15% |
| AD-12264 | 37% | 6% | 10% | 1% | 10% | 4% |
| AD-12265 | 40% | 8% | 17% | 1% | 20% | 10% |
| AD-12266 | 33% | 9% | 9% | 1% | 8% | 4% |
| AD-12267 | 34% | 13% | 11% | 1% | 6% | 2% |
| AD-12268 | 34% | 6% | 11% | 1% | 9% | 2% |
| AD-12269 | 54% | 6% | 33% | 4% | 29% | 7% |
| AD-12270 | 52% | 5% | 29% | 4% | 27% | 6% |
| AD-12271 | 53% | 7% | 27% | 3% | 19% | 6% |
| AD-12272 | 85% | 15% | 57% | 7% | 51% | 16% |
| AD-12273 | 36% | 6% | 26% | 2% | 30% | 5% |
| AD-12274 | 75% | 21% | 40% | 2% | 50% | 19% |
| AD-12275 | 29% | 9% | 8% | 1% | 8% | 4% |
| AD-12276 | 45% | 19% | 15% | 2% | 16% | 12% |
| AD-12277 | 58% | 17% | 32% | 2% | 55% | 14% |
| AD-12278 | 120% | 35% | 96% | 10% | 124% | 38% |
| AD-12279 | 47% | 29% | 17% | 1% | 12% | 4% |
| AD-12280 | 2% | 0% | 3% | 1% | | |
| AD-12281 | 2% | 0% | 5% | 2% | | |

TABLE 2B-continued

| duplex name | 1st single dose screen @ 50 nM [% resudual mRNA] | SDs 1st screen (among quadruplicates) | 2nd single dose screen @ 25 nM [% resudual mRNA] | SDs 2nd screen (among quadruplicates) | 3rd single dose screen @25 nM | SDs 3rd screen (among quadruplicates) |
|---|---|---|---|---|---|---|
| AD-12282 | 3% | 0% | 25% | 5% | | |
| AD-12283 | 3% | 1% | 35% | 4% | | |
| AD-12284 | 5% | 2% | 49% | 8% | | |
| AD-12285 | 7% | 7% | 21% | 26% | | |
| AD-12286 | 28% | 34% | 12% | 7% | | |
| AD-12287 | 40% | 21% | 51% | 23% | | |
| AD-12288 | 26% | 7% | 155% | 146% | | |
| AD-12289 | 43% | 21% | 220% | 131% | | |
| AD-12290 | 2% | 1% | 81% | 23% | | |
| AD-12291 | 4% | 1% | 70% | 3% | | |
| AD-12292 | 2% | 3% | 6% | 2% | | |
| AD-12293 | 4% | 2% | 36% | 3% | | |
| AD-12294 | 10% | 6% | 38% | 3% | | |
| AD-12295 | 29% | 31% | 37% | 3% | | |
| AD-12296 | 82% | 4% | 89% | 2% | | |
| AD-12297 | 75% | 3% | 65% | 2% | | |
| AD-12298 | 73 | 4% | 60% | 3% | | |
| AD-12299 | 76% | 4% | 65% | 4% | | |
| AD-12300 | 36% | 4% | 15% | 1% | | |
| AD-12301 | 33% | 4% | 18% | 2% | | |
| AD-12302 | 66% | 5% | 65% | 3% | | |
| AD-12303 | 35% | 6% | 17% | 2% | | |
| AD-12304 | 70% | 8% | 70% | 6% | | |
| AD-12305 | 63% | 8% | 80% | 7% | | |
| AD-12306 | 23% | 6% | 20% | 3% | | |
| AD-12307 | 78% | 10% | 58% | 5% | | |
| AD-12308 | 27% | 8% | 15% | 2% | | |
| AD-12309 | 58% | 11% | 42% | 3% | | |
| AD-12310 | 106% | 23% | 80% | 2% | | |
| AD-12311 | 73% | 12% | 60% | 2% | | |
| AD-12312 | 39% | 3% | 36% | 3% | | |
| AD-12313 | 64% | 9% | 49% | 6% | | |
| AD-12314 | 28% | 7% | 14% | 6% | | |
| AD-12315 | 31% | 7% | 13% | 2% | | |
| AD-12316 | 42% | 5% | 14% | 2% | | |
| AD-12317 | 34% | 9% | 15% | 5% | | |
| AD-12318 | 46% | 4% | 28% | 4% | | |
| AD-12319 | 77% | 3% | 56% | 4% | | |
| AD-12320 | 55% | 7% | 41% | 3% | | |
| AD-12321 | 21% | 3% | 10% | 2% | | |
| AD-12322 | 27% | 8% | 30% | 12% | | |
| AD-12323 | 26% | 7% | 35% | 18% | | |
| AD-12324 | 27% | 8% | 27% | 14% | | |
| AD-12325 | 32% | 12% | 32% | 22% | | |
| AD-12326 | 42% | 22% | 45% | 41% | | |
| AD-12327 | 36% | 14% | 37% | 32% | | |
| AD-12328 | 45% | 2% | 31% | 3% | | |
| AD-12329 | 61% | 4% | 34% | 3% | | |
| AD-12330 | 63% | 5% | 38% | 4% | | |
| AD-12331 | 50% | 2% | 26% | 5% | | |
| AD-12332 | 80% | 4% | 51% | 7% | | |
| AD-12333 | 34% | 6% | 12% | 2% | | |
| AD-12334 | 27% | 2% | 18% | 3% | | |
| AD-12335 | 84% | 6% | 60% | 7% | | |
| AD-12336 | 45% | 4% | 36% | 4% | | |
| AD-12337 | 30% | 7% | 19% | 2% | | |

TABLE 3

| sequence (5'-3') | SEQ ID NO. | sequence (5'-3') | SEQ ID NO. | duplex name | single dose screen @ 25 nM [% residual mRNA] | SDs 2nd screen (among quadruplicates) |
|---|---|---|---|---|---|---|
| ccAuuAcuAcAGuAGcAcuTsT | 582 | AGUGCuACUGuAGuAAUGGTsT | 583 | AD-14085 | 19% | 1% |
| AucuGGcAAccAuAuuucuTsT | 584 | AGAAAuAUGGUUGCcAGAUTsT | 585 | AD-14086 | 38% | 1% |
| GAuAGcuAAAuuAAAccAATsT | 586 | UUGGUUuAAUUuAGCuAUCTsT | 587 | AD-14087 | 75% | 10% |
| AGAuAccAuuAcuAcAGuATsT | 588 | uACUGuAGuAAUGGuAUCUTsT | 589 | AD-14088 | 22% | 8% |
| GAuuGuucAucAcAuuGGcGTsT | 590 | CGCcAAUUGAUGAAcAAUCTsT | 591 | AD-14089 | 70% | 12% |
| GcuuucuccucGGcucAcuTsT | 592 | AGuGAGCCGAGGAGAAAGCTsT | 593 | AD-14090 | 79% | 11% |
| GGAGGAuuGGcuGAcAAGATsT | 594 | UCUUGUcAGCcAAUCCUCCTsT | 595 | AD-14091 | 29% | 3% |
| uAAuGAAGAGuAuAccuGGTsT | 596 | CcAGGuAuACUCUUcAUuATsT | 597 | AD-14092 | 23% | 2% |
| uuucAccAAAccAuuuGuATsT | 598 | uAcAAAUGGUUUGGUGAAATsT | 599 | AD-14093 | 60% | 2% |
| cuuAuuAAGGAGuAuAcGGTsT | 600 | CCGuAuACUCCUuAAuAAGTsT | 601 | AD-14094 | 11% | 3% |
| GAAAucAGAuGGAcGuAAGTsT | 602 | CUuACGUCcAUCUGAUUUCTsT | 603 | AD-14095 | 10% | 2% |
| cAGAuGucAGcAuAAGcGATsT | 604 | UCGCUuAUGCUGAcAUCUGTsT | 605 | AD-14096 | 27% | 2% |
| AucuAAcccuAGuuGuAucTsT | 606 | GAuAcAACuAGGGUuAGAUTsT | 607 | AD-14097 | 45% | 6% |
| AAGAGcuuGuuAAAAucGGTsT | 608 | CCGAUUUuAAcAAGCUCUUTsT | 609 | AD-14098 | 50% | 10% |
| uuAAGGAGuAuAcGGAGGATsT | 610 | UCCUCCGuAuACUCCUuAATsT | 611 | AD-14099 | 12% | 4% |
| uuGcAAuGuAAAuAcGuATsT | 612 | AuACGuAUUuAcAUUGcAATsT | 613 | AD-14100 | 49% | 7% |
| ucuAAcccuAGuuGuAuccTsT | 614 | GGAuAcAACuAGGGUuAGATsT | 615 | AD-14101 | 36% | 1% |
| cAuGAucuuuuucucGAuTsT | 616 | AUCGAGAAAAGAuAcAUGTsT | 617 | AD-14102 | 49% | 3% |
| GAuGucAGcAuAAGcGAuGTsT | 618 | cAUCGCUuAUGCUGAcAUCTsT | 619 | AD-14103 | 74% | 5% |
| ucccAAcAGGuAcGAcAccTsT | 620 | GGUGUCGuACCUGUUGGGATsT | 621 | AD-14104 | 27% | 3% |
| uGcucAcGAuGAGuuuAGuTsT | 622 | ACuAAAACUcAUCGUGAGcATsT | 623 | AD-14105 | 34% | 4% |
| AGAGcuuGuuAAAAucGGATsT | 624 | UCCGAUUUuAAcAAGCUCUTsT | 625 | AD-14106 | 9% | 2% |
| GcGuAcAAGAAcAucuAuATsT | 626 | uAuAGAUGUUCUUGuACGCTsT | 627 | AD-14107 | 5% | 1% |
| GAGGuuGuAAGccAAuGuuTsT | 628 | AAcAUUGGCUuAcAACCUCTsT | 629 | AD-14108 | 15% | 1% |
| AAcAGGuAcGAcAccAcAGTsT | 630 | CUGUGGUGUCGuACCUGUUTsT | 631 | AD-14109 | 91% | 2% |
| AAcccuAGuuGuAucccucTsT | 632 | GAGGGAuAcAACuAGGGUUTsT | 633 | AD-14110 | 66% | 5% |
| GcAuAAGcGAuGGAuAAuATsT | 634 | uAUuAUCcAUCGCUuAUGCTsT | 635 | AD-14111 | 33% | 3% |
| AAGcGAuGGAuAuAccAuATsT | 636 | uAGGuAUuAUCcAUCGCUUTsT | 637 | AD-14112 | 51% | 3% |
| uGAuccGuAcGAAAAGAATsT | 638 | UUCUUUUCGuAcAGGAUCATsT | 639 | AD-14113 | 22% | 3% |
| AAAAcAuuGGccGuucuGUTsT | 640 | CcAGAACGGCcAAUGUUUUTsT | 641 | AD-14114 | 117% | 8% |
| cuuGGAGGGcGuAcAAGAATsT | 642 | UUCUUGuACGCCCUCcAAGTsT | 643 | AD-14115 | 50% | 8% |
| GGcGuAcAAGAAcAucuAuTsT | 644 | AuAGAUGUUCUUGuACGCCTsT | 645 | AD-14116 | 14% | 3% |
| AcucuGAGuAcAuuGGAAuTsT | 646 | AUUCcAAUGuACUcAGAGUTsT | 647 | AD-14117 | 12% | 4% |
| uuAuuAAGGAGuAuAcGGATsT | 648 | UCCGuAuACUCCUuAAuAATsT | 649 | AD-14118 | 26% | 4% |
| uAAGGAGuAuAcGGAGGAGTsT | 650 | CUCCUCCGuAuACUCCUuATsT | 651 | AD-14119 | 24% | 5% |
| AAAucAAuAGucAAcuAAATsT | 652 | UUuAGUUGAcuAUUGAUUUTsT | 653 | AD-14120 | 8% | 1% |
| AAucAAuAGucAAcuAAAGTsT | 654 | CUUuAGUUGACuAUUGAUUTsT | 655 | AD-14121 | 24% | 2% |
| uucucAcGAuAcuGuAGAATsT | 656 | UuAcAcAGuAucGUGAGAATsT | 657 | AD-14122 | 10% | 1% |
| uGuGAAAcAcucuGAuAAATsT | 658 | UUuAUcAGAGUGUUUcAcATsT | 659 | AD-14123 | 8% | 1% |
| AGAuGuGAAucucuGAAcATsT | 660 | UGUUcAGAGAUUcAcAUCUTsT | 661 | AD-14124 | 9% | 2% |
| AGGuuGuAAGccAAuGuuGTsT | 662 | cAAcAUUGGCUuAcAACCUTsT | 663 | AD-14125 | 114% | 6% |
| uGAGAAAAcAGAuGGAcGuTsT | 664 | ACGUCcAUCUGAUUUUCuATsT | 665 | AD-14126 | 9% | 1% |
| AGAAAucAGAuGGAcGuAATsT | 666 | UuACGUCcAUCUGAUUUCUTsT | 667 | AD-14127 | 57% | 6% |
| AuAcccAAcAGGuAcGAcTsT | 668 | GUCGuACCUGUUGGGAuAUTsT | 669 | AD-14128 | 104% | 6% |
| cccAAcAGGuAcGAcAccATsT | 670 | UGGUGUCGuACCUGUUGGGTsT | 671 | AD-14129 | 21% | 2% |
| AGuAuAcuGAAGAAccucuTsT | 672 | AGAGGUUCUUcAGuAuACUTsT | 673 | AD-14130 | 57% | 6% |
| AuAuAucAGccGGGcGuATsT | 674 | GCGCCCGGCUGAuAuAuAUTsT | 675 | AD-14131 | 93% | 6% |
| AAucuAAcccuAGuuGuAuTsT | 676 | AuAcAACuAGGGUuAGAUUTsT | 677 | AD-14132 | 75% | 8% |
| cuAAcccuAGuuGuAucccTsT | 678 | GGGAuAcAACuAGGGUuAGTsT | 679 | AD-14133 | 66% | 4% |
| cuAGuuGuAucccuccuuuTsT | 680 | AAAGGAGGGAuAcAACuAGTsT | 681 | AD-14134 | 44% | 6% |
| AGAcAcAGuAcuAAuAAGGcuTsT | 682 | AGCcAUuAGuAcUGUGUCUTsT | 683 | AD-14135 | 55% | 6% |
| GAAGcucAcAAuGAuuuAATsT | 684 | UuAAAUcAUUGUGAGCUUCTsT | 685 | AD-14136 | 29% | 3% |
| AcAuGuAucuuuuucucGATsT | 686 | UCGAGAAAAGAuAcAUGUTsT | 687 | AD-14137 | 40% | 3% |
| ucGAuucAAAucuuAAcccTsT | 688 | GGGUuAAGAUUUGAAUCGATsT | 689 | AD-14138 | 39% | 5% |
| ucuuAAcccuuAGGAcucuTsT | 690 | AGAGUCcAAGGGUuAAGACUsT | 691 | AD-14139 | 71% | 11% |
| GcucAcGAuGAGuuuAGuGTsT | 692 | cACuAAACUcAUCGUGAGCTsT | 693 | AD-14140 | 43% | 15% |
| cAuAAGcGAuGGAuAAuAcTsT | 694 | GuAUuAUCcAUCGCUuAUGTsT | 695 | AD-14141 | 33% | 6% |
| AuAAGcGAuGGAuAAuAccTsT | 696 | GGuAUuAUCcAUCGCUuAUTsT | 697 | AD-14142 | 51% | 14% |
| ccuAAuAAAcGcccucAGTsT | 698 | CUGAGGGcAGUUuAUuAGGTsT | 699 | AD-14143 | 42% | 1% |
| ucGGAAAGuuGAAcuuGGuTsT | 700 | ACcAAGUUcAACUUUCCGATsT | 701 | AD-14144 | 4% | 4% |
| GAAAAcAuuGGccGuucuGTsT | 702 | cAGAACGGCcAAUGUUUUCTsT | 703 | AD-14145 | 92% | 5% |
| AAGAcuAucuucuAAGuuTsT | 704 | AACUuAGAAGAUcAGUCUUTsT | 705 | AD-14146 | 13% | 2% |
| GAGcuuGuuAAAAucGGAATsT | 706 | UUCCGAUUUuAAcAAGCUCTsT | 707 | AD-14147 | 8% | 1% |
| AcAuuGGccGuucuGGAGcTsT | 708 | GCUCcAGAACGGCcAAUGUTsT | 709 | AD-14148 | 80% | 7% |
| AAGAAcucuAAAuuGcATsT | 710 | UGcAAuuAuGAUGUUCUUTsT | 711 | AD-14149 | 44% | 7% |
| AAAuGuGucuAcucAuGuuTsT | 712 | AAcAUGAGuAGAcAcAUUUTsT | 713 | AD-14150 | 32% | 29% |
| uGucuAcucAuGuuucucATsT | 714 | UGAGAAAcAUGAGuAGAcATsT | 715 | AD-14151 | 75% | 11% |
| GuAcuGuGuAAcAAucuATsT | 716 | AGAUUGUuAcAcAGuAACTsT | 717 | AD-14152 | 8% | 5% |
| uAuAcuGuGuAAcAAucuATsT | 718 | uAGAUUGUuAcAcAGuAUATsT | 719 | AD-14153 | 17% | 11% |
| cuuGuAGuGuccAGGAAATsT | 720 | UUUCCUGGAcACuACuAAGTsT | 721 | AD-14154 | 16% | 4% |
| ucAGAuGGAcGuAAGGcAGTsT | 722 | CUGCCUuACGUCcAUCUGATsT | 723 | AD-14155 | 11% | 1% |
| AGAuAAAuuGAuAGcAcAATsT | 724 | UUGUGCuAUcAAUUuAUCUTsT | 725 | AD-14156 | 10% | 1% |

TABLE 3-continued

| sequence (5'-3') | SEQ ID NO. | sequence (5'-3') | SEQ ID NO. | duplex name | single dose screen @ 25 nM [% residual mRNA] | SDs 2nd screen (among quadruplicates) |
|---|---|---|---|---|---|---|
| cAAcAGGuAcGAcAccAcATsT | 726 | UGUGGUGUCGuACCUGUUGTsT | 727 | AD-14157 | 29% | 3% |
| uGcAAuGuAAAuAcGuAuuTsT | 728 | AAuACGuAUUuAcAUUGcATsT | 729 | AD-14158 | 51% | 3% |
| AGucAGAAuuuuAucuAGATsT | 730 | UCuAGAuAAAAUUCUGACUTsT | 731 | AD-14159 | 53% | 5% |
| cuAGAAAucuuuuAAcAccTsT | 732 | GGUGUuAAAAGAUUUCuAGTsT | 733 | AD-14160 | 40% | 3% |
| AAuAAAucuAAcccuAGuuTsT | 734 | AACuAGGGUuAGAUUuAUUTsT | 735 | AD-14161 | 83% | 7% |
| AAuuuucuGcucAcGAuGATsT | 736 | UcAUCGUGAGcAGAAAAUUTsT | 737 | AD-14162 | 44% | 6% |
| GcccucAGuAAAuccAuGGTsT | 738 | CcAUGGAUUuACUGAGGGCTsT | 739 | AD-14163 | 57% | 3% |
| AcGuuuAAAAcGAGAucuuTsT | 740 | AAGAUCUCGUUUuAAACGUTsT | 741 | AD-14164 | 4% | 1% |
| AGGAGAuAGAAcGuuuAAATsT | 742 | UUuAAACGUUCuAUCCCUTsT | 743 | AD-14165 | 11% | 1% |
| GAccGucAuGGcGucGcAGTsT | 744 | CUGCGACGCcAUGACGGUCTsT | 745 | AD-14166 | 90% | 5% |
| AccGucAuGGcGucGcAGcTsT | 746 | GCUGCGACGCcAUGACGGUTsT | 747 | AD-14167 | 49% | 1% |
| GAAcGuuuAAAAcGAGAucTsT | 748 | GAUCUCGUUUuAAAGUUCTsT | 749 | AD-14168 | 12% | 2% |
| uuGAGcuuAAcAuAGGuAATsT | 750 | UuACCuAUGUuAAGCUcAATsT | 751 | AD-14169 | 66% | 4% |
| AcuAAAuuGAucucGuAGATsT | 752 | UCuACGAGAUcAAUUuAGUTsT | 753 | AD-14170 | 52% | 6% |
| ucGuAGAAuuAucuuAAuATsT | 754 | uAUuAAGAuAAUUCuACGATsT | 755 | AD-14171 | 42% | 4% |
| GGAGAuAGAAcGuuuAAAATsT | 756 | UUUuAAACGUUCuAUCUCCTsT | 757 | AD-14172 | 3% | 1% |
| AcAAcuuAuuGGAGGuuGUTsT | 758 | AcAACCUCcAuAAGUUGUTsT | 759 | AD-14173 | 29% | 2% |
| uGAGcuuAAcAuAGGuAAATsT | 760 | UUuACCuAUGUuAAGCUcATsT | 761 | AD-14174 | 69% | 2% |
| AucucGuAGAAuuAucuuATsT | 762 | uAAGAuAAUUCuACGAGAUTsT | 763 | AD-14175 | 53% | 3% |
| cuGcGuGcAGucGGuccucTsT | 764 | GAGGACCGACUGcACGcAGTsT | 765 | AD-14176 | 111% | 4% |
| cACGcAGcGcccGAGAGuATsT | 766 | uACUCUCGGGCGCUGCGUGTsT | 767 | AD-14177 | 87% | 6% |
| AGuAccAGGGAGAcuccGGTsT | 768 | CCGGAGUCUCCCUGGuACUTsT | 769 | AD-14178 | 59% | 2% |
| AcGGAGGAGAuAGAAcGuuTsT | 770 | AACGUUCuAUCUCCUCCGUTsT | 771 | AD-14179 | 9% | 2% |
| AGAAcGuuuAAAAcGAGAuTsT | 772 | AUCUCGUUUuAAACGUUCUTsT | 773 | AD-14180 | 43% | 2% |
| AAcGuuuAAAAcGAGAucuTsT | 774 | AGAUCUCGUUUuAAACGUUTsT | 775 | AD-14181 | 70% | 10% |
| AGcuuGAGcuuAAcAuAGGTsT | 776 | CCuAUGUuAAGCUcAAGCUTsT | 777 | AD-14182 | 100% | 7% |
| AGcuuAAcAuAGGuAAAuATsT | 778 | uAUUuACCuAUGUuAAGCUTsT | 779 | AD-14183 | 60% | 5% |
| uGAGAcuAcAAAAccuAucTsT | 780 | GAuAGGUUUUGuAGCUCuATsT | 781 | AD-14184 | 129% | 6% |
| uAGuuGuAuccuccuuuuATsT | 782 | uAAAGGAGGGAuAcAACuATsT | 783 | AD-14185 | 62% | 4% |
| AccAcccAGAcAucuGcAGTsT | 784 | AGUcAGAUGUCUGGGUGGUTsT | 785 | AD-14186 | 42% | 3% |
| AGAAAcuAAAuuGAucucGTsT | 786 | CGAGAUcAAUUuAGUUUCUTsT | 787 | AD-14187 | 123% | 12% |
| ucucGuAGAAuuAucuuAATsT | 788 | UuAAGAuAAUUCuACGAGATsT | 789 | AD-14188 | 38% | 2% |
| cAAcuuAuuGGAGGuuGuATsT | 790 | uAcAACCUCcAuAAGUUGTsT | 791 | AD-14189 | 13% | 1% |
| uuGuAucccuccuuuuAAGTsT | 792 | ACUuAAAAGGAGGGAuAcAATsT | 793 | AD-14190 | 59% | 3% |
| ucAcAAcuuAuuGGAGGuuTsT | 794 | AACCUCcAuAAGUUGUGATsT | 795 | AD-14191 | 93% | 3% |
| AGAAcuGuAcucuucucAGTsT | 796 | CUGAGAAGAGuAcAGUUCUTsT | 797 | AD-14192 | 45% | 5% |
| GAGcuuAAcAuAGGuAAAuTsT | 798 | AUUuACCuAUGUuAAGCUCTsT | 799 | AD-14193 | 57% | 3% |
| cAccAAcAucuGuccuuuGTsT | 800 | CuAAGGAcAGAUGUUGGUGTsT | 801 | AD-14194 | 51% | 4% |
| AAAGcccAcuuuAGAGuAuTsT | 802 | AuACUCuAAAGUGGGCUUUTsT | 803 | AD-14195 | 77% | 5% |
| AAGcccAcuuuAGAGuAuATsT | 804 | uAuACUCuAAAGUGGGCUUTsT | 805 | AD-14196 | 42% | 6% |
| GAccuuAuuuGGuAAucuGTsT | 806 | cAGAUuACcAAAuAAGGUCTsT | 807 | AD-14197 | 15% | 2% |
| GAuuAcGuAcucAAGAcuTsT | 808 | AGUCUUGAGuAcAUuAAUCTsT | 809 | AD-14198 | 12% | 2% |
| cuuuAAGAGGccuAAcucATsT | 810 | UGAGUuAGGCCUCUuAAAGTsT | 811 | AD-14199 | 18% | 2% |
| uuAAAccAAAcccuAuuGATsT | 812 | UcAAuAGGGUUUGGUUuAATsT | 813 | AD-14200 | 72% | 9% |
| ucuGuuGGAGAucuAuAAuTsT | 814 | AUuAuAGAUCUCcAAcAGATsT | 815 | AD-14201 | 9% | 3% |
| cuGAuGuuucuGAGAGAcuTsT | 816 | AGUCUCUcAGAAAcAUcAGTsT | 817 | AD-14202 | 25% | 3% |
| GcAuAcucuAGucGuuccCTsT | 818 | GGGAACGACuAGAGuAUGCTsT | 819 | AD-14203 | 21% | 1% |
| GuuccuuAucGAGAAucuATsT | 820 | uAGAUUCUCGAuAAGGAACTsT | 821 | AD-14204 | 4% | 2% |
| GcAcuuGGAucucucAcAuTsT | 822 | AUGUGAGAGAUCcAAGUGCTsT | 823 | AD-14205 | 5% | 1% |
| AAAAAAGGAcuAGAuGGcTsT | 824 | GCcAUCuAGUCCUUUUUUTsT | 825 | AD-14206 | 79% | 6% |
| AGAGcAGAuuAccucuGcGTsT | 826 | CGcAGAGGuAAUCUGCUCUTsT | 827 | AD-14207 | 55% | 2% |
| AGcAGAuuAccucuGcGAGTsT | 828 | CUCGcAGAGGuAAUCUGCUTsT | 829 | AD-14208 | 100% | 4% |
| cccuGAcAGAGuucAcAAATsT | 830 | UUUGUGAACUCUGUcAGGGTsT | 831 | AD-14209 | 34% | 3% |
| GuuuAccGAAGuGuuGuuTsT | 832 | AAAcAACACUUCGGuAAACTsT | 833 | AD-14210 | 13% | 2% |
| uuAcAGuAcAcAAcAAGGATsT | 834 | UCCUUGUUGUGuACUGuAATsT | 835 | AD-14211 | 9% | 1% |
| AcuGAucGuAAGAAGGcATsT | 836 | UGCCUUCUuACGAUCcAGUTsT | 837 | AD-14212 | 20% | 3% |
| GAGcAGAuuAccucuGcGATsT | 838 | UCGcAGAGGuAAUCUGCUCTsT | 839 | AD-14213 | 48% | 5% |
| AAAAGAAGuuAGuGuAcGATsT | 840 | UCGuAcACuAACUUCUUUUTsT | 841 | AD-14214 | 28% | 18% |
| GAccAuuuAAuuuGGcAGATsT | 842 | UCUGCcAAAUuAAAUGGUCTsT | 843 | AD-14215 | 132% | 0% |
| GAGAGGAGuGAuAAuuAAATsT | 844 | UUuAAUuAUcACUCCUCUCTsT | 845 | AD-14216 | 3% | 0% |
| cuGGAGGAuuGGcuGAcAATsT | 846 | UUGUcAGCcAAUCCUCcAGTsT | 847 | AD-14217 | 19% | 1% |
| cucuAGucGuucccAcucATsT | 848 | UGAGUGGGAACGACuAGAGTsT | 849 | AD-14218 | 67% | 8% |
| GAuAccAuuAcuAcAGuAGTsT | 850 | CuACUGuAGuAAUGGuAUCTsT | 851 | AD-14219 | 76% | 4% |
| uucGucuGcGAAGAAGAAATsT | 852 | UUUCUUCUUCGcAGACGAATsT | 853 | AD-14220 | 33% | 8% |
| GAAAAGAAGuuGuGuAcGTsT | 854 | CGuAcACuAACUUCUUUUCTsT | 855 | AD-14221 | 25% | 2% |
| uGAuGuuuAccGAAGuGuuTsT | 856 | AAcACUUCGGuAAAcAUcATsT | 857 | AD-14222 | 7% | 2% |
| uGuuuGcccAAAuucuGGAuTsT | 858 | AUCcAGAAUUGGAcAAAcATsT | 859 | AD-14223 | 19% | 2% |
| AuGAAGAGuAuAccuGGGATsT | 860 | UCCcAGGuAuACUCUUcAUTsT | 861 | AD-14224 | 13% | 1% |
| GcuAcucuGAuGAAuGcAuTsT | 862 | AUGcAUUcAUcAGAGuAGCTsT | 863 | AD-14225 | 15% | 2% |
| GcccuuGuAGAAAGAAcAcTsT | 864 | GUGUUCUUUCuAcAAGGGCTsT | 865 | AD-14226 | 11% | 0% |
| ucAuGuccuuAucGAGAATsT | 866 | UUCUCGAuAAGGAcAUGATsT | 867 | AD-14227 | 5% | 1% |
| GAAuAGGGuuAcAGAGuuGTsT | 868 | cAACUCUGuAACCCuAUUCTsT | 869 | AD-14228 | 34% | 3% |

TABLE 3-continued

| sequence (5'-3') | SEQ ID NO. | sequence (5'-3') | SEQ ID NO. | duplex name | single dose screen @ 25 nM [% residual mRNA] | SDs 2nd screen (among quadruplicates) |
|---|---|---|---|---|---|---|
| cAAAcuGGAucGuAAGAAGTsT | 870 | CUUCUuACGAUCcAGUUUGTsT | 871 | AD-14229 | 15% | 2% |
| cuuAuuuGGuAAucuGcuGTsT | 872 | cAGcAGAUuACcAAAuAAGTsT | 873 | AD-14230 | 20% | 1% |
| AGcAAuGuGGAAAccuAAcTsT | 874 | GUuAGGUUUCcAcAUUGCUTsT | 875 | AD-14231 | 18% | 1% |
| AcAAuAAAGcAGAcccAuuTsT | 876 | AAUGGGUCUGCUUuAUUGUTsT | 877 | AD-14232 | 21% | 1% |
| AAccAcuuAGuAGuGuccATsT | 878 | UGGAcACuACuAAGUGGUUTsT | 879 | AD-14233 | 106% | 12% |
| AGucAAGAGccAucuGuAGTsT | 880 | CuAcAGAUGGCUCUUGACUTsT | 881 | AD-14234 | 35% | 3% |
| cucccuAGAcuucccuAuuTsT | 882 | AAuAGGGAAGUCuAGGGAGTsT | 883 | AD-14235 | 45% | 4% |
| AuAGcuAAAuuAAAccAAATsT | 884 | UUUUGGUUuAAUUuAGCuAUTsT | 885 | AD-14236 | 23% | 3% |
| uGGcuGGuAuAAuuccAcGTsT | 886 | CGUGGAAUuAuACcAGCcATsT | 887 | AD-14237 | 79% | 9% |
| uuAuuuGGuAAucuGcuGuTsT | 888 | AcAGcAGAUuACcAAAuAATsT | 889 | AD-14238 | 92% | 7% |
| AAcuAGAuGGcuuucucAGTsT | 890 | CUGAGAAAGCcAUCuAGUUTsT | 891 | AD-14239 | 20% | 2% |
| ucAuGGcGucGcAGccAAATsT | 892 | UUUGGCUGCGACGCcAUGATsT | 893 | AD-14240 | 71% | 6% |
| AcuGGAGGAuuGGcuGAcATsT | 894 | UGUcAGCcAAUCCUCcAGUTsT | 895 | AD-14241 | 14% | 1% |
| cuAuAAuuGcAcuAucuuuTsT | 896 | AAAGAuAGUGcAAUuAuAGTsT | 897 | AD-14242 | 11% | 2% |
| AAAGGucAccuAuGAAGATsT | 898 | UCUUcAUuAGGUGACCUUUTsT | 899 | AD-14243 | 11% | 1% |
| AuGAAuGcAucucuAGucTsT | 900 | GACuAGAGAuGCAUUcAUTsT | 901 | AD-14244 | 15% | 2% |
| AAcAAuuuGAAuAAAGccuGTsT | 902 | cAGGCUuAUUcAAAuUGUUTsT | 903 | AD-14245 | 80% | 7% |
| AAGAAGGcAGuuGAccAAcTsT | 904 | GUUGGUcAACAGCCUUCUUTsT | 905 | AD-14246 | 57% | 5% |
| GAuAcuAAAAGAAcAAucATsT | 906 | UGAUUGUUCUUUuAGuAUCTsT | 907 | AD-14247 | 9% | 3% |
| AuAcuGAAAAucAAuAGucTsT | 908 | GACuAUUGAUUUUcAGuAUTsT | 909 | AD-14248 | 39% | 4% |
| AAAAAGGAAcuAGAuGGcuTsT | 910 | AGCcAUCuAGUUCCUUUUUTsT | 911 | AD-14249 | 64% | 2% |
| GAAcuAGAuGGcuuucucATsT | 912 | UGAGAAAGCcAUCuAGUUCTsT | 913 | AD-14250 | 18% | 2% |
| GAAAccuAAcuGAAGAccuTsT | 914 | AGGUCUUcAGUuAGGUUUCTsT | 915 | AD-14251 | 56% | 6% |
| uAcccAucAAcAcuGGuAATsT | 916 | UuACCAGUGUUGAUGGGuATsT | 917 | AD-14252 | 48% | 6% |
| AuuuuGAuAucuAcccAuuTsT | 918 | AAUGGGuAGAuAUcAAAAUTsT | 919 | AD-14253 | 39% | 5% |
| AucccuAuAGuucAcuuuGTsT | 920 | cAAAGUGAACuAAGGGAUUTsT | 921 | AD-14254 | 44% | 8% |
| AuGGGcuAuAAuuGcAcuATsT | 922 | uAGUGcAAUuAuAGCCcAUTsT | 923 | AD-14255 | 108% | 8% |
| AGAuuAccucuGcGAGcccTsT | 924 | GGGCUCGcAGAGGuAAUCUTsT | 925 | AD-14256 | 108% | 6% |
| uAAuccAcGuAcccuucATsT | 926 | UGAAGGGuACGUGGAAUuATsT | 927 | AD-14257 | 23% | 2% |
| GucGuucccAcucAGuuuTsT | 928 | AAAAcuGAGuGGGAACGACTsT | 929 | AD-14258 | 21% | 3% |
| AAAucAAucccuGuuGAcuTsT | 930 | AGUcAAcAGGGAUUGAUUUTsT | 931 | AD-14259 | 19% | 2% |
| ucAuAGAGcAAAGAAcAuATsT | 932 | uAUGUUCUUUGCUCuAUGATsT | 933 | AD-14260 | 10% | 1% |
| uuAcuAcAGuAGcAcuuGGTsT | 934 | CcAAGUGCuACUGuAGuAATsT | 935 | AD-14261 | 76% | 3% |
| AuGuGGAAAccuAAcuGAATsT | 936 | UUcAGUuAGGUUUCcAcAUTsT | 937 | AD-14262 | 13% | 2% |
| uGuGGAAAccuAAcuGAAGTsT | 938 | CUUcAGUuAGGUUUCcAcATsT | 939 | AD-14263 | 14% | 2% |
| uGuccuuAAAuGAAAGGGTsT | 940 | CCCUUUcAUUuAAGGAAGATsT | 941 | AD-14264 | 65% | 3% |
| uGAAGAAccucuAAGucAATsT | 942 | UUGACUuAGAGGUUCUUcATsT | 943 | AD-14265 | 13% | 1% |
| AGAGGucuAAAGuGGAAGATsT | 944 | UCUUCcACUUuAGACCUCUTsT | 945 | AD-14266 | 18% | 3% |
| AuAcuAcccAuuuuucuGTsT | 946 | cAGAAAAUGGGuAGAuAUTsT | 947 | AD-14267 | 50% | 9% |
| uAAGccuGAAGuGAAucAGTsT | 948 | CUGAUUcACUUcAGGCUuATsT | 949 | AD-14268 | 13% | 3% |
| AGAuGcAGAccAuuuAAuuTsT | 950 | AAUuAAAUGGUCUGcAUCUTsT | 951 | AD-14269 | 19% | 4% |
| AGuGuuuGuccAAAucTsT | 952 | GAAUUGGAcAAAcAAcACUTsT | 953 | AD-14270 | 11% | 2% |
| cuAuAAuGAAGAGcuuuuuTsT | 954 | AAAAAGCUCUUcAUuAuAGTsT | 955 | AD-14271 | 11% | 1% |
| AGAGGAGuGAuAAuuAAAGTsT | 956 | CUUuAAUuAUcACUCCUCUTsT | 957 | AD-14272 | 7% | 1% |
| uuucucuGuAcAAuAcAuTsT | 958 | AUGuAUUGuAAcAGAGAAATsT | 959 | AD-14273 | 14% | 2% |
| AAcAucuAuAAuuGcAAcATsT | 960 | UGUUGcAAUuAuAGAUGUUTsT | 961 | AD-14274 | 73% | 4% |
| uGcuAGAAGuAcAuAAGAcTsT | 962 | GUCUuAUGuACUUcuAGcATsT | 963 | AD-14275 | 10% | 1% |
| AAuGuAcucAAGAcuGAucTsT | 964 | GAUcAGUCUUGACuAcAUUTsT | 965 | AD-14276 | 89% | 2% |
| GuAcucAAGAcuGAucuucTsT | 966 | GAAGAUcAGUCUUGAGuACTsT | 967 | AD-14277 | 7% | 1% |
| cAcucuGAuAAAcucAAuGTsT | 968 | cAUUGAGUUuAUcAGAGUGTsT | 969 | AD-14278 | 12% | 1% |
| AAGAGcAGAuuAcccucGcTsT | 970 | GcAGAGGuAAUCUGCUCUUTsT | 971 | AD-14279 | 104% | 3% |
| ucuGcGAGcccAGAucAAcTsT | 972 | GUUGAUCUGGGCUCGcAGATsT | 973 | AD-14280 | 21% | 2% |
| AAcuuGAGccuuGuGuAuATsT | 974 | uAuAcAcAAGGCUcAAGUUTsT | 975 | AD-14281 | 43% | 3% |
| GAAuAuAuAucAGccGGTsT | 976 | CCGGCUGAuAuAuAUUCTsT | 977 | AD-14282 | 45% | 6% |
| uGucAucccuAuAGuucAcTsT | 978 | GUGAACuAuAGGGAuGAcTsT | 979 | AD-14283 | 35% | 5% |
| GAucGGcAAccAuAuuucTsT | 980 | GAAAuAUGGUUGCcAGAUCTsT | 981 | AD-14284 | 58% | 3% |
| uGGcAAccAuAuuucuGGATsT | 982 | UCcAGAAAuAUGGUUGCcATsT | 983 | AD-14285 | 48% | 3% |
| GAuGuuuAccGAAGuGuuGTsT | 984 | cAAcACUUCGGuAAAcAUCTsT | 985 | AD-14286 | 49% | 3% |
| uuccuuAucGAGAAcuAATsT | 986 | UuAGAAUUCUCGAuAAGGAATsT | 987 | AD-14287 | 6% | 1% |
| AGcuuAuuuGcuuucuGGATsT | 988 | UCcAGAAAGcAAUuAAGCUTsT | 989 | AD-14288 | 50% | 2% |
| uuGcuAuuAuGGGAGAccATsT | 990 | UGGUCUCCcAuAAuAGcAATsT | 991 | AD-14289 | 48% | 1% |
| GucAuGGcGucGcAGccAATsT | 992 | UUGGCUGCGACGCcAUGACTsT | 993 | AD-14290 | 112% | 7% |
| uAAuuGcAcuAucuuuGcGTsT | 994 | CGcAAAGAuAGUGcAAUuATsT | 995 | AD-14291 | 77% | 2% |
| cuAucuuuGcGuAuGGccATsT | 996 | UGGCcAuACGcAAAGAuAGTsT | 997 | AD-14292 | 80% | 6% |
| ucccuAuAGuucAcuuuGTsT | 998 | AcAAAGUGAACuAuAGGGATsT | 999 | AD-14293 | 58% | 2% |
| ucAAccuuuAAuucAcuuGTsT | 1000 | cAAGUGAAUuAAAGGUUGATsT | 1001 | AD-14294 | 77% | 2% |
| GGcAAccAuAuuucuGGATsT | 1002 | UUCcAGAAAuAUGGUUGCCTsT | 1003 | AD-14295 | 62% | 2% |
| AuGuAcucAAGAcuGAucuTsT | 1004 | AGAUcAGUCUUGAGuAcAUTsT | 1005 | AD-14296 | 59% | 4% |
| GcAGAccAuuuAAuuuGGcTsT | 1006 | GCcAAAUuAAAUGGUCUGCTsT | 1007 | AD-14297 | 37% | 1% |
| ucuGAGAGAcuAcAGAuGuTsT | 1008 | AcAUCUGuAGUCUCUcAGATsT | 1009 | AD-14298 | 21% | 1% |
| uGcucAuAGAGcAAAGAAcTsT | 1010 | GUUCUUUGCUCuAUGAGcATsT | 1011 | AD-14299 | 6% | 1% |
| AcAuAAGAccuuAuuuGGuTsT | 1012 | ACcAAAuAAGGUCUuAUGUTsT | 1013 | AD-14300 | 17% | 2% |

TABLE 3-continued

| sequence (5'-3') | SEQ ID NO. | sequence (5'-3') | SEQ ID NO. | duplex name | single dose screen @ 25 nM [% residual mRNA] | SDs 2nd screen (among quadru-plicates) |
|---|---|---|---|---|---|---|
| uuuGuGcuGAuucuGAuGGTsT | 1014 | CcAUcAGAAUcAGcAcAAATsT | 1015 | AD-14301 | 97% | 6% |
| ccAucAAcAcuGGuAAGAATsT | 1016 | UUCUuACcAGUGUUGAUGGTsT | 1017 | AD-14302 | 13% | 1% |
| AGAcAAuuccGGAuGuGGATsT | 1018 | UCcAcAUCCGGAAUUGUCUTsT | 1019 | AD-14303 | 13% | 3% |
| GAAcuuGAGccuuGuGAuATsT | 1020 | AuAcAcAAGGCUcAAGUUCTsT | 1021 | AD-14304 | 38% | 2% |
| uAAuuuGGcAGAGcGGAAATsT | 1022 | UUUCCGCUCUGCcAAAUuATsT | 1023 | AD-14305 | 14% | 2% |
| uGGAuGAAGuuAuuAuGGGTsT | 1024 | CCcAuAAuAACUUcAUCcATsT | 1025 | AD-14306 | 22% | 4% |
| AucuAcAuGAAcuAcAAGATsT | 1026 | UCUUGuAGUUcAUGuAGAUTsT | 1027 | AD-14307 | 26% | 6% |
| GGuAuuuuGAucuGGcAATsT | 1028 | UUGCcAGAUcAAAAAuACCTsT | 1029 | AD-14308 | 62% | 8% |
| cuAAuGAAGAGuAAccuGTsT | 1030 | cAGGuAuACUCUUcAUuAGTsT | 1031 | AD-14309 | 52% | 5% |
| uuuGAGAAAcuuAcuGAuATsT | 1032 | uAUcAGuAAGuuUCUcAAATsT | 1033 | AD-14310 | 32% | 3% |
| cGAuAAGAuAGAAGAucAATsT | 1034 | UUCAUCUUCuAUCUuAUCGTsT | 1035 | AD-14311 | 23% | 2% |
| cuGGcAAccAuAuuucGGTsT | 1036 | CcAGAAAuAUGGUUGCcAGTsT | 1037 | AD-14312 | 49% | 6% |
| uAGGuAccAuuAcuAcAGuTsT | 1038 | ACUGUAGuAAUGGuAUCuATsT | 1039 | AD-14313 | 69% | 4% |
| GuAuuAAAuuGGGuuucAuTsT | 1040 | AUGAAACCcAAUUuAuACTsT | 1041 | AD-14314 | 52% | 3% |
| AAGAccuuAuuuGGuAucTsT | 1042 | GAUuACcAAAuAAGGUCUUTsT | 1043 | AD-14315 | 66% | 4% |
| GcuGuuGAuAAGAGAGcucTsT | 1044 | GAGCUCUCUuAUcAAcAGCTsT | 1045 | AD-14316 | 19% | 4% |
| uAcucAuGuuucucAGAuuTsT | 1046 | AAUCUGAGAAAcAUGAGuATsT | 1047 | AD-14317 | 16% | 5% |
| cAGAuGGAcGuAAGGcAGcTsT | 1048 | GCUGCCUuACGUCcAUCUGTsT | 1049 | AD-14318 | 52% | 11% |
| uAucccAAcAGGuAcGAcATsT | 1050 | UGUCGuACCUGUUGGGAUTsT | 1051 | AD-14319 | 28% | 11% |
| cAuuGcuAuuAuGGGAGAcTsT | 1052 | GUCUCCcAuAAuAGcAAUGTsT | 1053 | AD-14320 | 52% | 10% |
| cccucAGuAAAuccAuGGuTsT | 1054 | ACcAUGGAUUuACUGAGGGTsT | 1055 | AD-14321 | 53% | 6% |
| GGucAuuAcuGcccuuGuATsT | 1056 | uAcAAGGGcAGuAAUGACCTsT | 1057 | AD-14322 | 20% | 2% |
| AAccAcucAAAAAcAuuuGTsT | 1058 | cAAAUGUUUUUGAGUGGUUTsT | 1059 | AD-14323 | 116% | 6% |
| uuuGcAAGuuAuGAAucuTsT | 1060 | AGAUUcAUuAcAAUUGcAAATsT | 1061 | AD-14324 | 14% | 2% |
| uuAuuucAGuAGucAGAATsT | 1062 | UUCUGAcUACUGAAAuAATsT | 1063 | AD-14325 | 50% | 2% |
| uuuucucGAuucAAAucuuTsT | 1064 | AAGAUUuGAUCGAGAAAATsT | 1065 | AD-14326 | 47% | 3% |
| GuAcGAAAAGAAGuuGuGTsT | 1066 | cACuAACUUCUUUUCGuACTsT | 1067 | AD-14327 | 18% | 2% |
| uuuAAAAcGAGAucuuGcuTsT | 1068 | AGcAAGAUCUCGUUUuAAATsT | 1069 | AD-14328 | 19% | 1% |
| GAAuuGAuuAAuGuAcucATsT | 1070 | UGAGuAcAUuAAUcAAUUCTsT | 1071 | AD-14329 | 94% | 10% |
| GAuGGAcGuAAGGcAGcucTsT | 1072 | GAGCUGCCUuACGUCcAUCTsT | 1073 | AD-14330 | 60% | 4% |
| cAucuGAcuAAuGGcucuGTsT | 1074 | cAGAGCcAUuAGUcAGAUGTsT | 1075 | AD-14331 | 54% | 7% |
| GuGAuccuGuAcGAAAAGATsT | 1076 | UCUUUUCGuAcAGGAUcACTsT | 1077 | AD-14332 | 22% | 4% |
| AGcucuuAuuAAGGAGuAuTsT | 1078 | AuACUCCUuAAuAAGAGCUTsT | 1079 | AD-14333 | 70% | 10% |
| GcucuuAuuAAGGAGuAuATsT | 1080 | uAuACUCCUuAAuAAGAGCTsT | 1081 | AD-14334 | 18% | 3% |
| ucuuAuuAAGGAGuAuAcGTsT | 1082 | CGuAuACUCCUuAAuAAGATsT | 1083 | AD-14335 | 38% | 6% |
| uAuuAAGGAGuAuAcGGAGTsT | 1084 | CUCCGuAuACUCCUuAAuATsT | 1085 | AD-14336 | 16% | 3% |
| cuGcAGcccGuGAGAAAATsT | 1086 | UUUUUCUcACGGGCUGcAGTsT | 1087 | AD-14337 | 65% | 4% |
| ucAAGAcuGAucuucuAAGTsT | 1088 | CUuAGAAGAUcAGUCUUGATsT | 1089 | AD-14338 | 18% | 0% |
| cuucuAAGuucAcuGGAAATsT | 1090 | UUUCcAGUGAACUuAGAAGTsT | 1091 | AD-14339 | 20% | 4% |
| uGcAAGuuAuGAAucuuuTsT | 1092 | AAAGAUUcAUuAACUUGcATsT | 1093 | AD-14340 | 24% | 1% |
| AAucuAAGGAuAuAGucAATsT | 1094 | UUGAcuAuAUCCUuAGAUUTsT | 1095 | AD-14341 | 27% | 3% |
| AucucuGAAcAcAAGAAcATsT | 1096 | UGUUCUUGUGUUcAGAGAUTsT | 1097 | AD-14342 | 13% | 1% |
| uuccAAcAGuGGGuAucuTsT | 1098 | AGAuACCcACUGUUcAGAATsT | 1098 | AD-14343 | 19% | 1% |
| AGuuAuuuAucccAucAATsT | 1100 | UUGAuGGGuAuAAAuAACUTsT | 1101 | AD-14344 | 23% | 2% |
| AuGcAAAcuGuucAGAAATsT | 1102 | UUUCUGAAcAGUUuAGcAUTsT | 1103 | AD-14345 | 21% | 4% |
| cuAcAGAGcAcuuGGuuAcTsT | 1104 | GuAACcAAGUGCUCUGuAGTsT | 1105 | AD-14346 | 18% | 2% |
| uAuAAuAcAGccGGGcGTsT | 1106 | CGCGCCCGGCCGuAuAuATsT | 1107 | AD-14347 | 67% | 2% |
| AuGuAAAuAcGuAuuucuATsT | 1108 | uAGAAAuACGuAUUuAcAUTsT | 1109 | AD-14348 | 39% | 3% |
| uuuuucucGAuucAAAucuTsT | 1110 | AGAUUuGAAUCGAGAAAATsT | 1111 | AD-14349 | 83% | 6% |
| AAucuuAAcccuuAGGAcuTsT | 1112 | AGUCcUAAGGGUuAAGAUUTsT | 1113 | AD-14350 | 54% | 2% |
| ccuuAGGAcucuGuAuuuTsT | 1114 | AAAuACcAGAGUCCuAAGGTsT | 1115 | AD-14351 | 57% | 8% |
| AAuAAAcuGcccucAGuAATsT | 1116 | UuACUGAGGGcAGUUuAUUTsT | 1117 | AD-14352 | 82% | 3% |
| GAuccuGuAcGAAAAGAAGTsT | 1118 | CUUCUUUUCGuAcAGGAUCTsT | 1119 | AD-14353 | 2% | 1% |
| AAuGuAuccuGuAcGAAATsT | 1120 | UUUCGuAcAGGAUcAcAUUTsT | 1121 | AD-14354 | 18% | 11% |
| GuGAAAAcAUUGGccGuucTsT | 1122 | GAACGGCcAAUGUUUUcACTsT | 1123 | AD-14355 | 2% | 1% |
| cuuGAGGAAAcucuGAGuATsT | 1124 | uACUcAGAGUUUCCUcAAGTsT | 1125 | AD-14356 | 8% | 2% |
| cGuuuAAAAcGAGAucuuGTsT | 1126 | cAAGAUCUCGUUUuAAACGTsT | 1127 | AD-14357 | 6% | 3% |
| uuAAAAcGAGAucuuGcuTsT | 1128 | cAGcAAGAUCUCGUUUuAATsT | 1129 | AD-14358 | 98% | 17% |
| AAAGAuAuucuGcGucuccTsT | 1130 | GGAGACcAGAuAcAUCUUUTsT | 1131 | AD-14359 | 10% | 1% |
| cAGAAAAuGuGucuAcucATsT | 1132 | UGAGuAGAcAcAUUUUCUGTsT | 1133 | AD-14360 | 6% | 4% |
| cAGGAAuuGAuuAAuGuAcTsT | 1134 | GuAcAUuAAUcAAUUCCUGTsT | 1135 | AD-14361 | 30% | 5% |
| AGucAAcuAAAGcAuuuuTsT | 1136 | AAAuUGCUUuAGUUGACUTsT | 1137 | AD-14362 | 20% | 2% |
| uGuGAAAcAAucuAcAuGuTsT | 1138 | UcAUGuAGAUUGUUUcAcATsT | 1139 | AD-14363 | 60% | 6% |
| AuAccAuuuGuuccuuGGuTsT | 1140 | ACcAAGGAAcAAAUGGuAUTsT | 1141 | AD-14364 | 12% | 9% |
| GcAGAAAucuAAGGAuAuATsT | 1142 | uAuAUCCUuAGAUUUCUGCTsT | 1143 | AD-14365 | 5% | 2% |
| uGGcuucucAcAGGAAcucTsT | 1144 | GAGUUCCUGUGAGAAGCcATsT | 1145 | AD-14366 | 28% | 5% |
| GAGAuGuGAAucucuGAAcTsT | 1146 | GUUcAGAGAUUcAcAUCUCTsT | 1147 | AD-14367 | 42% | 4% |
| uGuAAGccAAuGuuGuGAGTsT | 1148 | CUcAcAAcAUUGGCUuAcATsT | 1149 | AD-14368 | 93% | 12% |
| AGccAAuGuuGuGAGGcuuTsT | 1150 | AAGCCUcAcAAcAUUGGCUTsT | 1151 | AD-14369 | 65% | 4% |
| uuuGuGAGGcuucAAGuucATsT | 1152 | UGAACUUGAAGCCUcAcAATsT | 1153 | AD-14370 | 5% | 2% |
| AGGcAGcucAuGAGAAAcATsT | 1154 | UGUUUCUcAUGAGCUGCCUTsT | 1155 | AD-14371 | 54% | 5% |
| AuAAAuuGAuAGcAcAAAATsT | 1156 | UUUUGUGCuAUcAAUUuAUTsT | 1157 | AD-14372 | 4% | 1% |

TABLE 3-continued

| sequence (5'-3') | SEQ ID NO. | sequence (5'-3') | SEQ ID NO. | duplex name | single dose screen @ 25 nM [% residual mRNA] | SDs 2nd screen (among quadruplicates) |
|---|---|---|---|---|---|---|
| AcAAAAucuAGAAcuuAAuTsT | 1158 | AUuAAGUUCuAGAUUUUGUTsT | 1159 | AD-14373 | 5% | 1% |
| GAuAucccAAcAGGuAcGATsT | 1160 | UCGuACCUGUUGGGAuAUCTsT | 1161 | AD-14374 | 92% | 6% |
| AAGuuAuuuAuAcccAucATsT | 1162 | UGAUGGGuAuAAAuAACUUTsT | 1163 | AD-14375 | 76% | 4% |
| uGuAAAuAcGuAuuucuAGTsT | 1164 | CuAGAAAuACGuAUUuAcATsT | 1165 | AD-14376 | 70% | 5% |
| ucuAGuuuucAuAuAAAGuTsT | 1166 | ACUUuAuAUGAAAAcuAGATsT | 1167 | AD-14377 | 48% | 4% |
| AuAAAGuAGuucuuuuAuATsT | 1168 | uAuAAAAGAACuACUUuAUTsT | 1169 | AD-14378 | 48% | 3% |
| ccAuuuGuAGAGcuAcAAATsT | 1170 | UUUGuAGCUCuAcAAAUGGTsT | 1171 | AD-14379 | 44% | 5% |
| uAuuucAGuAGucAGAAuTsT | 1172 | AUUCUGACuACUGAAAAuATsT | 1173 | AD-14380 | 35% | 16% |
| AAAucuAAcccuAGuuGuATsT | 1174 | uAcAACuAGGGUuAGAUUUTsT | 1175 | AD-14381 | 44% | 5% |
| cuuuAGAGuAuAcAuuGcuTsT | 1176 | AGcAAUGuAuACUCuAAAGTsT | 1177 | AD-14382 | 28% | 1% |
| AucuGAcuAAuGGcucuGuTsT | 1178 | AcAGAGCcAUuAGUcAGAUTsT | 1179 | AD-14383 | 55% | 11% |
| cAcAAuGAuuuAAGGAcuGTsT | 1180 | cAGUCCUuAAAUcAUUGUGTsT | 1181 | AD-14384 | 48% | 9% |
| ucuuuuucucGAuucAAAuTsT | 1182 | AUUuGAAUCGAGAAAAAGATsT | 1183 | AD-14385 | 36% | 2% |
| cuuuuucucGAuucAAAucTsT | 1184 | GAUUuGAAUCGAGAAAAAGTsT | 1185 | AD-14386 | 41% | 7% |
| AuuuucGcucAcGAuGAGTsT | 1186 | CUcAUCGUGAGcAGAAAAUTsT | 1187 | AD-14387 | 38% | 3% |
| uuucuGcucAcGAuGAGuuTsT | 1188 | AACUcAUCGUGAGcAGAAATsT | 1189 | AD-14388 | 50% | 4% |
| AGAGcuAcAAAAccuAuccTsT | 1190 | GGAuAGGUUUUGuAGCUCUTsT | 1191 | AD-14389 | 98% | 6% |
| GAGccAAAGGuAcAccAcuTsT | 1192 | AGUGGUGuACCUUUGGCUCTsT | 1193 | AD-14390 | 43% | 0% |
| GccAAAGGuAcAccAcuAcTsT | 1194 | GuAGUGGUGuACCUUUGGCTsT | 1195 | AD-14391 | 48% | 4% |
| GAAcuGuAcucuucucAGcTsT | 1196 | GCUGAGAAGAGuAcAGUUCTsT | 1197 | AD-14392 | 44% | 3% |
| AGGuAAAuAucAccAAcAuTsT | 1198 | AUGUUGGUGAuAUUuACCUTsT | 1199 | AD-14393 | 37% | 2% |
| AGcuAcAAAAccuAuccuuTsT | 1200 | AAGGAuAGGUUUUGuAGCUTsT | 1201 | AD-14394 | 114% | 7% |
| uGuAAAGcAuuuAAuuccTsT | 1202 | GGAAUuAAAUGCUUUcAcATsT | 1203 | AD-14395 | 55% | 4% |
| GcccAcuuuAGAGuAuAcATsT | 1204 | UGuAuACUCuAAAGUGGGCTsT | 1205 | AD-14396 | 49% | 5% |
| uGuGccAcAcuccAAGaccTsT | 1206 | GGUCUUGGAGUGUGGcAcATsT | 1207 | AD-14397 | 71% | 6% |
| AAAcuAAuuGAucucGuATsT | 1208 | uACGAGAUcAAUUuAGUUUTsT | 1209 | AD-14398 | 81% | 7% |
| uGAucucGuAGAAuuAucuTsT | 1210 | AGAuAAUUCuACGAGAUcATsT | 1211 | AD-14399 | 38% | 4% |
| GcGuGcAGucGGuccuccATsT | 1212 | UGGAGGACCGACUGcACGCTsT | 1213 | AD-14400 | 106% | 8% |
| AAAGuuuAGAGAcAucuGATsT | 1214 | UcAGAUGUCUCuAAACUUUTsT | 1215 | AD-14401 | 47% | 3% |
| cAGAAGGAuAuGuAcAAATsT | 1216 | UUUGuAcAuAUUCCUUCUGTsT | 1217 | AD-14402 | 31% | 1% |
| cGcccGAGAGuAccAGGGATsT | 1218 | UCCCUGGuACUCUCGGGCGTsT | 1219 | AD-14403 | 105% | 4% |
| cGGAGGAGAuAGAAcGuuuTsT | 1220 | AAACGUUCuAUCUCCUCCGTsT | 1221 | AD-14404 | 3% | 1% |
| AGAuAGAAcGuuuAAAAcGTsT | 1222 | CGUUUuAAACGUUCuAUCUTsT | 1223 | AD-14405 | 15% | 1% |
| GGAAcAGGAAcuucAcAAcTsT | 1224 | GUuGuGAAGUUCCuGUUCCTsT | 1225 | AD-14406 | 44% | 5% |
| GuGAGccAAAGGuAcAccATsT | 1226 | UGGGUGuACCUUUGGCUcACTsT | 1227 | AD-14407 | 41% | 4% |
| AuccuccuAGAcuucccuTsT | 1228 | AGGGAAGUCuAGGGAGGAUTsT | 1229 | AD-14408 | 104% | 3% |
| cAcAcuccAAGAccuGuGcTsT | 1230 | GcAcAGGUCUUGGAGUGUGTsT | 1231 | AD-14409 | 67% | 4% |
| AcAGAAGGAuAuGuAcAATsT | 1232 | UUGuAcAuAUUCCUUCUGUTsT | 1233 | AD-14410 | 22% | 1% |
| uuAGAGAcAUCUGAcuuuGTsT | 1234 | cAAAGUcAGAUGUCUCuAATsT | 1235 | AD-14411 | 29% | 3% |
| AAuuGAucucGuAGAAuuATsT | 1236 | uAAUUCuACGAGAUcAAUUTsT | 1237 | AD-14412 | 31% | 4% |

---

We claim:

1. A double-stranded ribonucleic acid (dsRNA) for inhibiting the expression of a human kinesin family member 11 (Eg5) gene in a cell, wherein said dsRNA comprises a sense strand comprising a first sequence and an antisense strand comprising a second sequence complementary to SEQ ID NO:1311, wherein said first sequence is complementary to said second sequence and wherein said dsRNA is between 15 and 30 base pairs in length.

2. The dsRNA of claim 1, wherein said dsRNA comprises at least one modified nucleotide.

3. The dsRNA of claim 2, wherein said modified nucleotide is chosen from the group of: a 2'-O-methyl modified nucleotide, a nucleotide comprising a 5'-phosphorothioate group, and a terminal nucleotide linked to a cholesteryl derivative or dodecanoic acid bisdecylamide group.

4. The dsRNA of claim 2, wherein said modified nucleotide is chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide.

5. An isolated cell comprising the dsRNA of claim 1.

6. A pharmaceutical composition for inhibiting the expression of the Eg5 gene comprising the dsRNA of claim 1.

7. The pharmaceutical composition of claim 6, further comprising a second dsRNA that inhibits the expression of the VEGF gene wherein the second dsRNA comprises a sense strand consisting of the sequence of SEQ ID NO:1242, and an antisense strand consisting of the sequence of SEQ ID NO:1243.

8. A method for inhibiting expression of a human kinesin family member 11 (Eg5) gene in a cell, the method comprising:
(a) introducing into the cell the dsRNA of claim 1; and
(b) maintaining the cell produced in step (a) for a time sufficient to obtain degradation of the mRNA transcript of the Eg5 gene, thereby inhibiting expression of the Eg5 gene in the cell.

9. The method of claim 8, wherein a second dsRNA that inhibits the expression of VEGF is introduced into said cell wherein the second dsRNA comprises a sense strand consisting of the sequence of SEQ ID NO:1242, and an antisense strand consisting of the sequence of SEQ ID NO:1243.

10. A method of treating or managing pathological processes mediated by human kinesin family member 11 (Eg5) expression comprising administering to a patient in need of such treatment or management a therapeutically effective amount of the dsRNA of claim 1.

11. The method of claim 10 further comprising administering a second dsRNA that inhibits the expression of VEGF wherein the second dsRNA comprises a sense strand consisting of the sequence of SEQ ID NO:1242, and an antisense strand consisting of the sequence of SEQ ID NO:1243.

12. A vector for inhibiting the expression of a human kinesin family member 11 (Eg5) gene in a cell, said vector comprising a regulatory sequence operably linked to a nucleotide sequence that encodes at least one strand of a dsRNA, wherein one of the strands of said dsRNA is substantially complementary to SEQ ID NO:1311 and wherein said dsRNA is less than 30 base pairs in length.

13. An isolated cell comprising the vector of claim 12.

14. The dsRNA of claim 1, wherein said dsRNA, upon contact with a cell expressing said Eg5, inhibits expression of said Eg5 gene by at least 40%.

15. The dsRNA of claim 1, wherein said dsRNA is 19-21 base pairs in length.

16. The vector of claim 12, wherein said dsRNA, upon contact with a cell expressing said Eg5, inhibits expression of said Eg5 gene by at least 40%.

17. The vector of claim 12, wherein said dsRNA is 19-21 base pairs in length.

18. The pharmaceutical composition of claim 6, wherein the dsRNA is duplex AD12115 consisting of a sense strand consisting of SEQ ID NO:135 and an antisense strand consisting of SEQ ID NO:136.

19. The pharmaceutical composition of claim 7, wherein the dsRNA of claim 1 is duplex AD12115 consisting of a sense strand consisting of SEQ ID NO:135 and an antisense strand consisting of SEQ ID NO:136.

20. The method of claim 9, wherein said second dsRNA comprises a sense strand consisting of the sequence of SEQ ID NO:1242, and an antisense strand consisting of the sequence of SEQ ID NO:1243.

21. The dsRNA of claim 1, wherein the dsRNA is duplex AD12115 consisting of a sense strand consisting of SEQ ID NO:135 and an antisense strand consisting of SEQ ID NO:136.

22. The dsRNA of claim 21, wherein each strand is modified as follows to include a 2'-O-methyl ribonucleotide as indicated by a lower case letter "c" or "u" and a phosphorothioate as indicated by a lower case letter "s":
SEQ ID NO:135 is ucGAGAAucuAAAcuAAcuTsT
SEQ ID NO:136 is AGUuAGUUuAGAUUCUCGATsT.

23. A composition comprising the dsRNA of claim 1 and a second dsRNA that inhibits the expression of the VEGF gene, wherein the second dsRNA that inhibits the expression of VEGF comprises a sense strand consisting of the sequence of SEQ ID NO:1242, and an antisense strand consisting of the sequence of SEQ ID NO:1243.

24. The composition of claim 22, wherein the dsRNA of claim 1 is duplex AD12115 consisting of a sense strand consisting of SEQ ID NO:135 and an antisense strand consisting of SEQ ID NO:136.

25. The composition of claim 23, wherein the sense strand and antisense strand of the dsRNA of claim 1 are modified as follows to include a 2'-O-methyl ribonucleotide as indicated by a lower case letter "c" or "u" and a phosphorothioate as indicated by a lower case letter "s":
SEQ ID NO:135 is ucGAGAAucuAAAcuAAcuTsT
SEQ ID NO:136 is AGUuAGUUuAGAUUCUCGATsT.

26. The composition of claim 22 wherein the sense strand and antisense strand of the second dsRNA that inhibits the expression of VEGF are modified as follows to include a 2'-O-methyl ribonucleotide as indicated by a lower case letter "c" or "u" and a phosphorothioate as indicated by a lower case letter "s":
GcAcAuAGGAGAGAuGAGCUsU (SEQ ID NO:1242)
AAGCUcAUCUCUCCuAuGuGCusG (SEQ ID NO:1243).

27. The composition of claim 22, wherein the dsRNA of claim 1 is duplex AD12115 consisting of a sense strand consisting of SEQ ID NO:135 and an antisense strand consisting of SEQ ID NO:136 and the second dsRNA that inhibits the expression of VEGF comprises a sense strand consisting of the sequence of SEQ ID NO:1242 and an antisense strand consisting of the sequence of SEQ ID NO:1243.

28. The composition of claim 26, wherein the sense and antisense strands of the dsRNA of claim 1 and the sense strand and antisense strand of the second dsRNA that inhibits the expression of VEGF are modified as follows to include a 2'-O-methyl ribonucleotide as indicated by a lower case letter "c" or "u" and a phosphorothioate as indicated by a lower case letter "s":

SEQ ID NO:135 is ucGAGAAucuAAAcuAAcuTsT
SEQ ID NO:136 is AGUuAGUUuAGAUUCUCGATsT
GcAcAuAGGAGAGAuGAGCUsU (SEQ ID NO:1242)
AAGCUcAUCUCUCCuAuGuGCusG (SEQ ID NO:1243).

29. A pharmaceutical composition comprising the composition of claim 22.

30. At least one vector for inhibiting the expression of a human kinesin family member 11 (Eg5) gene and a VEGF gene in a cell, said vector comprising a regulatory sequence operably linked to a nucleotide sequence that encodes at least one strand of a first dsRNA and at least one strand of a second dsRNA, wherein one strand of said first dsRNA is substantially complementary to SEQ ID NO:1311 and one strand of said second dsRNA is substantially complementary to SEQ ID NO:1242 and wherein said first and second dsRNAs are less than 30 base pairs in length.

31. An isolated cell comprising the vector of claim 30.

32. The dsRNA of claim 2, comprising at least one 2'-O-Me ribonucleotide and at least one phosphorothioate.

33. The dsRNA of claim 22, comprising at least one 2'-O-Me ribonucleotide and at least one phosphorothioate.

\* \* \* \* \*

UNITED STATES PATENT AND TRADEMARK OFFICE
CERTIFICATE OF CORRECTION

PATENT NO. : 7,718,629 B2  Page 1 of 1
APPLICATION NO. : 11/694215
DATED : May 18, 2010
INVENTOR(S) : David Bumcrot et al.

It is certified that error appears in the above-identified patent and that said Letters Patent is hereby corrected as shown below:

In claim 24, Column 604, line 34, please delete "of claim 22" and replace with --of claim 23--.

In claim 25, Column 604, line 38, please delete "of claim 23" and replace with --of claim 24--.

In claim 26, Column 604, line 45, please delete "of claim 22" and replace with --of claim 23--.

In claim 27, Column 604, line 54, please delete "of claim 22" and replace with --of claim 23--.

In claim 28, Column 604, line 61, please delete "of claim 26" and replace with --of claim 27--.

In claim 29, Column 605, line 7, please delete "of claim 22" and replace with --of claim 23--.

Signed and Sealed this

Third Day of August, 2010

David J. Kappos
*Director of the United States Patent and Trademark Office*